(12) United States Patent
Cheung et al.

(10) Patent No.: US 9,181,266 B2
(45) Date of Patent: Nov. 10, 2015

(54) 2-PIPERIDIN-1-YL-ACETAMIDE COMPOUNDS FOR USE AS TANKYRASE INHIBITORS

(75) Inventors: Atwood Kim Cheung, Cambridge, MA (US); Donovan Noel Chin, Cambridge, MA (US); Jianmei Fan, Cambridge, MA (US); Karen Marie Miller-Moslin, Princeton, NJ (US); Michael David Shultz, Cambridge, MA (US); Troy D Smith, Cambridge, MA (US); Ronald Charles Tomlinson, Sudbury, MA (US); Bakary-Barry Toure, Cambridge, MA (US); Michael Scott Visser, Cambridge, MA (US); Zhuoliang Chen, Belmont, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/154,161

(22) PCT Filed: Jul. 13, 2012

(86) PCT No.: PCT/US2012/046673
§ 371 (c)(1),
(2), (4) Date: May 27, 2014

(87) PCT Pub. No.: WO2013/012723
PCT Pub. Date: Jan. 24, 2013

(65) Prior Publication Data
US 2015/0025070 A1    Jan. 22, 2015

Related U.S. Application Data

(60) Provisional application No. 61/507,308, filed on Jul. 13, 2011.

(51) Int. Cl.
| C07D 401/12 | (2006.01) |
| C07D 409/14 | (2006.01) |
| A61K 31/453 | (2006.01) |
| A61K 31/4545 | (2006.01) |
| C07D 491/052 | (2006.01) |
| C07D 493/04 | (2006.01) |

(52) U.S. Cl.
CPC .......... *C07D 491/052* (2013.01); *A61K 31/453* (2013.01); *A61K 31/4545* (2013.01); *C07D 401/12* (2013.01); *C07D 409/14* (2013.01); *C07D 493/04* (2013.01)

(58) Field of Classification Search
CPC .. C07D 401/12; C07D 409/14; A61K 31/453; A61K 31/4545
USPC .......... 544/117, 253, 278, 287, 319; 514/234.2, 258.1, 260.1, 266.22, 269
See application file for complete search history.

(56) References Cited

U.S. PATENT DOCUMENTS

| 2004/0132718 A1 | 7/2004 | Jacobson et al. |
| 2005/0075347 A1 | 4/2005 | Albrecht et al. |
| 2005/0085476 A1 | 4/2005 | Seko et al. |
| 2005/0159431 A1 | 7/2005 | Albrecht et al. |
| 2008/0269234 A1 | 10/2008 | Gandhi et al. |
| 2009/0163545 A1 | 6/2009 | Goldfarb |

FOREIGN PATENT DOCUMENTS

| EP | 1142881 A1 | 10/2001 |
| EP | 1 396 488 A1 | 3/2004 |
| WO | 99/011624 A1 | 3/1999 |
| WO | WO 0248117 A1 | 6/2002 |
| WO | 02/094790 A1 | 11/2002 |
| WO | WO 03049678 A2 | 6/2003 |
| WO | WO 03063874 A1 | 8/2003 |
| WO | 03/080581 A1 | 10/2003 |
| WO | WO 2004087677 A2 | 10/2004 |
| WO | WO 2004111014 A1 | 12/2004 |
| WO | 2005/061460 A1 | 7/2005 |
| WO | 2006/004925 A1 | 1/2006 |
| WO | WO 2006003146 A1 | 1/2006 |
| WO | WO 2005018557 A2 | 3/2006 |

(Continued)

OTHER PUBLICATIONS

Simone, Oncology: Introduction, Cecil Textbook of Medicine, 20th Edition, vol. 1, pp. 1004-1101 O, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Huang, Shih-Min A., et al., Nature08356, Oct. 2009, vol. 461, doi:1038, "Tankyrase inhibition stabilizes axin and antagonizes Wnt signalling".

(Continued)

*Primary Examiner* — Deepak Rao
(74) *Attorney, Agent, or Firm* — Qian Zhang

(57) ABSTRACT

The present invention provides for compounds of formula (I):

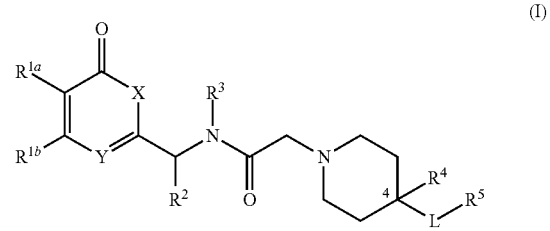

(I)

wherein $R^1$-$R^5$ and L are defined herein. The present invention also provides for pharmaceutical compositions and combinations comprising a compound of formula (I) as well as for the use of such compounds as tankyrase inhibitors and in the treatment of Wnt signaling and tankyrase 1 and 2 signaling related disorders which include, but are not limited to, cancer.

13 Claims, No Drawings

(56) References Cited

FOREIGN PATENT DOCUMENTS

| WO | 2007/002701 A2 | 1/2007 |
| WO | 2007/127726 A2 | 11/2007 |
| WO | 2009/059994 A2 | 5/2009 |
| WO | 2009/061131 A2 | 5/2009 |
| WO | 2009/118382 A1 | 10/2009 |

OTHER PUBLICATIONS

Bae et al., Tankyrase 1 interacts with Mcl-1 proteins and inhibits their regulation of apoptosis. J Biol Chem. Feb. 14, 2003;278(7):5195-204. Epub Dec. 9, 2002.

Barker et al., Mining the Wnt pathway for cancer therapeutics. Nat Rev Drug Discov. Dec. 2006;5(12):997-1014. Review.

Behrens et al., Functional interaction of an axin homolog, conductin, with beta-catenin, APC, and GSK3beta. Science. Apr. 24, 1998;280(5363):596-9.

Chang et al., Poly(ADP-ribose) is required for spindle assembly and structure. Nature. Dec. 2, 2004;432(7017):645-9.

Chang et al., NuMA is a major acceptor of poly(ADP-ribosyl)ation by tankyrase 1 in mitosis. Biochem J. Oct. 15, 2005;391(Pt 2):177-84.

Chi et al., Tankyrase is a golgi-associated mitogen-activated protein kinase substrate that interacts with IRAP in GLUT4 vesicles. J Biol Chem. Dec. 8, 2000;275(49):38437-44.

Clevers, Wnt/beta-catenin signaling in development and disease. Cell. Nov. 3, 2006;127(3):469-80.

Cook et al., Role for the related poly(ADP-Ribose) polymerases tankyrase 1 and 2 at human telomeres. Mol Cell Biol. Jan. 2002;22(1):332-42.

Dynek et al., Resolution of sister telomere association is required for progression through mitosis. Science. Apr. 2, 2004;304(5667):97-100.

Fancy et al., Axin2 as regulatory and therapeutic target in newborn brain injury and remyelination. Nat Neurosci. Jun. 26, 2011;14(8):1009-16.

Hahn et al. Inhibition of telomerase limits the growth of human cancer cells. Nat Med. 1999;5(10):1164-70.

Hart et al., Downregulation of beta-catenin by human Axin and its association with the APC tumor suppressor, beta-catenin and GSK3 beta. Curr Biol. May 7, 1998;8(10):573-81.

Kishida et al., Axin prevents Wnt-3a-induced accumulation of beta-catenin. Oncogene. Jan. 28, 1999;18(4):979-85.

Kwon et al., Mechanisms to suppress multipolar divisions in cancer cells with extra centrosomes. Genes Dev. Aug. 15, 2008;22(16):2189-203.

Lammi et al., Mutations in AXIN2 cause familial tooth agenesis and predispose to colorectal cancer. Am J Hum Genet. May 2004;74(5):1043-50. Epub Mar. 23, 2004.

Lee et al., The roles of APC and Axin derived from experimental and theoretical analysis of the Wnt pathway. PLoS Biol. Oct. 2003;1(1):E10. Epub Oct. 13, 2003.

Li et al., Herpes simplex virus requires poly(ADP-ribose) polymerase activity for efficient replication and induces extracellular signal-related kinase-dependent phosphorylation and ICP0-dependent nuclear localization of tankyrase 1. J Virol., Jan. 2012; 86(1):492-503. Epub Oct. 19, 2011.

Liu et al., Efficient total synthesis of (S)-14-azacamptothecin. Chem Asian J. Jun. 1, 2010;5(6):1382-8.

Liu et al., Mutations in AXIN2 cause colorectal cancer with defective mismatch repair by activating beta-catenin/TCF signalling. Nat Genet. Oct. 2000;26(2):146-7.

Miyaki et al., Characteristics of somatic mutation of the adenomatous polyposis coli gene in colorectal tumors. Cancer Res. Jun. 1, 1994;54(11):3011-20.

Miyoshi et al., Somatic mutations of the APC gene in colorectal tumors: mutation cluster region in the APC gene. Hum Mol Genet. Jul. 1992;1(4):229-33.

Polakis, The many ways of Wnt in cancer. Curr Opin Genet Dev. Feb. 2007;17(1):45-51.

Powell et al., APC mutations occur early during colorectal tumorigenesis. Nature. Sep. 17, 1992;359(6392):235-7.

Salic et al., Control of beta-catenin stability: reconstitution of the cytoplasmic steps of the wnt pathway in *Xenopus* egg extracts. Mol Cell. Mar. 2000;5(3):523-32.

Seimiya et al., Tankyrase 1 as a target for telomere-directed molecular cancer therapeutics. Cancer Cell. Jan. 2005;7(1):25-37.

Smith et al., Tankyrase, a poly(ADP-ribose) polymerase at human telomeres. Science. Nov. 20, 1998;282(5393):1484-7.

Taniguchi et al., Mutational spectrum of beta-catenin, AXIN1, and AXIN2 in hepatocellular carcinomas and hepatoblastomas. Oncogene. Jul. 18, 2002;21(31):4863-71.

Ulsamer et al., Axin pathway activity regulates in vivo pY654-β-catenin accumulation and pulmonary fibrosis. J Biol Chem. Feb. 10, 2012;287(7):5164-72.

Yeh et al., Hypermetabolism, hyperphagia, and reduced adiposity in tankyrase-deficient mice. Diabetes. Nov. 2009;58(11):2476-85.

\* cited by examiner

2-PIPERIDIN-1-YL-ACETAMIDE COMPOUNDS FOR USE AS TANKYRASE INHIBITORS

FIELD OF THE INVENTION

The present invention relates to novel 2-piperidin-1-yl-acetamide compounds, pharmaceutical compositions containing them, and the use of such compounds as tankyrase inhibitors and in the treatment of Wnt signaling and tankyrase 1 and 2 signaling related disorders which include, but are not limited to, cancer.

BACKGROUND OF THE INVENTION

The evolutionarily conserved canonical Wnt/β-catenin signal transduction cascade controls many aspects of metazoan development. Context-dependent activation of the pathway is involved in embryonic cell fate decisions, stem cell regulation and tissue homeostasis (Clevers, H. *Cell* 2006, 127, 469-80).

A key feature of the Wnt/β-catenin pathway is the regulated proteolysis of the downstream effector β-catenin by the β-catenin destruction complex. The principal constituents of the β-catenin destruction complex are adenomatous polyposis coli (APC), Axin, and GSK3α/β. In the absence of Wnt pathway activation, cytosolic β-catenin is constitutively phosphorylated and targeted for degradation. Upon Wnt stimulation, the β-catenin destruction complex disassociates, which leads to the accumulation of nuclear β-catenin and transcription of Wnt pathway responsive genes.

Inappropriate activation of the pathway, mediated by over expression of Wnt proteins or mutations affecting components of the β-catenin destruction complex, thus leading to stabilization of β-catenin, has been observed in many cancers. Notably, truncating mutations of the tumour suppressor APC are the most prevalent genetic alterations in colorectal carcinomas (Miyaki, M. et al. *Cancer Res* 1994, 54, 3011-20; Miyoshi, Y. et al. *Hum Mol Genet* 1992, 1, 229-33; and Powell, S. M. et al. *Nature* 1992, 359, 235-7). In addition, Axin1 and Axin2 mutations have been identified in patients with hepatocarcinomas and colorectal cancer respectively (Taniguchi, K. et al. *Oncogene* 2002, 21, 4863-71; Liu, W. et al. *Nat Genet* 2000, 26, 146-7; Lammi, L. et al. *Am J Hum Genet* 2004, 74, 1043-50). These somatic mutations result in Wnt-independent stabilization of β-catenin and constitutive activation of β-catenin-mediated transcription.

Deregulated Wnt pathway activity has also been implicated in many other cancers (Polakis, P. *Curr Opin Genet Dev* 2007, 17, 45-51; and Barker, N. et al. *Nat Rev Drug Discov* 2006, 5, 997-1014), including colorectal, melanoma, breast, liver, lung and gastric cancers. Other disorders associated with aberrant Wnt signaling include osteoporosis, osteoarthritis, polycystic kidney disease, pulmonary fibrosis, diabetes, schizophrenia, vascular disease, cardiac disease, non-oncogenic proliferative diseases, and neurodegenerative diseases such as Alzheimer's disease.

The efficient assembly of the multi-protein β-catenin destruction complex is dependent on the steady state levels of its principal constituents. Axin has been reported to be the concentration-limiting factor in regulating the efficiency of the β-catenin destruction complex (Salic, A., et al. *Mol Cell* 2000, 5, 523-32; and Lee, E. et al. *PLoS Biol* 2003, 1, E10) and increased expression of Axin can enhance β-catenin degradation in cell lines expressing truncated APC (Behrens, J. et al. *Science* 1998, 280, 596-9; Kishida, M. et al. *Oncogene* 1999, 18, 979-85; and Hart, M. J., et al. *Curr Biol* 1998, 8, 573-81). Thus, it is likely that Axin protein levels need to be tightly regulated to ensure proper Wnt pathway signaling.

It has recently been found that β-catenin degradation can be promoted by stablising Axin through the inhibition of the poly-ADP-ribose polymerase (PARP) enzymes tankyrase 1 and tankyrase 2, as explained in WO 2009/059994 and Huang et al., (Huang S. M., et al. *Nature* 2009, 461, 614-620). Both tankyrase isoforms interact with a highly conserved domain of Axin and stimulate its degradation through the ubiquitin-proteasome pathway. This previously unknown mechanism for stabilising Axin protein, thereby enhancing β-catenin degradation, can be exploited for treating Wnt signaling-related disorders. Axin proteins are essential regulators of a spectrum of physiological processes, including brain oligodendrocyte progenitor cell differentiation for remyelination (Fancy, S., et al. *Nature NeuroSci* 2011, 14, 1009-1017), and epithelial-to-mesenchymal transition during pulmonary fibrosis (Ulsamer, A., et al. *J Bio Chem* 2012, 287, 5164-5172). Thus, by way of stabilizing Axin proteins, Tankyrase inhibitors could be used as a therapy for remyelination post brain injury and pulmonary fibrosis.

Tankyrase has several binding protein partners, including TRF1, a double-stranded telomeric repeat binding protein (Smith, S., et al. *Science* 1998, 282, 1484-1487); NuMA, an essential protein in mitotic spindle assembly (Chang, W., et al. *Biochem J*, 2005, 391, 177-184); IRAP, an integral membrane protein involved in glucose uptake in response to insulin (Chi, N. W., et al. *J Biol Chem* 2000, 275, 38437-38444); and Mcl-1, a pro-apoptotic protein (Bae, J., et al. *J Biol Chem* 2003, 278, 5195-5204).

By way of its various interacting proteins, tankyrase proteins have been implicated in different biological functions. Tankyrase poly (ADP-ribosyl)ates TRF1, releasing it from telomeres and enhancing telomere access to telomerase. Thus, tankyrase functions as a positive regulator for telomere elongation by telomerase, supported by the findings that long-term overexpression of tankyrase leads to telomere elongation (Cook, B. D., et al *Mol Cell Biol* 2002, 22, 332-242). Telomere maintenance by telomerase has been attributed to the uncontrolled proliferation of cancer cells (Hahn, W. C., et al, *Nat Med* 1999, 5, 1164-1169). Tankyrase could be a target for cancer therapy by inhibiting the telomere accessibility for telomerase. Tankyrase inhibition could be used as an effective cancer therapy to treat patients with a wide spectrum of cancers, including leukemia, lymphoma, multiple myeloma, lung, and breast cancer.

Tankyrase also plays a role in cell mitosis by: 1) poly(ADP-ribosyl)ating NuMA during mitosis and regulating its functions at spindle poles (Chang, W., et al. *Biochem J* 2005, 391, 177-184); 2) by regulating spindle assembly and structure (Chang, P., et al. *Nature* 2004, 432, 645-649); and 3) by maintaining sister chromatid resolution at telomeres (Dynek, J., et al. *Science* 2004, 304, 97-100). Inhibition of tankyrase leads to cell mitotic arrest or senescence, and thus could be exploited for treating diseases that have abnormal mitotic division, such as cancer. Examples include breast, lung, ovarian, leukemia, lymphoma, and melanoma. In addition, tankyrase 1 was identified as a gene required for centrosome clustering, a mechanism that cancer cells with supernumerary centrosomes employs to suppress multipolar mitosis and enable bipolar mitosis (Kwon, M., et al. *Genes Dev* 2008, 22, 2189-2203). Thus inhibition of tankyrase could be exploited for treating cancers with centrosome amplification, including both solid and haematological cancers, examples include breast, bladder, lung, colon, and leukemia.

Moreover, One of the cellular localizations of tankyrase is at the Golgi apparatus co-localizing with the glucose transporter GLUT4 vesicles where tankyrase is associated with IRAP, and tankyrase is implicated in the regulation of GLUT4 trafficking in adipocytes (Chi, N. W., et al. *J Biol Chem* 2000, 275, 38437-38444). Tankyrase-deficient mice exhibit reduced adiposity and increased energy expenditure by increases in both fatty acid oxidation and insulin-stimulated glucose utilization (Yeh, T., et al. *Diabetes* 2009). This supports tankyrase involvement in energy homeostasis in mammals and inhibiting tankyrase can be exploited for treating metabolic diseases, such as obesity.

Tankyrase has been reported to be a host protein targeted by Herpes Simplex Virus (HSV), modulated by HSV through hyperphosphorylation, nuclear transport and proteasomal degradation (Li Z., et al. *J of Virol* 2012, 86, 492-503). More importantly, efficient HSV viral replication requires the enzymatic activity of tankyrase proteins. Inhibition of tankyrase activity by inhibitor XAV939 (WO 2009/059994, Huang, S. M., et al. *Nature* 2009, 461, 614-620) suppressed HSV viral protein expression and decreased viral growth. Thus, inhibition of tankyrase can be exploited as anti-viral therapeutics, including but not limited to treatment of HSV infection.

Consequently, compounds that inhibit tankyrase (TNKS) and/or Wnt Signaling may be useful for treatment of diseases mediated by such inhibitions.

SUMMARY OF THE INVENTION

The present invention provides for compounds of formula (I):

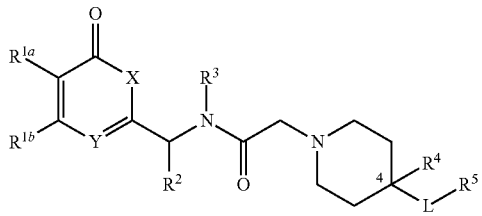

(I)

wherein $R^1$-$R^5$ and L are defined herein. The present invention also provides for pharmaceutical compositions and combinations comprising a compound of formula (I) as well as for the use of such compounds as tankyrase inhibitors and in the treatment of Wnt signaling and tankyrase 1 and 2 signaling related disorders which include, but are not limited to, cancer.

DETAILED DESCRIPTION OF THE INVENTION

The present invention provides for compounds of formula (I)

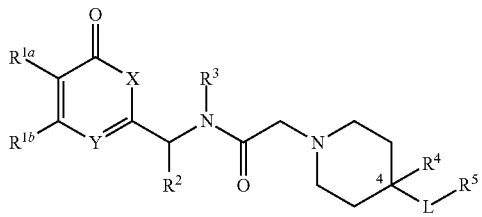

(I)

wherein:
X is NH or O;
Y is N or CH;
$R^{1a}$ and $R^{1b}$ are each independently $C_{1-3}$ alkyl; or
$R^{1a}$ and $R^{1b}$ are joined together with the atoms to which they are attached forming an optionally substituted $C_{5-7}$ cycloalkenyl ring, an optionally substituted 3,6-dihydro-2H-pyranyl ring, or an optionally substituted 1,2,3,6-tetrahydropyridinyl ring,
wherein said $C_{5-7}$ cycloalkenyl, 3,6-dihydro-2H-pyranyl, and 1,2,3,6-tetrahydropyridinyl are each optionally substituted with one to three substituents each independently selected from the group consisting of: halo, hydroxy, $C_{1-3}$ alkyl, and benzyl;
$R^2$ is H or $C_{1-3}$ alkyl;
$R^3$ is hydrogen, $C_{1-3}$ haloalkyl, $C_{3-6}$ alkynyl, or $C_{1-6}$ alkyl optionally substituted with one substituent selected from the group consisting of: methoxy, cyano, $C_{3-5}$ cycloalkyl, optionally substituted phenyl, optionally substituted 5-10 membered heteroaryl, and 5-6 membered heterocyclyl,
wherein said phenyl, 5-10 membered heteroaryl and 5-6 membered heterocyclyl are each optionally substituted with one or two substituents each independently selected from the group consisting of: halo, $C_{1-3}$ alkoxy, cyano, and morpholinyl-S(O)$_2$—; and
$R^4$ is hydrogen, L is C(O),

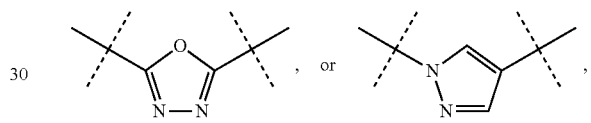

and
$R^5$ is optionally substituted phenyl, optionally substituted 5-6 membered heteroaryl, optionally substituted 2,3-dihydrobenzofuran-6-yl, optionally substituted benzyl[1,3]dioxol-5-yl; optionally substituted 1,2,3,4-tetrahydro-quinolin-1-yl, or optionally substituted 1,2,3,4-tetrahydro-isoquinolin-2-yl,
wherein each $R^5$ is optionally substituted with one or two substituents each independently selected from the group consisting of:
(a) halo,
(b) hydroxy,
(c) $C_{1-6}$ alkyl,
(d) $C_{1-3}$ haloalkyl,
(e) $C_{1-3}$ alkoxy optionally substituted with one methoxy, $C_{3-5}$ cycloalkyl, or phenyl,
(f) $C_{1-3}$ haloalkoxy,
(g) $C_{3-6}$ alkynyloxy,
(h) tetrahydropyranyl-O—, and
(i) $C_{1-3}$ alkyl-C(O)NH—;
or
$R^4$ is hydrogen, L is absent, and $R^5$ is optionally substituted benzo[d]isoxazol-3-yl, optionally substituted 1H-indazol-3-yl, or optionally substituted 1,3-dihydro-benzimidazol-2-one-1-yl, wherein each $R^5$ is optionally substituted with one or two substituents each independently selected from the group consisting of: halo, hydroxy, $C_{1-6}$ alkyl, $C_{1-3}$ haloalkyl, and $C_{1-3}$ alkoxy;
or
$R^4$ and L-$R^5$, wherein L is C(O), are joined together with the atoms to which they are attached forming an optionally substituted indan-1-one-2-yl group or an optionally substituted 3,4-dihydro-2H-naphthalen-1-one-2-yl each of which are attached to the piperidine ring of formula (I) through spiro carbon 4 and are optionally substituted with one to three substituents each independently selected from the group consisting of: halo and $C_{1-6}$ alkoxy.

As used herein, the term "alkyl" refers to a fully saturated branched or unbranched hydrocarbon moiety having up to 6 carbon atoms. Alkyl groups may be optionally substituted with one or more substituents as defined. Unless otherwise provided, alkyl refers to hydrocarbon moieties having 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

As used herein, the term "alkoxy" refers to an alkyl moiety attached through an oxygen bridge (i.e. a —O—$C_{1-6}$ alkyl wherein alkyl is defined herein). Alkoxy groups may be optionally substituted with one or more substituents as defined. Typically, alkoxy groups have 1 to 6 carbon atoms. Representative examples of alkoxy include, but are not limited to, methoxy, ethoxy, propoxy, 2-propoxy, butoxy, tert-butoxy, pentyloxy, hexyloxy.

As used herein, the term "alkynyl" refers to an unsaturated branched or unbranched hydrocarbon chain having the specified number of carbon atoms and having one or more carbon-carbon triple bonds within the chain. For example $C_{3-6}$ alkynyl refers to an alkynyl groups having from 3 to 6 carbon atoms. Alkynyl groups can have one or more triple bonds. Representative examples of alkynyl groups include, but are not limited to, propynyl, butynyl, pentynyl, and hexynyl.

As used herein, the term "alkynyloxy" refers to an alkyl moiety attached through an oxygen bridge (i.e. a —O—$C_{3-6}$ alkynyl wherein alkynyl is defined herein). Typically, alkynyloxy groups have 3 to 6 carbon atoms. Representative examples of alkynyloxy include, but are not limited to, propynyloxy, butynyloxy, pentynyloxy, and hexynyloxy.

As used herein, the term "cycloalkyl" refers to a 3 to 5 membered monocyclic saturated hydrocarbon ring system. Cycloalkyl groups may be optionally substituted with one or more substituents as defined herein. Cycloalkyl includes cyclobutyl, cyclopentyl, cyclohexyl, and cycloheptyl.

As used herein, the term "cycloalkenyl" refers to a 5 to 7 membered monocyclic unsaturated, but not aromatic, hydrocarbon ring system. Cycloalkenyl groups may be optionally substituted with one or more substituents as defined here. Cycloalkenyl includes cyclopentenyl, cyclohexenyl, and cycloheptenyl.

As used herein, the term "halo" refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "haloalkyl" refers to an alkyl as defined herein, which is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms.

As used herein, the term "heteroatoms" refers to nitrogen (N), oxygen (O) or sulfur (S) atoms, in particular nitrogen or oxygen.

As used herein, the term "heteroaryl" refers to a 5-10 membered monocyclic- or bicyclic aromatic ring system, having 1 to 4 heteroatoms selected from N, O or S. Heteroaryl groups containing more than one heteroatom may contain different heteroatoms unless specified otherwise. Heteroaryl groups may be optionally substituted with one or more substituents as defined herein. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2,3-, or 4-pyridyl, 3- or 4-pyridazinyl, 3-, 4-, or 5-pyrazinyl, 2-pyrazinyl, and 2-, 4-, or 5-pyrimidinyl. The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido [2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b] thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

As used herein the term "heterocyclyl" refers to a 5 to 7 membered monocyclic saturated or unsaturated ring containing from 1 to 3 heteroatoms. Heterocyclyl rings are not aromatic. Heterocyclyl containing more than one heteroatom may contain different heteroatoms. Heterocyclyl groups may be optionally substituted with one or more substituents as defined herein. Examples of heterocyclyl include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

When any group or moiety, such as alkyl, heteroaryl, heterocyclyl or phenyl, is defined herein as being "optionally substituted with one, one or two, or one to three substituents each independently selected from the group consisting of" it is understood that the group or moiety is unsubstituted or substituted with one, one or two, or one to three substituents, wherein each substituent is independently selected from the recited group of substituents.

The skilled artisan will appreciate that salts, including pharmaceutically acceptable salts, of the compounds according to formula (I) may be prepared. These salts may be prepared in situ during the final isolation and purification of the compound, or by separately reacting the purified compound in its free acid or free base form with a suitable base or acid, respectively.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Solvates, including pharmaceutically acceptable solvates, of the compounds of formula (I) may also be prepared. "Solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

As used herein, the term "pharmaceutically acceptable" means a compound which is suitable for pharmaceutical use. Salts and solvates (e.g. hydrates and hydrates of salts) of compounds of the invention which are suitable for use in medicine are those where in the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

The compounds of formula (I), including salts and solvates thereof, may exist in crystalline forms, non-crystalline forms, or mixtures thereof. The compound or salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

The invention also includes various isomers of the compounds of formula (I). "Isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of formula (I) may have one or more asymmetric carbon atom and may occur as racemates, racemic mixtures and as individual enantiomers or diastereomers. All such isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of a compound of formula (I) can be present in racemic or enantiomerically enriched, for example the (R)-, (S)- or (R,S)-configuration. In certain embodiments, each asymmetric atom has at least 50 enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of formula (I) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The invention includes unlabeled forms as well as isotopically labeled forms of compounds of formula (I). Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Representative Embodiments

Various embodiments of the invention are described herein. It will be recognized that features specified in each embodiment may be combined with other specified features to provide for further embodiments.

In one embodiment of the present invention X is NH and Y is N.

In another embodiment of the present invention $R^{1a}$ and $R^{1b}$ are both methyl.

In another embodiment $R^{1a}$ and $R^{1b}$ are joined together with the atoms to which they are attached forming an optionally substituted $C_{5-7}$ cycloalkenyl ring, an optionally substituted 3,6-dihydro-2H-pyranyl ring, or an optionally substituted 1,2,3,6-tetrahydropyridinyl ring. Suitably $R^{1a}$ and $R^{1b}$ are joined together with the atoms to which they are attached forming an $C_{5-7}$ cycloalkenyl ring, an 3,6-dihydro-2H-pyranyl ring, or an 1,2,3,6-tetrahydropyridinyl ring.

In another embodiment of the present invention X is NH, Y is N, and $R^{1a}$ and $R^{1b}$ are joined together with the atoms to which they are attached forming an optionally substituted 3,6-dihydro-2H-pyranyl ring, preferably an unsubstituted 3,6-dihydro-2H-pyranyl ring. In another embodiment X is NH, Y is N, and $R^{1a}$ and $R^{1b}$ form an optionally substituted, preferably unsubstituted, 4-oxo-4,5,7,8-tetrahydro-3H-pyrano[4,3-d]pyrimidin-2-yl group of the following formula:

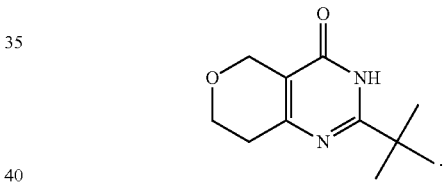

In another embodiment $R^2$ is H or methyl. Suitably $R^2$ is H.

In another embodiment $R^3$ is H, $C_{1-3}$ haloalkyl, $C_{3-6}$ alkynyl, or unsubstituted $C_{1-6}$ alkyl. For example $R^3$ is H, methyl, neopentyl, 2-methyl-butyl, isobutyl, prop-2-ynyl, n-propyl, 2-fluoro-ethyl, 2,2-difluoroethyl, or 2,2,2-trifluoroethyl. Suitably $R^3$ is H or unsubstituted $C_{1-6}$ alkyl.

In another embodiment $R^3$ is optionally substituted $C_{1-6}$ alkyl. Suitably $R^3$ is 1-phenyl-ethyl, cyclopropylmethyl, 4-fluorobenzyl, 4-methoxybenzyl, benzo[d]thiazol-2-ylmethyl, 3-methoxybenzyl, 3-fluorobenzyl, pyridin-4-ylmethyl, pyridin-3-ylmethyl, tetrahydrofurany-2-ylmethyl, 4-fluorophenylethyl, 2,4-difluorophenylethyl, benzyl, cyclopropylethyl, cyanomethyl, 5-cyano-thiophen-2-ylmethyl, 5-(morpholine-4-sulfonyl)-thiophen-2-ylmethyl, 1-thiophen-2-ylethyl, or 2-methoxyethyl.

In another embodiment $R^4$ is H, L is C(O), and $R^5$ is optionally substituted phenyl, optionally substituted 5-6 membered heteroaryl; optionally substituted 2,3-dihydrobenzofuran-6-yl, optionally substituted benzyl[1,3]dioxol-5-yl; optionally substituted 1,2,3,4-tetrahydro-quinolin-1-yl, or optionally substituted 1,2,3,4-tetrahydro-isoquinolin-2-yl. Suitably $R^5$ is pyridinyl, 2,3-dihydrobenzofuran-6-yl, benzyl[1,3]dioxol-5-yl, 1,2,3,4-tetrahydro-quinolin-1-yl, or 1,2,3,4-tetrahydro-isoquinolin-2-yl. Suitably $R^5$ is optionally substituted phenyl. More suitably $R^5$ is phenyl optionally substituted with one substituent selected from the group consisting of: halo, suitably fluoro or chloro, or $C_{1-3}$ alkoxy. Even more suitably $R^5$ is 4-fluorophenyl, 4-chlorophenyl, 4-isopropoxyphenyl, 4-methoxyphenyl, 4-ethoxyphenyl, 4-trifluoromethoxyphenyl, 2-methoxyphenyl, 3-methoxyphenyl, 3-trifluoromethoxyphenyl, 4-trifluoromethylphenyl, 4-phenoxy-benzoyl, 4-but-2-ynyloxy-benzoyl, 4-methylphenyl, 4-propoxyphenyl, 4-cyclopropylmethoxyphenyl, 4-cyclobutylmethoxyphenyl, 4-tetrahydro-pyran-4-yloxyphenyl, (2-cyclopropylethoxy)phenyl, 2-methoxy-ethoxyphenyl, 3,4-dimethoxyphenyl, 4-methoxy-3-methylphenyl, 3-chloro-4-methoxyphenyl, or 4-ethoxy-3-fluorophenyl, In another embodiment $R^4$ and $L-R^5$, wherein L is C(O), are joined together with the atoms to which they are attached forming an optionally substituted indan-1-one-2-yl group or an optionally substituted 3,4-dihydro-2H-naphthalen-1-one-2-yl both of which are attached to the piperidine ring of formula (I) through spiro carbon 4 and are optionally substituted with one to three substituents, suitably one substituent, each independently selected from the group consisting of: halo, for example fluoro, and $C_{1-6}$ alkoxy, for example methoxy.

Specific compounds of the present invention include:

2-(4-(4-Fluorobenzoyl)piperidin-1-yl)-N-((4-oxo-4,5,7,8-tetrahydro-3H-pyrano[4,3-d]pyrimidin-2-yl)methyl)acetamide;

2-[4-(4-Chloro-benzoyl)-piperidin-1-yl]-N-(4-oxo-3,5,7,8-tetrahydro-4H-pyrano[4,3-d]-pyrimidin-2-ylmethyl)-acetamide;

2-[4-(4-Isopropoxy-benzoyl)-piperidin-1-yl]-N-(4-oxo-3,5,7,8-tetrahydro-4H-pyrano[4,3-d]pyrimidin-2-ylmethyl)-acetamide;

2-[4-(4-Fluoro-benzoyl)-piperidin-1-yl]-N-(4-oxo-3,5,7,8-tetrahydro-4H-pyrano[4,3-d]pyrimidin-2-ylmethyl)-N—((R)-1-phenyl-ethyl)-acetamide;

N-Cyclopropylmethyl-2-[4-(4-methoxy-benzoyl)-piperidin-1-yl]-N-(4-oxo-3,5,7,8-tetrahydro-4H-pyrano[4,3-d]pyrimidin-2-ylmethyl)-acetamide;

2-(4-(4-Methoxybenzoyl)piperidin-1-yl)-N-((4-oxo-4,5,6,7,8,9-hexahydro-3H-cyclohepta[d]pyrimidin-2-yl)methyl)acetamide;

N-(Cyclopropylmethyl)-2-(4-(4-methoxybenzoyl)piperidin-1-yl)-N-((4-oxo-4,5,6,7,8,9-hexahydro-3H-cyclohepta[d]pyrimidin-2-yl)methyl)acetamide;

N-(Cyclopropylmethyl)-2-(4-(4-methoxybenzoyl)piperidin-1-yl)-N-((4-oxo-3,4,5,6,7,8-hexahydroquinazolin-2-yl)methyl)acetamide;

2-(4-(4-Methoxybenzoyl)piperidin-1-yl)-N-((4-oxo-3,4,5,6,7,8-hexahydroquinazolin-2-yl)methyl)acetamide;

2-(4-(4-Fluorobenzoyl)piperidin-1-yl)-N-((4-oxo-3,4,5,6,7,8-hexahydroquinazolin-2-yl)methyl)acetamide;

2-(4-(4-Methoxybenzoyl)piperidin-1-yl)-N-((4-oxo-4,5,6,7-tetrahydro-3H-cyclopenta[d]pyrimidin-2-yl)methyl)acetamide;

N-((4,5-Dimethyl-6-oxo-1,6-dihydropyrimidin-2-yl)methyl)-2-(4-(4-methoxybenzoyl)piperidin-1-yl)acetamide;

2-(4-(4-Fluorobenzoyl)piperidin-1-yl)-N-((4-oxo-4,5,7,8-tetrahydro-3H-pyrano[4,3-d]pyrimidin-2-yl)methyl)-N-(thiophen-2-ylmethyl)acetamide;

2-(4-(4-Fluorobenzoyl)piperidin-1-yl)-N-neopentyl-N-((4-oxo-4,5,7,8-tetrahydro-3H-pyrano[4,3-d]pyrimidin-2-yl)methyl)acetamide;

2-(4-(4-Fluorobenzoyl)piperidin-1-yl)-N-(4-fluorobenzyl)-N-((4-oxo-4,5,7,8-tetrahydro-3H-pyrano[4,3-d]pyrimidin-2-yl)methyl)acetamide;

2-(4-(4-Fluorobenzoyl)piperidin-1-yl)-N-(4-methoxybenzyl)-N-((4-oxo-4,5,7,8-tetrahydro-3H-pyrano[4,3-d]pyrimidin-2-yl)methyl)acetamide;

N-(Benzo[d]thiazol-2-ylmethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;

2-(4-(4-Fluorobenzoyl)piperidin-1-yl)-N-(3-methoxybenzyl)-N-((4-oxo-4,5,7,8-tetrahydro-3H-pyrano[4,3-d]pyrimidin-2-yl)methyl)acetamide;

2-(4-(4-Fluorobenzoyl)piperidin-1-yl)-N-(3-fluorobenzyl)-N-((4-oxo-4,5,7,8-tetrahydro-3H-pyrano[4,3-d]pyrimidin-2-yl)methyl)acetamide;

2-(4-(4-Fluorobenzoyl)piperidin-1-yl)-N-((4-oxo-4,5,7,8-tetrahydro-3H-pyrano[4,3-d]pyrimidin-2-yl)methyl)-N-(pyridin-4-ylmethyl)acetamide;

2-(4-(4-Fluorobenzoyl)piperidin-1-yl)-N-((4-oxo-4,5,7,8-tetrahydro-3H-pyrano[4,3-d]pyrimidin-2-yl)methyl)-N-(pyridin-3-ylmethyl)acetamide;

2-(4-(4-Fluorobenzoyl)piperidin-1-yl)-N-((4-oxo-4,5,7,8-tetrahydro-3H-pyrano[4,3-d]pyrimidin-2-yl)methyl)-N-(pyridin-2-ylmethyl)acetamide;

2-[4-(4-Fluoro-benzoyl)-piperidin-1-yl]-N-(4-oxo-3,5,7,8-tetrahydro-4H-pyrano[4,3-d]pyrimidin-2-ylmethyl)-N—((S)-1-phenyl-ethyl)-acetamide;

N-Cyclopropylmethyl-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide;

2-[4-(4-Fluoro-benzoyl)-piperidin-1-yl]-N—((S)-2-methylbutyl)-N-(4-oxo-3,5,7,8-tetrahydro-4H-pyrano[4,3-d]pyrimidin-2-ylmethyl)-acetamide;

2-(4-(4-Fluorobenzoyl)piperidin-1-yl)-N-isobutyl-N-((4-oxo-4,5,7,8-tetrahydro-3H-pyrano[4,3-d]pyrimidin-2-yl)methyl)acetamide;

2-(4-(4-Fluorobenzoyl)piperidin-1-yl)-N-((4-oxo-4,5,7,8-tetrahydro-3H-pyrano[4,3-d]pyrimidin-2-yl)methyl)-N-(prop-2-ynyl)acetamide;

(S)-2-(4-(4-Fluorobenzoyl)piperidin-1-yl)-N-((4-oxo-4,5,7,8-tetrahydro-3H-pyrano[4,3-d]pyrimidin-2-yl)methyl)-N-((tetrahydrofuran-2-yl)methyl)acetamide;

(R)-2-(4-(4-Fluorobenzoyl)piperidin-1-yl)-N-((4-oxo-4,5,7,8-tetrahydro-3H-pyrano[4,3-d]pyrimidin-2-yl)methyl)-N-((tetrahydrofuran-2-yl)methyl)acetamide;

2-(4-(4-Fluorobenzoyl)piperidin-1-yl)-N-methyl-N-((4-oxo-4,5,7,8-tetrahydro-3H-pyrano[4,3-d]pyrimidin-2-yl)methyl)acetamide;

(S)—N-sec-Butyl-2-(4-(4-fluorobenzoyl)piperidin-1-yl)-N-((4-oxo-4,5,7,8-tetrahydro-3H-pyrano[4,3-d]pyrimidin-2-yl)methyl)acetamide;

(R)—N-sec-Butyl-2-(4-(4-fluorobenzoyl)piperidin-1-yl)-N-((4-oxo-4,5,7,8-tetrahydro-3H-pyrano[4,3-d]pyrimidin-2-yl)methyl)acetamide;

2-(4-(4-Fluorobenzoyl)piperidin-1-yl)-N-isopropyl-N-((4-oxo-4,5,7,8-tetrahydro-3H-pyrano[4,3-d]pyrimidin-2-yl)methyl)acetamide;

2-(4-(4-Fluorobenzoyl)piperidin-1-yl)-N-((4-oxo-4,5,7,8-tetrahydro-3H-pyrano[4,3-d]pyrimidin-2-yl)methyl)-N-propylacetamide;

(S)-2-(4-(4-Fluorobenzoyl)piperidin-1-yl)-N-(1-(4-fluorophenyl)ethyl)-N-((4-oxo-4,5,7,8-tetrahydro-3H-pyrano[4,3-d]pyrimidin-2-yl)methyl)acetamide;

(R)-2-(4-(4-Fluorobenzoyl)piperidin-1-yl)-N-(1-(4-fluorophenyl)ethyl)-N-((4-oxo-4,5,7,8-tetrahydro-3H-pyrano[4,3-d]pyrimidin-2-yl)methyl)acetamide;

N-(1-(2,4-Difluorophenyl)ethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;

N-Benzyl-2-(4-(4-fluorobenzoyl)piperidin-1-yl)-N-((4-oxo-4,5,7,8-tetrahydro-3H-pyrano[4,3-d]pyrimidin-2-yl)methyl)acetamide;

2-(4-(4-Fluorobenzoyl)piperidin-1-yl)-N-(2-fluorobenzyl)-N-((4-oxo-4,5,7,8-tetrahydro-3H-pyrano[4,3-d]pyrimidin-2-yl)methyl)acetamide;

N-(2,4-Difluorobenzyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;

(R)—N-(1-Cyclopropylethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;

(S)—N-(1-Cyclopropylethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;

N-Cyanomethyl-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide;

2-[4-(4-Fluoro-benzoyl)-piperidin-1-yl]-N-(2-fluoro-ethyl)-N-(4-oxo-3,5,7,8-tetrahydro-4H-pyrano[4,3-d]pyrimidin-2-ylmethyl)-acetamide;

N-(2,2-Difluoro-ethyl)-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide;

N-(5-Cyano-thiophen-2-ylmethyl)-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide;

2-[4-(4-Fluoro-benzoyl)-piperidin-1-yl]-N-[5-(morpholine-4-sulfonyl)-thiophen-2-ylmethyl]-N-(4-oxo-3,5,7,8-tetrahydro-4H-pyrano[4,3-d]pyrimidin-2-ylmethyl)-acetamide;

2-[4-(4-Fluoro-benzoyl)-piperidin-1-yl]-N-(4-oxo-3,5,7,8-tetrahydro-4H-pyrano[4,3-d]pyrimidin-2-ylmethyl)-N-(2,2,2-trifluoro-ethyl)-acetamide;

2-[4-(4-Fluoro-benzoyl)-piperidin-1-yl]-N-(4-oxo-3,5,7,8-tetrahydro-4H-pyrano[4,3-d]pyrimidin-2-ylmethyl)-N-(1-thiophen-2-yl-ethyl)-acetamide;

N-(2,2-Difluoro-ethyl)-2-[4-(4-methoxy-benzoyl)-piperidin-1-yl]-N-(4-oxo-3,5,7,8-tetrahydro-4H-pyrano[4,3-d]pyrimidin-2-ylmethyl)-acetamide;

2-(4-(6-Fluorobenzo[d]isoxazol-3-yl)piperidin-1-yl)-N-((4-oxo-4,5,7,8-tetrahydro-3H-pyrano[4,3-d]pyrimidin-2-yl)methyl)acetamide;

N-(4-Oxo-3,5,7,8-tetrahydro-4H-pyrano[4,3-d]pyrimidin-2-ylmethyl)-2-[4-(5-phenyl-[1,3,4]oxadiazol-2-yl)-piperidin-1-yl]-acetamide;

2-(4-Benzoyl-piperidin-1-yl)-N-(2-methoxy-ethyl)-N-(4-oxo-3,5,7,8-tetrahydro-4H-pyrano[4,3-d]pyrimidin-2-ylmethyl)-acetamide;

2-[4-(4-Methoxy-benzoyl)-piperidin-1-yl]-N-(2-methoxy-ethyl)-N-(4-oxo-3,5,7,8-tetrahydro-4H-pyrano[4,3-d]pyrimidin-2-ylmethyl)-acetamide;

2-{4-[5-(4-Fluoro-phenyl)-[1,3,4]oxadiazol-2-yl]-piperidin-1-yl}-N-(4-oxo-3,5,7,8-tetrahydro-4H-pyrano[4,3-d]pyrimidin-2-ylmethyl)-acetamide;

2-{4-[5-(4-Methoxy-phenyl)-[1,3,4]oxadiazol-2-yl]-piperidin-1-yl}-N-(4-oxo-3,5,7,8-tetrahydro-4H-pyrano[4,3-d]pyrimidin-2-ylmethyl)-acetamide;

2-[4-(6-Fluoro-1H-indazol-3-yl)-piperidin-1-yl]-N-(4-oxo-3,5,7,8-tetrahydro-4H-pyrano[4,3-d]pyrimidin-2-ylmethyl)acetamide;

2-[4-(6-Methoxy-1H-indazol-3-yl)-piperidin-1-yl]-N-(4-oxo-3,5,7,8-tetrahydro-4H-pyrano[4,3-d]pyrimidin-2-ylmethyl)-acetamide;

N-(4-Oxo-3,5,7,8-tetrahydro-4H-pyrano[4,3-d]pyrimidin-2-ylmethyl)-2-[4-(4-phenyl-pyrazol-1-yl)-piperidin-1-yl]-acetamide;

2-{4-[4-(4-Methoxy-phenyl)-pyrazol-1-yl]-piperidin-1-yl}-N-(4-oxo-3,5,7,8-tetrahydro-4H-pyrano[4,3-d]pyrimidin-2-ylmethyl)-acetamide;

2-(5-Fluoro-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide;

N-(Cyclopropylmethyl)-2-(5-fluoro-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide;

N-(Cyclopropylmethyl)-2-(5-methoxy-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide;

N-(2,2-Difluoro-ethyl)-2-(5-methoxy-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide;

2-(1-oxo-3,4-dihydro-1H-spiro[naphthalene-2,4'-piperidine]-1'-yl)-N-((4-oxo-4,5,7,8-tetrahydro-3H-pyrano[4,3-d]pyrimidin-2-yl)methyl)acetamide;

2-(4-(4-Ethoxybenzoyl)piperidin-1-yl)-N-((4-oxo-4,5,7,8-tetrahydro-3H-pyrano[4,3-d]pyrimidin-2-yl)methyl)acetamide;

2-(4-(4-Methoxybenzoyl)piperidin-1-yl)-N-((4-oxo-4,5,7,8-tetrahydro-3H-pyrano[4,3-d]pyrimidin-2-yl)methyl)acetamide;

2-(4-Benzoyl-piperidin-1-yl)-N-(2,2-difluoro-ethyl)-N-(4-oxo-3,5,7,8-tetrahydro-4H-pyrano[4,3-d]pyrimidin-2-ylmethyl)-acetamide;

2-[4-(4-Chloro-benzoyl)-piperidin-1-yl]-N-(2,2-difluoro-ethyl)-N-(4-oxo-3,5,7,8-tetrahydro-4H-pyrano[4,3-d]pyrimidin-2-ylmethyl)-acetamide;

N-Cyclopropylmethyl-N-(4-oxo-3,5,7,8-tetrahydro-4H-pyrano[4,3-d]pyrimidin-2-ylmethyl)-2-[4-(4-trifluoromethoxy-benzoyl)-piperidin-1-yl]-acetamide;

N-(2,2-Difluoro-ethyl)-N-(4-oxo-3,5,7,8-tetrahydro-4H-pyrano[4,3-d]pyrimidin-2-ylmethyl)-2-[4-(4-trifluoromethoxy-benzoyl)-piperidin-1-yl]-acetamide;

N-(2,2-Difluoro-ethyl)-2-[4-(2-methoxy-benzoyl)-piperidin-1-yl]-N-(4-oxo-3,5,7,8-tetrahydro-4H-pyrano[4,3-d]pyrimidin-2-ylmethyl)-acetamide;

N-(2,2-Difluoro-ethyl)-2-[4-(3-methoxy-benzoyl)-piperidin-1-yl]-N-(4-oxo-3,5,7,8-tetrahydro-4H-pyrano[4,3-d]pyrimidin-2-ylmethyl)-acetamide;

N-(2,2-Difluoro-ethyl)-N-(4-oxo-3,5,7,8-tetrahydro-4H-pyrano[4,3-d]pyrimidin-2-ylmethyl)-2-[4-(3-trifluoromethoxy-benzoyl)-piperidin-1-yl]-acetamide;

N-(2,2-Difluoro-ethyl)-N-(4-oxo-3,5,7,8-tetrahydro-4H-pyrano[4,3-d]pyrimidin-2-ylmethyl)-2-[4-(4-trifluoromethyl-benzoyl)-piperidin-1-yl]-acetamide;

N-Cyclopropylmethyl-N-(4-oxo-3,5,7,8-tetrahydro-4H-pyrano[4,3-d]pyrimidin-2-ylmethyl)-2-[4-(pyridine-2-carbonyl)-piperidin-1-yl]-acetamide;

N-Cyclopropylmethyl-N-(4-oxo-3,5,7,8-tetrahydro-4H-pyrano[4,3-d]pyrimidin-2-ylmethyl)-2-[4-(4-phenoxy-benzoyl)-piperidin-1-yl]-acetamide;

2-[4-(4-But-2-ynyloxy-benzoyl)-piperidin-1-yl]-N-cyclopropylmethyl-N-(4-oxo-3,5,7,8-tetrahydro-4H-pyrano[4,3-d]pyrimidin-2-ylmethyl)-acetamide;

N-((4-Oxo-4,5,7,8-tetrahydro-3H-pyrano[4,3-d]pyrimidin-2-yl)methyl)-2-(4-(1,2,3,4-tetrahydroisoquinoline-2-carbonyl)piperidin-1-yl)acetamide;

2-(4-(6-Methoxy-1,2,3,4-tetrahydroquinoline-1-carbonyl)piperidin-1-yl)-N-((4-oxo-4,5,7,8-tetrahydro-3H-pyrano[4,3-d]pyrimidin-2-yl)methyl)acetamide;

2-(4-(5-Chloro-1,2,3,4-tetrahydroisoquinoline-2-carbonyl)piperidin-1-yl)-N-((4-oxo-4,5,7,8-tetrahydro-3H-pyrano[4,3-d]pyrimidin-2-yl)methyl)acetamide;

2-(4-(2-Oxo-2,3-dihydro-1H-benzo[d]imidazol-1-yl)piperidin-1-yl)-N-((4-oxo-4,5,7,8-tetrahydro-3H-pyrano[4,3-d]pyrimidin-2-yl)methyl)acetamide;

2-[4-(4-Methyl-benzoyl)-piperidin-1-yl]-N-(4-oxo-3,5,7,8-tetrahydro-4H-pyrano[4,3-d]pyrimidin-2-ylmethyl)-acetamide;

N-(4-Oxo-3,5,7,8-tetrahydro-4H-pyrano[4,3-d]pyrimidin-2-ylmethyl)2-[4-(4-propoxy-benzoyl)-piperidin-1-yl]-acetamide;

2-[4-(4-Cyclopropylmethoxy-benzoyl)-piperidin-1-yl]-N-(4-oxo-3,5,7,8-tetrahydro-4H-pyrano[4,3-d]pyrimidin-2-ylmethyl)-acetamide;
2-[4-(4-Cyclobutylmethoxy-benzoyl)-piperidin-1-yl]-N-(4-oxo-3,5,7,8-tetrahydro-4H-pyrano[4,3-d]pyrimidin-2-ylmethyl)-acetamide;
N-(4-Oxo-3,5,7,8-tetrahydro-4H-pyrano[4,3-d]pyrimidin-2-ylmethyl)-2-{4-[4-(tetrahydro-pyran-4-yloxy)-benzoyl]-piperidin-1-yl}-acetamide;
2-{4-[4-(2-Methoxy-ethoxy)-benzoyl]-piperidin-1-yl}-N-(4-oxo-3,5,7,8-tetrahydro-4H-pyrano[4,3-d]pyrimidin-2-ylmethyl)-acetamide;
2-{4-[4-(2-Cyclopropyl-ethoxy)-benzoyl]-piperidin-1-yl}-N-(4-oxo-3,5,7,8-tetrahydro-4H-pyrano[4,3-d]pyrimidin-2-ylmethyl)-acetamide;
2-[4-(3,4-Dimethoxy-benzoyl)-piperidin-1-yl]-N-(4-oxo-3,5,7,8-tetrahydro-4H-pyrano[4,3-d]pyrimidin-2-ylmethyl)-acetamide;
2-[4-(2,3-Dihydro-benzofuran-5-carbonyl)-piperidin-1-yl]-N-(4-oxo-3,5,7,8-tetrahydro-4H-pyrano[4,3-d]pyrimidin-2-ylmethyl)-acetamide;
2-[4-(Benzo[1,3]dioxole-5-carbonyl)-piperidin-1-yl]-N-(4-oxo-3,5,7,8-tetrahydro-4H-pyrano[4,3-d]pyrimidin-2-ylmethyl)-acetamide;
2-[4-(4-Methoxy-3-methyl-benzoyl)-piperidin-1-yl]-N-(4-oxo-3,5,7,8-tetrahydro-4H-pyrano[4,3-d]pyrimidin-2-ylmethyl)-acetamide;
2-[4-(3-Chloro-4-methoxy-benzoyl)-piperidin-1-yl]-N-(4-oxo-3,5,7,8-tetrahydro-4H-pyrano[4,3-d]pyrimidin-2-ylmethyl)-acetamide;
2-[4-(4-Ethoxy-3-fluoro-benzoyl)-piperidin-1-yl]-N-(4-oxo-3,5,7,8-tetrahydro-4H-pyrano[4,3-d]pyrimidin-2-ylmethyl)-acetamide;
2-[4-(4-methoxy-benzoyl)-piperidin-1-yl]-N-(1-oxo-5,8-dihydro-1H,6H-pyrano[3,4-c]pyran-3-ylmethyl)-acetamide;
2-[4-(4-Methoxy-benzoyl)-piperidin-1-yl]-N-(8-oxo-3,4,7,8-tetrahydro-1H-pyrano[3,4-c]pyridin-6-ylmethyl)-acetamide; and
2-(4-(4-Fluorobenzoyl)piperidin-1-yl)-N-methyl-N-(1-(4-oxo-4,5,7,8-tetrahydro-3H-pyrano[4,3-d]pyrimidin-2-yl)ethyl)acetamide.

ENUMERATED EMBODIMENTS

Embodiment 1

A compound according to formula (I)

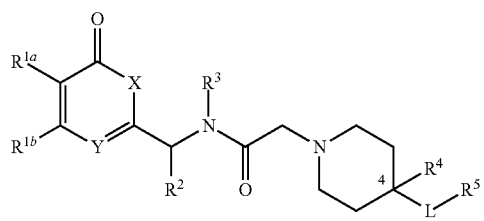

wherein:
X is NH or O;
Y is N or CH;
$R^{1a}$ and $R^{1b}$ are each independently $C_{1-3}$ alkyl; or
$R^{1a}$ and $R^{1b}$ are joined together with the atoms to which they are attached forming an optionally substituted $C_{5-7}$ cycloalkenyl ring, an optionally substituted 3,6-dihydro-2H-pyranyl ring, or an optionally substituted 1,2,3,6-tetrahydropyridinyl ring, wherein said $C_{5-7}$ cycloalkenyl, 3,6-dihydro-2H-pyranyl, and 1,2,3,6-tetrahydropyridinyl are each optionally substituted with one to three substituents each independently selected from the group consisting of: halo, hydroxy, $C_{1-3}$ alkyl, and benzyl;
$R^2$ is H or $C_{1-3}$ alkyl;
$R^3$ is hydrogen, $C_{1-3}$ haloalkyl, $C_{3-6}$ alkynyl, or $C_{1-6}$ alkyl optionally substituted with one substituent selected from the group consisting of: methoxy, cyano, $C_{3-5}$ cycloalkyl, optionally substituted phenyl, optionally substituted 5-10 membered heteroaryl, and 5-6 membered heterocyclyl,
wherein said phenyl, 5-10 membered heteroaryl and 5-6 membered heterocycloalkyl are each optionally substituted with one or two substituents each independently selected from the group consisting of: halo, $C_{1-3}$ alkoxy, cyano, and morpholinyl-$S(O)_2$—; and
$R^4$ is hydrogen, L is C(O),

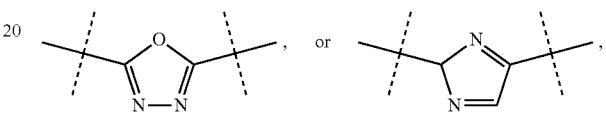

and
$R^5$ is optionally substituted phenyl, optionally substituted 5-6 membered heteroaryl, optionally substituted 2,3-dihydrobenzofuran-6-yl, optionally substituted benzyl[1,3]dioxol-5-yl; optionally substituted 1,2,3,4-tetrahydro-quinolin-1-yl, or optionally substituted 1,2,3,4-tetrahydro-isoquinolin-2-yl,
wherein each $R^5$ is optionally substituted with one or two substituents each independently selected from the group consisting of:
(a) halo,
(b) hydroxy,
(c) $C_{1-6}$ alkyl,
(d) $C_{1-3}$ haloalkyl,
(e) $C_{1-3}$ alkoxy optionally substituted with one methoxy, $C_{3-5}$ cycloalkyl, or phenyl,
(f) $C_{1-3}$ haloalkoxy,
(g) $C_{3-6}$ alkynyloxy,
(h) tetrahydropyranyl-O—, and
(i) $C_{1-3}$ alkyl-C(O)NH—;
or
$R^4$ is hydrogen, L is absent, and $R^5$ is optionally substituted benzo[d]isoxazol-3-yl, optionally substituted 1H-indazol-3-yl, or optionally substituted 1,3-dihydro-benzimidazol-2-one-1-yl, wherein each $R^5$ is optionally substituted with one or two substituents each independently selected from the group consisting of: halo, hydroxy, $C_{1-6}$ alkyl, $C_{1-3}$ haloalkyl, and $C_{1-3}$ alkoxy;
or
$R^4$ and L-$R^5$, wherein L is C(O), are joined together with the atoms to which they are attached forming an optionally substituted indan-1-one-2-yl group or an optionally substituted 3,4-dihydro-2H-naphthalen-1-one-2-yl each of which are attached to the piperidine ring of formula (I) through spiro carbon 4 and are optionally substituted with one to three substituents each independently selected from the group consisting of: halo and $C_{1-6}$ alkoxy; or a pharmaceutically acceptable salt thereof.

Embodiment 2

The compound according to embodiment 1 wherein X is NH and Y is N; or a pharmaceutically acceptable salt thereof.

Embodiment 3

The compound according to embodiment 1 or 2 wherein $R^{1a}$ and $R^{1b}$ are both methyl; or a pharmaceutically acceptable salt thereof.

Embodiment 4

The compound according to embodiment 1 or 2 wherein $R^{1a}$ and $R^{1b}$ are joined together with the atoms to which they are attached forming an optionally substituted $C_{5-7}$ cycloalkenyl ring, an optionally substituted 3,6-dihydro-2H-pyranyl ring, or an optionally substituted 1,2,3,6-tetrahydropyridinyl ring; or a pharmaceutically acceptable salt thereof.

Embodiment 5

The compound according to any one of embodiments 1, 2, and 4 wherein $R^{1a}$ and $R^{1b}$ are joined together with the atoms to which they are attached forming an optionally substituted 3,6-dihydro-2H-pyranyl ring; or a pharmaceutically acceptable salt thereof.

Embodiment 6

The compound according to any one of embodiments 1-5 wherein $R^2$ is H or methyl; or a pharmaceutically acceptable salt thereof.

Embodiment 7

The compound according to any one of embodiments 1-6 wherein $R^3$ is H, $C_{1-3}$ haloalkyl, $C_{3-6}$ alkynyl, or unsubstituted $C_{1-6}$ alkyl; or a pharmaceutically acceptable salt thereof.

Embodiment 8

The compound according to any one of embodiments 1-7 wherein $R^3$ is optionally substituted $C_{1-6}$ alkyl; or a pharmaceutically acceptable salt thereof.

Embodiment 9

The compound according to any one of embodiments 1-8 wherein $R^4$ is H, L is C(O), and $R^5$ is optionally substituted phenyl, optionally substituted 5-6 membered heteroaryl; optionally substituted 2,3-dihydrobenzofuran-6-yl, optionally substituted benzyl[1,3]dioxol-5-yl; optionally substituted 1,2,3,4-tetrahydro-quinolin-1-yl, or optionally substituted 1,2,3,4-tetrahydro-isoquinolin-2-yl; or a pharmaceutically acceptable salt thereof.

Embodiment 10

The compound according to embodiment 9 wherein $R^5$ is optionally substituted phenyl; or a pharmaceutically acceptable salt thereof.

Embodiment 11

The compound according to any one of embodiments 1-8 wherein $R^4$ and L-$R^5$, wherein L is C(O), are joined together with the atoms to which they are attached forming an optionally substituted indan-1-one-2-yl group or an optionally substituted 3,4-dihydro-2H-naphthalen-1-one-2-yl both of which are attached to the piperidine ring of formula (I) through spiro carbon 4 and are optionally substituted with one to three substituents each independently selected from the group consisting of: halo and $C_{1-6}$ alkoxy; or a pharmaceutically acceptable salt thereof.

General Synthetic Procedures

The compounds of the present invention may be made by a variety of methods, including standard chemistry. Illustrative general synthetic methods are set out below and specific compounds of the invention as prepared are given in the Examples.

The compounds of formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formula (I).

Those skilled in the art will recognize if a stereocenter exists in the compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-interscience, 1994).

The compounds described herein may be made from commercially available starting materials or synthesized using known organic, inorganic, and/or enzymatic processes.

Scheme 1: Synthesis of 2-Aminomethyl-3H-pyrimidinones

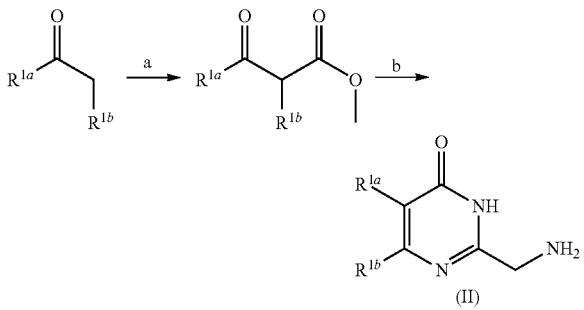

a) KOtBu, CO(OMe)$_2$; b) i. Benzyl 2-amino-2-iminoethyl-carbamate hydrochloride, NaOEt, EtOH ii. H$_2$, Pd/C, MeOH Intermediate II is prepared from appropriately substituted β-keto esters which can be obtained from commercial sources or prepared from suitable ketones by reaction with potassium tert-butoxide in methyl carbonate. Pyrimidinone formation is accomplished by reaction of the β-keto ester with benzyl 2-amino-2-iminoethylcarbamate hydrochloride and a base, such as an alkoxide base, such as sodium ethoxide in a polar solvent, such as a polar protic solvent, such as ethanol. Hydrogenolysis of the Cbz protecting group, accomplished by a suitable catalyst, such as palladium on carbon or palladium hydroxide, in a suitable solvent, such as methanol reveals the primary amine.

Scheme 2: Alternate Synthesis of 2-Aminomethyl-3H-pyrimidinones

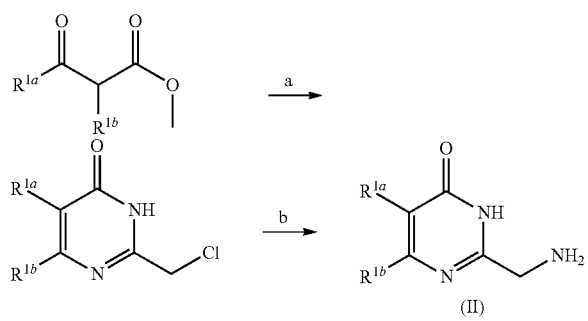

a) TEA, 2-chloroacetamidine, MeOH; b) i. NaN₃, H₂O/acetone ii. Ph₃P, THF

There are other methods for making aminomethyl pyrimidinones including the conversion of β-keto esters to chloromethylpyrimidinones, via 2-chloromethyl acetamide in the presence of a suitable base, such as triethylamine, in a suitable solvent, such as methanol. Formation of the azide can be achieved by reacting the chloromethylpyrimidinone with an azide source, such as sodium azide, in a suitable solvent, such as a water and acetone co-solvent system. Reduction of the azide under suitable reaction conditions, such as treatment with triphenylphosphine, in a suitable solvent, such as THF can also provide 2-aminomethyl-3H-pyrimidinones.

Scheme 3:

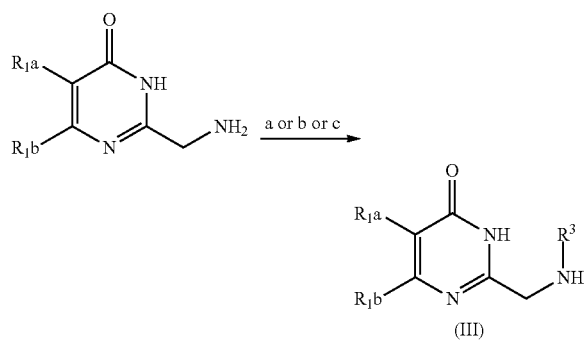

a) R³—CHO, SiCNBH₃, AcOH, EtOH; b) R³CH₂Br, TEA, DMF or R³CH₂X, 120° C. for 5 min Secondary amine (III) can be prepared via reductive amination with the appropriate aldehyde or via alkylation with the appropriate alkyl halide using standard organic chemistry methods.

Scheme 4: Synthesis of 2-alkylaminomethyl-3,4a,5,7,8,8a-hexahydro-pyrano[4,3-d]pyrimidin-4-ones

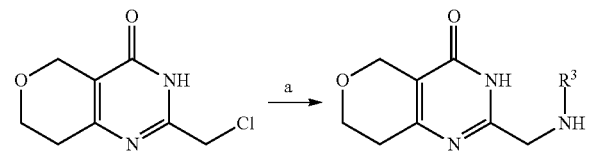

a) R³NH₂, TEA 120° C., 5 min; or R³NH₂, TEA or DIEA, EtOH, 65° C. for 15 h

The formation of 2-alkylaminotmethyl-3,4a,5,7,8,8a-hexahydro-pyrano[4,3-d]pyrimidin-4-ones can be accomplished by a variety of methods, including alkylation of an appropriately substituted amine, with a suitable alkylating agent facilitated with either excess amine, or with the use of a suitable base, such as triethylamine, in a suitable solvent, such as ethanol at temperatures between 0-150° C.

Scheme 5: Synthesis of 2-alkylaminomethyl-3,4a,5,7,8,8a-hexahydro-pyrano[4,3-d]pyrimidin-4-ones

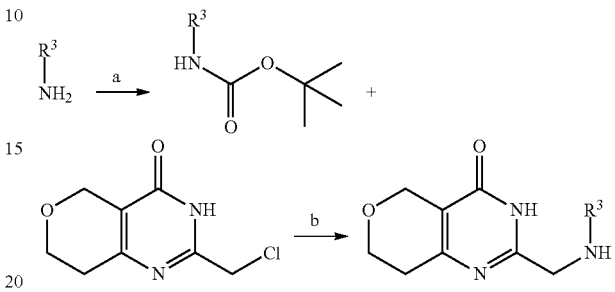

a) di-tert-butyl dicarbonate, TEA, DCM or di-tert-butyl dicarbonate, β-cyclodextrin, water; b) i. BocNHR², NaH, THF or DMF ii. HCl, dioxane, MeOH The formation of 2-alkylaminotmethyl-3,4a,5,7,8,8a-hexahydro-pyrano[4,3-d]pyrimidin-4-ones can be accomplished by a variety of methods, including alkylation of an appropriately substituted Boc-protected amine, with a suitable alkylating agent in the presence of a suitable base, such as sodium hydride or KHMDS, in a suitable solvent, such as THF or DMF at temperatures between −78-50° C.

Scheme 6: Synthesis of spiro[indene-2,4'-piperidin]-1(3H)-one

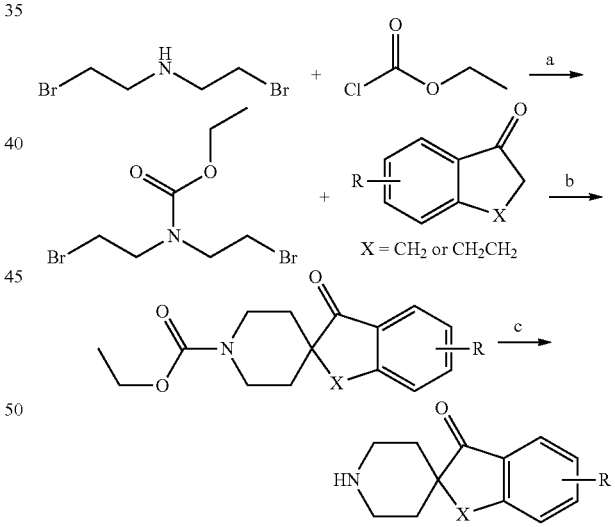

a) NaOH, H₂O; b) NaH, DMF, 50° C.; c) 6 N HCl, reflux

The formation of substituted spiro[indene-2,4'-piperidin]-1(3H)-ones can be accomplished by a variety of methods, including those described below. A suitable bis-(2-bromo-ethyl)-carbamic acid alkyl ester, such as bis-(2-bromo-ethyl)-carbamic acid ethyl ester can by synthesized by protection of bis-(2-bromo-ethyl)-amine with a suitable protecting group, such as a carbamate, such as ethyl carbamate, via reaction with carbamoylating agents, such as alkyl chloroformates, such as ethyl chloroformate, in a suitable solvent, such as water, in the presence of a base, such as NaOH at temperatures from −40° C. to 40° C. Formation of the protected spiro[indene-2,4'-piperidin]-1(3H)-ones can be accomplished by reacting a suitable ketone, such as a substituted indanone, with a strong base, such as sodium hydride, in a polar solvent, such as DMF at temperatures from 0° C. to 100° C. Deprotection of the piperidinyl nitrogen can be accomplished via a variety of methods, such as such as treatment with a strong acid or base, such as 6 N HCl at temperatures between 0° C. and 100° C.

Scheme 7: Synthesis of 4-(5-aryl-[1,3,4]oxadiazol-2-yl)-piperidine analogs

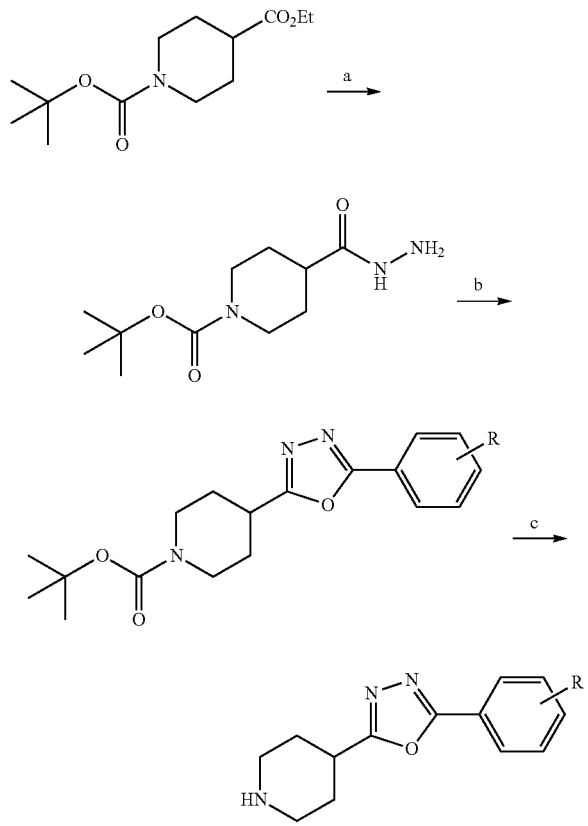

a) NH$_2$NH$_2$, EtOH, reflux; b) ArC(NH)OEt, EtOH, reflux; c) TFA, DCM

The synthesis of 4-(5-aryl-heteroaryl)-piperidine analogs, such as 4-(5-phenyl-[1,3,4]oxadiazol-2-yl)-piperidine can be accomplished by a variety of means. A heterocycle, such as an oxadiazole, may be generated by converting a suitably protected piperidinyl intermediate, such as 1-tert-butyl 4-ethylpiperidine-1,4-dicarboxylate to a heterocyclic precursor, such as a hydrazide, by treatment with a suitable reagent, such as hydrazine hydrate, in a suitable solvent, such as ethanol at temperatures between 20° C. and reflux. This heterocycle can then be formed from this heterocyclic precursor by reaction with a suitable reagent, such as an imidic acid alkyl ester, such as benzimidic acid ethyl ester hydrochloride, under suitable conditions, such as heating at reflux, in a suitable solvent, such as ethanol. Depending on the choice of protecting group, if any, on the piperidinyl intermediate, a further deprotection step may be required, such as the removal of a Boc group, with a suitable reagent, such as an acid, such as TFA, in a suitable solvent, such as DCM.

Scheme 8: Synthesis of 4-benzoyl-piperidinylones via Friedel-Craft reaction

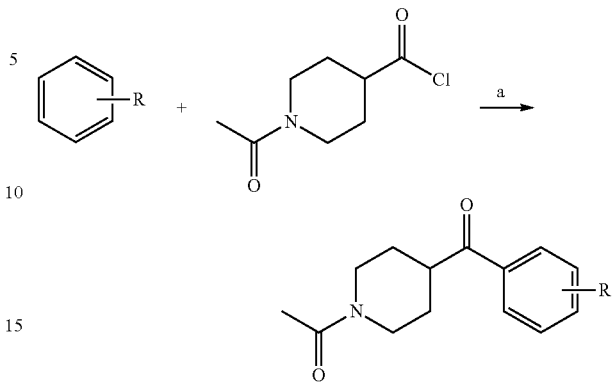

a) AlCl$_3$ or MeAlCl$_2$, −20° C. to 150° C., neat or in DCM or 1,2-dichloroethane)

There are a variety of methods to prepare 4-benzoyl-piperidinylones, including Friedel-Craft acylating conditions, such as reacting a suitable acid chloride, such as 1-acetylpiperidine-4-carbonyl chloride, with a suitably substituted benzene derivative, such as 1,3-difluorobenzene, using a Lewis acid catalyst, such as an alkylaluminum chloride or AlCl$_3$, either neat or in a suitable solvent, such as 1,2-dichloroethane, at temperatures from −20 to 150° C.

Scheme 9: Synthesis of 4-aryl-piperidinylones from Weinreb Amides

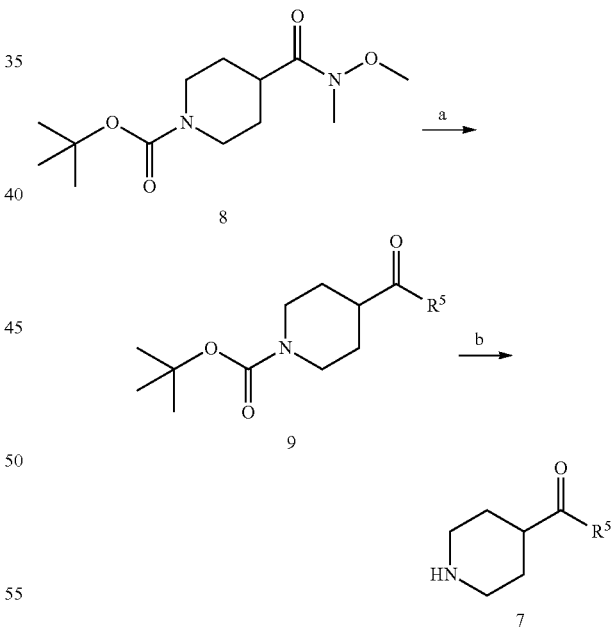

a) Ar—Br, nBuLi, THF, −78° C. or Ar—MgBr, THF, 0° C.; b) TFA, DCM

The synthesis of 7 can be achieved by way of the Weinreb ketone synthesis as shown in Scheme 9. In this scheme, Weinreb amide 8 is treated with a Grignard reagent or an organometallic reagent such as n-butyllithium in the presence of R$^5$—Br to form ketone 9. The tert-butyl protecting group of 9 is removed through the addition of trifluoroacetic acid in dichloromethane to yield the secondary amine 7.

Scheme 10: Synthesis of aryl-piperidin-4-yl-methanone analogs via thiol ester-boronic acid cross-coupling

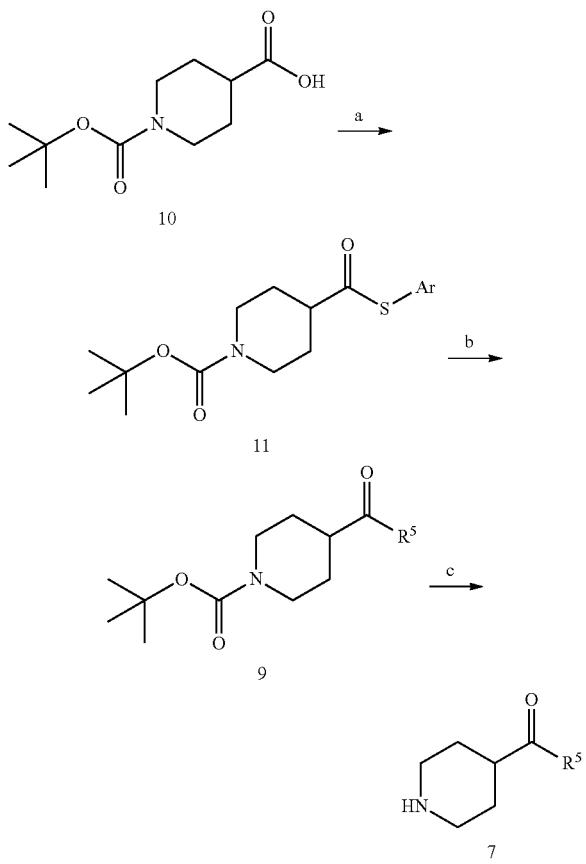

a) ArSH (Ar=Ph or 4-MePh), HATU, DIEA, DMF; b) R—B(OH)2), Pd$_2$(dba)$_3$, ligand TFP, copper (I) thiophene-2-carboxylate, DME, 50° C.; c) TFA, DCM or 4 N HCl, dioxane The synthesis of 7 can also be achieved through a thioester boronic acid cross coupling reaction as shown in Scheme 10. Thioester 11 is achieved through the treatment of 10 with the appropriate aryl thiol in the presence of HATU, DIEA and DMF. 11 is converted into ketone 12 through the addition of the appropriate boronic acid in the presence of a palladium metal catalyst such as Pd$_2$(dba)$_3$ in the presence of tris(2-furyl)phosphine and copper (I) thiophene-2-carboxylate in dimethoxyethane (DME). The tert-butyl protecting group of 9 is removed through the addition of trifluoroacetic acid in dichloromethane to yield the secondary amine 7.

Scheme 11: Synthesis of piperidin-1-yl acetic acids

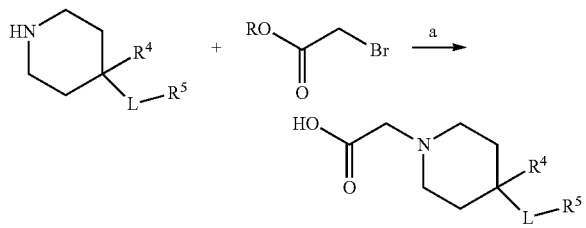

a) i. TEA, MeCN, reflux; ii. (optional) NaOH or LiOH, MeOH/H$_2$O

The synthesis of substituted piperidin-1-yl acetic acids from an appropriately substituted piperidine can be accomplished by a variety of methods, including alkylation of the piperidine with an acetic acid synthon, such as an ester of a halo acetic acid or a halo acetic acid, such as ethyl 2-bromoacetate or bromoacetic acid, in the presence of a base, such as an amine base, such as triethylamine, in an appropriate solvent, such as acetonitrile at a suitable temperature, such as refluxing. Following this alkylation, the acetic acid ester is hydrolyzed with a suitable reagent, such as an alkali base, such as aqueous NaOH, in a polar solvent, such as ethanol at temperatures from 0° C. to 100° C.

Scheme 12: Synthesis of 4-(4-alkoxy-benzoyl)-piperidin-1-yl]-acetic acid analogs

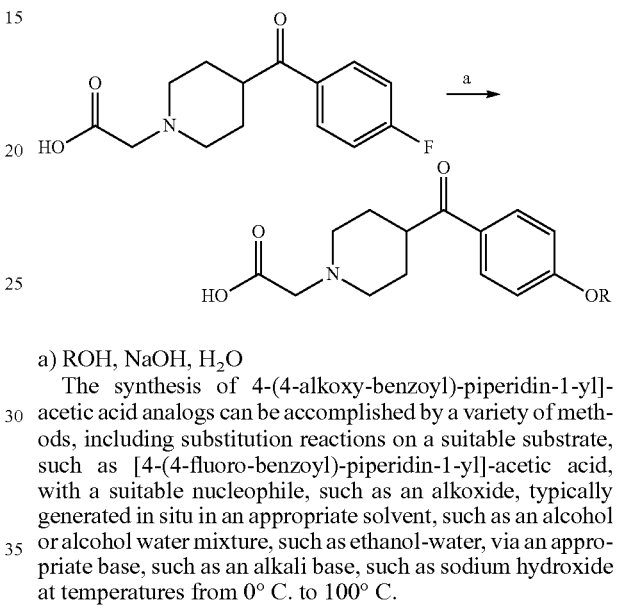

a) ROH, NaOH, H$_2$O

The synthesis of 4-(4-alkoxy-benzoyl)-piperidin-1-yl]-acetic acid analogs can be accomplished by a variety of methods, including substitution reactions on a suitable substrate, such as [4-(4-fluoro-benzoyl)-piperidin-1-yl]-acetic acid, with a suitable nucleophile, such as an alkoxide, typically generated in situ in an appropriate solvent, such as an alcohol or alcohol water mixture, such as ethanol-water, via an appropriate base, such as an alkali base, such as sodium hydroxide at temperatures from 0° C. to 100° C.

Scheme 13:

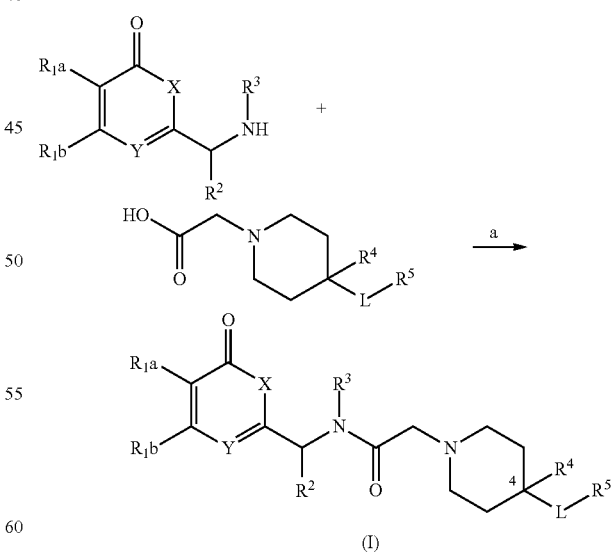

a) EDCl, HOBt or HATU, TEA or DIPEA, DCM or DMF

Compounds of formula (I) can be synthesized by a variety of methods, including the formation of an amide bond. Amide bonds can be formed by a variety of methods, including the use of suitable activating agents, such as a carbodiimide, such as EDCl, with reagents that help form a reactive intermediate, such as an activated ester, with a suitable reagent, such as HOBt or HATU, in the presence of a base, such as triethylamine or DIEA, in a suitable solvent, such as DCM or DMF.

Compositions

In another aspect, the present invention provides a pharmaceutical composition comprising a compound of formula (I), or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
- a) diluents, e.g., lactose, dextrose, sucrose, mannitol, sorbitol, cellulose and/or glycine;
- b) lubricants, e.g., silica, talcum, stearic acid, its magnesium or calcium salt and/or polyethyleneglycol; for tablets also
- c) binders, e.g., magnesium aluminum silicate, starch paste, gelatin, tragacanth, methylcellulose, sodium carboxymethylcellulose and/or polyvinylpyrrolidone; if desired
- d) disintegrants, e.g., starches, agar, alginic acid or its sodium salt, or effervescent mixtures; and/or
- e) absorbents, colorants, flavors and sweeteners.

Tablets may be either film coated or enteric coated according to methods known in the art.

Suitable compositions for oral administration include an effective amount of a compound of formula (I), or a pharmaceutically acceptable salt thereof, in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

Methods of Use

The compounds of formula (I) are tankyrase inhibitors and therefore may be useful in the treatment of diseases mediated by tanykyrase, including Wnt signaling related disorders and tankyrase 1 and 2 (TNKS/TNKS2) signaling related disorders.

Wnt signaling related disorders include diseases and conditions associated with aberrant Wnt signaling including but not limited to Wnt signaling-related cancers (e.g., colorectal cancer, malignant medulloblastoma and other primary CNS malignant neuroectodermal tumors, rhabdomyosarcoma, lung cancer, in particular small cell lung cancer, gut-derived tumors, including but not limited to cancer of the esophagus, stomach, pancreas, and biliary duct system, prostate and bladder cancers, and liver cancer); other, non-oncogenic proliferative diseases, such as proliferative skin disorders (e.g., psoriasis, dermatitis); osteoporosis; osteoarthritis; fibrosis; schizophrenia; vascular disease; cardiac disease; neurodegenerative diseases such as Alzheimer's disease; remyelination, including remyelination after brain and/or spinal code injury; and pulmonary fibrosis. Aberrant upregulation of Wnt signaling is associated with cancer, osteoarthritis, and polycystic kidney disease, while aberrant down regulation of Wnt signaling has been linked to osteoporosis, obesity, diabetes, and neuronal degenerative diseases.

Tankyrase signaling related disorders include diseases and conditions associated with aberrant tankyrase 1 and 2 signaling, including but not limited to cancer (e.g., leukemia, lymphoma, melanoma, multiple myeloma, lung, ovarian, and breast cancer) metabolic diseases and viral infection (e.g. Herpes Simplex Virus infection).

The term "a therapeutically effective amount" of a compound of the present invention refers to an amount of a compound of formula (I) that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of a compound of formula (I) when administered to a subject, is effective to (1) at least partially alleviating, inhibiting, preventing and/or ameliorating a condition, or a disorder or a disease (i) mediated by tankyrase, or (ii) associated with tankyrase activity, or (iii) characterized by activity (normal or abnormal) of tankyrase; or (2) reducing or inhibiting the activity of tankyrase or (3) reducing or inhibiting the expression of tankyrase. In another non-limiting embodiment, the term "a therapeutically effective amount" refers to the amount of a compound of formula (I) when administered to a cell, or a tissue, or a non-cellular biological material, or a medium, is effective to at least partially reducing or inhibiting the activity of tankyrase; or at least partially reducing or inhibiting the expression of tankyrase.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

Thus, as a further embodiment, the present invention provides the use of a compound of formula (I) or a pharmaceutically acceptable salt thereof, in therapy. In a further embodiment, the therapy is selected from a disease which may be treated by tankyrase inhibition. In one embodiment the disease is a Wnt signaling related disorder. In another embodiment the disease is a tankyrase signaling related disorder. In another embodiment, the disease is cancer, in particular a cancer selected from the group consisting of leukemia, melanoma, multiple myeloma, lymphoma, lung cancer, esophageal cancer, stomach cancer, pancreas cancer, biliary duct system cancer, ovarian cancer, breast cancer, prostate cancer, bladder cancer, colon cancer and liver cancer. In another embodiment, the disease is cancer, in particular, a cancer selected from the group consisting of leukemia, lung cancer, pancreas cancer, breast cancer and colon cancer. In another embodiment the disease is a cancer selected from the group consisting of colon, pancreas, and breast.

In another embodiment, the invention provides a use of a compound of formula (I), or a pharmaceutically acceptable salt thereof, in that manufacture of a medicament for the treatment of a disease mediated by tankyrase inhibition. In one embodiment the disease is a Wnt signaling related disorder. In another embodiment the disease is a tankyrase signaling related disorder. In another embodiment, the disease is cancer, in particular a cancer selected from the group consisting of leukemia, melanoma, multiple myeloma, lymphoma, lung cancer, esophageal cancer, stomach cancer, pancreas cancer, biliary duct system cancer, ovarian cancer, breast cancer, prostate cancer, bladder cancer, colon cancer and liver cancer. In another embodiment, the disease is cancer, in particular a cancer selected from the group consisting of leukemia, lung cancer, pancreas cancer, breast cancer and colon cancer. In another embodiment the disease is a cancer selected from the group consisting of colon, pancreas, and breast.

In another embodiment, the invention provides a method for the treatment of a disease mediated by tankyrase inhibition comprising administration of a therapeutically effective amount of a compound of formula (I) or a pharmaceutically acceptable salt thereof to a subject in need thereof. In one embodiment the disease is a Wnt signaling related disorder. In another embodiment the disease is a tankyrase signaling related disorder. In a further embodiment, the disease is cancer, in particular a cancer selected from the group consisting of leukemia, melanoma, multiple myeloma, lymphoma, lung cancer, esophageal cancer, stomach cancer, pancreas cancer, biliary duct system cancer, ovarian cancer, breast cancer, prostate cancer, bladder cancer, colon cancer and liver cancer. In another embodiment, the disease is cancer, in particular a cancer selected from the group consisting of leukemia, lung cancer, pancreas cancer, breast cancer and colon cancer. In another embodiment the disease is a cancer selected from the group consisting of colon, pancreas, and breast.

Combinations

The compounds of the present invention may be administered either simultaneously with, or before or after, one or more other therapeutic agent(s). The compounds of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by TNKS inhibition. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by tankyrase inhibition wherein the medicament is prepared for administration with another therapeutic agent. The invention also provides the use of another therapeutic agent for treating a disease or condition mediated by tankyrase inhibition, wherein the medicament is administered with a compound of formula (I).

The invention also provides a compound of formula (I) for use in a method of treating a disease or condition mediated by tankyrase inhibition, wherein the compound of formula (I) is prepared for administration with another therapeutic agent. The invention also provides another therapeutic agent for use in a method of treating a disease or condition mediated by tankyrase inhibition, wherein the other therapeutic agent is prepared for administration with a compound of formula (I). The invention also provides a compound of formula (I) for use in a method of treating a disease or condition mediated by tankyrase inhibition, wherein the compound of formula (I) is administered with another therapeutic agent. The invention also provides another therapeutic agent for use in a method of treating a disease or condition mediated by tankyrase inhibition, wherein the other therapeutic agent is administered with a compound of formula (I).

The invention also provides the use of a compound of formula (I) for treating a disease or condition mediated by tankyrase inhibition, wherein the patient has previously (e.g. within 24 hours) been treated with another therapeutic agent. The invention also provides the use of another therapeutic agent for treating a disease or condition mediated by tankyrase inhibition, wherein the patient has previously (e.g. within 24 hours) been treated with a compound of formula (I).

In one embodiment, the other therapeutic agent is selected from the group of, but not limited to Hedgehog antagonists, PI3K inhibitors, MEK inhibitors, tyrosine kinase inhibitors, IAP (Inhibitors of Apoptosis Proteins) inhibitors, alkylating agents, anti-metabolites, microtubule inhibitors, telomerase inhibitors, PARP inhibitors, and RAF inhibitors.

An example of a Hedgehog antagonist is 2-chloro-N-[4-chloro-3-(2-pyridinyl)phenyl]-4-(methylsulfonyl)-benzamide (also known as GDC-0449, and described in PCT Publication No. WO 06/028958) and Erismodegib (also known as LDE225).

Some examples of PI3K inhibitors include: 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730) and 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806).

An example of a Mitogen-activated protein kinase kinase (MEK) inhibitor is XL-518 (Cas No. 1029872-29-4, available from ACC Corp.).

Some examples of tyrosine kinase inhibitors include: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), pazopanib (also known as Armala™ sold under the tradename Votrient® by GlaxoSmithKline), and imatinib and imatinib mesylate (sold under the tradenames Gilvec® and Gleevec® by Novartis).

An example of an IAP (Inhibitors of Apoptosis Proteins) inhibitor is (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide (also known as LCL161 and described in PCT Publication No. WO2008/016893).

Some examples of alkylating agents include: temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, and TESPA and TSPA, sold under the tradename Thioplex®.

Some examples of Anti-metabolites include: claribine (2-chlorodeoxyadenosine, sold under the tradename Ieustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodim (MTX), sold under the tradenames Rheumatrex® and Trexall™), and pentostatin (sold under the tradename Nipent®).

Some examples of microtubule inhibitors are vinorelbine (sold under the trade name Navelbine®), vindesine (sold under the trade name Eldisine®), estramustine (sold under the trade name Emcyt®), vincristine (Oncovin®), triclabendazole (Egaten®), secnidazole, quinfamide, podophyllotoxin, mebendazole, griseofulvin, flubendazole, eribulin, colchicine, ciclobendazole, cabazitaxel, albendazole, and vinorelbine.

An example of a telomerase inhibitor is imetelstat.

Some examples of PARP inhibitors include: olaparib (from Astrazeneca), iniparib (also known as BSI-201), AGO14699 (Pfizer), veliparib (also known as ABT-888 from Enzo), and MK4827 (Merck).

Some examples of RAF inhibitors include: 2-Chloro-5-[2-Phenyl-5-(4-pyridinyl)-1H-imidazol-4-yl]phenol (also known as L-779450), 3-(dimethylamino)-N-[3-[(4-hydroxybenzoyl)amino]-4-methylphenyl]-benzamide (also known as ZM-336372) and sorafenib (marketed as Nexavar® by Bayer).

INTERMEDIATES AND EXAMPLES

The following examples are intended to be illustrative only and not limiting in any way.

Abbreviations used are those conventional in the art or the following:
AcOH acetic acid
BOC tertiary butyl carboxy
C Celsius
d doublet
dd doublet of doublets
DCM dichloromethane
DIEA diethylisopropylamine
DME 1,4-dimethoxyethane
DMF N,N-dimethylformamide
DMSO dimethylsulfoxide
EtOAc ethyl acetate
EtOH ethanol
EDCL 1-ethyl-3-(3'-dimethylaminopropyl)carbodiimide
g gram
h hour(s)
HBTU 1-[bis(dimethylamino)methylene]-1H-benzotriazoliumhexafluorophosphate(1-) 3-oxide
HOBt 1-hydroxy-7-azabenzotriazole
HPLC high pressure liquid chromatography
IR infrared spectroscopy
kg kilogram
L liter
LCMS liquid chromatography and mass spectrometry
MTBE methyl tert butyl either
MeOH methanol
MS mass spectrometry
MW microwave
m multiplet
min minutes
mL milliliter(s)
μM micromolar
m/z mass to charge ratio
nm nanometer
nM nanomolar
N normal
NMR nuclear magnetic resonance
Pa pascal
Pd/C palladium on carbon
rac racemic
RP-HPLC reverse phase-high pressure liquid chromatography
s singlet
t triplet
TEA triethylamine
TLC thin layer chromatography
TFA trifluoroacetic acid
THF tetrahydrofuran Intermediate 1

4-Oxo-tetrahydro-pyran-3-carboxylic acid methyl ester

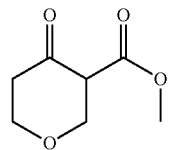

To a solution of tetrahydro-pyran-4-one (1.3 kg, 12.98 mol) and carbonic acid dimethyl ester (11.69 kg, 129.8 mol) was added solid potassium tert-butoxide (1.89 kg, 16.08 mol) in portions at −10° C. over 2 h under nitrogen protection. The suspension was stirred at room temperature 10 h after the addition. LCMS (215 nm) indicated that tetrahydro-pyran-4-one had been completely consumed. The reaction was acidified by HCl (2 N) to pH 6~7 and then the phases were separated. The organic phase was washed with water (3 L×2) and the combined aqueous phases were extracted with MTBE (2.5 L×2). The combined organic phase was concentrated under reduced pressure at 25° C. to remove most of MTBE. The residue was distilled out by oil pump (~200 Pa) at 74° C. to give the title compound as colorless oil (545 g, 26.3%). CHN analysis: calculated (results). C, 53.16 (53.10), H, 6.37 (6.245), N, 0.00 (0.00).

Intermediate 2

Benzyl 2-amino-2-iminoethylcarbamate hydrochloride

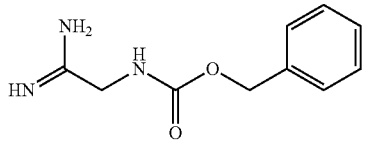 [SMILES: N=C(N)CNC(=O)OCc1ccccc1]

To a solution of benzyl cyanomethylcarbamate (65.4 g, 344 mmol) in methanol was added sodium methoxide (7.86 mL, 34.4 mmol, 25% in methanol). The mixture was stirred at ambient temperature for 24 h. Ammonium chloride (18.4 g, 344 mmol) was then added. The mixture was stirred at ambient temperature for another 24 h, and concentrated under reduced pressure. The resulting material was added into hexane/ethyl acetate (1:1) (240 mL) and ether (50 mL), stirred at ambient temperature for 1.5 h, then filtered to provide the title compound as a pale colored solid (78.8 g, 94% yield). $^1$H NMR (400 MHz, DMSO-$d_6$) δ 8.79 (br. s., 4H), 7.78 (t, J=5.5 Hz, 1H), 7.24-7.47 (m, 5H), 5.07 (s, 2H), 3.98 (d, J=5.5 Hz, 2H). MS m/z 208.2 (M+1), retention time=0.64 min.

Intermediate 3

Benzyl (4-oxo-4,5,7,8-tetrahydro-3H-pyrano[4,3-d]pyrimidin-2-yl)methylcarbamate

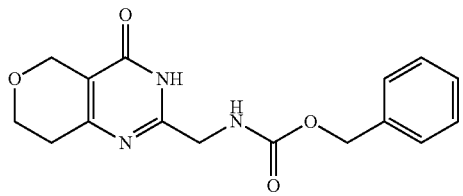 [SMILES: O=C(NCc1nc2c(c(=O)[nH]1)COCC2)OCc1ccccc1]

To a solution of methyl 4-oxotetrahydro-2H-pyran-3-carboxylate (51.1 g, 323 mmol) and benzyl 2-amino-2-iminoethylcarbamate hydrochloride (78.8 g, 323 mmol) in anhydrous ethanol was added sodium ethoxide (122 mL, 323 mmol, 21% in ethanol). The mixture was mechanically stirred, heated at reflux for 24 h, cooled down to ambient temperature, and filtered to give the title compound (55.6 g, 55% yield). $^1$H NMR (400 MHz, DMSO-$d_6$) δ 12.40 (br. s., 1H), 7.69 (t, J=5.8 Hz, 1H), 7.15-7.44 (m, 5H), 4.99-5.08 (m, 2H), 4.35 (s, 2H), 4.04-4.11 (m, 2H), 3.84 (t, J=5.3 Hz, 2H), 2.48-2.57 (m, 2H). MS m/z 316.2 (M+1), retention time=1.10 min.

Alternate Procedure

To benzyl 2-amino-2-iminoethylcarbamate (1.77 g, 8.54 mmol) in methanol (67.5 mL) was added methyl 4-oxotetrahydro-2H-pyran-3-carboxylate (1.35 g, 8.54 mmol) and potassium carbonate (3.54 g, 25.6 mmol). The reaction mixture was stirred 15 h at room temperature. The solution was filtered and concentrated under vacuum. Purification was accomplished on a 100 g Isco column with 0% to 10% methanol in dichloromethane over 20 column volumes to give title compound (1.63 g, 59% yield). Exact mass calculated for $C_{16}H_{17}N_3O_4$ 315.3. found 316.2 (ESI, M+H); $^1$H NMR (400 MHz, MeOD) δ ppm 7.17-7.46 (m, 5H) 5.11 (s, 2H) 4.47 (br. s., 2H) 4.22 (s, 2H) 3.92 (t, J=5.31 Hz, 2H) 2.65 (br. s., 2H).

Intermediate 4

2-aminomethyl-3,5,7,8-tetrahydro-pyrano[4,3-d]pyrimidin-4-one

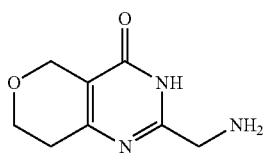 [SMILES: NCc1nc2c(c(=O)[nH]1)COCC2]

A solution of benzyl (4-oxo-4,5,7,8-tetrahydro-3H-pyrano[4,3-d]pyrimidin-2-yl)methylcarbamate (55.5 g, 176 mmol) in methanol (4 L) was degassed several times under nitrogen then palladium on carbon (1.87 g, 1.76 mmol, 10% on carbon) was added slowly under nitrogen atmosphere. The mixture was stirred under a hydrogen balloon at ambient temperature until TLC showed complete consumption of starting material. Filtration through a pad of Celite and evaporation of solvent provided the title compound (32 g, >99% yield). $^1$H NMR (400 MHz, CD$_3$OD) δ 4.49 (s, 2H), 3.93 (t, J=5.5 Hz, 2H), 3.77 (s, 2H), 2.66 (t, J=5.5 Hz, 2H). MS m/z 182.2 (M+1), retention time=0.39 min.

Alternate Procedure

To benzyl (4-oxo-4,5,7,8-tetrahydro-3H-pyrano[4,3-d]pyrimidin-2-yl)methylcarbamate (1.63 g, 51.7 mmol) in methanol (70 mL) was added 10% palladium hydroxide (726 mg, 0.52 mmol) and the mixture was stirred under 1 atm of H$_2$ for 4 h. The solution was filtered through celite and concentrated under vacuum to give 2-aminomethyl-3,5,7,8-tetrahydropyrano[4,3-d]pyrimidin-4-one (707 mg, 75% yield). $^1$H NMR (400 MHz, DMSO-$d_6$) δ ppm 4.34 (s, 2H) 3.83 (t, J=5.56 Hz, 2H) 3.54 (s, 2H) 2.54 (t, J=5.56 Hz, 2H).

Intermediate 5

2-(Aminomethyl)-5,6,7,8-tetrahydroquinazolin-4(3H)-one

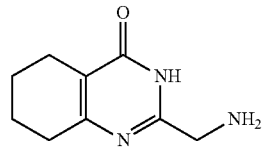 [SMILES: NCc1nc2c(c(=O)[nH]1)CCCC2]

The title compound (370 mg, 36% yield) was prepared following the general procedures of Intermediates 2-4 from ethyl 2-oxocyclohexanecarboxylate (1.0 mL, 6.2 mmol). MS m/z 180.3 (M+1), retention time=0.42 min.

Intermediate 6

2-(Aminomethyl)-6,7-dihydro-3H-cyclopenta[d]pyrimidin-4(5H)-one

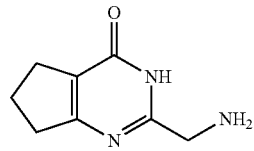 [SMILES: NCc1nc2c(c(=O)[nH]1)CCC2]

The title compound (716 mg) was prepared following the general procedures of Intermediates 2-4 from methyl 2-oxocyclopentanecarboxylate (1.52 mL, 11.5 mmol). MS m/z 165.9 (M+1), retention time=0.38 min.

Intermediate 7

2-(Aminomethyl)-5,6-dimethylpyrimidin-4(3H)-one

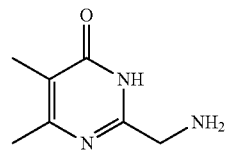

The title compound (420 mg) was prepared following the general procedures of Intermediates 2-4 from ethyl 2-methyl-3-oxobutanoate (1.84 mL, 11.5 mmol).

Intermediate 8

2-(Aminomethyl)-6,7,8,9-tetrahydro-3H-cyclohepta[d]pyrimidin-4(5H)-one

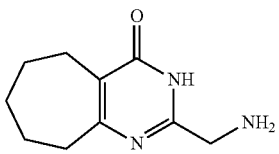 [SMILES: NCc1nc2c(c(=O)[nH]1)CCCCC2]

The title compound (260 mg, 22% yield) was prepared following the general procedures of Intermediates 2-4 from methyl 2-oxocycloheptanecarboxylate (0.97 mL, 6.2 mmol). MS m/z 194.0 (M+1), retention time=1.06 min.

Intermediate 9

2-Chloro-acetamidine

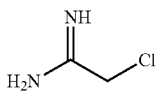

Sodium (18.3 g, 0.795 mol) was completely dissolved in 2 L of MeOH at 25° C. and stirred for 1 hour. To the solution was then added chloro-acetonitrile (600 g, 7.95 mol) dropwise in 1 hour under the protection of $N_2$. After being stirred at about 20° C. for an additional hour, $NH_4Cl$ (514 g, 8.73 mol) was added in portions over 45 minutes (the solution turned to yellow and then red, and then a black liquid was obtained), the reaction mixture was then allowed to stir at 15-20° C. for 16 hours. After filtration, the filtrate was concentrated to give a residue, which was triturated with MTBE (1 L×2) to give the title compound as a black solid (988 g, 96%).

Intermediate 10

2-Chloromethyl-3,5,7,8-tetrahydro-pyrano[4,3-d]pyrimidin-4-one

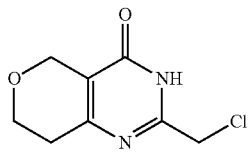 [SMILES: O=c1[nH]c(CCl)nc2c1COCC2]

A mixture of crude 4-oxo-tetrahydro-pyran-3-carboxylic acid methyl ester (1780 g, 11 mol) and $NEt_3$ (830 g, 8.2 mol) in MeOH (3560 mL) was cooled to 0° C. under $N_2$. A solution of 2-chloro-acetamidine (567 g, 4.4 mol) in 890 mL of MeOH was added dropwise over 50 minutes. The reaction mixture was stirred at 0° C. for 30 minutes and then at about 20° C. for 16 hours. LCMS at 215 nm and TLC (DCM:MeOH=10:1) analysis showed that most of 4-oxo-tetrahydro-pyran-3-carboxylic acid methyl ester was consumed. The mixture was then filtered and concentrated to give black oil, which was subsequently purified by flash column chromatography on silica gel and eluted with DCM to give yellow solid/oil mixture, which was further triturated with MTBE (1200 mL) and $H_2O$: $CH_3CN$: EA=1:1:2 (~600 mL) to give the title compound as a white solid (318 g). MS m/z 201.2 (M+H). CHN analysis: calculated (results). C, 47.89 (47.95), H, 4.52 (4.401), N, 13.96 (13.76).

Intermediate 11

2-(azidomethyl)-7,8-dihydro-3H-pyrano[4,3-d]pyrimidin-4(5H)-one

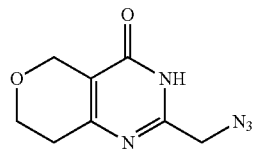 [SMILES: [N-]=[N+]=NCc1nc2c(c(=O)[nH]1)COCC2]

To a solution of 2-chloromethyl-3,5,7,8-tetrahydro-pyrano[4,3-d]pyrimidin-4-one (20.6 g, 103 mmol) in acetone (513 mL) was added an aqueous solution of sodium azide (7.01 g, 108 mmol in 32 mL water). Reaction was stirred at room temperature for 36 h. Mixture was split into three equal volumes and each was diluted with dichloromethane (500 mL) and brine was added (100 mL) and the layers were separated. The aqueous fractions were combined and extracted with dichloromethane (5×100 mL). The combined organic layers were concentrated in vacuo. The resulting residue was taken up in dichloromethane (200 mL) and evaporated to dryness three times to yield 19.25 g of a yellow-white solid. 1H NMR (400 MHz, DMSO-d6) δ ppm 2.59 (t, J=5.56 Hz, 2H) 3.85 (t, J=5.56 Hz, 2H) 4.28 (s, 2H) 4.36 (s, 2H) 12.58 (br. s., 1H)

Intermediate 4

2-aminomethyl-3,5,7,8-tetrahydro-pyrano[4,3-d]pyrimidin-4-one

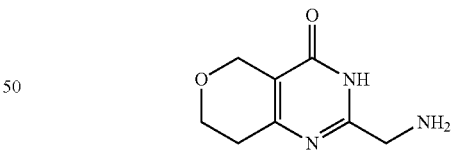

To a solution of 2-(azidomethyl)-7,8-dihydro-3H-pyrano[4,3-d]pyrimidin-4(5H)-one (19 g, 92 mmol) in THF (945 mL) at 35° C. was added triphenylphosphine (26.5 g, 101 mmol). Gas evolution was noted immediately and after approximately 40 minutes a fine precipitate formed. The reaction was allowed to stir for 1.5 h then 18.17 mL water was added. After an addition 2 h the reaction mixture was cooled to room temperature, filtered twice, concentrated to approximately ⅓ of the original volume and filtered once more. The solid material was washed with THF to yield a total of 15.82 g of the title compound. 1H NMR (400 MHz, MeOD) δ ppm 2.66 (t, J=5.56 Hz, 2H) 3.76 (s, 2H) 3.94 (t, J=5.56 Hz, 2H) 4.49 (s, 2H)

Intermediate 12

2-{[(Thiophen-2-ylmethyl)-amino]-methyl}3,5,7,8-tetrahydro-pyrano[4,3-d]pyrimidin-4-one

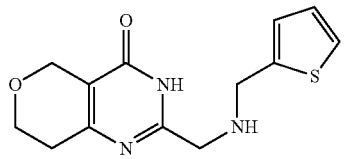 [SMILES: O=c1[nH]c(CNCc2cccs2)nc2c1COCC2]

A mixture of thiophene-2-carbaldehyde (0.021 mL, 0.22 mmol), 2-aminomethyl-3,5,7,8-tetrahydro-pyrano[4,3-d]pyrimidin-4-one (40 mg, 0.22 mmol), and siliabond cyanoborohydride (240 mg, 0.24 mmol, 1 mmol/g) in ethanol (1 mL) was stirred at ambient temperature for 10 minutes. Acetic acid (0.013 mL, 0.22 mmol) was then added, and the mixture was stirred at ambient temperature for another 5 minutes. The reaction mixture was concentrated in vacuo and purified via flash column chromatography (ethyl acetate:hexane, 10:90 to 100:0, methanol: dichloromethane, 1:99 to 10:90) to provide the title compound (30 mg, 49% yield). m/z 278.1 (M+1), retention time=0.89 min.

Alternate Procedure

To 2-aminomethyl-3,5,7,8-tetrahydro-pyrano[4,3-d]pyrimidin-4-one (100 mg, 0.552 mmol) in methylene chloride (5 mL) was added thiophene-2-carbaldehyde (62 mg, 0.552 mmol), sodium triacetoxyborohydride (351 mg, 1.66 mmol) and drop of acetic acid. The solution was stirred for 4 hr. The solvent was removed under vacuum, and the crude product was loaded on a Isco 12 g column. Elution with 0% to 10% methanol in methylene chloride over 15 column volumes afforded the title compound (95 mg, 61% yield). Exact mass calculated for $C_{13}H_{15}N_3O_2S$ 277.3. found 278.2 (ESI, M+H); $^1$H NMR (400 MHz, MeOD) δ ppm 7.58 (d, J=5.05 Hz, 1H) 7.33 (d, J=3.03 Hz, 1H) 7.07-7.16 (m, 1H) 4.63 (s, 2H) 4.47 (s, 2H) 4.24 (s, 2H) 3.94 (t, J=5.56 Hz, 2H) 2.73 (t, J=5.56 Hz, 2H).

Intermediate 13

2-((4-Fluorobenzylamino)methyl)-7,8-dihydro-3H-pyrano[4,3-d]pyrimidin-4(5H)-one

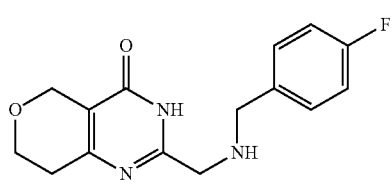 [SMILES: O=c1[nH]c(CNCc2ccc(F)cc2)nc2c1COCC2]

A mixture of 2-aminomethyl-3,5,7,8-tetrahydro-pyrano[4,3-d]pyrimidin-4-one (150 mg, 0.83 mmol) and 1-(bromomethyl)-4-fluorobenzene (83 µL 0.66 mmol) was heated via microwave in ethanol (5 mL) at 120° C. for 5 minutes. The reaction mixture was concentrated in vacuo and the residue was purified via flash column chromatography (ethyl acetate: hexane, 20:80 to 100:0 and then methanol: dichloromethane, 1:99 to 30:70) to provide the title compound (160 mg, 67% yield). MS m/z 290.2 (M+1), retention time=1.04 min

Intermediate 14

2-((Cyclopropylmethylamino)methyl)-6,7,8,9-tetrahydro-3H-cyclohepta[d]pyrimidin-4(5H)-one

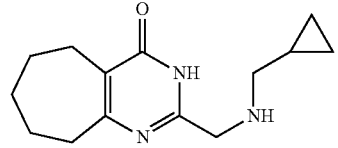 [SMILES: O=c1[nH]c(CNCC2CC2)nc2c1CCCCC2]

The title compound was prepared according to the general procedure of Intermediate 13 from (bromomethyl)cyclopropane (0.042 mL, 0.44 mmol). It was used directly in the next step without purification. MS m/z 248.0 (M+1), retention time=1.34 min.

Intermediate 15

2-(Neopentylamino)methyl)-7,8-dihydro-3H-pyrano[4,3-d]pyrimidin-4(5H)-one

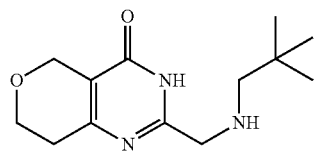 [SMILES: CC(C)(C)CNCc1nc2c(c(=O)[nH]1)COCC2]

A mixture of 2-(chloromethyl)-7,8-dihydro-3H-pyrano[4,3-d]pyrimidin-4(5H)-one (130 mg, 0.63 mmol), 2,2-dimethylpropan-1-amine (74 µL 0.63 mmol), and triethylamine (0.264 mL, 1.90 mmol) was microwave at 120° C. for 5 minutes. The reaction mixture was concentrated in vacuo and the residue was purified via flash column chromatography (ethyl acetate:hexane, 20:80 to 100:0 and then methanol: dichloromethane, 1:99 to 10:90) to provide the title compound (50 mg, 32% yield). MS m/z 252.2 (M+1), retention time=1.02 min.

Intermediate 16

2-[((R)-1-Phenyl-ethylamino)-methyl]-3,5,7,8-tetrahydro-pyrano[4,3-d]pyrimidin-4-one

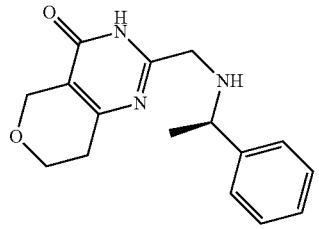 [SMILES: C[C@@H](NCc1nc2c(c(=O)[nH]1)COCC2)c1ccccc1]

To 2-chloromethyl-3,5,7,8-tetrahydro-pyrano[4,3-d]pyrimidin-4-one (50 mg, 0.249 mmol) in ethanol (2 mL) was added (R)-1-phenyl-ethylamine (66 mg, 0.545 mmol, 2 eq) and the solution was heated at 65° C. for 15 h. The cooled solution was concentrated under vacuum and the resulting oil was taken up in methanol, added to a strong cation exchange (SCX) column and washed with methanol (50 mL). The product was eluted with 1 N ammonia in methanol (50 mL) and concentrated under vacuum. The crude product was absorbed onto Silica Gel (500 mg), added to a Biotage SNAP-10 g column and eluted with 1% to 10% methanol in dichloromethane over 12 column volumes to give: 2-[((R)-1-phenylethylamino)-methyl]-3,5,7,8-tetrahydro-pyrano[4,3-d]pyrimidin-4-one (20 mg, 28% yield). Exact mass calculated for $C_{16}H_{19}N_3O_2$ 285.15. found 286.5 (ESI, M+H).

Intermediate 17

2-[(Cyclopropylmethyl-amino)-methyl]-3,5,7,8-tetrahydro-pyrano[4,3-d]pyrimidin-4-one

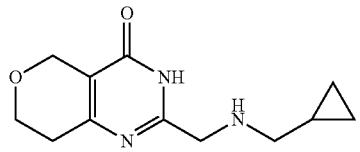 [SMILES: O=c1[nH]c(CNCC2CC2)nc2c1COCC2]

To a solution of 2-chloromethyl-3,5,7,8-tetrahydro-pyrano[4,3-d]pyrimidin-4-one (1.0 g, 4.98 mmol) in ethanol (30 mL) was added cyclopropylmethylamine (2.13 g, 29.9 mmol). The mixture was then heated at 45° C. for 60 hours. The reaction was then stopped and the mixture was concentrated under high vacuum for 24 h. The remaining semi-solid was subjected to column chromatography (Silica gel, 0-10% methanol in dichloromethane) to give 2-[(cyclopropylmethyl-amino)-methyl]-3,5,7,8-tetrahydro-pyrano[4,3-d]pyrimidin-4-one as a light brown solid (540 mg, 2.30 mmol, 46% yield) that was directly used in the next step. m/z=236.4 (M+H).

Alternate Procedure

To a solution of 2-chloromethyl-3,5,7,8-tetrahydro-pyrano[4,3-d]pyrimidin-4-one (1 g, 5 mmol, 1 eq.) and DIEA (4.35 mL, 24.9 mmol, 5 eq.) in 7 mL of EtOH was added cyclopropylmethylamine (1.4 g, 20 mmol, 4 eq.). The resulting mixture was heated at 65° C. overnight. After 18 h, the reaction mixture was concentrated in vacuo to give an oil that was purified by silica gel column chromatography (100% $CH_2Cl_2$) to give the title compound as a white solid (0.23 g, 20%). $^1$H NMR (400 MHz, chloroform-d) δ ppm 4.37-4.42 (m, 2H), 3.95 (s, 1H), 3.80-3.88 (m, 3H), 2.63-2.72 (m, 1H), 2.54-2.63 (m, 3H), 0.89-1.05 (m, 1H), 0.42-0.54 (m, 2H), 0.14-0.26 (m, 2H). Exact mass calculated for $C_{12}H_{18}N_3O_2$ 236.1. MS (ESI) m/z 236.9 (M+H)$^+$. Retention time: 0.56 min (5-95% $CH_3CN/H_2O$ over 2 min with 0.1% formic acid, Inertsil 3×3 mm C-8-3 column with flow rate of 2 mL/min).

Intermediate 18 tert-butyl cyclopropylmethylcarbamate

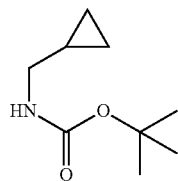

To 1.5 L of water at 0° C. was added beta-cyclodextrin (0.798 g, 0.703 mmol) and cyclopropylmethanamine (50 g, 703 mmol). To this was added slowly di-tert-butyl dicarbonate (153 g, 703 mmol). The reaction was allowed to stir for 16 h then transferred to a separatory funnel. The aqueous layer was separated and extracted with ethyl acetate (3×200 mL). The organic layers were combined, washed with water and then brine. The organics were dried with MgSO4, filtered and concentrated in vacuo to a clear, near colorless oil. The oil was taken up into heptane, cooled in a dry ice/isopropanol batch to form a solid suspension which was then filtered, washed with cold heptane and dried in vacuo (68 g).

Alternate Procedure

Cyclopropylmethyl-carbamic acid tert-butyl ester (91 g, 79%) was synthesized from cyclopropyl-methylamine (50 g, 703 mmol, 1.05 eq.) and di-tert-butyl dicarbonate (146 g, 670 mmol, 1 eq.) (Synlett 206, 1110).

Intermediate 19 tert-butyl cyclopropylmethyl((4-oxo-4,5,7,8-tetrahydro-3H-pyrano[4,3-d]pyrimidin-2-yl)methyl)carbamate

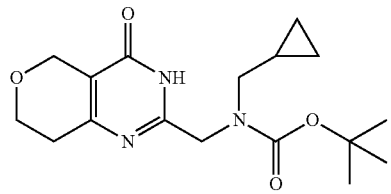 [SMILES: CC(C)(C)OC(=O)N(Cc1nc2c(c(=O)[nH]1)COCC2)CC1CC1]

To a stirred solution of NaH (11.96 g, 299 mmol) in 260 mL DMF at 0° C. was sequentially added 2-(chloromethyl)-7,8-dihydro-3H-pyrano[4,3-d]pyrimidin-4(5H)-one (20 g, 100 mmol) and tert-butyl cyclopropylmethylcarbamate (17.07 g, 100 mmol) in small portions in order to maintain the internal temperature at or below 5° C. The reaction mixture was allowed to warm to room temperature slowly with continued stirring over 12 h. The reaction was cooled to 0 C and water was added slowly (~250 mL total). The reaction mixture was concentrated in vacuo, taken up in ethyl acetate, filtered and concentrated to a red oil. The material was purified on a pad of silica gel, loading with 20% ethyl acetate in heptanes and eluting with 100% ethyl acetate via a sharp gradient. The title compound was obtained as an off-white solid (20.79 g).

Intermediate 17

2-[(Cyclopropylmethyl-amino)-methyl]-3,5,7,8-tetrahydro-pyrano[4,3-d]pyrimidin-4-one

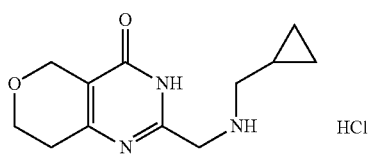 [SMILES: O=c1[nH]c(CNCC2CC2)nc2c1COCC2 ; Cl]

tert-butyl cyclopropylmethyl((4-oxo-4,5,7,8-tetrahydro-3H-pyrano[4,3-d]pyrimidin-2-yl)methyl)carbamate (5.639 g, 16.81 mmol) was dissolved in 4 N HCl in dioxane (40 mL) and stirred at room temperature after approximately 5 min a white suspension formed and the reaction was allowed to stir overnight. 100 mL diethyl ether was added and the reaction mixture was filtered, washed with diethyl ether (2×25 mL) and dried in vacuo to yield the title compound as a white solid (4.819 g).

Intermediate 20 tert-Butyl thiophen-2-ylmethylcarbamate

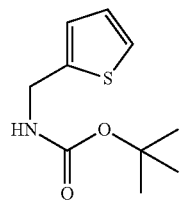

To a solution of thiophen-2-ylmethanamine (4.73 g, 41.8 mmol) in dichloromethane (50 mL) was added di-tert-butyl dicarbonate (9.12 g, 41.8 mmol) and triethylamine (5.54 mL, 39.7 mmol) at 0° C. The mixture was stirred at ambient temperature for 24 h, washed with water and extracted with dichloromethane. The combined organic layers were dried over sodium sulfate, concentrated in vacuo and purified via flash column chromatography (ethyl acetate:hexane, 10:90 to 100:0) to provide the title compound (8.2 g, 92% yield). $^1$H NMR (400 MHz, CDC$_3$) δ ppm 7.21 (d, J=6.0 Hz, 1H), 6.85-7.01 (m, 2H), 4.89 (br. s., 1H), 4.48 (d, J=5.5 Hz, 2H), 1.46 (s, 9H). MS m/z 158.0 (M-100 (M-Boc)), retention time=1.41 min.

Intermediate 21 tert-Butyl (4-oxo-4,5,7,8-tetrahydro-3H-pyrano[4,3-c]pyrimidin-2-yl)methyl(thiophen-2-ylmethyl)carbamate

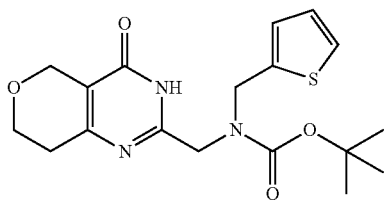 [SMILES: CC(C)(C)OC(=O)N(Cc1nc2c(c(=O)[nH]1)COCC2)Cc1cccs1]

To a solution of tert-butyl thiophen-2-ylmethylcarbamate (1.8 g, 8.2 mmol) in tetrahydrofuran (40 mL) was added sodium hydride (1.5 g, 37 mmol, 60% in mineral oil) and stirred at ambient temperature for 10 minutes. 2-(Chloromethyl)-7,8-dihydro-3H-pyrano[4,3-d]pyrimidin-4(5H)-one (1.5 g, 7.5 mmol) was then added and the reaction mixture was stirred at ambient temperature for 48 h. The reaction mixture was washed with brine and extracted with ethyl acetate three times. The combined organic layer was dried over sodium sulfate, concentrated in vacuo and purified via flash column chromatography (ethyl acetate:hexane, 10:90 to 100:0) to provide the title compound (450 mg, 16% yield). $^1$H NMR (400 MHz, CDC$_3$) δ 10.62 (br. s., 1H), 7.13-7.36 (m, 1H), 6.80-7.06 (m, 2H), 4.62 (br. s., 2H), 4.56 (s, 2H), 4.28 (s, 2H), 3.94 (t, J=5.5 Hz, 2H), 2.66 (t, J=5.5 Hz, 2H), 1.55 (br. s., 6H), 1.46 (s, 3H). MS m/z 378.2 (M+1), retention time=1.38 min.

Intermediate 12

2-((Thiophen-2-ylmethylamino)methyl)-7,8-dihydro-3H-pyrano[4,3-d]pyrimidin-4(5H)-one

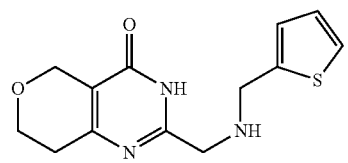 [SMILES: O=c1[nH]c(CNCc2cccs2)nc2c1COCC2]

To a solution of tert-butyl (4-oxo-4,5,7,8-tetrahydro-3H-pyrano[4,3-d]pyrimidin-2-yl)methyl(thiophen-2-ylmethyl)carbamate (0.87 g, 2.3 mmol) in methanol (5 mL) was added hydrochloride acid (2.3 mL, 4M in dioxane). The mixture was stirred at ambient temperature for 24 h, filtered and washed with ether to give the title compound as a white solid (710 mg, 98% yield).

Intermediate 22

2-[((S)-1-Phenyl-ethylamino)-methyl]-3,5,7,8-tetrahydro-pyrano[4,3-d]pyrimidin-4-one

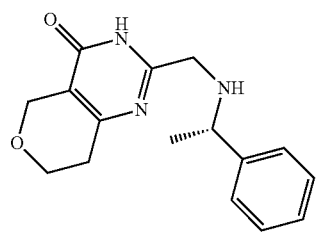 [SMILES: C[C@H](NCc1nc2c(c(=O)[nH]1)COCC2)c1ccccc1]

Following the general procedure of Intermediate 16, the title compound was prepared (51.4 mg) from (S)-1-phenylethylamine (66 mg, 0.548 mmol). Exact mass calculated for C$_{16}$H$_{19}$N$_3$O$_2$ 285.15. found 286.5 (ESI, M+H).

Intermediate 23

(S)-2((2-Methylbutylamino)methyl)-7,8-dihydro-3H-pyrano[4,3-d]pyrimidin-4(5H)-one

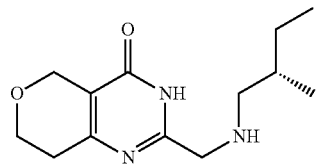 [SMILES: CC[C@H](C)CNCc1nc2c(c(=O)[nH]1)COCC2]

Following the general procedure of Intermediate 16, the title compound was prepared (36.1 mg) from (S)-2-methylbutan-1-amine (48 mg, 0.548 mmol). Exact mass calculated for $C_{13}H_{21}N_3O_2$ 251.3. found 252.3 (ESI, M+H).

Intermediate 24

2-((Isobutylamino)methyl)-7,8-dihydro-3H-pyrano[4,3-d]pyrimidin-4(5H)-one

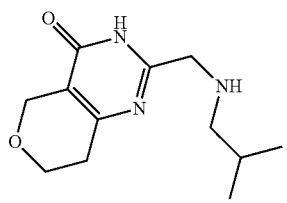 [SMILES: CC(C)CNCc1nc2c(c(=O)[nH]1)COCC2]

Following the general procedure of Intermediate 16, the title compound was prepared (13.7 mg) (40 mg, 0.548 mmol). Exact mass calculated for $C_{12}H_{19}N_3O_2$ 237.30. found 238.4 (ESI, M+H).

Intermediate 25

2-((Prop-2-ynylamino)methyl)-7,8-dihydro-3H-pyrano[4,3-d]pyrimidin-4(5H)-one

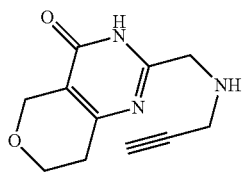 [SMILES: C#CCNCc1nc2c(c(=O)[nH]1)COCC2]

Following the general procedure of Intermediate 16, the title compound was prepared (47 mg) from prop-2-yn-1-amine (30 mg, 0.548 mmol). Exact mass calculated for $C_{11}H_{13}N_3O_2$ 219.2. found 220.3 (ESI, M+H).

Intermediate 26

(S)-2-(((Tetrahydrofuran-2-yl)methylamino)methyl)-7,8-dihydro-3H-pyrano[4,3-d]pyrimidin-4(5H)-one

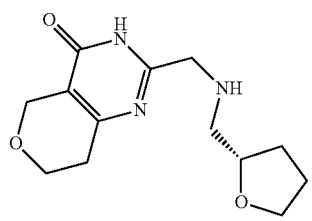 [SMILES: O=c1[nH]c(CNC[C@@H]2CCCO2)nc2c1COCC2]

Following the general procedure of Intermediate 16, the title compound was prepared (46.9 mg) from (S)-(tetrahydrofuran-2-yl)methanamine (56 mg, 0.458 mmol). Exact mass calculated for $C_{13}H_{19}N_3O_2$ 265.3. found 266.3 (ESI, M+H).

Intermediate 27

(R)-2-(((Tetrahydrofuran-2-yl)methylamino)methyl)-7,8-dihydro-3H-pyrano[4,3-d]pyrimidin-4(5H)-one

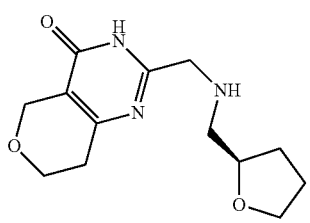 [SMILES: O=c1[nH]c(CNC[C@H]2CCCO2)nc2c1COCC2]

Following the general procedure of Intermediate 16, the title compound was prepared (43.6 mg) from (R)-(tetrahydrofuran-2-yl)methanamine (56 mg, 0.458 mmol). Exact mass calculated for $C_{13}H_{19}N_3O_2$ 265.3. found 266.3 (ESI, M+H).

Intermediate 28

2-((Methylamino)methyl)-7,8-dihydro-3H-pyrano[4,3-d]pyrimidin-4(5H)-one

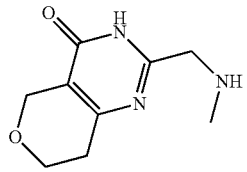

Following the general procedure of Intermediate 16, the title compound was prepared (30.7 mg) from 30% methanamine in water (57 mg, 0.548 mmol). Exact mass calculated for $C_9H_{13}N_3O_2$ 195.2. found 196.3 (ESI, M+H).

Intermediate 29

(S)-2-((sec-Butylamino)methyl)-7,8-dihydro-3H-pyrano[4,3-d]pyrimidin-4(5H)-one

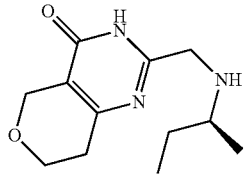 [SMILES: CC[C@H](C)NCc1nc2c(c(=O)[nH]1)COCC2]

Following the general procedure of Intermediate 16, the title compound was prepared (30.2 mg) from (S)-2-methylbutan-1-amine (48 mg, 0.548 mmol). Exact mass calculated for $C_{12}H_{19}N_3O_2$ 237.2. found 238.4 (ESI, M+H).

Intermediate 30

(R)-2-((sec-Butylamino)methyl)-7,8-dihydro-3H-pyrano[4,3-c]pyrimidin-4(5H)-one

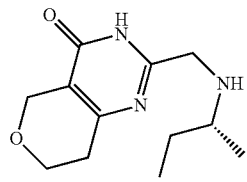 [SMILES: CC[C@@H](C)NCc1nc2c(c(=O)[nH]1)COCC2]

Following the general procedure of Intermediate 16, the title compound was prepared (35.3 mg) from (R)-2-methylbutan-1-amine (48 mg, 0.548 mmol). Exact mass calculated for $C_{12}H_{19}N_3O_2$ 237.2. found 238.4 (ESI, M+H).

Intermediate 31

2-((Isopropylamino)methyl)-7,8-dihydro-3H-pyrano[4,3-d]pyrimidin-4(5H)-one

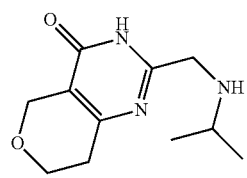 [SMILES: CC(C)NCc1nc2c(c(=O)[nH]1)COCC2]

Following the general procedure of Intermediate 16, the title compound was prepared (38 mg) from propan-2-amine (32 mg, 0.548 mmol). Exact mass calculated for $C_{11}H_{17}N_3O_2$ 223.2. found 224.3 (ESI, M+H).

Intermediate 32

2-((Propylamino)methyl)-7,8-dihydro-3H-pyrano[4,3-d]pyrimidin-4(5H)-one

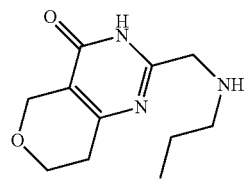 [SMILES: CCCNCc1nc2c(c(=O)[nH]1)COCC2]

Following the general procedure of Intermediate 16, the title compound was prepared (41 mg) from propylamine (32 mg, 0.548 mmol). Exact mass calculated for $C_{11}H_{17}N_3O_2$ 223.2. found 224.3 (ESI, M+H).

Intermediate 33

(S)-2-((1-(4-Fluorophenyl)ethylamino)methyl)-7,8-dihydro-3H-pyrano[4,3-d]pyrimidin-4(5H)-one

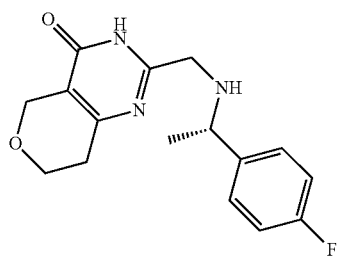 [SMILES: C[C@H](NCc1nc2c(c(=O)[nH]1)COCC2)c1ccc(F)cc1]

Following the general procedure of Intermediate 16, the title compound was prepared (53 mg) from (S)-1-(4-fluorophenyl)ethanamine (139 mg, 0.997 mmol). Exact mass calculated for $C_{16}H_{18}FN_3O_2$ 303.3. found 304.3 (ESI, M+H).

Intermediate 34

(R)-2-((1-(4-Fluorophenyl)ethylamino)methyl)-7,8-dihydro-3H-pyrano[4,3-d]pyrimidin-4(5H)-one

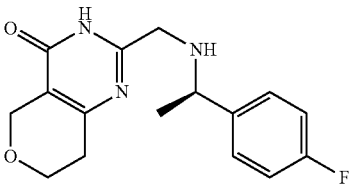 [SMILES: C[C@@H](NCc1nc2c(c(=O)[nH]1)COCC2)c1ccc(F)cc1]

Following the general procedure of Intermediate 16, the title compound was prepared (60 mg) from (R)-1-(4-fluorophenyl)ethanamine (139 mg, 0.997 mmol). Exact mass calculated for $C_{16}H_{18}FN_3O_2$ 303.3. found 304.3 (ESI, M+H).

Intermediate 35

2-((1-(2,4-Difluorophenyl)ethylamino)methyl)-7,8-dihydro-3H-pyrano[4,3-d]pyrimidin-4(5H)-one

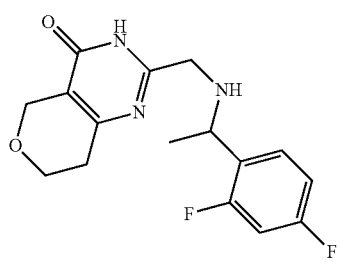 [SMILES: CC(NCc1nc2c(c(=O)[nH]1)COCC2)c1ccc(F)cc1F]

Following the general procedure of Intermediate 16, the title compound was prepared (60 mg) from 1-(2,4-difluorophenyl)ethanamine (157 mg, 0.997 mmol). Exact mass calculated for $C_{16}H_{17}F_2N_3O_2$ 321.3. found 322.3 (ESI, M+H).

Intermediate 36

2-((Benzylamino)methyl)-7,8-dihydro-3H-pyrano[4,3-d]pyrimidin-4(5H)-one

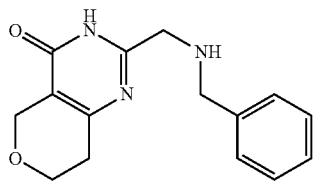 [SMILES: O=c1[nH]c(CNCc2ccccc2)nc2c1COCC2]

Following the general procedure of Intermediate 16, the title compound was prepared (30 mg) from phenylmethanamine (107 mg, 0.996 mmol). Exact mass calculated for $C_{15}H_{17}N_3O_2$ 271.3. found 272.4 (ESI, M+H).

Intermediate 37

2-((2-Fluorobenzylamino)methyl)-7,8-dihydro-3H-pyrano[4,3-c]pyrimidin-4(5H)-one

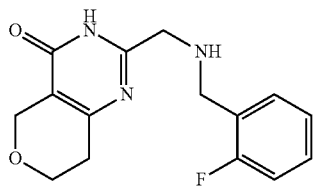 [SMILES: O=c1[nH]c(CNCc2ccccc2F)nc2c1COCC2]

Following the general procedure of Intermediate 16, the title compound was prepared (50 mg) from (2-fluorophenyl)methanamine (125 mg, 0.997 mmol). Exact mass calculated for $C_{15}H_{16}FN_3O_2$ 289.3. found 290.3 (ESI, M+H).

Intermediate 38

2-((2,4-Difluorobenzylamino)methyl)-7,8-dihydro-3H-pyrano[4,3-d]pyrimidin-4(5H)-one

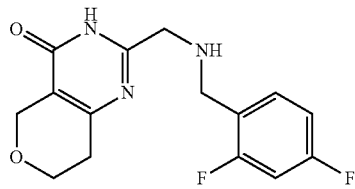 [SMILES: O=c1[nH]c(CNCc2ccc(F)cc2F)nc2c1COCC2]

Following the general procedure of Intermediate 16, the title compound was prepared (33 mg) from (2,4-difluorophenyl)methanamine (143 mg, 0.997 mmol). Exact mass calculated for $C_{15}H_{15}F_2N_3O_2$ 307.3. found 308.3 (ESI, M+H).

Intermediate 39

(R)-2-((1-Cyclopropylethylamino)methyl)-7,8-dihydro-3H-pyrano[4,3-c]pyrimidin-4(5H)-one

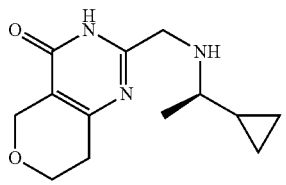 [SMILES: C[C@@H](NCc1nc2c(c(=O)[nH]1)COCC2)C1CC1]

Following the general procedure of Intermediate 16, the title compound was prepared (22 mg) from (R)-1-cyclopropylethanamine (85 mg, 0.997 mmol). Exact mass calculated for $C_{13}H_{19}N_3O_2$ 249.3. found 250.5 (ESI, M+H).

Intermediate 40

(S)-2-((1-Cyclopropylethylamino)methyl)-7,8-dihydro-3H-pyrano[4,3-d]pyrimidin-4(5H)-one

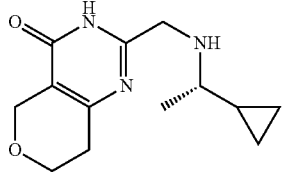 [SMILES: C[C@H](NCc1nc2c(c(=O)[nH]1)COCC2)C1CC1]

Following the general procedure of Intermediate 16, the title compound was prepared (26 mg) from (S)-1-cyclopropylethanamine[85 mg, 0.997 mmol]. Exact mass calculated for $C_{13}H_{19}N_3O_2$ 249.3. found 250.5 (ESI, M+H).

Intermediate 41

[(4-Oxo-3,5,7,8-tetrahydro-4H-pyrano[4,3-d]pyrimidin-2-ylmethyl)-amino]-acetonitrile

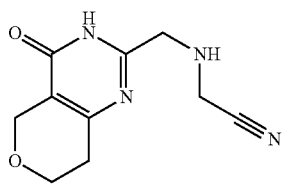 [SMILES: N#CCNCc1nc2c(c(=O)[nH]1)COCC2]

Following the general procedure of Intermediate 16, the title compound was prepared (25 mg) from amino-acetonitrile (50 mg, 1 mmol, 4 eq.). Exact mass calculated for $C_{10}H_{12}N_4O_2$ 220.3. found 221.5 (ESI, M+H)

Intermediate 42

2-[(2-Fluoro-ethylamino)-methyl]-3,5,7,8-tetrahydro-pyrano[4,3-d]pyrimidin-4-one Following the general procedure of Intermediate 18, the title compound was prepared (0.013 g) from 2-fluoroethanamine (0.024 g, 0.239 mmol, 4 eq.).

Intermediate 43

2-((2,2-Difluoroethylamino)methyl)-7,8-dihydro-3H-pyrano[4,3-d]pyrimidin-4(5H)-one Following the general procedure of Intermediate 18, the title compound was prepared (0.17 g) from 2,2-difluoroethanamine (0.24 g, 3.0 mmol, 4 eq.).

Intermediate 44

5-(((4-oxo-4,5,7,8-tetrahydro-3H-pyrano[4,3-d]pyrimidin-2-yl)methylamino)methyl)thiophene-2-carbonitrile Following the general procedure of Intermediate 18, the title compound was prepared (0.22 g) from 5-(aminomethyl)thiophene-2-carbonitrile (0.41 g, 3.0 mmol, 4 eq.).

Intermediate 45

2-(((5-(morpholinosulfonyl)thiophen-2-yl)methylamino)methyl)-7,8-dihydro-3H-pyrano[4,3-d]pyrimidin-4(5H)-one Following the general procedure of Intermediate 18, the title compound was prepared (0.07 g) from (5-(morpholinosulfonyl)thiophen-2-yl)methanamine (1.05 g, 4 mmol, 4 eq.).

Intermediate 46

2-(2,2,2-trifluoroethylamino)methyl)-7,8-dihydro-3H-pyrano[4,3-d]pyrimidin-4(5H)-one Following the general procedure of Intermediate 18, the title compound was prepared (0.022 g) from 2,2,2-trifluoroethanamine (0.40 g, 4 mmol, 4 eq.).

Intermediate 47

2-((1-(thiophen-2-yl)ethylamino)methyl)-7,8-dihydro-3H-pyrano[4,3-d]pyrimidin-4(5H)-one Following the general procedure of Intermediate 18, the title compound was prepared (0.015 g) from 1-(thiophen-2-yl)ethanamine (0.25 g, 2.0 mmol, 4 eq.).

Intermediate 48

2-Chloropropanimidamide hydrochloride

The title compound (5.2 g) was prepared according to same procedure as intermediate 2 from 2-chloropropanenitrile (3.5 g, 39 mmol). MS m/z 500.4 (M+1), retention time=1.36 min.

Intermediate 49

2-(1-Chloroethyl)-7,8-dihydro-3H-pyrano[4,3-d]pyrimidin-4(5H)-one

A mixture of methyl 4-oxotetrahydro-2H-pyran-3-carboxylate (1.0 g, 6.3 mmol), 2-chloropropanimidamide hydrochloride (0.9 g, 6.3 mmol), and triethylamine (3.52 mL, 25.4 mmol) was stirred at ambient temperature for 24 h. The mixture was concentrated in vacuo to give the title compound (1.4 g), which was used directly to the next step without further purification. MS m/z 215.2 (M+1), retention time=1.27 min.

Intermediate 50

2-(1-(Methylamino)ethyl)-7,8-dihydro-3H-pyrano[4,3-d]pyrimidin-4(5H)-one

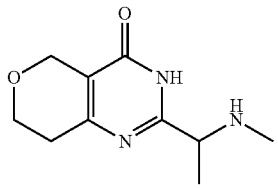

To a solution of 2-(1-chloroethyl)-7,8-dihydro-3H-pyrano[4,3-d]pyrimidin-4(5H)-one (270 mg, 1.3 mmol) in methanol (1 mL) was added methylamine in water (1.1 mL, 13 mmol, 40%). The mixture was heated via microwave at 110° C. for 10 min., concentrated in vacuo and purified via reverse phase chromatography (Acetonitrile:water) to provide the title compound (260 mg). MS m/z 210.3 (M+1), retention time=0.54 min.

Intermediate 51

2-(Chloromethyl)-5,6,7,8-tetrahydroquinazolin-4(3H)-one

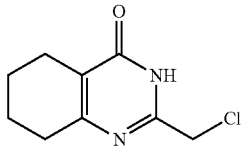 [SMILES: O=c1[nH]c(CCl)nc2c1CCCC2]

To a solution of ethyl 2-cyclohexanone-carboxylate (5.5 g, 32 mmol) in methanol was added chloroacetamidine hydrochloride (4.2 g, 32 mmol) and triethylamine (14 mL, 97 mmol). The mixture was stirred at ambient temperature for 60 h. It was then concentrated under reduced pressure and purified via flash column chromatography (ethyl acetate:hexane, 10:90 to 100:0) to provide product (0.82 g, 13% yield). $^1$H NMR (400 MHz, CD$_3$OD) δ 4.40 (s, 2H), 2.61 (t, J=6.3 Hz, 2H), 2.45 (t, J=6.3 Hz, 2H), 1.68-1.87 (m, 4H). MS m/z 199.2 (M+1), retention time=0.94 min.

Intermediate 52

Bis-(2-bromo-ethyl)-carbamic acid ethyl ester

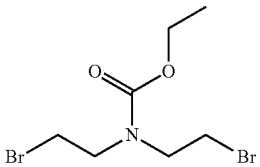

To a stirred solution of bis-(2-bromo-ethyl)-amine (1 g, 3.21 mmol) in water (10 mL) at 0° C. was added ethyl chloroformate (0.293 mL, 3.08 mmol) and then NaOH (4.01 mL, 8.02 mmol), and stirred for 10 min at 0° C. The reaction mixture was acidified by 2 N HCl to pH 5, and extracted three times with 20 mL of ethyl acetate, dried over Na$_2$SO$_4$ and concentrated in vacuo. The crude product was purified by flash chromatography (gradient of 85:15 to 70:30 heptane/ethyl acetate in 30 min) to give the title compound (287 mg, 0.947 mmol, 29.5% yield). MS calculated for C$_7$H$_{14}$Br$_2$NO$_2$ 304.0. found (ESI) m/z 304.2 (M+H)$^+$, retention time 0.56 min.

Intermediate 53

Ethyl 5-fluoro-1-oxo-1,3-dihydrospiro[indene-2,4'-piperidine]-1'-carboxylate

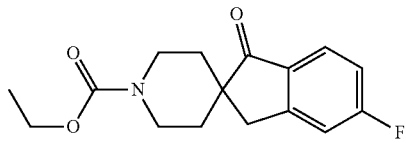 [SMILES: CCOC(=O)N1CCC2(CC1)Cc1cc(F)ccc1C2=O]

To a stirred solution of 5-fluoro-1-indanone (302 mg, 2.013 mmol) and bis-(2-bromo-ethyl)-carbamic acid ethyl ester (188 mg, 0.645 mmol, 32.1% yield) in DMF (5 mL) at 50° C. was added NaH (121 mg, 5.03 mmol) by small portions. After being stirred at 50° C. for 16 hr, the reaction was cooled to 25° C. The reaction was diluted with 15 mL of ethyl acetate and washed twice with 10 ml of water, dried over Na$_2$SO$_4$ and concentrated in vacuo. The crude product was purified by flash column (gradient of 85:15 to 60:40 heptane/ethyl acetate in 20 min to give the title compound (188 mg, 0.645 mmol, 32.1 yield). MS calculated for C$_{16}$H$_{19}$FNO$_3$ 292.3. found (ESI) m/z 292.4 (M+H)$^+$, retention time 1.46 min.

Intermediate 54

5-Fluorospiro[indene-2,4'-piperidin]-1(3H)-one

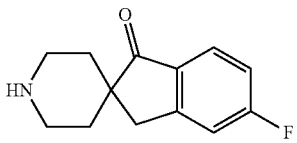 [SMILES: O=C1c2ccc(F)cc2CC12CCNCC2]

To a stirred solution of ethyl 5-fluoro-1-oxo-1,3-dihydrospiro[indene-2,4'-piperidine]-1'-carboxylate (188 mg, 0.645 mmol) in HCl (19.61 μL, 0.645 mmol) was heated at 100° C. over night. The reaction mixture was concentrated to dryness without any further purification to give the title compound (160 mg, 97% yield). MS calculated for C$_{13}$H$_{15}$FNO 220.3. found (ESI) m/z 220.0 (M+H)$^+$, retention time 0.51 min.

Intermediate 55

2-(5-Fluoro-1-oxo-1,3-dihydrospiro[indene-2,4'-piperidine]-1'-yl)acetic acid

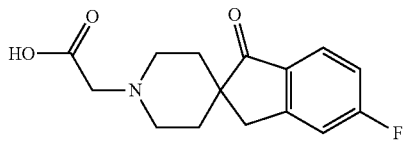 [SMILES: O=C(O)CN1CCC2(CC1)Cc1cc(F)ccc1C2=O]

A stirred solution of 5-fluorospiro[indene-2,4'-piperidin]-1(3H)-one (160 mg, 0.626 mmol), bromoacetic acid (113 mg, 0.813 mmol) and triethylamine (0.436 mL, 3.13 mmol) in acetonitrile (2 mL) was heated at 80° C. for 3 h, then cooled to 25° C. The reaction mixture was diluted with 20 mL of ethyl acetate and washed with 5 mL of water, dried over $Na_2SO_4$ and concentrated to dryness without any further purification to give the title compound (174 mg, 0.626 mmol, 100% yield). MS calculated for $C_{15}H_{17}FNO_3$ 278.3. found (ESI) m/z 278.4 (M+H)$^+$, retention time 0.81 min.

Intermediate 56

Ethyl 5-methoxy-1-oxo-1,3-dihydrospiro[indene-2,4'-piperidine]-1'-carboxylate

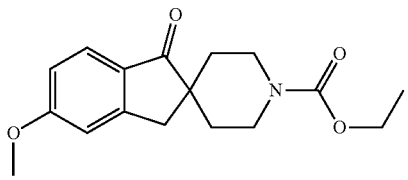 [SMILES: CCOC(=O)N1CCC2(CC1)Cc1cc(OC)ccc1C2=O]

To a stirred solution of 5-methoxy-1-indanone (1.0 g, 6.17 mmol) and bis-(2-bromo-ethyl)-carbamic acid ethyl ester (1.87 g, 6.17) in DMF (10 mL) at 50° C. was added NaH (0.370 g, 15.4 mmol) by small portions. After being stirred at 50° C. for 16 hr, the reaction was cooled to ambient temperature. The reaction was diluted with 15 mL of ethyl acetate and washed twice with 10 mL of water, dried over $Na_2SO_4$ and concentrated in vacuo. The crude product was purified by flash column (gradient of 85:15 to 60:40 heptane/ethyl acetate over 30 min) to give the title compound (590 mg, 1.945 mmol). MS calculated for $C_{17}H_{22}NO_4$ 304.4. found (ESI) m/z 304.2 (M+H)$^+$, retention time 1.56 min.

Intermediate 57

5-Methoxyspiro[indene-2,4'-piperidin]-1(3H)-one

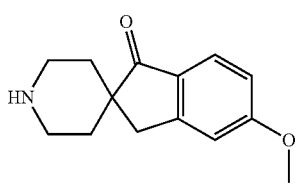 [SMILES: COc1ccc2c(c1)CC1(CCNCC1)C2=O]

A stirred solution of ethyl 5-methoxy-1-oxo-1,3-dihydrospiro[indene-2,4'-piperidine]-1'-carboxylate (590 mg, 1.95 mmol) in HCl (6.5 mL, 38.9 mmol) was heated at 100° C. overnight. The reaction mixture was concentrated to dryness to give the title compound (511 mg, 2.21 mmol) without any additional purification. MS calculated for $C_{14}H_{17}NO_2$ 232.3. found (ESI) m/z 232.4 (M+H)$^+$, retention time 0.90 min.

Intermediate 58

2-(5-Methoxy-1-oxo-1,3-dihydrospiro[indene-2,4'-piperidine]-1'-yl)acetic acid

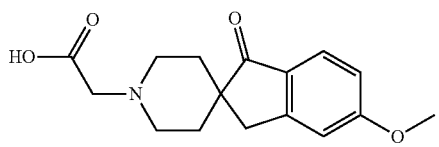 [SMILES: COc1ccc2c(c1)CC1(CCN(CC(=O)O)CC1)C2=O]

A stirred solution of 5-methoxyspiro[indene-2,4'-piperidin]-1(3H)-one (511 mg, 1.93 mmol), bromoacetic acid (349 mg, 2.51 mmol) and DIPEA (1.013 mL, 5.80 mmol) in DMF (5 mL) was heated at 100° C. for 20 min via microwave. The reaction mixture was diluted with 20 mL of ethyl acetate, washed with 5 mL of water, dried over $Na_2SO_4$ and concentrated in vacuo. The crude product was purified by flash column (gradient of 100:0 to 85:15 $CH_2Cl_2$/MeOH with 5% $NH_4OH$ over 20 min) to give the title compound (368 mg, 1.272 mmol). MS calculated for $C_{16}H_{19}NO_4$ 290.3. found (ESI) m/z 290.1 (M+H)$^+$, retention time 1.10 min.

Intermediate 59

Ethyl 1-oxo-3,4-dihydro-1H-spiro[naphthalene-2,4'-piperidine]-1'-carboxylate

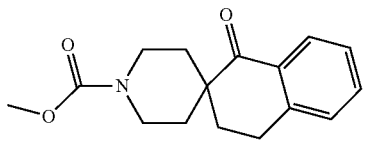 [SMILES: COC(=O)N1CCC2(CCc3ccccc3C2=O)CC1]

To a stirred solution of α-tetralone (289 mg, 1.98 mmol) and bis-(2-bromo-ethyl)-carbamic acid ethyl ester (600 mg, 1.98 mmol) in DMF (2 mL) at 50° C. was added NaH (119 mg, 4.95 mmol) by small portions. After being stirred at 50° C. for 12 h, the reaction was cooled to 25° C. The reaction mixture was diluted with 15 mL of ethyl acetate and washed twice with 10 mL of water, dried over $Na_2SO_4$ and concentrated. The crude product was purified via flash chromatography (gradient of 85:15 to 60:40 heptane/ethyl acetate over 20 min) to give the title compound (85 mg, 0.296 mmol) as a white solid. MS calculated for $C_{17}H_{22}NO_3$ 288.4. found (ESI) m/z 288.7 (M+H)$^+$, retention time 1.58 min.

Intermediate 60

3,4-Dihydro-1H-spiro[naphthalene-2,4'-piperidin]-1-one

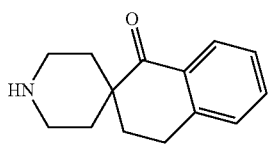

A solution of ethyl 1-oxo-3,4-dihydro-1H-spiro[naphthalene-2,4'-piperidine]-1'-carboxylate (85 mg, 0.296 mmol) in HCl (6 N, 2.46 mL, 14.8 mmol) was heated at 100° C. overnight. The reaction mixture was cooled to 25° C., and concentrated to dryness to give the HCl salt of title compound (72. mg, 0.286 mmol) as a white. MS calculated for $C_{14}H_{18}NO$ 216.13. found (ESI) m/z 216.7 (M+H)$^+$, retention time 0.69 min.

Intermediate 61

Ethyl 2-(1-oxo-3,4-dihydro-1H-spiro[naphthalene-2,4'-piperidine]-1'-yl)acetate

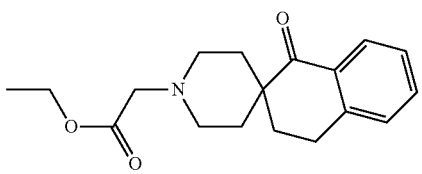 [SMILES: CCOC(=O)CN1CCC2(CCc3ccccc3C2=O)CC1]

A solution of 3,4-dihydro-1H-spiro[naphthalene-2,4'-piperidin]-1-one (72 mg, 0.286 mmol), ethyl bromoacetate (62.1 mg, 0.37 mmol) and triethylamine (0.20 mL, 1.43 mmol) in acetonitrile (5 ml) was heated at 80° C. for 3 h. The reaction was cooled to 25° C. and diluted with 20 mL of ethyl acetate and washed twice with 10 mL of water, dried over $Na_2SO_4$ and concentrated. The crude product was purified by flash chromatography (gradient of 85:15 to 60:40 heptane/ethyl acetate over 20 min) to give the title compound as a white solid. MS calculated for $C_{18}H_{24}NO_3$ 302.4. found (ESI) m/z 302.5 (M+H)$^+$, retention time 0.81 min.

Intermediate 62

2-(1-Oxo-3,4-dihydro-1H-spiro[naphthalene-2,4'-piperidine]-1'-yl)acetic acid

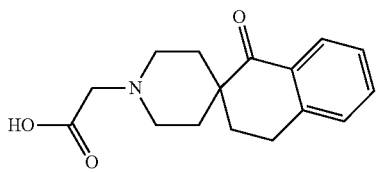 [SMILES: O=C(O)CN1CCC2(CCc3ccccc3C2=O)CC1]

To a stirred solution of ethyl 2-(1-oxo-3,4-dihydro-1H-spiro[naphthalene-2,4'-piperidine]-1'-yl)acetate (71 mg, 0.236 mmol) in EtOH (2 mL) at 25° C. was added NaOH (2 N, 1.39 mL, 2.78 mmol). After being stirred at 25° C. for 16 h, the reaction mixture was extracted with 5 mL of $CH_2Cl_2$. The aqueous layer was basified with 2 M HCl to pH 5, and extracted three times with 10 mL of ethyl acetate, dried over $Na_2SO_4$ and concentrated. The crude product was purified by flash chromatography (gradient of 100% $CH_2Cl_2$ to 90:10 $CH_2Cl_2$/ethyl acetate over 20 min) to give the title compound (37 mg, 0.135 mmol). MS calculated for $C_{16}H_{20}NO_3$ 274.3. found (ESI) m/z 271.4 (M+H)$^+$, retention time 0.93 min.

Intermediate 63

4-Hydrazinocarbonyl-piperidine-1-carboxylic acid tert-butyl ester

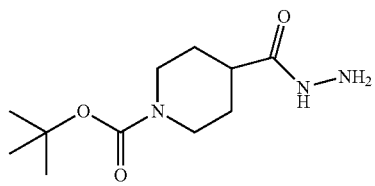 [SMILES: CC(C)(C)OC(=O)N1CCC(C(=O)NN)CC1]

To a stirred solution of 1-tert-butyl 4-ethylpiperidine-1,4-dicarboxylate (10 g, 38.9 mmol, 1.0 eq) in EtOH (100 mL) was added hydrazine hydrate (18.67 g, 389 mmol, 10 eq.) and the mixture was refluxed for 8 h. The reaction was cooled to room temperature and evaporation of the solvent gave a viscous liquid which was dissolved in $CH_2Cl_2$, washed with water (3×50 mL) then brine (50 mL). The organic layers were combined, dried over $Na_2SO_4$, the solvent evaporated leaving a yellowish oil, which upon addition of a few drops of acetonitrile and re-evaporation, yielded the title compound (8.6 g, 35.3 mmol) MS (m/z, MH−): 242.2.

Intermediate 64

4-(5-Phenyl[1,3,4]oxadiazol-2-yl)-piperidine-1-carboxylic acid tert-butyl ester)

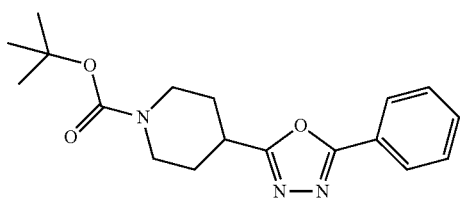 [SMILES: CC(C)(C)OC(=O)N1CCC(c2nnc(-c3ccccc3)o2)CC1]

To a stirred solution of 4-hydrazinocarbonyl-piperidine-1-carboxylic acid tert-butyl ester (1.15 g, 4.73 mmol, 1.0 eq) in EtOH (15 mL) was added benzimidic acid ethyl ester hydrochloride (921 mg, 4.96 mmol, 1.05 eq.) and the reaction mixture was refluxed for 48 h. The inorganic precipitate was filtered off, washed with ethyl acetate, and the solvent of the mother liquor was evaporated in vacuo. The residue was purified by column chromatography (ethyl acetate/heptanes) to give the title compound as a white solid (327 mg, 0.99 mmol). MS (m/z, MH+): 330.2

Intermediate 65

4-(5-Phenyl-[1,3,4]oxadiazol-2-yl)-piperidine

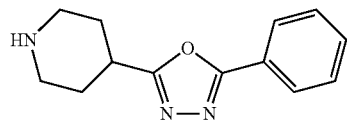 [SMILES: c1ccc(-c2nnc(C3CCNCC3)o2)cc1]

To a solution of 4-(5-phenyl-[1,3,4]oxadiazol-2-yl)-piperidine-1-carboxylic acid tert-butyl ester (795 mg, 2.41 mmol, 1.0 eq) in $CH_2Cl_2$ was added TFA (1.5 mL, 19.5 mmol, 8 eq). The reaction was stirred for 1 h and 7 N $NH_3$ in MeOH (2 mL) was added dropwise for the pH to reach 7. The solvent was evaporated in vacuo giving the title product as a white solid (553 mg) which was used without further purification for the next step. MS (m/z, MH+): 230.3

Intermediate 66

[4-(5-Phenyl-[1,3,4]oxadiazol-2-yl)-piperidin-1-yl]-acetic acid ethyl ester

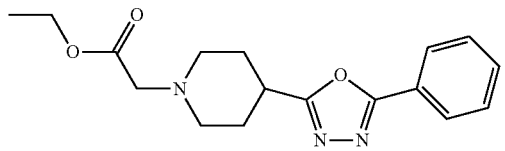 [SMILES: CCOC(=O)CN1CCC(c2nnc(-c3ccccc3)o2)CC1]

To a solution of 4-(5-phenyl-[1,3,4]oxadiazol-2-yl)-piperidine (388 mg, 1.69 mmol, 1.0 eq) in acetonitrile (4 mL) were added $Et_3N$ (0.542 mL, 3.89 mmol, 2.3 eq.) then methyl 2-bromoacetate (0.203 mL, 2.2 mmol, 1.3 eq.). The reaction mixture was stirred for 4 h, diluted with ethyl acetate (15 mL), washed with water (2×50 mL) and brine (30 mL).

The organic layers were combined, dried over $Na_2SO_4$ and the solvent evaporated in vacuo, leaving a clear oil, which solidified upon being dried overnight under high vacuum to give the title compound (358 mg, 1.19 mmol). No further purification was necessary. MS (m/z, MH+): 302.0

Intermediate 67

[4-(5-Phenyl[1,3,4]oxadiazol-2-yl)-piperidin-1-yl]-acetic acid

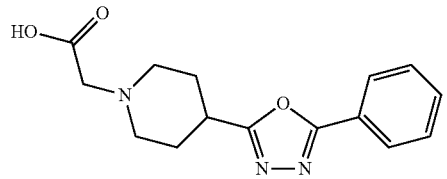 [SMILES: O=C(O)CN1CCC(c2nnc(-c3ccccc3)o2)CC1]

To a stirred solution of [4-(5-phenyl-[1,3,4]oxadiazol-2-yl)-piperidin-1-yl]-acetic acid ethyl ester in EtOH was added NaOH (36.6 mg, 0.916 mmol, 2 eq) in water (0.421 mL). The mixture was stirred for 4 h and the cloudy suspension was treated dropwise with 2.3 mL of 1N HCl until pH ~7. The solvent was evaporated in vacuo to yield the title compound in quantitative yield used without further purification. $^1$H NMR (400 MHz, DMSO-$d_6$) δ ppm 7.99 (d, J=7.58 Hz, 2H) 7.56-7.64 (m, 3H) 2.92-3.08 (m, 5H) 2.29-2.42 (m, 2H) 2.01-2.12 (m, 2H) 1.80-1.96 (m, 2H). MS (m/z, MH+): 288.3.

Intermediate 68

1-[4-(2,4-Difluoro-benzoyl)-piperidin-1-yl]-ethanone

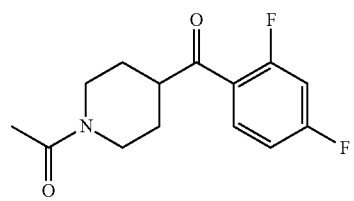 [SMILES: CC(=O)N1CCC(C(=O)c2ccc(F)cc2F)CC1]

To a rapidly stirred slurry of aluminum chloride (3.3 g, 24.7 mmol) and 1,3-difluorobenzene (10 mL) at ambient temperature was added 1-acetylpiperidine-4-carbonyl chloride (2.5 g, 13.2 mmol). The reaction mixture was heated at reflux (100° C.) for 1.5 hours and then poured into 30 mL of ice water, the mixture was extracted with DCM (50 ml) and the organic layer was washed with water and dried over $Na_2SO_4$. The solvent was removed in vacuo to give an oil. Trituration of the oil with pentane gave the title product (1.75 g, 6.22 mmol, 47%) as a white solid. MS (ESI) m/z 268.3 (M+H+); HPLC (Novapak 150×3.9 mm C-18 column: mobile phase: 35-90% acetonitrile/water with 0.1% TFA, at 2 mL/min over 2 min.) t 1.04 min.

Intermediate 69

4-(Pyridine-2-carbonyl)-piperidine-1-carboxylic acid tert-butyl ester

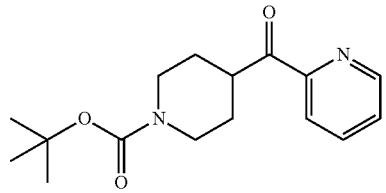 [SMILES: CC(C)(C)OC(=O)N1CCC(C(=O)c2ccccn2)CC1]

To a solution of 2-bromopyridine (0.89 g, 5.62 mmol) in THF (10 mL) at −78° C. was added n-BuLi (2.81 mL, 1.6 M in THF, 5.62 mmol). The reaction was stirred for 30 minutes prior to the addition of 4-(methoxy-methyl-carbamoyl)-piperidine-1-carboxylic acid tert-butyl ester (0.77 g, 2.81 mmol) as a solution in 5 mL of THF. The reaction was then stirred at room temperature for 30 minutes and then 1 hour at 60° C. The reaction was then quenched by adding a saturated solution of sodium bicarbonate and then extracted with 2×50 mL ethyl acetate. The combined organic layers was dried on magnesium sulfate and concentrated under vacuum to afford an orange oily solid which was purified via silica gel chromatography (gradient: ethyl acetate/hexane; 0:1 to 3:5) to afford the title compound as a white solid (290 mg). $^1$H NMR (400 MHz, $CDC_3$) δ 8.70 (d, J=6.6 Hz, 1H), 8.05 (d, J=8.6 Hz, 1H), 7.86 (t, J=7.6 Hz, 1H), 7.46 (t, J=6.2 Hz, 1H), 4.25-4.13 (m, 2H), 4.09-4.00 (m, 1H), 2.94 (t, J=12.6 Hz, 2H), 1.91 (d, J=11.6 Hz, 2H), 1.69-1.65 (m, 2H), 1.50 (s, 9H). LRMS m/z ES+=290.8 (M+H), retention time 1.78.

Intermediate 70

4-(4-Methoxy-3-methyl-benzoyl)-piperidine-1-carboxylic acid tert-butyl ester

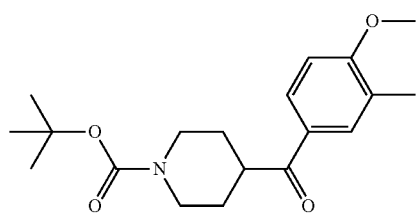 [SMILES: COc1ccc(C(=O)C2CCN(C(=O)OC(C)(C)C)CC2)cc1C]

A solution of 4-(methoxy-methyl-carbamoyl)-piperidine-1-carboxylic acid tert-butyl ester (3.0 g, 11.02 mmol in 30 mL THF) was cooled to 0° C., then (4-methoxy-3-methylphenyl) magnesium bromide was added dropwise via a syringe under $N_2$ and the reaction mixture was stirred at the same temperature for 1.5 h, then gradually warmed up to room temperature over 1 h when the reaction was judged complete by LCMS. 40 mL of saturated aqueous $NH_4Cl$ was added slowly then the aqueous solution was extracted with ethyl acetate (2×50 mL). The combined organic phases were washed with brine, dried over $Na_2SO_4$ and the solvent was removed to yield the crude product. Purification by flash chromatography gave the title compound as a white solid (1.97 g, 5.62 mmol, 51% yield). MS (ESI) m/z 334.4 (M+H$^+$); HPLC (Novapak 150×3.9 mm C-18 column: mobile phase: 35-90% acetonitrile/water with 0.1% TFA, at 2 mL/min over 2 min.) t 1.57 min. $^1$H NMR (400 MHz, CDCL$_3$) δ ppm 1.48 (s, 9H) 1.62-1.91 (m, 4H) 2.27 (s, 3H) 2.78-3.02 (m, 2H) 3.27-3.46 (m, 1H) 3.91 (s, 3H) 4.12-4.27 (m, 2H) 6.87 (d, J=8.59 Hz, 1H) 7.77 (t, 2H).

Intermediate 71

Piperidin-4-yl-pyridin-2-yl-methanone

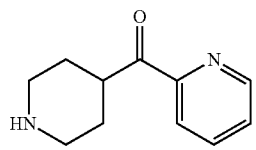 [SMILES: O=C(c1ccccn1)C1CCNCC1]

To a solution of compound 4-(pyridine-2-carbonyl)-piperidine-1-carboxylic acid tert-butyl ester (260 mg, 0.90 mmol) in dichloromethane (10 mL) was then added TFA (0.69 mL, 8.95 mmol) the reaction was then stirred at 25° C. for 3 hours and the solvent was removed under vacuum and the crude material was co-evaporated 3 times with dichloromethane to remove most of the remaining TFA, affording crude the title compound as an orange oil (170 mg, 100%). The crude material was used directly in the next step without subsequent purification. LRMS m/z ES+=190.8 (M+H), retention time 0.60.

Intermediate 72

1-[4-(6-Fluoro-1H-indazol-3-yl)-piperidin-1-yl]-ethanone

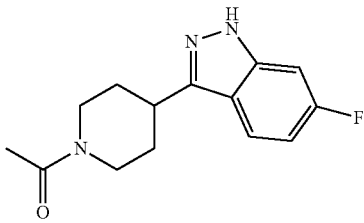 [SMILES: CC(=O)N1CCC(c2n[nH]c3cc(F)ccc23)CC1]

A solution of 1-[4-(2,4-difluoro-benzoyl)-piperidin-1-yl]-ethanone (1.7 g, 6.4 mmol), 6 mL of hydrazine hydrate and 13 mL of n-BuOH was refluxed for 48 hours. The reaction mixture was concentrated in vacuo, the residue was diluted with water (30 mL) and then extracted with ethyl acetate (50 mL). The solvent was removed in vacuo to yield the crude product as an oil. It was washed with heptane and the solvent was filtered to yield the title product (0.60 g, 2.3 mmol, 36% yield) as a white solid. MS (ESI) m/z 261.6 (M+H$^+$); HPLC (Novapak 150×3.9 mm C-18 column: mobile phase: 35-90% acetonitrile/water with 0.1% TFA, at 2 mL/min over 2 min.) t 1.44 min.

Intermediate 73

6-Fluoro-3-piperidin-4-yl-1H-indazole

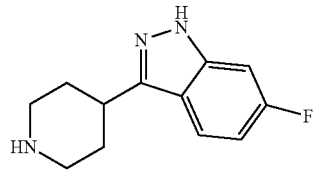 [SMILES: Fc1ccc2c(C3CCNCC3)n[nH]c2c1]

A solution of 1-[4-(6-fluoro-1H-indazol-3-yl)-piperidin-1-yl]-ethanone (0.60 g, 2.3 mmol) in 4 mL of 6 N HCl was stirred at reflux for 6 hours. It was frozen at −78° C. and lyophilized for 24 hours to yield the title compound as a white solid (0.61 g, 2.7 mmol, >99% yield). MS (ESI) m/z 219.9 (M+H$^+$); HPLC (Novapak 150×3.9 mm C-18 column: mobile phase: 35-90% acetonitrile/water with 0.1% TFA, at 2 mL/min over 2 min.) t 0.96 min.

Intermediate 74

4-Phenylsulfanylcarbonyl-piperidine-1-carboxylic acid tert-butyl ester

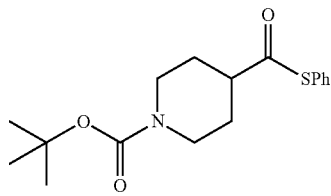

To a solution of piperidine-1,4-dicarboxylic acid mono-tert-butyl ester (5.0 g, 21.81 mmol), diisopropylethylamine (5.64 g, 43.6 mmol) in 40 mL of DMF were added HATU (9.2 g, 24.0 mmol) and benzenethiol (2.7 g, 24.0 mmol). The reaction mixture was stirred at ambient temperature for 15 hours. The reaction mixture was quenched with water (50 mL), then extracted with DCM (50 mL). The combined organic layers were washed with water and saturated aqueous NaCl solution, dried over $Na_2SO_4$, filtered and concentrated in vacuo to yield the crude product. (6.85 g, 20.25 mmol) as a yellow oil. MS (ESI) m/z 321.8 (M+H$^+$); HPLC (Novapak 150×3.9 mm C-18 column: mobile phase: 35-90% acetonitrile/water with 0.1% TFA, at 2 mL/min over 2 min.) retention time=1.66 min.

Intermediate 75

4-p-Tolylsulfanylcarbonyl-piperidine-1-carboxylic acid tert-butyl ester

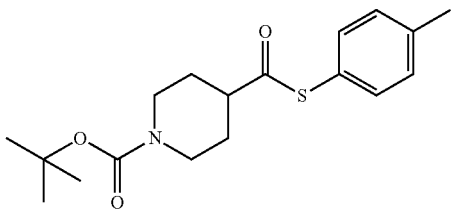 [SMILES: Cc1ccc(SC(=O)C2CCN(C(=O)OC(C)(C)C)CC2)cc1]

To a solution of piperidine-1,4-dicarboxylic acid mono-tert-butyl ester (5 g, 21.8 mmol, 1 eq.) and DIEA (7.6 mL, 44 mmol, 2 eq.) in DMF was added HATU (9.12 g, 24 mmol, 1.1 eq.) and stirred at room temperature for 30 min. Methylbenzenethiol (3 g, 24 mmol, 1.1 eq.) in 45 mL of DMF was added and the resulting mixture was stirred at room temperature overnight. After 18 h, the reaction mixture was concentrated in vacuo to give an oil. This oil was purified by silica gel column chromatography (0-20% ethyl acetate/heptane) to give the title compound as a white solid (6.6 g, 90% yield). $^1$H NMR (400 MHz, chloroform-d) δ ppm 7.28 (m, 4H), 4.13 (m, 2H), 2.81 (m, 3H), 2.39 (s, 3H), 1.97 (m, 2H), 1.73 (m, 2H), 1.48 (s, 9H), MS (ESI) m/z 336.6 (M+H)$^+$. Exact mass calculated for $C_{18}H_{26}N_1O_3S$, 336.2. MS (ESI) m/z 279.9 (M+H without t-butyl). Retention time: 1.27 min (5-95% $CH_3CN$/$H_2O$ over 2 min with 0.1% formic acid, Inertsil 3×3 mm C-8-3 column with flow rate of 2 mL/min).

Intermediate 76

4-(2,3-Dihydro-benzofuran-5-carbonyl)-piperidine-1-carboxylic acid tert-butyl ester

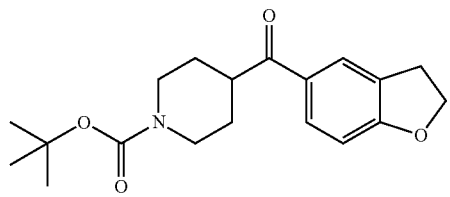 [SMILES: CC(C)(C)OC(=O)N1CCC(C(=O)c2ccc3c(c2)CCO3)CC1]

To a mixture of 2,3-dihydro-1-benzofuran-5-ylboronic acid (0.56 g, 1.56 mmol), ligand TFP (0.07 g, 0.3 mmol), Pd$_2$dba$_3$ (0.28 g, 0.30 mmol), copper (I) thiophene-2-carboxylate (0.45 g, 2.4 mmol) was added a solution of 4-phenylsulfanylcarbonyl-piperidine-1-carboxylic acid tert-butyl ester (0.5 g, 1.6 mmol) in 15 mL of DME while purging with N$_2$ at 50° C. After 18 hours the reaction mixture was diluted with ethyl acetate, filtered through celite then concentrated in vacuo. Purification by flash chromatography gave the title compound (0.5 g, 1.4 mmol, 87% yield). MS (ESI) m/z 331.8 (M+H$^+$); HPLC (Novapak 150×3.9 mm C-18 column: mobile phase: 35-90% acetonitrile/water with 0.1% TFA, at 2 mL/min over 2 min.) t 1.54 min.

Intermediate 77

(2,3-Dihydro-benzofuran-5-yl-piperidin-4-yl-methanone

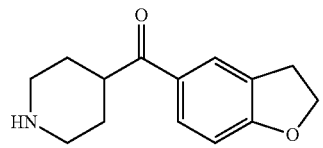 [SMILES: O=C(c1ccc2c(c1)CCO2)C1CCNCC1]

To a solution of 4-(2,3-dihydro-benzofuran-5-carbonyl)-piperidine-1-carboxylic acid tert-butyl ester (0.50 g, 1.5 mmol) in 10 mL of DCM, was added 1 mL of TFA. The reaction mixture was stirred at ambient temperature for 2.5 hours, then solvent was removed by reduced pressure to yield the title product (0.3 g, 1.2 mmol, 77% yield). MS (ESI) m/z 232.3 (M+H$^+$); HPLC (Novapak 150×3.9 mm C-18 column: mobile phase: 35-90% acetonitrile/water with 0.1% TFA, at 2 mL/min over 2 min.) t 1.14 min.

Intermediate 78

4-(2-Trifluoromethoxy-benzoyl)-piperidine-1-carboxylic acid tert-butyl ester

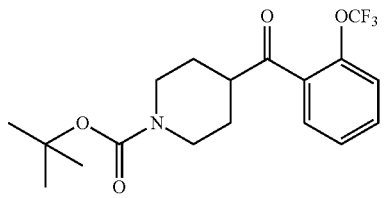 [SMILES: CC(C)(C)OC(=O)N1CCC(C(=O)c2ccccc2OC(F)(F)F)CC1]

To a mixture of 2-trifluoromethoxy-phenyl-boronic acid (0.307 g, 2.24 mmol, 1.5 eq.), ligand TFP (0.069 g, 0.298 mmol, 0.2 eq.), Pd$_2$(dba)$_3$ (0.154 g, 0.149 mmol, 0.1 eq.), copper (I) thiophene-2-carboxylate (0.426 g, 2.24 mmol, 1.5 eq.) was added a solution of p-tolylsulfanylcarbonyl-piperidine-1-carboxylic acid tert-butyl ester (0.479 g, 1.49 mmol, 1 eq.) in 15 mL of DME while purging with N2 at room temperature. After 18 h stirring at room temperature, the reaction mixture was diluted with ethyl acetate and filtered through celite. The filtrate was concentrated to give an oil. This oil was purified by silica gel column chromatography (10% ethyl acetate/heptane) to give the title compound as a white solid (0.5 g, 86%). Exact mass calculated for $C_{18}H_{23}F_3N_1O_4$ 374.2. MS (ESI) m/z 274.3 [(M-100)H]+.

Intermediate 79

Piperidin-4-yl-(2-trifluoromethoxy-phenyl)-methanone

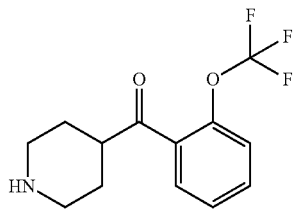 [SMILES: O=C(c1ccccc1OC(F)(F)F)C1CCNCC1]

To a solution of 4-(2-trifluoromethoxy-benzoyl)-piperidine-1-carboxylic acid tert-butyl ester (0.5 g, 1.34 mmol, 1 eq.) in 1 mL of dichloromethane was added 10 mL of 4 N HCl in dioxane and stirred at room temperature overnight. After 18 h, the reaction mixture was concentrated and triturated with diethyl ether to give the title compound as a white solid (0.365 g, 88%). Exact mass calculated for $C_{13}H_{13}F_3N_1O_2$ 274.1. MS (ESI) m/z 274.3 (M+H)$^+$.

Intermediate 80

Ethyl 2-(4-(4-fluorobenzoyl)piperidin-1-yl)acetate

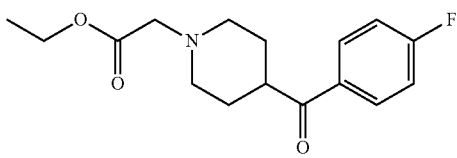 [SMILES: CCOC(=O)CN1CCC(C(=O)c2ccc(F)cc2)CC1]

To a solution of (4-fluorophenyl)(piperidin-4-yl)methanone hydrochloride (51.8 g, 213 mmol) in acetonitrile (400 mL) was added ethyl 2-bromoacetate (38.2 mL, 345 mmol) and triethylamine (70 mL, 506 mmol). The mixture was heated at reflux for 5 h, the solvent was evaporated under reduced pressure and purified via flash column chromatography (ethyl acetate:hexane, 10:90 to 100:0) to provide product (52.7 g, 85% yield). $^1$H NMR (400 MHz, CDC$_3$) δ 7.98 (dd, J=8.5, 5.5 Hz, 2H), 7.16 (t, J=8.5 Hz, 2H), 4.22 (q, J=7.2 Hz, 2H), 3.16-3.27 (m, 1H), 3.03 (d, J=11.5 Hz, 2H), 2.43 (td, J=11.2, 3.3 Hz, 2H), 1.81-2.09 (m, 4H), 1.51-1.73 (m, 2H), 1.30 (t, J=7.3 Hz, 3H). MS m/z 294.4 (M+1), retention time=1.94 min.

Intermediate 81

2-(4-(4-Fluorobenzoyl)piperidin-1-yl)acetic acid

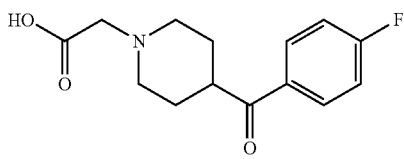 [SMILES: O=C(O)CN1CCC(C(=O)c2ccc(F)cc2)CC1]

To a solution of ethyl 2-(4-(4-Fluorobenzoyl)piperidin-1-yl)acetate (52.7 g, 180 mmol) in ethanol (300 mL) was added sodium hydroxide solution in water (1.8 M, 300 mL). The mixture was stirred at ambient temperature for 24 h then neutralized with HCl (37%) until pH 5~7. The solvent was evaporated under reduced pressure, dissolved with methanol and methylene chloride, and filtered. The resulting solution was evaporated to give the title compound as a white solid (47.7 g, >99% yield). $^1$H NMR (400 MHz, CD$_3$OD) δ 8.11 (dd, J=8.8, 5.3 Hz, 2H), 7.26 (t, J=8.8 Hz, 2H), 3.57-3.85 (m, 5H), 3.21 (t, J=11.0 Hz, 2H), 1.96-2.18 (m, 4H). MS m/z 266.3 (M+1), retention time=0.87 min.

Intermediate 82

4-(4-Isopropoxy-benzoyl)-piperidin-1-yl]-acetic acid

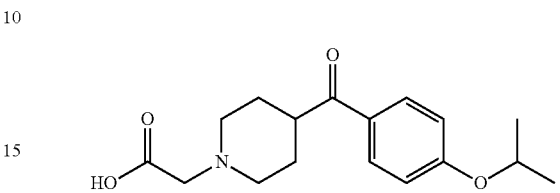

To a solution of 2-[4-(4-fluoro-benzoyl)-piperidin-1-yl]-acetic acid (0.30 g, 1.13 mmol) in 5 mL of 2-propanol was added 4 mL of 10 M NaOH, the reaction mixture was stirred at reflux (90° C.) for 15 h. The organic solvent was removed by reduced pressure, the aqueous layer was neutralized to pH 4 by using 1 M HCl (6 mL). The solvent was removed under reduced pressure to yield the title product that was carried on to the next step without further purification. MS (ESI) m/z 306.3 (M+H$^+$); HPLC (Novapak 150×3.9 mm C-18 column: mobile phase: 35-90% acetonitrile/water with 0.1% TFA, at 2 mL/min over 2 min.) t 1.36 min.

Intermediate 83

2-(4-(4-Ethoxybenzoyl)piperidin-1-yl)acetic acid

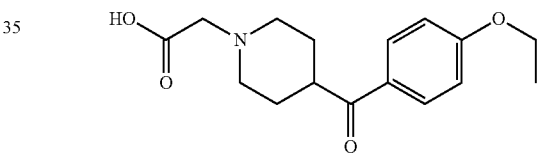

To a solution of 2-(4-(4-fluorobenzoyl)piperidin-1-yl)acetic acid (600 mg, 2.26 mmol) in ethanol (20 mL) was added sodium hydroxide (400 mg, 10.0 mmol) in water (2 mL) and heated at 80° C. for 24 h. The reaction mixture was neutralized with aqueous hydrochloric acid (1 N), the solvent was evaporated under reduced pressure and used to the next step directly. MS m/z 292.3 (M+1), retention time=0.99 min.

Intermediate 84

[4-(4-Methoxy-benzoyl)-piperidin-1-yl]-acetic acid ethyl ester

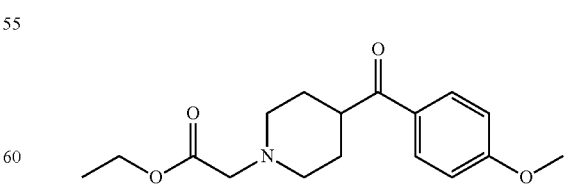

To a solution of 4-methoxy-phenyl-piperidin-4-yl-methanone (20 g, 78 mmol, 1 eq.) in 313 mL of acetonitrile was added triethylamine (22 mL, 156 mmol, 2 eq.), followed by ethyl 2-bromoacetate (9.5 mL, 86 mmol, 1.1 eq.) dropwise. The resulting mixture was heated at 85° C. overnight. After 18

Intermediate 85

[4-(4-Methoxy-benzoyl)-piperidin-1-yl]-acetic acid

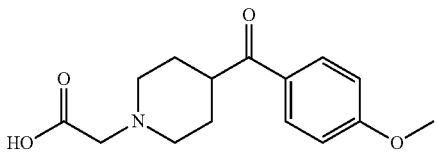 [SMILES: COc1ccc(C(=O)C2CCN(CC(=O)O)CC2)cc1]

To a solution of [4-(4-methoxy-benzoyl)-piperidin-1-yl]-acetic acid ethyl ester (11.7 g, 38 mmol, 1 eq.) in 154 mL of EtOH was added a solution of NaOH (3.07 g, 77 mmol, 2 eq.) in 154 mL of $H_2O$. The resulting mixture was stirred at room temperature overnight. After 18 h, the reaction mixture was concentrated and treated with 1 N HCl to pH 5. The resulting mixture was freeze dried using lyophilizer to remove $H_2O$. The resulting yellow solids were washed with dichloromethane/methanol and filtered off NaCl. The filtrate was concentrated to give the title compound as a white solid (11 g, 38 mmol). Exact mass calculated for $C_{15}H_{20}N_1O_4$ 278.1. MS (ESI) m/z 278.8 (M+H)$^+$.

Intermediate 86

[4-(2-trifluoromethoxy-benzoyl)-piperidin-1-yl]-acetic acid ethyl ester

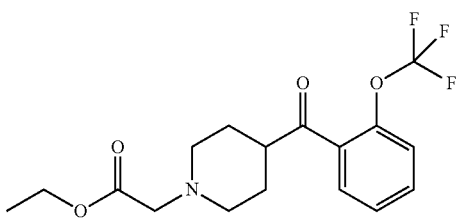 [SMILES: CCOC(=O)CN1CCC(C(=O)c2ccccc2OC(F)(F)F)CC1]

To a solution of piperidin-4-yl-(2-trifluoromethoxy-phenyl)-methanone in 5 mL of acetonitrile was added Et$_3$N (0.3 mL, 2.4 mmol, 2 eq.), followed by ethyl 2-bromoacetate (0.14 mL, 1.3 mmol, 1.1 eq.) added dropwise and heated at 85° C. overnight. After 18 h, the reaction mixture was concentrated in vacuo, diluted with saturated NaHCO$_3$ (100 mL) and extracted with ethyl acetate (3×50 mL). The combine organic layers were washed with brine, dried over anhydrous Na$_2$SO$_4$ and concentrated in vacuo to give a dark oil. This oil was purified by silica gel column chromatography (30-50% ethyl acetate/heptane) to give the title as a light brown oil (0.36 g, 85%). Exact mass calculated for $C_{18}H_{22}F_3N_1O_4$ 360.1. MS (ESI) m/z 360.7 (M+H)$^+$.

Intermediate 87

[4-(2-Trifluoromethoxy-benzoyl)-piperidin-1-yl]-acetic acid

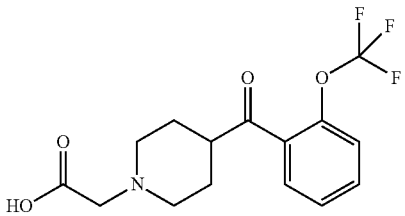 [SMILES: O=C(O)CN1CCC(C(=O)c2ccccc2OC(F)(F)F)CC1]

To a solution of [4-(2-trifluoromethoxy-benzoyl)-piperidin-1-yl]-acetic acid ethyl ester (0.36 g, 1 mmol, 1 eq.) in 5 mL of EtOH was added a solution of NaOH (0.08 g, 2 mmol, 2 eq.) in 5 mL of H$_2$O. The resulting mixture was stirred at room temperature overnight. After 18 h, the reaction mixture was concentrated and treated with 1 N HCl to pH 5. The resulting mixture was freeze dried using a lyophilizer to remove H$_2$O. The resulting yellow solids were washed with dichloromethane/methanol and filtered off NaCl. The filtrate was concentrated to give the title compound as a white solid (0.33 g, 99%). Exact mass calculated for $C_{15}H_{19}F_3N_1O_4$ 332.1. MS (ESI) m/z 332.4 (M+H)$^+$.

Intermediate 88

[4-(4-Chloro-benzoyl)-piperidin-1-yl]-acetic acid ethyl ester

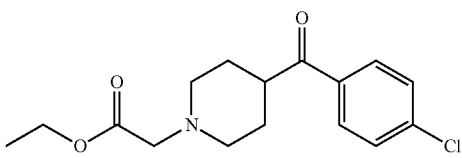 [SMILES: CCOC(=O)CN1CCC(C(=O)c2ccc(Cl)cc2)CC1]

To a suspension of (4-chloro-phenyl)-piperidin-4-yl-methanone (1.0 g, 3.8 mmol) and bromo-acetic acid ethyl ester (0.71 g, 4.2 mmol) in acetonitrile (10 mL) was added triethylamine (0.78 g, 7.7 mmol), the reaction mixture was stirred at 85° C. for 15 h. The reaction mixture was cooled to ambient temperature, the solvent was removed, the residue was redissolved in DCM (20 mL), washed with water (20 mL), the organic layers were then washed with brine (20 mL) and dried over Na$_2$SO$_4$. Purification by flash chromatography gave the title compound as a white solid (1.01 g, 3.10 mmol, 81% yield). MS (ESI) m/z 310.3 (M+H$^+$); HPLC (Novapak 150×3.9 mm C-18 column: mobile phase: 35-90% acetonitrile/water with 0.1% TFA, at 2 mL/min over 2 min.) t 1.45 min.

h, the reaction mixture was diluted with saturated NaHCO$_3$ (150 mL) and extracted with ethyl acetate (3×500 mL). The combined organic layers were washed with brine, dried over anhydrous Na$_2$SO$_4$, filtered, and concentrated in vacuo to give an oil. This oil was purified by silica gel column chromatography (10-20% acetone/heptane) to give the title compound as a white solid (11.7 g, 49% yield). Exact mass calculated for $C_{17}H_{24}N_1O_4$ 306.2. MS (ESI) m/z 306.4 (M+H)$^+$.

Intermediate 89

[4-(4-Chloro-benzoyl)-piperidin-1-yl]-acetic acid

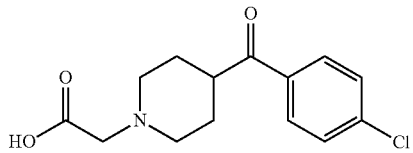 [SMILES: O=C(O)CN1CCC(C(=O)c2ccc(Cl)cc2)CC1]

To a stirred solution of [4-(4-chloro-benzoyl)-piperidin-1-yl]-acetic acid ethyl ester (1.0 g, 3.03 mmol) in 12 mL of THF and 4 mL of MeOH, was added LiOH (0.39 g, 16.14 mmol in 3 mL of water). After 3 h at ambient temperature the solvent was removed in vacuo, then diluted with 20 mL of water (pH 14). The residue was treated with 12 mL of 1 N HCl (pH 4), frozen at −78° C. then lyophilized for 24 hours to yield the title product (1.33 g, 4.70 mmol, >99% yield) with LiCl salt. MS (ESI) m/z 282.3 (M+H$^+$); HPLC (Novapak 150×3.9 mm C-18 column: mobile phase: 35-90% acetonitrile/water with 0.1% TFA, at 2 mL/min over 2 min.) t 1.26 min.

Intermediate 90

[4-(6-Fluoro-1H-indazol-3-yl)-piperidin-1-yl]-acetic acid ethyl ester

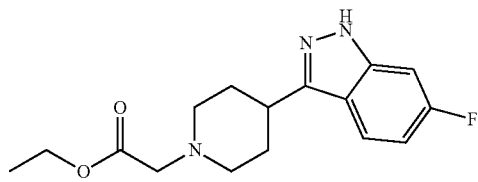 [SMILES: CCOC(=O)CN1CCC(c2n[nH]c3cc(F)ccc23)CC1]

To a suspension of ethyl 2-bromoacetate (0.55 g, 3.3 mmol) and 6-fluoro-3-piperidin-4-yl-1H-indazole (0.60 g, 2.7 mmol in 10 mL of acetonitrile) was added Et$_3$N (1.4 g, 13.7 mmol) and the reaction mixture was stirred at 85° C. for 15 hours. The reaction mixture was cooled to ambient temperature and the solvent was removed in vacuo. The residue was redissolved in DCM (50 mL), washed with water, brine, dried over Na$_2$SO$_4$ and concentrated in vacuo. Purification by flash chromatography gave the title compound (0.29 g, 0.90 mmol) as a white solid. MS (ESI) m/z 306.9 (M+H$^+$); HPLC (Novapak 150×3.9 mm C-18 column: mobile phase: 35-90% acetonitrile/water with 0.1% TFA, at 2 mL/min over 2 min.) t 1.54 min.

Intermediate 91

[4-(6-Fluoro-1H-indazol-3-yl)-piperidin-1-yl]-acetic acid

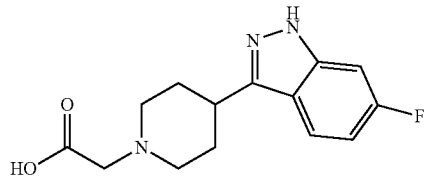 [SMILES: O=C(O)CN1CCC(c2n[nH]c3cc(F)ccc23)CC1]

To a solution of [4-(6-fluoro-1H-indazol-3-yl)-piperidin-1-yl]-acetic acid ethyl ester (0.29 g, 0.90 mmol in 6 mL of THF and 2 mL of methanol) was added LiOH.H$_2$O (0.21 g, 4.9 mmol in 3 mL of water) and the reaction mixture was stirred at ambient temperature for 1.5 hours. The solvent was removed in vacuo then diluted with 20 mL of water (pH 14). The residue was treated with 12 mL of 1 N HCl (pH 4), frozen at −78° C. and lyophilized for 24 hours to yield the title compound as the LiCl salt (0.31 g, 1.0 mmol). MS (ESI) m/z 279.0 (M+H$^+$); HPLC (Novapak 150×3.9 mm C-18 column: mobile phase: 35-90% acetonitrile/water with 0.1% TFA, at 2 mL/min over 2 min.) t 0.90 min.

Intermediate 92

Ethyl 2-(4-benzoylpiperidin-1-yl)acetate

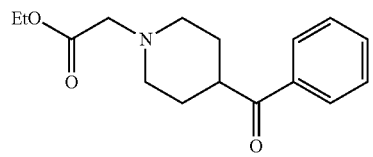 [SMILES: O=C(O)CN1CCC(C(=O)c2ccccc2)CC1]

Following the general procedure of Intermediate 86, the title compound was prepared (1.93 g) from phenyl(piperidin-4-yl)methanone (2 g, 11 mmol, 1 eq.). Exact mass calculated for C$_{16}$H$_{22}$N$_1$O$_3$ 276.2. MS (ESI) m/z 276.1 (M+H)$^+$.

Intermediate 93

2-(4-benzoylpiperidin-1-yl)acetic acid

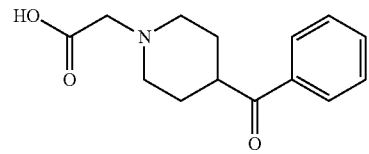

Following general procedure of Intermediate 87, the title compound was prepared (1.0 g) from ethyl 2-(4-benzoylpiperidin-1-yl)acetate (1.93 g, 7.01 mmol, 1 eq.). Exact mass calculated for C$_{14}$H$_{18}$N$_1$O$_3$ 248.1. MS (ESI) m/z 248.1 (M+H)$^+$.

Intermediate 94

1-tert-butoxycarbonylmethyl-piperidine-4-carboxylic acid methyl ester

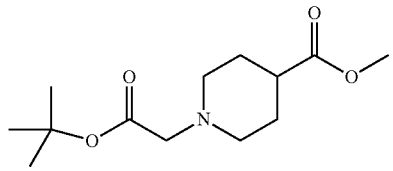 [SMILES: COC(=O)C1CCN(CC(=O)OC(C)(C)C)CC1]

To a solution of piperidine-4-carboxylic acid methyl ester (10 g, 70 mmol, 1 eq.) and Et$_3$N (19.5 mL, 140 mmol, 2 eq.) in 150 mL of THF was added bromo-acetic acid tert-butyl ester (13.6 g, 70 mmol, 1 eq.) in 150 mL of THF. The resulting mixture was heated at reflux overnight. After 18 h, the resulting mixture was concentrated and purified by silica gel column chromatography (98/1/1 CH$_2$Cl$_2$/MeOH/NH$_4$OH) to give the title compound as a yellow oil (0.84 g). Exact mass calculated for $C_{13}H_{24}N_1O_4$ 258.2. MS (ESI) m/z 258.6 $(M+H)^+$.

Intermediate 95

1-{[Cyclopropylmethyl-(4-oxo-3,4a,5,7,8,8a-hexahydro-4H-pyrano[4,3-d]pyrimidin-2-ylmethyl)-carbamoyl]-methyl}-piperidine-4-carboxylic acid methyl ester

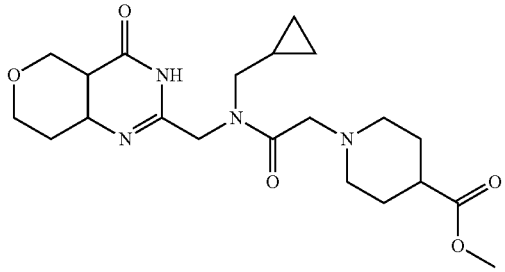 [SMILES: COC(=O)C1CCN(CC(=O)N(CC2=NC3CCOCC3C(=O)N2)CC2CC2)CC1]

To a solution of 1-tert-butoxycarbonylmethyl-piperidine-4-carboxylic acid methyl ester (0.65 g, 2.53 mmol, 1 eq.) in 2.5 mL of dichloromethane was added TFA (2.53 mL, 32.8 mmol, 13 eq.). The resulting mixture was stirred at room temperature overnight. After 18 h, the reaction mixture was concentrated and dried under high vacuum. To this oil (0.52 g, 2.22 mmol, 1 eq.) was added DIEA (1.16 mL, 6.66 mmol, 3 eq.) in 5 mL of DMF, followed by HATU (1.69 g, 4.44 mmol, 2 eq.). The resulting mixture was stirred at room temperature for 30 min. 2-[(Cyclopropylmethyl-amino)-methyl]-3,4a,5,7,8,8a-hexahydro-pyrano[4,3-d]pyrimidin-4-one (0.7 g, 2.22 mmol, 1 eq.) in 5 mL of DMF was added and the resulting mixture was stirred at room temperature overnight. After 18 h, the reaction mixture was quenched with $H_2O$ (25 mL) and extracted with dichloromethane (3×50 mL). The combined organic layer was concentrated and purified via preparative HPLC (20-100% $CH_3CN/H_2O$ over 10 min with 0.1% TFA, sun fire C18 OBD 50×50 mm column with flow rate of 60 mL/min) to give the title compound as a white solid (0.69 g). Exact mass calculated for $C_{21}H_{33}N_4O_5$ 421.2. MS (ESI) m/z 421.6 $(M+H)^+$.

Intermediate 96

1-{[Cyclopropylmethyl-(4-oxo-3,4a,5,7,8,8a-hexahydro-4H-pyrano[4,3-d]pyrimidin-2-ylmethyl)-carbamoyl]-methyl}-piperidine-4-carboxylic acid

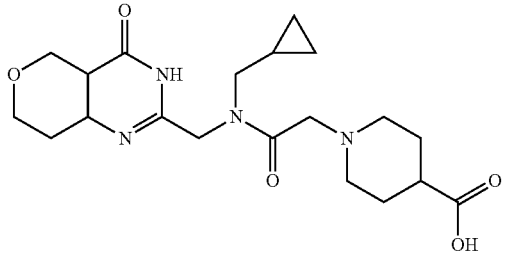 [SMILES: O=C(O)C1CCN(CC(=O)N(CC2=NC3CCOCC3C(=O)N2)CC2CC2)CC1]

To a solution of 1-{[cyclopropylmethyl-(4-oxo-3,4a,5,7,8,8a-hexahydro-4H-pyrano[4,3-d]pyrimidin-2-ylmethyl)-carbamoyl]-methyl}-piperidine-4-carboxylic acid methyl ester (0.6 g, 1.43 mmol, 1 eq.) in 3 mL of MeOH was added a solution of NaOH (0.13 g, 5.43 mmol, 3.8 eq.) in 3 mL of $H_2O$. The resulting mixture was stirred at room temperature overnight. After 18 h, the reaction mixture was concentrated and treated with 1 N HCl to pH 5. The resulting mixture was freeze dried using lyophilizer to remove $H_2O$. The resulting white solids were washed with dichloromethane/methanol and filtered to remove NaCl. The filtrate was concentrated to give the title compound as a white solid (0.53 g, 92%). Exact mass calculated for $C_{23}H_{31}N_4O_3$ 407.2. MS (ESI) m/z 407.6 $(M+H)^+$.

Intermediate 97

1-{[Cyclopropylmethyl-(4-oxo-3,4a,5,7,8,8a-hexahydro-4H-pyrano[4,3-d]pyrimidin-2-ylmethyl)-carbamoyl]-methyl}-piperidine-4-carbothioic acid S-phenyl ester

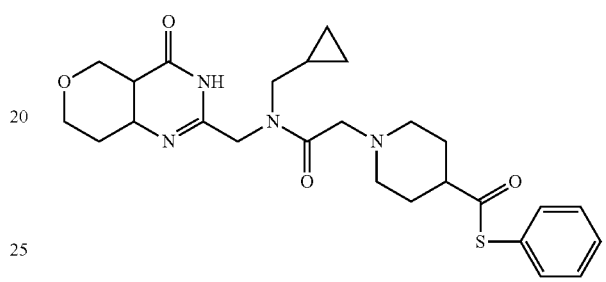

To a solution of 1-{[cyclopropylmethyl-(4-oxo-3,4a,5,7,8,8a-hexahydro-4H-pyrano[4,3-d]pyrimidin-2-ylmethyl)-carbamoyl]-methyl}-piperidine-4-carboxylic acid (0.5 g, 1.24 mmol, 1 eq.) in 5 mL of DMF was added DIEA (0.432 mL, 2.47 mmol, 2 eq.), thiophenol (0.14 mL, 1.36 mmol, 1.1 eq.), followed by HATU (0.517 g, 1.36 mmol, 1.1 eq.) at 0° C. The resulting mixture was allowed to warm to room temperature and stirred overnight. After 18 h, the reaction mixture was concentrated in vacuo to give an oil. This oil was purified by silica gel column chromatography (98/1/1 to 95/4/1 dichloromethane/MeOH/NH$_4$OH) to give the title compound as an orange sticky oil (0.4 g). $^1$H NMR (400 MHz, chloroform-d) δ ppm 7.48-7.58 (m, 2H), 7.33-7.48 (m, 3H), 4.54-4.64 (m, 2H), 4.48-4.54 (m, 1H), 4.34-4.46 (m, 1H), 3.91-4.06 (m, 2H), 3.23-3.42 (m, 3H), 2.92-3.08 (m, 1H), 2.80-2.89 (m, 1H), 2.54-2.76 (m, 2H), 2.18-2.37 (m, 2H), 1.60-1.84 (m, 6H), 0.92-1.01 (m, 1H), 0.41-0.63 (m, 2H), 0.19-0.35 (m, 2H). Exact mass calculated for $C_{26}H_{33}N_4O_4S_1$ 497.2. MS (ESI) m/z 497.2 $(M+H)^+$ (5-95% $CH_3CN/H_2O$ over 2 min with 0.1% formic acid, Inertsil 3×3 mm C-8-3 column with flow rate of 2 mL/min).

Intermediate 98 tert-Butyl 4-(4-(trifluoromethoxy)benzoyl)piperidine-1-carboxylate

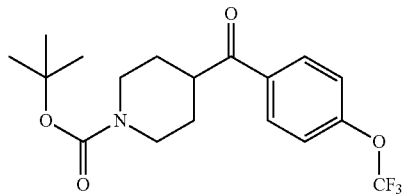 [SMILES: CC(C)(C)OC(=O)N1CCC(C(=O)c2ccc(OC(F)(F)F)cc2)CC1]

Following the general procedure of Intermediate 78, the title compound was prepared (0.38 g) from 4-(trifluoromethoxy)phenylboronic acid (0.46 g, 2.24 mmol, 1.5 eq.).

Exact mass calculated for $C_{18}H_{23}F_3N_1O_4$ 374.4. MS (ESI) m/z 317.8 (M+H without t-butyl).

Intermediate 99 tert-Butyl 4(2-methoxybenzoyl)piperidine-1-carboxylate

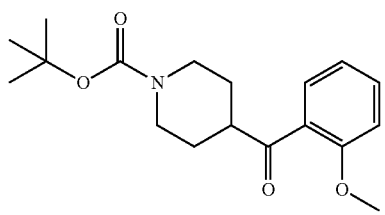 [SMILES: COc1ccccc1C(=O)C1CCN(C(=O)OC(C)(C)C)CC1]

Following the general procedure of Intermediate 78, the title compound was prepared (0.38 g) from tert-butyl 4-(phenylthiocarbonyl)piperidine-1-carboxylate (0.48 g, 1.49 mmol, 1 eq.). Exact mass calculated for $C_{18}H_{26}N_1O_4$ 320.2. MS (ESI) m/z 263.6 (M+H loss of t-butyl).

Intermediate 100 tert-Butyl 4-(3-methoxybenzoyl)piperidine-1-carboxylate

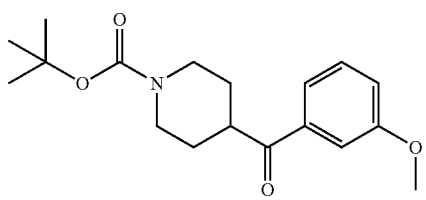 [SMILES: COc1cccc(C(=O)C2CCN(C(=O)OC(C)(C)C)CC2)c1]

Following the general procedure of Intermediate 78, the title compound was prepared (0.43 g) from tert-butyl 4-(phenylthiocarbonyl)piperidine-1-carboxylate (0.48 g, 1.49 mmol, 1 eq.). Exact mass calculated for $C_{18}H_{26}N_1O_4$ 320.2. MS (ESI) m/z 264.3 (M+H without t-butyl).

Intermediate 101 tert-Butyl 4-(3-(trifluoromethoxy)benzoyl)piperidine-1-carboxylate

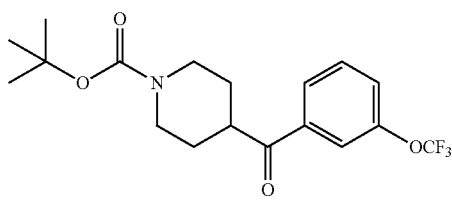 [SMILES: CC(C)(C)OC(=O)N1CCC(C(=O)c2cccc(OC(F)(F)F)c2)CC1]

Following the general procedure of Intermediate 78, the title compound was prepared (0.31 g) from tert-butyl 4-(phenylthiocarbonyl)piperidine-1-carboxylate (0.48 g, 1.5 mmol, 1 eq.). Exact mass calculated for $C_{18}H_{23}F_3N_1O_4$ 374.2. MS (ESI) m/z 318.3 (M+H without t-butyl).

Intermediate 102 tert-Butyl 4-(4-(trifluoromethyl)benzoyl)piperidine-1-carboxylate

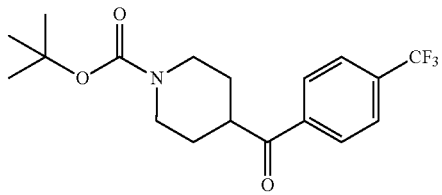 [SMILES: CC(C)(C)OC(=O)N1CCC(C(=O)c2ccc(C(F)(F)F)cc2)CC1]

Following the general procedure of Intermediate 78, the title compound was prepared (0.30 g) from 4-(trifluoromethyl)phenylboronic acid (0.48 g, 1.5 mmol, 1 eq.). Exact mass calculated for $C_{18}H_{23}F_3N_1O_3$ 358.2. MS (ESI) m/z 302.3 (M+H without t-butyl).

Intermediate 103

[4-(Pyridine-2-carbonyl)-piperidin-1-yl]-acetic acid ethyl ester

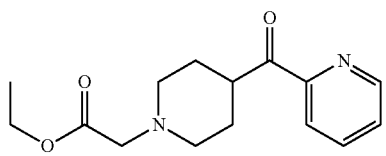 [SMILES: CCOC(=O)CN1CCC(C(=O)c2ccccn2)CC1]

To a solution of compound piperidin-4-yl-pyridin-2-yl-methanone (170 mg, 0.894 mmol) in 10 mL acetonitrile was added ethyl bromoacetate (0.13 mL, 1.12 mmol) and triethylamine (362 mg, 3.57 mmol). The reaction was heated at 80° C. for 16 hour. The combined organic layers were concentrated under vacuum to afford an orange oily solid. The residue was chromatographed on silica gel (gradient: methanol/dichloromethane; 0:1 to 1:9 over 20 minutes) to afford the title compound as a white solid (198 mg). 1H NMR (400 MHz, CDC$_3$) δ 8.68 (d, J=4.0 Hz, 1H), 8.06 (d, J=7.6 Hz, 1H), 7.89 (t, J=9.0 Hz, 1H), 7.52 (t, J=7.6 Hz, 1H), 4.33-4.27 (m, 2H), 3.92 (s, 2H), 3.70-3.72 (m, 2H), 3.59-3.53 (m, 2H), 2.34-2.28 (m, 4H), 1.34 (t, J=7.1 Hz, 3H). MS m/z ES+=276.8 (M+H), retention time 0.80.

Intermediate 104

[4-(Pyridine-2-carbonyl)-piperidin-1-yl]-acetic acid

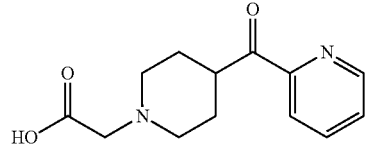 [SMILES: O=C(O)CN1CCC(C(=O)c2ccccn2)CC1]

To a solution of compound [4-(pyridine-2-carbonyl)-piperidin-1-yl]-acetic acid ethyl ester (198 mg, 0.72 mmol), in water (4 mL) and ethanol (4 mL) and was added 4N sodium hydroxide (0.36 mL, 1.43 mmol). The reaction was stirred at 25° C. for 48 hours and then heated at 40° C. for 3 hours. The reaction mixture was acidified with 1N HCl to pH 3 and the solvent was removed under vacuum. The residue was co-evaporated 3 times with acetonitrile to afford the title compound (178 mg). The crude product was used directly in the next step without subsequent purification. MS m/z ES+=248.8 (M+H), retention time 1.66.

Intermediate 105

Methyl 1-(2-tert-butoxy-2-oxoethyl)piperidine-4-carboxylate

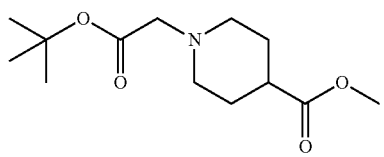 [SMILES: COC(=O)C1CCN(CC(=O)OC(C)(C)C)CC1]

To a mixture of methyl isonipecotate (10.0 g, 69.8 mmol) and triethylamine (19.5 mL, 140 mmol) in tetrahydrofuran (200 mL) was added tert-butyl bromoacetate (10.3 mL, 69.8 mmol). The solution was heated at reflux for 24 h, concentrated under reduced pressure and purified via flash column chromatography (ethyl acetate:hexane, 10:90 to 100:0, methanol: dichloromethane, 1:99 to 5:95) to provide the title compound (18 g). $^1$H NMR (400 MHz, CDC$_3$) δ 3.61 (s, 3H), 3.04 (s, 2H), 2.84 (d, J=11.5 Hz, 2H), 2.12-2.31 (m, 3H), 1.64-1.91 (m, 4H), 1.39 (s, 9H).

Intermediate 106

2-(4-(Methoxycarbonyl)piperidin-1-yl)acetic acid

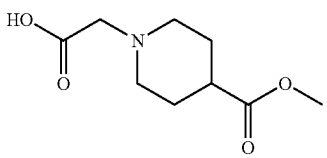

To a solution of methyl 1-(2-tert-butoxy-2-oxoethyl)piperidine-4-carboxylate (3.0 g, 12 mmol) in dichloromethane (9 mL) was added hydrochloric acid in 1,4-dioxane (4 M) and stirred at ambient temperature for 24 h. The final product was formed as a white solid, which was washed with ether and filtered (2.3 g). $^1$H NMR (400 MHz, DMSO-d$_6$) δ 4.09 (s, 2H), 3.64 (s, 3H), 3.46 (br. s., 2H), 3.11 (br. s., 2H), 2.67 (br. s., 1H), 1.82-2.12 (m, 4H)

Intermediate 107

Methyl 1-(2-oxo-2-((4-oxo-4,5,7,8-tetrahydro-3H-pyrano[4,3-d]pyrimidin-2-yl)methylamino)ethyl)piperidine-4-carboxylate

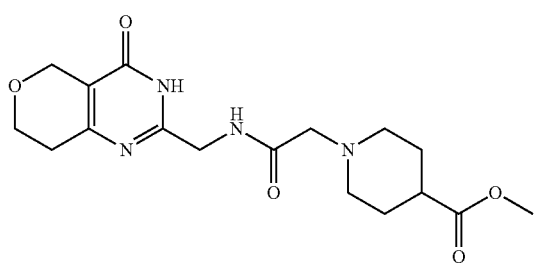 [SMILES: COC(=O)C1CCN(CC(=O)NCc2nc3c(c(=O)[nH]2)COCC3)CC1]

The title compound (1.2 g) was prepared according the general procedure of Example 1 from 2-(4-(methoxycarbonyl)piperidin-1-yl)acetic acid (2.2 g, 11 mmol) and 2-aminomethyl-3,5,7,8-tetrahydro-pyrano[4,3-d]pyrimidin-4-one (1.5 g, 8.3 mmol). MS m/z 365.3 (M+1), retention time=1.46 min.

Intermediate 108

1-(2-Oxo-2-((4-oxo-4,5,7,8-tetrahydro-3H-pyrano[4,3-d]pyrimidin-2-yl)methylamino)ethyl)piperidine-4-carboxylic acid

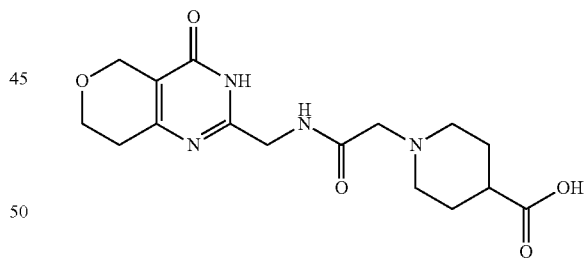

To a solution of methyl 1-(2-oxo-2-((4-oxo-4,5,7,8-tetrahydro-3H-pyrano[4,3-d]pyrimidin-2-yl)methylamino)ethyl)piperidine-4-carboxylate (1.2 g, 3.3 mmol) in methanol (5 mL) was added sodium hydroxide (0.4 g, 10 mmol) in water (5 mL). The mixture was stirred at ambient temperature for 24 h, neutralized with HCl (37%) until pH 5~7 and the solvent was evaporated under reduced pressure to give a white solid which was used directly to the next step. $^1$H NMR (400 MHz, CD$_3$OD) δ 4.48 (s, 2H), 4.38 (s, 2H), 3.95 (t, J=5.8 Hz, 2H), 3.24-3.36 (m, 1H), 3.10 (d, J=12.1 Hz, 2H), 2.67 (t, J=5.6 Hz, 2H), 2.45 (td, J=11.4, 2.5 Hz, 2H), 2.25-2.39 (m, 1H), 1.77-2.04 (m, 5H).

Intermediate 109

Piperidine-4-carbothioic acid S-phenyl ester

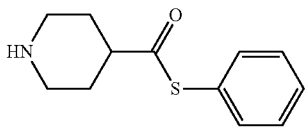

To a solution of 4-phenylsulfanylcarbonyl-piperidine-1-carboxylic acid tert-butyl ester (1.11 g, 3.45 mmol) in dichloromethane (10 mL) was then added TFA (2 mL) the reaction was then stirred at 25° C. for 2.5 hours and the solvent was removed under vacuum and the crude material was co-evaporated 3 times with dichloromethane to afford the title compound (750 mg, 3.31 mmol). The crude material was used directly in the next step without subsequent purification. MS (ESI) m/z 221.8 (M+H$^+$); HPLC (Insertsil ODS3 100×3 mm C-18 column: mobile phase: 5-95% acetonitrile/water with 0.1% TFA, at 1 mL/min over 7.75 min.), t=1.29 min.

Intermediate 110

(4-Phenylsulfanylcarbonyl-piperidin-1-yl)-acetic acid ethyl ester

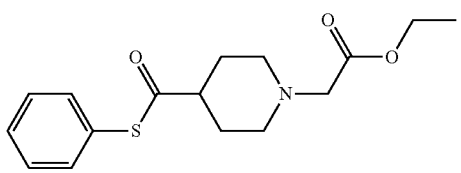 [SMILES: CCOC(=O)CN1CCC(C(=O)Sc2ccccc2)CC1]

To a solution of piperidine-4-carbothioic acid S-phenyl ester (0.65 g, 2.94 mmol) in acetonitrile (10 mL) was added ethyl 2-bromoacetate (0.49 g, 2.94 mmol) and triethylamine (1.49 g 14.7 mmol). The mixture was heated at 85° C. for 10 h, the solvent was evaporated under reduced pressure and purified via flash column chromatography (ethyl acetate:heptane) to provide product (0.81 g, 2.5 mmol). MS (ESI) m/z 307.8 (M+H+); HPLC (Insertsil ODS3 100×3 mm C-18 column: mobile phase: 5-95% acetonitrile/water with 0.1% TFA, at 1 mL/min over 7.75 min.), t=1.50 min.

Intermediate 111

[4-(4-Methoxy-3-methyl-benzoyl)-piperidin-1-yl]-acetic acid ethyl ester

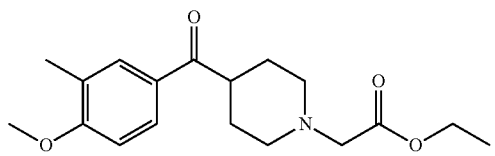 [SMILES: CCOC(=O)CN1CCC(C(=O)c2ccc(OC)c(C)c2)CC1]

To a mixture of 4-methoxy-3-methyl phenylboronic acid (0.32 g, 1.95 mmol), ligand TFP (0.06 g, 0.26 mmol), Pd$_2$dba$_3$ (0.12 g, 0.13 mmol), copper (I) thiophene-2-carboxylate (0.37 g, 2.0 mmol) was added a solution of (4-phenylsulfanylcarbonyl-piperidin-1-yl)-acetic acid ethyl ester (0.4 g, 1.3 mmol) in 6 mL of DME. It was stirred at RT for 16 hours, the reaction mixture was diluted with ethyl acetate, filtered through celite then concentrated in vacuo. Purification by flash chromatography gave the title compound (0.2 g, 0.6 mmol). MS (ESI) m/z 319.8 (M+H$^+$); HPLC (Novapak 150× 3.9 mm C-18 column: mobile phase: 35-90% acetonitrile/water with 0.1% TFA, at 2 mL/min over 2 min.) t 1.36 min.

Intermediate 112

[4-(4-Methoxy-3-methyl-benzoyl)-piperidin-1-yl]-acetic acid

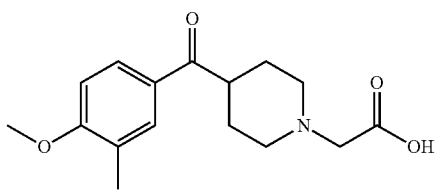 [SMILES: COc1ccc(C(=O)C2CCN(CC(=O)O)CC2)cc1C]

To a stirred solution of [4-(4-methoxy-3-methyl-benzoyl)-piperidin-1-yl]-acetic acid ethyl ester (0.19 g, 0.60 mmol) in 6 mL of THF and 2 mL of MeOH, was added LiOH (0.13 g, 3.0 mmol in 3 mL of water). After 1.5 hours at ambient temperature the solvent was removed in vacuo, then diluted with 20 mL of water (pH 14). The residue was treated with 12 mL of 1N HCl (pH 4), frozen at −78° C. then lyophilized for 24 hours to yield the title product (0.17 g, 0.54 mmol, 90%) with LiCl salt. MS (ESI) m/z 291.8 (M+H$^+$); HPLC (Novapak 150×3.9 mm C-18 column: mobile phase: 35-90% acetonitrile/water with 0.1% TFA, at 2 mL/min over 2 min.) t 1.58 min.

Intermediate 113

(8-Oxo-3,4,7,8-tetrahydro-1H-pyrano[8,4-c]pyridin-6-ylmethyl)-carbamic acid tert-butyl ester

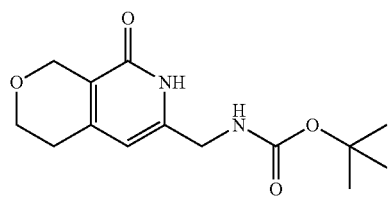 [SMILES: CC(C)(C)OC(=O)NCc1cc2c(c(=O)[nH]1)COCC2]

A stirred solution of (1-oxo-5,8-dihydro-1H,6H-pyrano[3,4-c]pyran-3-ylmethyl)-carbamic acid tert-butyl ester (160 mg, 0.57 mmol) in dimethylformamide (3 mL) in 28% ammonium hydroxide (6 mL) was heated at 90° C. for two hours, concentrated in vacuo then dried under a stream of nitrogen. The residue was dissolved in 50 mL ethyl acetate, washed three times with 20 mL saturated aqueous ammonium chloride solution then brine, dried over anhydrous sodium sulfate, filtered and concentrated in vacuo. Used crude product without further purification (73 mg). $^1$H NMR (400 MHz, MeOD) δ ppm 7.08-7.19 (br. s, 1H), 6.09 (s, 1H), 4.45-4.50 (m, 2H), 4.05-4.10 (m, 2H), 3.86 (t, J=5.6 Hz, 2H), 2.61-2.67 (m, 2H), 1.43 (s, 9H). MS (ESI) m/z 280.8 (M+1), retention time=0.77 min.

Intermediate 114

1-[4-(3,4-Dimethoxy-benzoyl)-piperidin-1-yl]-ethanone

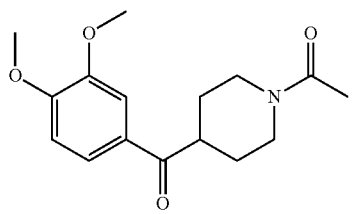 [SMILES: COc1ccc(C(=O)C2CCN(C(C)=O)CC2)cc1OC]

To a rapidly stirred slurry of aluminum chloride (1.1 g, 8.2 mmol) and 1,2-dimethoxybenzene (3.5 mL) at ambient temperature was added 1-acetylpiperidine-4-carbonyl chloride (0.8 g, 4.2 mmol). The reaction mixture was heated at reflux (100° C.) for 1.5 hours and then poured into 30 mL of ice water, the mixture was extracted with DCM (50 mL) and the organic layer was washed with water and dried over $Na_2SO_4$. The solvent was removed in vacuo to give an oil. Trituration of the oil with pentane gave the title product (0.88 g, 2.87 mmol) as a white solid. MS (ESI) m/z 292.4 (M+H$^+$); HPLC (Novapak 150×3.9 mm C-18 column: mobile phase: 35-90% acetonitrile/water with 0.1% TFA, at 2 mL/min over 2 min.) t 0.86 min.

Intermediate 115

(3,4-Dimethoxy-phenyl)-piperidin-4-yl-methanone

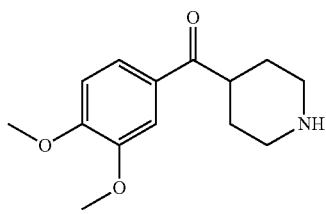 [SMILES: COc1ccc(C(=O)C2CCNCC2)cc1OC]

A solution of 1-[4-(3,4-dimethoxy-benzoyl)-piperidin-1-yl]-ethanone (0.50 g, 1.7 mmol) in 5 mL of 6 N HCl was stirred at reflux for 6 hours and then it was stirred at room temperature overnight. The solvent was removed in vacuo to yield the title compound (0.41 g, 1.65 mmol). MS (ESI) m/z 249.8 (M+H$^+$); HPLC (Novapak 150×3.9 mm C-18 column: mobile phase: 35-90% acetonitrile/water with 0.1% TFA, at 2 mL/min over 2 min.) t 0.91 min.

Intermediate 116

[4-(3,4-Dimethoxy-benzoyl)-piperidin-1-yl]-acetic acid ethyl ester

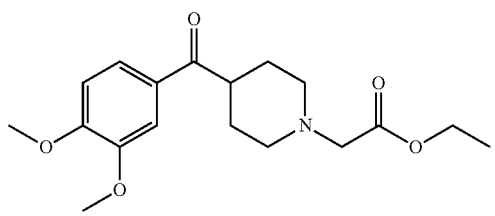 [SMILES: CCOC(=O)CN1CCC(C(=O)c2ccc(OC)c(OC)c2)CC1]

To a solution of (3,4-dimethoxy-phenyl)-piperidin-4-yl-methanone (0.51 g, 2.05 mmol) in acetonitrile (10 mL) was added ethyl 2-bromoacetate (0.41 g, 2.5 mmol) and triethylamine (1.04 g, 10.2 mmol). The mixture was heated at 85° C. overnight, the solvent was evaporated under reduced pressure and purified via flash column chromatography (ethyl acetate) to provide product as a white solid (0.45 g, 1.28 mmol). MS (ESI) m/z 335.8 (M+H$^+$); HPLC (Novapak 150×3.9 mm C-18 column: mobile phase: 35-90% acetonitrile/water with 0.1% TFA, at 2 mL/min over 2 min.) t 1.08 min.

Intermediate 117

[4-(3,4-Dimethoxy-benzoyl)-piperidin-1-yl]-acetic acid

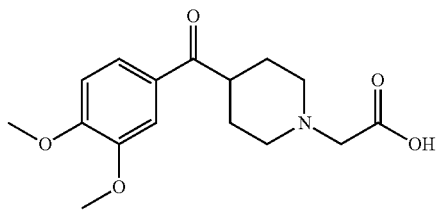 [SMILES: COc1ccc(C(=O)C2CCN(CC(=O)O)CC2)cc1OC]

To a solution of [4-(3,4-dimethoxy-benzoyl)-piperidin-1-yl]-acetic acid ethyl ester (0.45 g, 1.34 mmol in 6 mL of THF and 2 mL of methanol) was added LiOH.H$_2$O (0.28 g, 6.7 mmol in 3 mL of water) and the reaction mixture was stirred at ambient temperature for 1.5 hours. The solvent was removed in vacuo then diluted with 20 mL of water (pH 14). The residue was treated with 12 mL of 1 N HCl (pH 4), frozen at −78° C. and lyophilized for 24 hours to yield the title compound (0.40 g, 1.24 mmol). MS (ESI) m/z 308.3 (M+H+); HPLC (Novapak 150×3.9 mm C-18 column: mobile phase: 35-90% acetonitrile/water with 0.1% TFA, at 2 mL/min over 2 min.) t 1.16 min.

Intermediate 118

4-(2,3-Dihydro-benzofuran-5-carbonyl)-piperidine-1-carboxylic acid tert-butyl ester

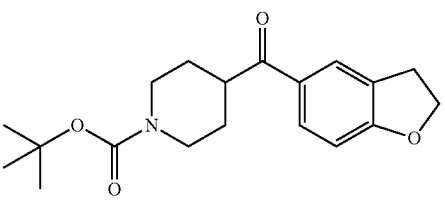 [SMILES: CC(C)(C)OC(=O)N1CCC(C(=O)c2ccc3c(c2)CCO3)CC1]

To a mixture of 2,3-dihydro-1-benzofuran-5-ylboronic acid (0.56 g, 1.56 mmol), ligand TFP (0.07 g, 0.3 mmol), Pd$_2$dba$_3$ (0.28 g, 0.30 mmol), copper (I) thiophene-2-carboxylate (0.45 g, 2.4 mmol) was added a solution of 4-phenylsulfanylcarbonyl-piperidine-1-carboxylic acid tert-butyl ester (0.5 g, 1.6 mmol) in 15 mL of DME while purging with N$_2$ at 50° C. After 18 hours the reaction mixture was diluted with ethyl acetate, filtered through celite then concentrated in vacuo. Purification by flash chromatography gave the title compound (0.5 g, 1.4 mmol). MS (ESI) m/z 331.8 (M+H$^+$);

HPLC (Novapak 150×3.9 mm C-18 column: mobile phase: 35-90% acetonitrile/water with 0.1% TFA, at 2 mL/min over 2 min.) t 1.54 min.

Intermediate 119

(2,3-Dihydro-benzofuran-5-yl-piperidin-4-yl-methanone)

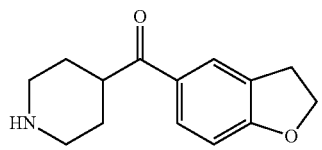

To a solution of 4-(2,3-dihydro-benzofuran-5-carbonyl)-piperidine-1-carboxylic acid tert-butyl ester (0.50 g, 1.5 mmol) in 10 mL of DCM, was added 1 mL of TFA. The reaction mixture was stirred at ambient temperature for 2.5 hours then the solvent was removed by reduced pressure to yield the title product (0.3 g, 1.3 mmol). MS (ESI) m/z 232.3 (M+H$^+$); HPLC (Novapak 150×3.9 mm C-18 column: mobile phase: 35-90% acetonitrile/water with 0.1% TFA, at 2 mL/min over 2 min.) t 1.14 min.

Intermediate 120

[4-(2,3-Dihydro-benzofuran-5-carbonyl)-piperidin-1-yl]-acetic acid ethyl ester

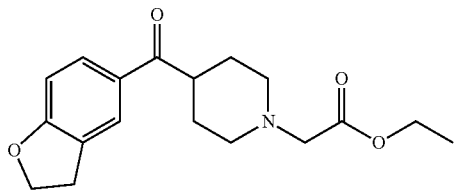 [SMILES: CCOC(=O)CN1CCC(C(=O)c2ccc3c(c2)CCO3)CC1]

To a solution of (2,3-dihydro-benzofuran-5-yl)-piperidin-4-yl-methanone (0.30 g, 1.30 mmol) in acetonitrile (10 mL) was added ethyl 2-bromoacetate (0.26 g, 1.6 mmol) and triethylamine (0.66 g, 6.5 mmol). The mixture was heated at 85° C. overnight, the solvent was evaporated under reduced pressure and purified via flash column chromatography (ethyl acetate:heptane) to provide desired product as a white solid (0.18 g, 0.54 mmol). MS (ESI) m/z 317.8 (M+H$^+$); HPLC (Novapak 150×3.9 mm C-18 column: mobile phase: 35-90% acetonitrile/water with 0.1% TFA, at 2 mL/min over 2 min.) t 1.22 min.

Intermediate 121

[4-(2,3-Dihydro-benzofuran-5-carbonyl)-piperidin-1-yl]-acetic acid

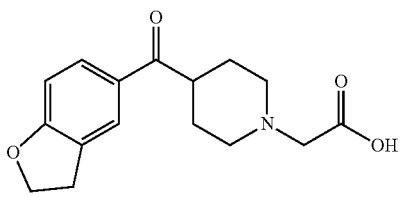 [SMILES: O=C(O)CN1CCC(C(=O)c2ccc3c(c2)CCO3)CC1]

To a solution of [4-(2,3-dihydro-benzofuran-5-carbonyl)-piperidin-1-yl]-acetic acid ethyl ester (0.18 g, 0.57 mmol in 6 mL of THF and 2 mL of methanol) was added LiOH.H$_2$O (0.12 g, 2.8 mmol in 3 mL of water) and the reaction mixture was stirred at ambient temperature for 1.5 hours. The solvent was removed in vacuo then diluted with 20 mL of water (pH 14). The residue was treated with 12 mL of 1 N HCl (pH 4), frozen at −78° C. and lyophilized for 24 hours to yield the title compound (0.16 g, 0.53 mmol). MS (ESI) m/z 289.7 (M+H$^+$); HPLC (Novapak 150×3.9 mm C-18 column: mobile phase: 35-90% acetonitrile/water with 0.1% TFA, at 2 mL/min over 2 min.) t 1.23 min.

Intermediate 122

4-(Benzo[1,3]dioxole-5-carbonyl)-piperidine-1-carboxylic acid tert-butyl ester

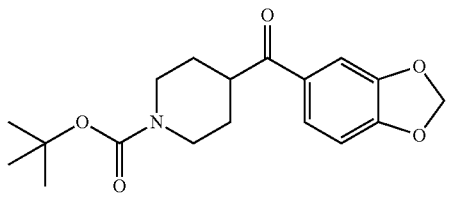 [SMILES: CC(C)(C)OC(=O)N1CCC(C(=O)c2ccc3c(c2)OCO3)CC1]

To a mixture of benzo[d][1,3]dioxol-5-ylboronic acid (0.39 g, 2.30 mmol), ligand TFP (0.07 g, 0.3 mmol), Pd$_2$dba$_3$ (0.14 g, 0.16 mmol), copper (I) thiophene-2-carboxylate (0.45 g, 2.4 mmol) was added a solution of 4-phenylsulfanyl-carbonyl-piperidine-1-carboxylic acid tert-butyl ester (0.5 g, 1.6 mmol) in 10 mL of THF while purging with N$_2$ at 50° C. After 18 hours the reaction mixture was diluted with ethyl acetate, filtered through celite then concentrated in vacuo. Purification by flash chromatography gave the title compound (0.52 g, 1.48 mmol). MS (ESI) m/z 333.8 (M+H$^+$); HPLC (Novapak 150×3.9 mm C-18 column: mobile phase: 35-90% acetonitrile/water with 0.1% TFA, at 2 mL/min over 2 min.) t 1.52 min.

Intermediate 123

Benzo[1,3]dioxol-5-yl-piperidin-4-yl-methanone

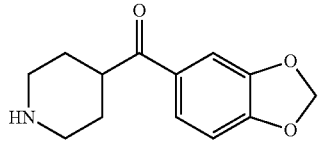

To a solution of 4-(benzo[1,3]dioxole-5-carbonyl)-piperidine-1-carboxylic acid tert-butyl ester (0.50 g, 1.5 mmol) in 10 mL of DCM, was added 2 mL of TFA. The reaction mixture was stirred at ambient temperature for 2.5 hours, then solvent was removed by reduced pressure to yield the title product (0.35 g, 1.35 mmol). MS (ESI) m/z 234.9 (M+H$^+$); HPLC (Novapak 150×3.9 mm C-18 column: mobile phase: 35-90% acetonitrile/water with 0.1% TFA, at 2 mL/min over 2 min.) t 1.11 min.

Intermediate 124

[4-(Benzo[1,3]dioxole-5-carbonyl)-piperidin-1-yl]-acetic acid ethyl ester

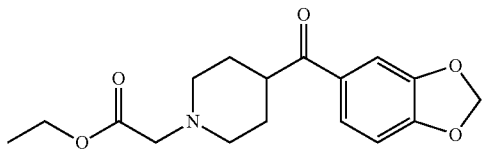 [SMILES: CCOC(=O)CN1CCC(C(=O)c2ccc3c(c2)OCO3)CC1]

To a solution of benzo[1,3]dioxol-5-yl-piperidin-4-yl-methanone (0.55 g, 2.40 mmol) in acetonitrile (10 mL) was added ethyl 2-bromoacetate (0.47 g, 2.8 mmol) and triethylamine (1.19 g, 11.8 mmol). The mixture was heated at 85° C. overnight, the solvent was evaporated under reduced pressure and purified via flash column chromatography (ethyl acetate:heptane) to provide product as a white solid (0.35 g, 1.04 mmol). MS (ESI) m/z 319.8 (M+H$^+$); HPLC (Novapak 150×3.9 mm C-18 column: mobile phase: 35-90% acetonitrile/water with 0.1% TFA, at 2 mL/min over 2 min.) t 1.26 min.

Intermediate 125

[4-(Benzo[1,3]dioxole-5-carbonyl)-piperidin-1-yl]-acetic acid

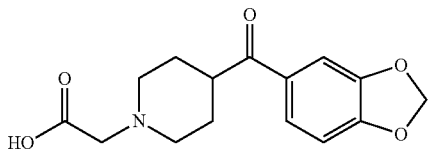 [SMILES: O=C(O)CN1CCC(C(=O)c2ccc3c(c2)OCO3)CC1]

To a solution of [4-(benzo[1,3]dioxole-5-carbonyl)-piperidin-1-yl]-acetic acid ethyl ester (0.35 g, 1.1 mmol in 6 mL of THF and 2 mL of methanol) was added LiOH.H$_2$O (0.23 g, 5.5 mmol in 3 mL of water) and the reaction mixture was stirred at ambient temperature for 1.5 hours. The solvent was removed in vacuo then diluted with 20 mL of water (pH 14). The residue was treated with 12 mL of 1 N HCl (pH 4), frozen at −78° C. and lyophilized for 24 hours to yield the title compound (0.30 g, 0.98 mmol). MS (ESI) m/z 292.9 (M+H$^+$); HPLC (Novapak 150×3.9 mm C-18 column: mobile phase: 35-90% acetonitrile/water with 0.1% TFA, at 2 mL/min over 2 min.) t 1.12 min.

Intermediate 126

Piperidine-4-carbothioic acid S-phenyl ester

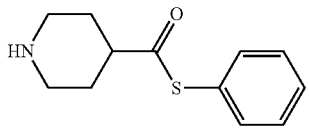 [SMILES: O=C(Sc1ccccc1)C1CCNCC1]

To a solution of 4-phenylsulfanylcarbonyl-piperidine-1-carboxylic acid tert-butyl ester (1.11 g, 3.45 mmol) in 10 mL of DCM, was added 2 mL of TFA. The reaction mixture was stirred at ambient temperature for 2.5 hours then solvent was removed by reduced pressure to yield the title product (0.75 g, 3.4 mmol). MS (ESI) m/z 221.8 (M+H$^+$); HPLC (Novapak 150×3.9 mm C-18 column: mobile phase: 35-90% acetonitrile/water with 0.1% TFA, at 2 mL/min over 2 min.) t 1.29 min.

Intermediate 127

(4-phenylsulfanylcarbonyl-piperidin-1-yl-acetic acid ethyl ester

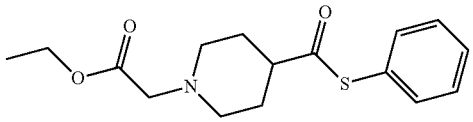 [SMILES: CCOC(=O)CN1CCC(C(=O)Sc2ccccc2)CC1]

To a solution of piperidine-4-carbothioic acid S-phenyl ester (0.65 g, 2.94 mmol) in acetonitrile (10 mL) was added ethyl 2-bromoacetate (0.49 g, 2.94 mmol) and triethylamine (1.49 g, 14.7 mmol). The mixture was heated at 85° C. overnight, the solvent was evaporated under reduced pressure and purified via flash column chromatography (ethyl acetate:heptane) to provide product as a white solid (0.81 g, 2.5 mmol). MS (ESI) m/z 307.8 (M+H$^+$); HPLC (Novapak 150×3.9 mm C-18 column: mobile phase: 35-90% acetonitrile/water with 0.1% TFA, at 2 mL/min over 2 min.) t 1.50 min

Intermediate 128

4-(4-Methoxy-3-methyl-benzoyl)-piperidin-1-yl]-acetic acid ethyl ester

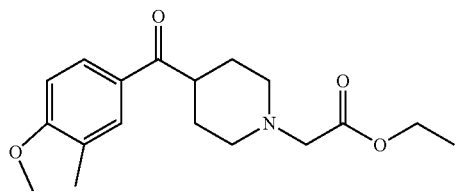 [SMILES: CCOC(=O)CN1CCC(C(=O)c2ccc(OC)c(C)c2)CC1]

To a mixture of 4-methoxy-3-methylphenylboronic acid (0.32 g, 1.95 mmol), ligand TFP (0.06 g, 0.26 mmol), Pd$_2$dba$_3$ (0.12 g, 0.13 mmol), copper (I) thiophene-2-carboxylate (0.37 g, 1.95 mmol) was added a solution of (4-phenylsulfanylcarbonyl-piperidin-1-yl)-acetic acid ethyl ester (0.4 g, 1.3 mmol) in 6 mL of DME, it was stirred at room temperature for 18 hours, the reaction mixture was diluted with ethyl acetate, filtered through celite then concentrated in vacuo. Purification by flash chromatography gave the title compound (0.20 g, 0.60 mmol). MS (ESI) m/z 319.8 (M+H$^+$); HPLC (Novapak 150×3.9 mm C-18 column: mobile phase: 35-90% acetonitrile/water with 0.1% TFA, at 2 mL/min over 2 min.) t 1.36 min.

Intermediate 129

[4-(4-Methoxy-3-methyl-benzoyl)-piperidin-1-yl]-acetic acid

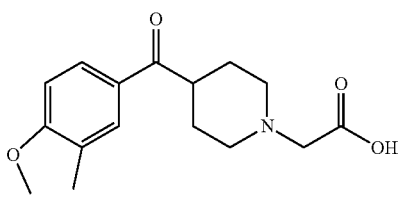 [SMILES: COc1ccc(C(=O)C2CCN(CC(=O)O)CC2)cc1C]

To a solution of 4-(4-methoxy-3-methyl-benzoyl)-piperidin-1-yl]-acetic acid ethyl ester (0.19 g, 0.60 mmol in 6 mL of THF and 2 mL of methanol) was added LiOH.H$_2$O (0.13 g, 3.0 mmol in 3 mL of water) and the reaction mixture was stirred at ambient temperature for 1.5 hours. The solvent was removed in vacuo then diluted with 20 mL of water (pH 14). The residue was treated with 12 mL of 1 N HCl (pH 4), frozen at −78° C. and lyophilized for 24 hours to yield the title compound (0.17 g, 0.54 mmol). MS (ESI) m/z 291.8 (M+H$^+$); HPLC (Novapak 150×3.9 mm C-18 column: mobile phase: 35-90% acetonitrile/water with 0.1% TFA, at 2 mL/min over 2 min.) t 1.58 min.

Intermediate 130

4-(3-Chloro-4-methoxy-benzoyl)-piperidine-1-carboxylic acid tert-butylester

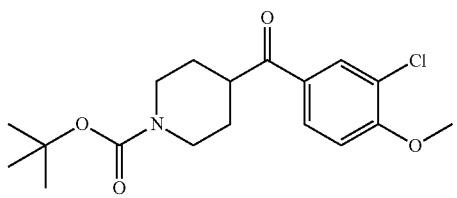 [SMILES: COc1ccc(C(=O)C2CCN(C(=O)OC(C)(C)C)CC2)cc1Cl]

To a mixture of 3-chloro-4-methoxyphenylboronic acid (0.87 g, 4.67 mmol), ligand TFP (0.14 g, 0.6 mmol), Pd$_2$dba$_3$ (0.29 g, 0.31 mmol), copper (I) thiophene-2-carboxylate (0.89 g, 4.7 mmol) was added a solution of 4-phenylsulfanyl-carbonyl-piperidine-1-carboxylic acid tert-butyl ester (1.0 g, 3.1 mmol) in 10 mL of THF while purging with N$_2$ at 50° C. After 18 hours the reaction mixture was diluted with ethyl acetate, filtered through celite then concentrated in vacuo. Purification by flash chromatography gave the title compound (1.02 g, 2.74 mmol). MS (ESI) m/z 354.0 (M+H$^+$); HPLC (Novapak 150×3.9 mm C-18 column: mobile phase: 35-90% acetonitrile/water with 0.1% TFA, at 2 mL/min over 2 min.) t 1.42 min.

Intermediate 131

(3-Chloro-4-methoxy-phenyl)-piperidin-4-yl-methanone

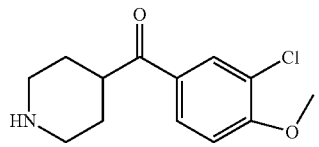 [SMILES: COc1ccc(C(=O)C2CCNCC2)cc1Cl]

To a solution of 4-(3-chloro-4-methoxy-benzoyl)-piperidine-1-carboxylic acid tert-butylester (1.1 g, 3.1 mmol) in 20 mL of 6N HCl, the reaction mixture was stirred at ambient temperature for 18 hours, then solvent was removed by reduced pressure to yield the title product (0.75 g, 2.8 mmol). MS (ESI) m/z 254.0 (M+H$^+$); HPLC (Novapak 150×3.9 mm C-18 column: mobile phase: 35-90% acetonitrile/water with 0.1% TFA, at 2 mL/min over 2 min.) t 1.39 min.

Intermediate 132

[4-(3-Chloro-4-methoxy-benzoyl)-piperidin-1-yl]-acetic acid ethyl ester

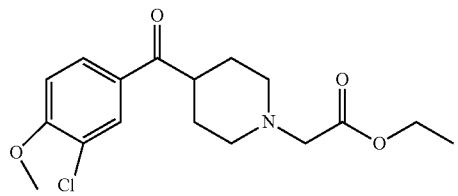 [SMILES: CCOC(=O)CN1CCC(C(=O)c2ccc(OC)c(Cl)c2)CC1]

To a solution of (3-chloro-4-methoxy-phenyl)-piperidin-4-yl-methanone (0.80 g, 3.15 mmol) in acetonitrile (10 mL) was added ethyl 2-bromoacetate (0.63 g, 3.8 mmol) and triethylamine (1.60 g, 15.8 mmol). The mixture was heated at 85° C. overnight, the solvent was evaporated under reduced pressure and purified via flash column chromatography (ethyl acetate: heptane) to provide product as a white solid (0.76 g, 2.1 mmol). MS (ESI) m/z 340.0 (M+H$^+$); HPLC (Novapak 150× 3.9 mm C-18 column: mobile phase: 35-90% acetonitrile/water with 0.1% TFA, at 2 mL/min over 2 min.) t 0.98 min.

Intermediate 133

[4-(3-Chloro-4-methoxy-benzoyl)-piperidin-1-yl]-acetic acid

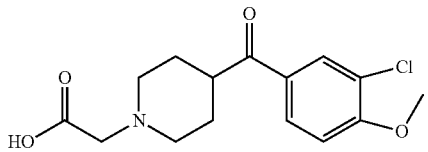 [SMILES: COc1ccc(C(=O)C2CCN(CC(=O)O)CC2)cc1Cl]

To a solution of [4-(3-chloro-4-methoxy-benzoyl)-piperidin-1-yl]-acetic acid ethyl ester (0.76 g, 2.24 mmol in 6 mL of THF and 2 mL of methanol) was added LiOH.H$_2$O (0.47 g, 11.2 mmol in 3 mL of water) and the reaction mixture was stirred at ambient temperature for 1.5 hours. The solvent was removed in vacuo then diluted with 20 mL of water (pH 14). The residue was treated with 12 mL of 1 N HCl (pH 4), frozen at −78° C. and lyophilized for 24 hours to yield the title compound (0.70 g, 2.1 mmol). MS (ESI) m/z 312.4 (M+H⁺); HPLC (Novapak 150×3.9 mm C-18 column: mobile phase: 35-90% acetonitrile/water with 0.1% TFA, at 2 mL/min over 2 min.) t 1.81 min.

Intermediate 134

4-(4-Ethoxy-3-fluoro-benzoyl)-piperidine-1-carboxylic acid tert-butyl ester

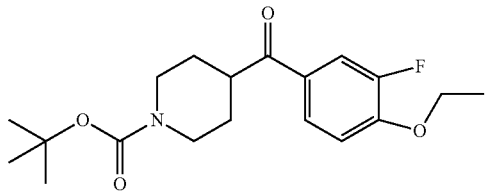 [SMILES: CCOc1ccc(C(=O)C2CCN(C(=O)OC(C)(C)C)CC2)cc1F]

To a mixture of 4-ethoxy-3-fluorophenylboronic acid (0.86 g, 4.67 mmol), ligand TFP (0.144 g, 0.62 mmol), Pd₂dba₃ (0.29 g, 0.31 mmol), copper (I) thiophene-2-carboxylate (0.89 g, 4.7 mmol) was added a solution of 4-phenylsulfanyl-carbonyl-piperidine-1-carboxylic acid tert-butyl ester (1.0 g, 3.11 mmol) in 10 mL of THF while purging with N₂ at 50° C. After 18 hours the reaction mixture was diluted with ethyl acetate, filtered through celite then concentrated in vacuo. Purification by flash chromatography gave the title compound (0.95 g, 2.57 mmol). MS (ESI) m/z 352.0 (M+H⁺); HPLC (Novapak 150×3.9 mm C-18 column: mobile phase: 35-90% acetonitrile/water with 0.1% TFA, at 2 mL/min over 2 min.) t 1.42 min.

Intermediate 135

(4-Ethoxy-3-fluoro-phenyl)-piperidin-4-yl-methanone

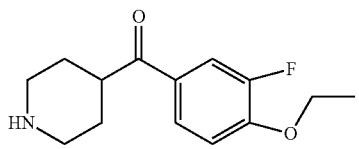 [SMILES: CCOc1ccc(C(=O)C2CCNCC2)cc1F]

To a solution of 4-(4-ethoxy-3-fluoro-benzoyl)-piperidine-1-carboxylic acid tert-butyl ester (0.95 g, 2.70 mmol) in 10 mL of DCM, was added 2 mL of TFA. The reaction mixture was stirred at ambient temperature for 2.5 hours, and then solvent was removed by reduced pressure to yield the title product (0.65 g, 2.46 mmol). MS (ESI) m/z 252.0 (M+H⁺); HPLC (Novapak 150×3.9 mm C-18 column: mobile phase: 35-90% acetonitrile/water with 0.1% TFA, at 2 mL/min over 2 min.) t 1.43 min.

Intermediate 136

[4-(4-Ethoxy-3-fluoro-benzoyl)-piperidin-1-yl]-acetic acid ethyl ester

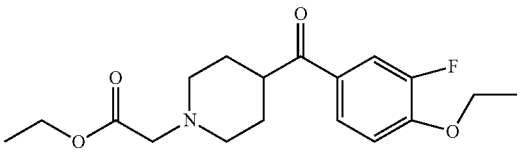 [SMILES: CCOC(=O)CN1CCC(C(=O)c2ccc(OCC)c(F)c2)CC1]

To a solution of (4-ethoxy-3-fluoro-phenyl)-piperidin-4-yl-methanone (0.65 g, 2.59 mmol) in acetonitrile (10 mL) was added ethyl 2-bromoacetate (0.52 g, 3.10 mmol) and triethylamine (1.31 g, 12.9 mmol). The mixture was heated at 85° C. overnight, the solvent was evaporated under reduced pressure and purified via flash column chromatography (ethyl acetate: heptane) to provide product as a white solid (0.61 g, 1.8 mmol). MS (ESI) m/z 338.0 (M+H⁺); HPLC (Novapak 150×3.9 mm C-18 column: mobile phase: 35-90% acetonitrile/water with 0.1% TFA, at 2 mL/min over 2 min.) t 1.18 min.

Intermediate 137

[4-(4-Ethoxy-3-fluoro-benzoyl)-piperidin-1-yl]-acetic acid

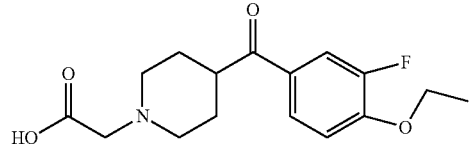 [SMILES: CCOc1ccc(C(=O)C2CCN(CC(=O)O)CC2)cc1F]

To a solution of [4-(4-ethoxy-3-fluoro-benzoyl)-piperidin-1-yl]-acetic acid ethyl ester (0.19 g, 0.56 mmol in 6 mL of THF and 2 mL of methanol) was added LiOH.H₂O (0.12 g, 2.8 mmol in 3 mL of water) and the reaction mixture was stirred at ambient temperature for 1.5 hours. The solvent was removed in vacuo then diluted with 20 mL of water (pH 14). The residue was treated with 12 mL of 1 N HCl (pH 4), frozen at −78° C. and lyophilized for 24 hours to yield the title compound (0.17 g, 0.55 mmol,). MS (ESI) m/z 310.4 (M+H⁺); HPLC (Novapak 150×3.9 mm C-18 column: mobile phase: 35-90% acetonitrile/water with 0.1% TFA, at 2 mL/min over 2 min.) t 1.86 min.

Intermediate 138

4-(4-Benzyloxy-benzoyl)-piperidine-1-carboxylic acid tert-butyl ester

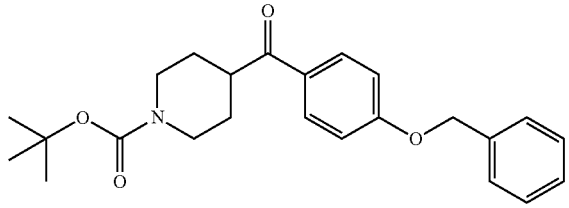 [SMILES: CC(C)(C)OC(=O)N1CCC(C(=O)c2ccc(OCc3ccccc3)cc2)CC1]

To 4-benzyloxybromobenzene (3.9 g, 14.7 mmol) in THF (50 mL) at −78° C. was added a 1.6 M solution of n-butyl-ithium in THF (9.18 mL, 14.7 mmol) and stirred at the same temperature for 30 minutes. A solution of 4-(methoxy-methyl-carbomoyl)-piperidine-1-carboxylic acid tert-butyl ester (2.0 g, 7.34 mmol) in THF (20 mL) was then added. The reaction was then allowed to warm to room temperature and then stirred 1 hour at 60° C. The reaction was quenched by adding a saturated solution of sodium bicarbonate (50 mL). The organic phase was then extracted 3×50 mL times with ethyl acetate. The combined organic phases were then dried on MgSO$_4$. The crude material was then purified on silica gel using a gradient from 0 to 40% ethyl acetate in heptane over 20 minutes to afford title compound (2.18 g). $^1$H NMR (400 MHz, CDC$_3$) δ: 7.95 (d, J=8.0 Hz, 2H), 7.47-7.35 (m, 5H), 7.04 (d, J=8.0 Hz, 2H), 5.16 (s, 2H), 4.24-4.12 (m, 2H), 3.41-3.33 (m, 1H), 2.97-2.85 (m, 2H), 1.89-1.68 (m, 4H), 1.49 (s, 9H). LRMS m/z: ES+=339.7 (M-tert-butyl+H) and 295.7 (M-BOC+H), retention time 1.98.

Intermediate 139

(4-Benzyloxy-phenyl)-piperidin-4-yl-methanone

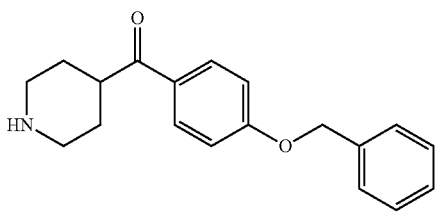 [SMILES: O=C(c1ccc(OCc2ccccc2)cc1)C1CCNCC1]

The a solution of 4-(4-benzyloxy-benzoyl)-piperidine-1-carboxylic acid tert-butyl ester (313 mg, 0.79 mmol) in dichloromethane (10 mL) was added TFA (0.61 mL, 7.9 mmol). The reaction was stirred for 3 hours and then the solvent removed under vacuum and placed under high vacuum to afford the title compound (234 mg). LRMS m/z: ES+=295.9 (M+H), retention time 1.18.

Intermediate 140

[4-(4-Benzyloxy-benzoyl)-piperidin-1-yl]-acetic acid ethyl ester

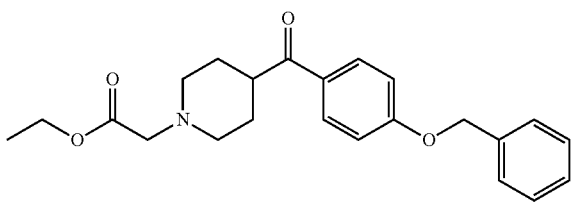 [SMILES: CCOC(=O)CN1CCC(C(=O)c2ccc(OCc3ccccc3)cc2)CC1]

To a solution of 4-benzyloxy-phenyl)-piperidin-4-yl-methanone (234 mg, 0.79 mmol) in acetonitrile (10 mL) was added ethyl bromoacetate (0.11 mL, 0.99 mmol) and triethylamine (0.55 mL, 3.96 mmol). The reaction was then stirred at 80° C. for 16 hours. The solvent was removed under vacuum and the crude material was loaded on silica gel and purified using a gradient from 0 to 10% methanol in dichloromethane over 20 minutes to afford the title compound (180 mg). $^1$H NMR (400 MHz, CDC$_3$) δ: 7.94 (d, J=8.0 Hz, 2H), 7.47-7.34 (m, 5H), 7.03 (d, J=8.0 Hz, 2H), 5.16 (s, 2H), 4.22 (q, J=7.1 and 6.4 Hz, 2H), 3.30 (s, 2H), 3.27-3.13 (m, 1H), 3.09-2.99 (m, 2H), 2.52-2.39 (m, 2H), 2.01-1.82 (m, 4H), 1.31 (t, J=7.2 Hz, 3H). LRMS m/z: ES+=382.5 (M+H), retention time=0.86.

Intermediate 141

[4-(4-Benzyloxy-benzoyl)-piperidin-1-yl]-acetic acid

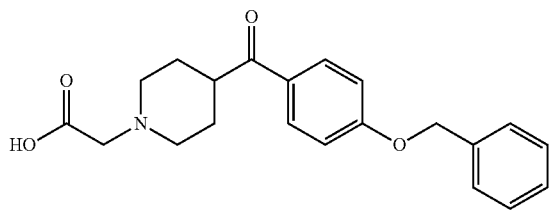 [SMILES: O=C(O)CN1CCC(C(=O)c2ccc(OCc3ccccc3)cc2)CC1]

To a solution of [4-(4-benzyloxy-benzoyl)-piperidin-1-yl]-acetic acid ethyl ester (180 mg, 0.47 mmol) in water (2 mL) and ethanol (2 mL) was added a 4N solution of NaOH (0.24 mL, 0.94 mmol). The reaction was heated up to 40° C. for 3 hours. The reaction was acidified to pH 3 using 1N HCl, then the solvent was then evaporated under vacuum to afford the crude title compound (260 mg). LRMS m/z: ES+=354.4 (M+H), retention time 1.11.

Intermediate 142

[4-(4-But-2-ynyloxy-benzoyl)-piperidin-1-yl]-acetic acid

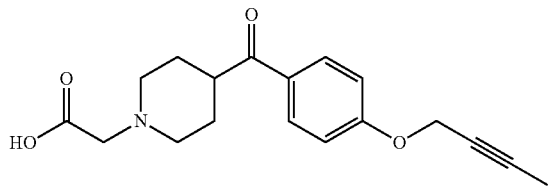 [SMILES: CC#CCOc1ccc(C(=O)C2CCN(CC(=O)O)CC2)cc1]

To a solution of [4-(4-fluoro-benzoyl)-piperidin-1-yl]-acetic acid (561 mg, 2.11 mmol) in water (10 mL) and was added 2-butyn-1-ol (3.71 g, 52.9 mmol) followed by a solution of 4N NaOH (3.44 mL, 13.8 mmol). The reaction was heated up to 80° C. for 72 hours. The reaction was acidified using 2N HCl to pH 5, then the solvent was then removed under vacuum to afford the crude title compound (2.0 g). LRMS m/z: ES+=315.9 (M+H), retention time 1.52.

Intermediate 143

(2-Methoxy-ethyl)-carbamic acid tert-butyl ester

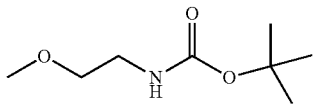

A mixture of 2-methoxyethanamine (5 g, 67 mmol), di-tert-butyl dicarbonate (14.67 g, 67.2 mmol) and triethylamine (9.3 mL, 67.2 mmol) was stirred for 8 h at room temperature. The solution was concentrated in vacuo to approximately half of the original volume then ethyl acetate and water were added. The organic layer was washed with water (2×200 mL), then brine (100 mL); the organic layers were combined, dried over Na₂SO₄ and the solvent was evaporated in vacuo to yield the title compound as an yellow oil (9.6 g), which was used without further purification. ¹H NMR (400 MHz, Chloroform-d) δ ppm 4.85-4.95 (br. s., 1H) 3.41-3.49 (m, 2H) 3.37 (s, 3H) 3.26-3.35 (m, 2H) 1.46 (s, 9H). MS (m/z, MH+ minus t-butyl group): 120.2

Intermediate 144

(2-Methoxy-ethyl)-(4-oxo-3,5,7,8-tetrahydro-4H-pyrano[4,3-d]pyrimidin-2-ylmethyl)-carbamic acid tert-butyl ester

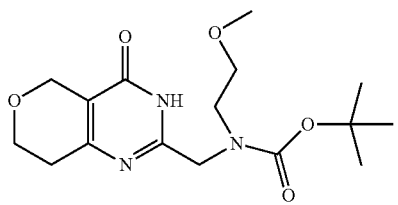 [SMILES: COCCN(Cc1nc2c(c(=O)[nH]1)COCC2)C(=O)OC(C)(C)C]

To a solution of tert-butyl 2-methoxyethylcarbamate (185 mg, 1.06 mmol) in anhydrous tetrahydrofuran (5 mL) was added sodium hydride (95%, 127 mg, 4.28 mmol) portionwise slowly, followed by 2-(chloromethyl)-7,8-dihydro-3H-pyrano[4,3-d]pyrimidin-4(5H)-one (212 mg, 1.6 mmol). The reaction mixture was stirred for 48 h. The reaction was quenched with water (approximately 3 mL) and the solvent evaporated. The residue was re-dissolved in acetonitrile and purified by column chromatography (100% dichloromethane for 5 min, then slow gradient up to 15% methanol in dichloromethane). The resulting clear oil was dissolved with 0.5 mL of acetonitrile and heated in vacuo to give the title compound as a white solid (179 mg). ¹H NMR (400 MHz, chloroform-d) δ ppm 4.60 (s, 2H) 4.21-4.34 (m, 2H) 3.91-4.01 (m, 3H) 3.66-3.79 (m, 2H) 3.51-3.66 (m, 6H) 2.71-2.80 (m, 2H) 1.48 (s, 3H) 1.35 (s, 6H). MS (m/z, MH+): 340.4

Intermediate 145

2-[(2-Methoxy-ethylamino)-methyl]-3,5,7,8-tetrahydro-pyrano[4,3-d]pyrimidin-4-one

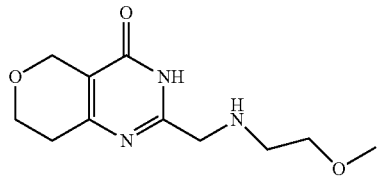 [SMILES: COCCNCc1nc2c(c(=O)[nH]1)COCC2]

To a solution of tert-butyl 2-methoxyethyl((4-oxo-4,5,7,8-tetrahydro-3H-pyrano[4,3-d]pyrimidin-2-yl)methyl)carbamate (257 mg, 0.545 mmol) in dioxane (5 mL) was added hydrochloric acid (4M in dioxane, 0.818 mL, 3.3 mmol) and the solution was stirred for 8 h. The precipitate was filtered and washed with ether. The residue was re-dissolved in ether, and stirred overnight (8 h) in ether. The precipitate was filtered and washed with ether to yield the title compound as a hydrochloride salt (107 mg). ¹H NMR (400 MHz, MeOD) δ ppm 4.50 (s, 2H) 4.27 (s, 2H) 3.90-4.03 (m, 3H) 3.66-3.77 (m, 2H) 3.43 (s, 3H) 3.35-3.41 (m, 3H) 2.74 (s, 2H). MS (m/z, MH+): 239.3

Intermediate 146 tert-butyl 4-(hydrazinecarbonyl)piperidine-1-carboxylate

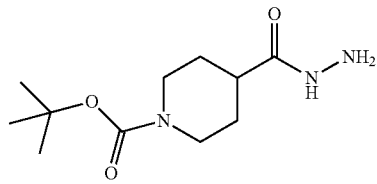 [SMILES: CC(C)(C)OC(=O)N1CCC(C(=O)NN)CC1]

To a stirred solution of 1-tert-butyl 4-ethylpiperidine-1,4-dicarboxylate (10 g, 38.9 mmol, 1.0 eq) in EtOH (100 mL) was added hydrazine hydrate (18.67 g, 389 mmol, 10 eq.) and the mixture was refluxed for 8 h. The reaction was cooled to room temperature and upon evaporation of the solvent gave a viscous liquid which was redissolved in CH₂Cl₂, washed with water (3×50 mL), then brine (50 mL). The organic layers were combined, dried over Na₂SO₄ and the solvent evaporated, leaving an yellowish oil, which upon addition of a few drops of ACN and re-evaporated yielded the title compound (8.6 g, 35.3 mmol). 1H NMR (400 MHz, MeOD) δ ppm 4.09 (d, J=13.14 Hz, 2H) 2.70-2.85 (br. s., 2H) 2.23-2.43 (m, 1H) 1.66-1.77 (m, 2H) 1.49-1.66 (m, 2H) 1.40-1.49 (m, 9H). MS (m/z, MH−): 242.2

Intermediate 147 tert-butyl 4-(5-(4-fluorophenyl)-1,3,4-oxadiazol-2-yl)piperidine-1-carboxylate

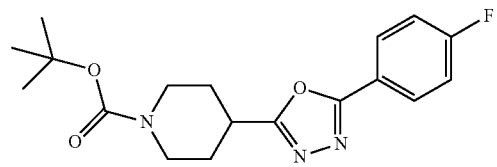 [SMILES: CC(C)(C)OC(=O)N1CCC(c2nnc(-c3ccc(F)cc3)o2)CC1]

A solution of tert-butyl 4-(hydrazinecarbonyl)piperidine-1-carboxylate (512 mg, 2.1 mmol) and benzimidic acid ethyl ester hydrochloride (471 mg, 2.3 mmol) in ethanol (25 mL) was refluxed for 24 h. The precipitate was filtered off, washed with acetonitrile, and the mother liquor was evaporated to give an oily pink residue, which was purified by column chromatography (0% heptanes to 50% ethyl acetate-heptanes gradient) to yield the title compound as a waxy solid (210 mg). ¹H NMR (400 MHz, chloroform-d) δ ppm 7.94-8.15 (m, 2H) 7.22 (s, 2H) 4.05-4.26 (m, 2H) 3.08-3.26 (m, 1H) 2.90-3.08 (m, 2H) 2.06-2.22 (m, 2H) 1.80-2.00 (m, 2H) 1.50 (s, 9H); MS (m/z, MH+): 348.3

Intermediate 148

4-[5-(4-Fluoro-phenyl)-[1,3,4]oxadiazol-2-yl]-piperidine

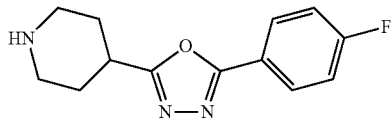 [SMILES: Fc1ccc(-c2nnc(C3CCNCC3)o2)cc1]

To a solution of tert-butyl 4-(5-(4-fluorophenyl)-1,3,4-oxadiazol-2-yl)piperidine-1-carboxylate (210 mg, 0.605 mmol) in dioxane (1 mL) was added 4N HCl in dioxane (0.756 mL, 3.0 mmol) and the mixture was stirred for 48 h. 1N NaOH (2.4 mL, 2.4 mmol) was added to neutralize the mixture. The solvent was evaporated, ether was added to the resulting white precipitate and the mixture sonicated. This white precipitate was filtered, washed with ether to give the title compound as a white powder as a NaCl salt (171 mg) and used without further purification. $^1$H NMR (400 MHz, chloroform-d) δ ppm 8.00-8.16 (m, 2H) 7.24-7.41 (m, 2H) 3.42-3.58 (m, 3H) 3.15-3.29 (m, 3H) 2.31-2.53 (m, 2H) 2.11 (m, 2H); MS (m/z, MH+): 248.3

Intermediate 149

{4-[5-(4-Fluoro-phenyl)-[1,3,4]oxadiazol-2-yl]-piperidin-1-yl}-acetic acid methyl ester

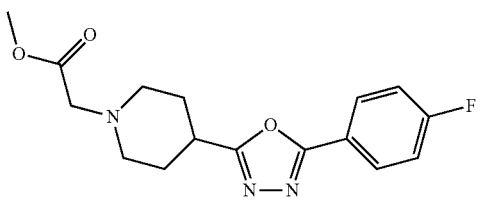 [SMILES: COC(=O)CN1CCC(c2nnc(-c3ccc(F)cc3)o2)CC1]

To a solution of 2-(4-fluorophenyl)-5-(piperidin-4-yl)-1,3,4-oxadiazole (160 mg, 0.55 mmol) in acetonitrile (15 mL) was added triethylamine (0.192 mL, 1.4 mmol), then methyl 2-bromoacetate (0.066 mL, 0.715 mmol). The mixture was stirred overnight at room temperature for 8 h. The white precipitate was filtered, washed with acetonitrile, then ether. The mother liquor which contained the desired product was evaporated yielding the title compound as a white solid (100 mg) which was used without further purification. $^1$H NMR (400 MHz, chloroform-d) δ ppm 8.03 (dd, J=9.09, 5.05 Hz, 2H) 7.19 (t, J=8.59 Hz, 2H) 3.74 (s, 3H) 3.30 (s, 2H) 2.93-3.10 (m, 3H) 2.35-2.54 (m, 2H) 2.12 (dd, 4H). MS (m/z, MH+): 320.5

Intermediate 150

{4-[5-(4-Fluoro-phenyl)-[1,3,4]oxadiazol-2-yl]-piperidin-1-yl}acetic acid

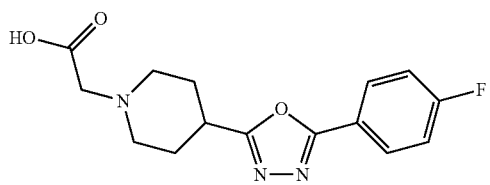 [SMILES: O=C(O)CN1CCC(c2nnc(-c3ccc(F)cc3)o2)CC1]

To a solution of methyl 2-(4-(5-(4-fluorophenyl)-1,3,4-oxadiazol-2-yl)piperidin-1-yl)acetate (97.8 mg, 0.306 mmol) in ethanol (1 mL) was added 2 N NaOH (1 mL). The cloudy reaction suspension was stirred for 4 h until LCMS confirmed the reaction was complete. The mixture was treated with 0.7 mL 1 N HCl dropwise until pH 7. The solvent was evaporated and the residue triturated with ether. The precipitate was filtered, washed with ether and dried under high vacuum, yielding the title compound as a white solid as a NaCl salt (130 mg) which was used without further purification. $^1$H NMR (400 MHz, chloroform-d) δ ppm 8.10 (dd, J=9.03, 5.02 Hz, 2H) 7.33 (t, J=8.78 Hz, 2H) 3.47 (br. s., 4H) 3.30 (s, 2H) 3.43-3.55 (br. s., 2H) 2.28-2.45 (m, 2H) 2.07-2.28 (m, 2H). MS (m/z, MH+): 306.3

Example 1

2-(4-(4-Fluorobenzoyl)piperidin-1-yl)-N-((4-oxo-4,5,7,8-tetrahydro-3H-pyrano[4,3-d]pyrimidin-2-yl)methyl)acetamide

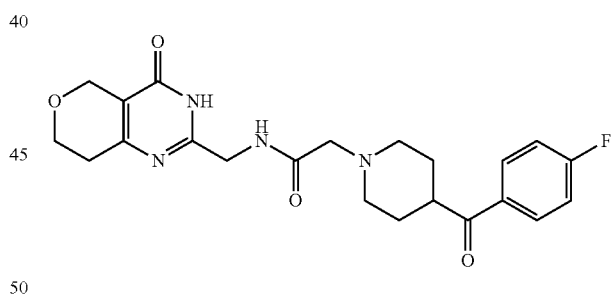

To a solution of 2-aminomethyl-3,5,7,8-tetrahydro-pyrano[4,3-d]pyrimidin-4-one (1.7 g, 9.6 mmol) and 2-(4-(4-fluorobenzoyl)piperidin-1-yl)acetic acid (2.7 g, 10 mmol) in dichloromethane (50 mL) was added 1-(3-dimethylaminopropyl)-3-ethylcarbodiimide hydrochloride (2.2 g, 11 mmol), 1-hydroxybenzotriazole (1.5 g, 9.6 mmol) and triethylamine (4.0 mL, 29 mmol). The mixture was stirred at ambient temperature for 24 hours. The reaction mixture was washed with ammonium chloride solution, concentrated in vacuo and purified via flash column chromatography (ethyl acetate:hexane, 10:90 to 100:0, methanol:dichloromethane, 1:99 to 10:90) to provide the title compound (2.2 g, 54% yield). $^1$H NMR (400 MHz, CDC$_3$) δ 11.12 (s, 1H), 8.07 (s, 1H), 7.99 (dd, J=9.0, 5.5 Hz, 2H), 7.18 (t, J=8.5 Hz, 2H), 4.58 (s, 2H), 4.41 (d, J=6.0 Hz, 2H), 3.97 (t, J=5.5 Hz, 2H), 3.22-3.35 (m, 1H), 3.10-3.22 (m, 2H), 2.94-3.07 (m, 2H), 2.66-2.75 (m, 2H), 2.31-2.48 (m, 2H), 1.80-1.99 (m, 4H). HRMS calculated for C$_{22}$H$_{23}$N$_4$O$_4$ 429.1938. found (ESI, [M+H]⁺), 429.1925. MS m/z 429.3 (M+1), retention time=1.28 min.

Example 2

2-[4-(4-Chloro-benzoyl)-piperidin-1-yl]-N-(4-oxo-3,5,7,8-tetrahydro-4H-pyrano[4,3-d]-pyrimidin-2-ylmethyl)-acetamide

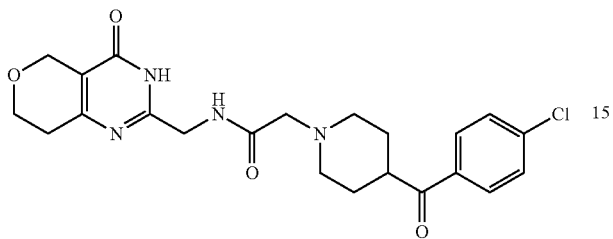

A solution of [4-(4-chloro-benzoyl)-piperidin-1-yl]-acetic acid (0.1 g, 0.36 mmol), EDCl (0.08 g, 0.43 mmol), HOBT (0.06 g, 0.43 mmol) and triethylamine (0.14 g, 1.4 mmol) in 20 mL of DMF, was stirred at ambient temperature for 20 min. then added 2-aminomethyl-3,5,7,8-tetrahydro-pyrano[4,3-d]pyrimidin-4-one (0.08 g, 0.43 mmol). The reaction mixture was stirred at ambient temperature for 15 hours. The reaction mixture was diluted with 50 mL of water, extracted with DCM (20 mL). The combined organic layers were washed with saturated aqueous NaHCO₃ solution. The organic layer was dried over Na₂SO₄, filtered and concentrated in vacuo to provide crude product. Purification by flash chromatography gave the title compound (37.2 mg, 0.084 mmol, 24% yield) as a white solid. MS (ESI) m/z 445.2 (M+H⁺); HPLC (Novapak 150×3.9 mm C-18 column: mobile phase: 35-90% acetonitrile/water with 0.1% TFA, at 2 mL/min over 2 min.) t 1.12 min. ¹H NMR (400 MHz, DMSO-d₆) δ ppm 1.61-1.83 (m, 6H), 2.21-2.30 (m, 1H), 2.50 (br. s., 2H), 2.94 (br. s., 1H), 2.99 (s, 2H), 3.32 (s, 2H), 3.35-3.46, (m, 1H), 3.83 (t, J=5.31 Hz, 1H), 4.19 (d, J=6.06 Hz, 1H), 4.34 (s, 2H), 7.60 (d, J=8.59 Hz, 2H), 8.00 (d, J=8.59 Hz, 2H), 8.20 (s, 1H) 12.40 (s, 1H). HRMS calculated for C₂₂H₂₆ClN₄O₄: 445.1643 (M+H). found (ESI, [M+H]⁺): 445.1658.

Example 3

2-[4-(4-Isopropoxy-benzoyl)-piperidin-1-yl]-N-(4-oxo-3,5,7,8-tetrahydro-4H-pyrano[4,3-c]pyrimidin-2-ylmethyl)-acetamide

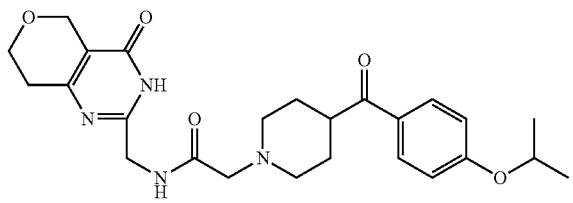 [SMILES: CC(C)Oc1ccc(C(=O)C2CCN(CC(=O)NCc3nc4c(c(=O)[nH]3)COCC4)CC2)cc1]

A solution of 4-(4-isopropoxy-benzoyl)-piperidin-1-yl]-acetic acid (0.1 g, 0.32 mmol), EDCl (0.08 g, 0.43 mmol), HOBT (0.06 g, 0.43 mmol) and triethylamine (0.14 g, 1.4 mmol) in 20 mL of DMF was stirred at ambient temperature for 20 min., then 2-aminomethyl-3,5,7,8-tetrahydro-pyrano[4,3-d]pyrimidin-4-one (0.08 g, 0.43 mmol) was added. The reaction mixture was stirred at ambient temperature for 15 hours. The reaction mixture was diluted with 50 mL of water, extracted with DCM (20 mL) and the combined organic layers were washed with saturated aqueous NaHCO₃ solution. The organic layer was dried over Na₂SO₄, filtered and concentrated in vacuo to provide crude product. Purification by flash chromatography gave the title compound (23.2 mg, 0.045 mmol, 14% yield) as a white solid. MS (ESI) m/z 469.5 (M+H⁺); HPLC (Novapak 150×3.9 mm C-18 column: mobile phase: 35-90% acetonitrile/water with 0.1% TFA, at 2 mL/min over 2 min.) t 1.31 min. ¹H NMR (400 MHz, DMSO-d₆) δ ppm 1.19-1.42 (m, 6H), 1.61-1.87 (m, 6H), 2.20-2.31 (m, 2H), 2.50 (br. s., 2H), 2.98 (br. s., 2H), 3.13-3.21 (m, 1H), 3.31 (br. s., 2H), 3.83 (d, 1H), 4.02-4.12 (m, 1H), 4.19 (br. s., 1H), 4.34 (br. s., 2H), 7.02 (d, 2H), 7.95 (d, 2H), 8.20 (s, 1H), 12.40 (s, 1H).

Example 4

2-[4-(4-Fluoro-benzoyl)-piperidin-1-yl]-N-(4-oxo-3,5,7,8-tetrahydro-4H-pyrano[4,3-c]pyrimidin-2-ylmethyl)-N—((R)-1-phenyl-ethyl)-acetamide

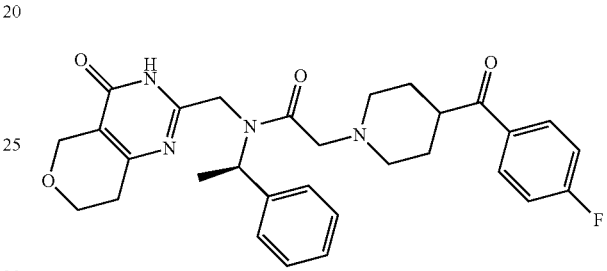

To 2-(4-(4-fluorobenzoyl)piperidin-1-yl)acetic acid (50 mg, 0.188 mmol) in DMF (1 mL) and diisoproplyethylamine (61 mg, 0.471 mmol) was added HATU (107 mg, 0.283 mmol) and the solution was stirred for 30 min. 2-[((R)-1-Phenyl-ethylamino)-methyl]-3,5,7,8-tetrahydro-pyrano[4,3-d]pyrimidin-4-one (20 mg, 0.29 mmol) in DMF (1 mL) was added and the reaction solution was stirred for 15 h. The product was purified directly on a Sunfire C18-5 μm (19×100 mm) column; eluting with 10% to 90% acetonitrile in water (0.1% TFA) over 10 min. Lyophilization afforded the title compound (50.7 mg, 42% yield). Exact mass calculated for C₃₀H₃₃FN₄O₄ 532.61. found 533.7 (ESI, M+H); ¹H NMR (600 MHz, DMSO-d₆) δ ppm 9.70 (br. s., 1H) 8.05-8.23 (m, 2H) 7.36-7.47 (m, 3H) 7.23-7.36 (m, 4H) 5.76-5.94 (m, 1H) 4.50-4.63 (m, 1H) 4.43 (dd, J=16.05, 3.21 Hz, 1H) 4.22-4.39 (m, 5H) 3.76-3.88 (m, 3H) 3.68-3.75 (m, 1H) 3.57-3.66 (m, 1H) 3.54 (d, J=11.71 Hz, 1H) 3.45 (d, J=11.33 Hz, 1H) 3.05-3.19 (m, 2H) 2.36-2.47 (m, 1H) 1.99-2.12 (m, 3H) 1.86-1.99 (m, 2H) 1.59-1.67 (m, 1H) 1.32-1.43 (m, 2H)

Example 5

N-Cyclopropylmethyl-2-[4-(4-methoxy-benzoyl)-piperidin-1-yl]-N-(4-oxo-3,5,7,8-tetrahydro-4H-pyrano[4,3-d]pyrimidin-2-ylmethyl)-acetamide

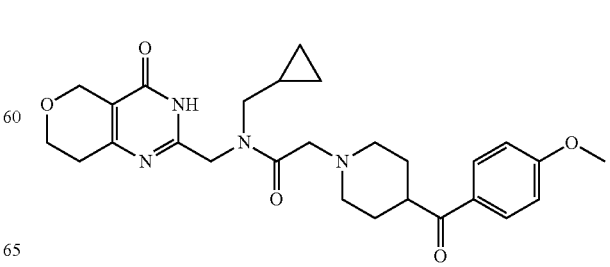

To a solution of [4-(4-methoxy-benzoyl)-piperidin-1-yl]-acetic acid (0.071 g, 0.26 mmol, 1 eq.) and DIEA (0.089 mL, 0.51 mmol, 2 eq.) in 2 mL of DMF was added HATU (0.107 g, 0.281 mmol, 1.1 eq.). The resulting mixture was stirred at room temperature for 30 min. 2-[(Cyclopropylmethyl-amino)-methyl]-3,5,7,8-tetrahydro-pyrano[4,3-d]pyrimidin-4-one (0.06 g, 0.26 mmol, 1 eq.) in 1 mL of DMF was added and the mixture was stirred at room temperature overnight. After 18 h, the reaction mixture was diluted with $H_2O$ (10 mL) and extracted with dichloromethane (3×50 mL). The combined organics were concentrated and purified by preparative HPLC (20-100% $CH_3CN/H_2O$ over 10 min with 0.1% TFA, sun fire C18 OBD 50×50 mm column with flow rate of 60 mL/min) to give the title compound as a white solid (0.03 g, 24%). $^1$H NMR (400 MHz, MeOD) δ ppm 7.94-8.07 (m, 2H), 6.98-7.10 (m, 2H), 4.64-4.70 (m, 1H), 4.54-4.60 (m, 1H), 4.44-4.52 (m, 2H), 4.28-4.37 (m, 1H), 3.94-3.99 (m, 1H), 3.91-3.95 (m, 2H), 3.88 (s, 3H), 3.67-3.80 (m, 2H), 3.40-3.61 (m, 1H), 3.33-3.40 (m, 2H), 3.09-3.27 (m, 2H), 2.50-2.72 (m, 2H), 1.92-2.26 (m, 4H), 0.83-1.15 (m, 1H), 0.12-0.67 (m, 4H). HRMS calculated for $C_{27}H_{35}N_4O_5$ 495.2607. found (ESI, [M+H]+) 495.2606. MS (ESI) m/z 495.3 $(M+H)^+$. Retention time: 2.89 min (5-95% $CH_3CN/H_2O$ over 7.75 min with 0.1% formic acid, Inertsil ODS3 100×3 mm C18 column with flow rate of 1.0 mL/min).

Alternate Procedure 1

To a well stirred suspension of 2-[(Cyclopropylmethyl-amino)-methyl]-3,5,7,8-tetrahydro-pyrano[4,3-d]pyrimidin-4-one (15.66 g, 57.6 mmol) in dichloromethane (600 mL) was added 2-(4-(4-methoxybenzoyl)piperidin-1-yl)acetic acid (16.45 g, 59.3 mmol), followed by triethylamine (24 mL, 173 mmol), 1H-benzo[d][1,2,3]triazol-1-ol hydrate (21.41 g, 140 mmol) and N1-((ethylimino)methylene)-N3,N3-dimethyl-propane-1,3-diamine hydrochloride (13.26 g, 69.2 mmol). The resulting yellow suspension was stirred for 12 h, filtered and then washed with water three times (250 mL, 150 mL, then 50 mL). The organic layer was washed twice with brine (50 mL), dried with $Na_2SO_4$, filtered and concentrated in vacuo (33.34 g). The residue was dissolved in 750 mL dichloromethane, and washed with a pH 9 $KHCO_3/K_2CO_3$ solution (2×100 mL). The organic layer was washed twice with brine (50 mL), dried with $Na_2SO_4$, filtered and concentrated in vacuo (23.4 g). The crude material was dissolved in approximately 25 mL MeOH resulting in an orange solution and placed in a freezer overnight to form a slurry. The mixture was filtered, washed with MeOH and dried in vacuo to yield 21.959 g of the title compound as a white solid. HRMS calculated for $C_{27}H_{34}N_4O_5$ 495.2607. found (ESI, [M+H]$^+$), 495.2607, retention time=3.717 min. CHN analysis: calculated (results). C, 65.57 (65.17), H, 6.93 (6.64), N, 11.33 (11.39).

Alternate Procedure 2

To [4-(4-methoxy-benzoyl)-piperidin-1-yl]-acetic acid (306 mg, 0.85 mmol) in DMF (3 mL) was added with HATU (485 mg, 1.28 mmol) and DIEA (0.37 mL, 275 mg, 2.12 mmol). This was sonicated, stirred for 30 min and then 2-[(cyclopropylmethyl-amino)-methyl]-3,5,7,8-tetrahydro-pyrano[4,3-d]pyrimidin-4-one (200 mg, 0.85 mmol) in 1 mL DMF was added to the mixture. Then it was stirred at room temperature for 16 hours and the mixture was concentrated to dryness. This was purified by silica gel column (eluted with 0-10% methanol in dichloromethane) followed by trituration with methanol to give a white solid as the title compound (93 mg, 0.19 mmol, 22% yield). m/z=495.3 (M+H).

Example 6

2-(4-(4-Methoxybenzoyl)piperidin-1-yl)-N-((4-oxo-4,5,6,7,8,9-hexahydro-3H-cyclohepta[d]pyrimidin-2-yl)methyl)acetamide

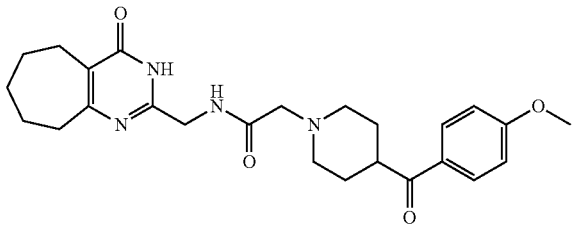 [SMILES: COc1ccc(C(=O)C2CCN(CC(=O)NCc3nc4c(c(=O)[nH]3)CCCCC4)CC2)cc1]

The title compound (89 mg, 44% yield) was prepared following the general procedure of Example 1 from 2-(4-(4-methoxybenzoyl)piperidin-1-yl)acetic acid (124 mg, 0.45 mmol) and 2-(aminomethyl)-6,7,8,9-tetrahydro-3H-cyclohepta[d]pyrimidin-4(5H)-one (87 mg, 0.45 mmol). $^1$H NMR (400 MHz, $CDC_3$) δ 11.36 (br. s., 1H), 8.01 (br. s., 1H), 7.83-7.89 (m, J=9.1 Hz, 2H), 6.85-6.91 (m, 2H), 4.30 (d, J=5.6 Hz, 2H), 3.81 (s, 3H), 3.12-3.29 (m, 1H), 2.97-3.12 (m, 2H), 2.92 (br. s., 2H), 2.55-2.83 (m, 4H), 2.30 (br. s., 2H), 1.67-1.94 (m, 6H), 1.40-1.67 (m, 4H). HRMS calculated for $C_{23}H_{32}N_4O_4$ 453.2502. found (ESI, [M+H]$^+$), 453.2509. Retention time=3.09.

Example 7

N-(Cyclopropylmethyl)-2-(4-(4-methoxybenzoyl)piperidin-1-yl)-N-((4-oxo-4,5,6,7,8,9-hexahydro-3H-cyclohepta[d]pyrimidin-2-yl)methyl)acetamide

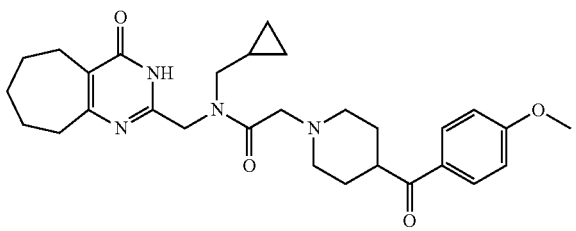 [SMILES: COc1ccc(C(=O)C2CCN(CC(=O)N(Cc3nc4c(c(=O)[nH]3)CCCCC4)CC3CC3)CC2)cc1]

The title compound (18 mg, 8% yield) was prepared following the general procedures of Example 1 from 2-(4-(4-methoxybenzoyl)piperidin-1-yl)acetic acid (124 mg, 0.45 mmol) and 2-((cyclopropylmethylamino)methyl)-6,7,8,9-tetrahydro-3H-cyclohepta[d]pyrimidin-4(5H)-one (104 mg, 0.45 mmol). $^1$H NMR (400 MHz, $CDC_3$) δ 7.85 (d, J=8.5 Hz, 2H), 6.70-6.97 (m, 2H), 4.41 (s, 1H), 4.34 (s, 1H), 3.68-3.91 (m, 3H), 3.41 (s, 3H), 3.33 (d, J=7.0 Hz, 1H), 3.07-3.29 (m, 4H), 2.91 (d, J=10.5 Hz, 2H), 2.57-2.79 (m, 4H), 2.50 (br. s., 1H), 2.12-2.37 (m, 1H), 2.04 (d, J=14.1 Hz, 2H), 1.76 (d, J=5.0 Hz, 4H), 1.36-1.65 (m, 1H), 0.75-1.04 (m, 1H), 0.46 (d, J=7.5 Hz, 1H), 0.26-0.41 (m, 1H), 0.15-0.26 (m, 1H), 0.12 (d, J=4.5 Hz, 1H). HRMS calculated for $C_{23}H_{38}N_4O_4$ 507.2971. found (ESI, [M+H]$^+$), 507.2975. Retention time=3.54.

Example 8

N-(Cyclopropylmethyl)-2-(4-(4-methoxybenzoyl)piperidin-1-yl)-N-((4-oxo-3,4,5,6,7,8-hexahydroquinazolin-2-yl)methyl)acetamide

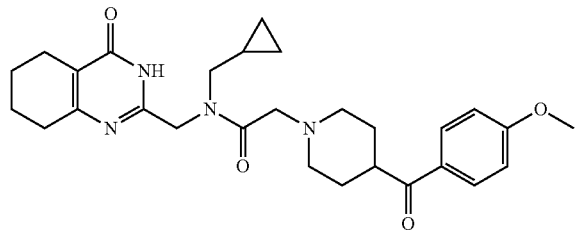 [SMILES: COc1ccc(C(=O)C2CCN(CC(=O)N(Cc3nc4c(c(=O)[nH]3)CCCC4)CC3CC3)CC2)cc1]

The title compound (26 mg, 1% yield) was prepared following the general procedure of Example 7 from 2-(4-(4-methoxybenzoyl)piperidin-1-yl)acetic acid and 2-[(cyclopropylmethyl-amino)-methyl]-5,6,7,8-tetrahydro-3H-quinazolin-4-one. $^1$H NMR (400 MHz, CD$_3$OD) δ 7.75-7.83 (m, J=9.1 Hz, 2H), 6.77-6.88 (m, J=9.1 Hz, 2H), 4.48 (s, 1H), 4.26-4.44 (m, 1H), 4.04-4.26 (m, 2H), 3.67 (s, 3H), 3.37-3.59 (m, 2H), 2.93-3.19 (m, 5H), 2.39 (t, J=5.6 Hz, 2H), 2.22 (t, J=5.8 Hz, 2H), 1.91 (br. s., 3H), 1.75-1.86 (m, 1H), 1.47-1.75 (m, 4H), 0.65-0.90 (m, 1H), 0.40 (q, J=6.1 Hz, 1H), 0.16-0.32 (m, 1H), 0.06-0.16 (m, 1H), −0.13-0.06 (m, 1H). HRMS calculated for C$_{28}$H$_{36}$N$_4$O$_4$ 493.2815. found (ESI, [M+H]$^+$), 493.2826. Retention time=3.50 min.

Example 9

2-(4-(4-Methoxybenzoyl)piperidin-1-yl)-N-((4-oxo-3,4,5,6,7,8-hexahydroquinazolin-2-yl)methyl)acetamide

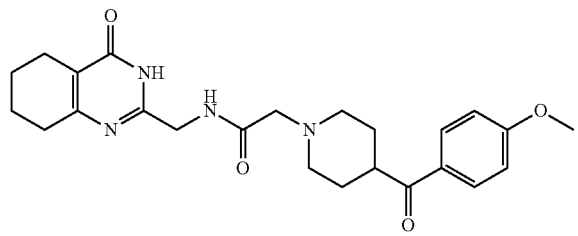 [SMILES: COc1ccc(C(=O)C2CCN(CC(=O)NCc3nc4c(c(=O)[nH]3)CCCC4)CC2)cc1]

The title compound (100 mg) was prepared following the general procedure of Example 1 from 2-(4-(4-methoxybenzoyl)piperidin-1-yl)acetic acid (265 mg, 0.67 mmol, 70% purity) and 2-(aminomethyl)-5,6,7,8-tetrahydroquinazolin-4(3H)-one (120 mg, 0.67 mmol). $^1$H NMR (400 MHz, CDC$_3$) δ 10.91 (br. s., 1H), 7.91 (br. s., 1H), 7.82-7.89 (m, 2H), 6.85-6.91 (m, J=8.6 Hz, 2H), 4.29 (d, J=6.1 Hz, 2H), 3.81 (s, 3H), 3.17 (d, J=6.6 Hz, 1H), 3.07 (br. s., 2H), 2.90 (br. s., 2H), 2.52 (t, J=6.1 Hz, 2H), 2.42 (t, J=6.1 Hz, 4H), 1.80 (br. s., 4H), 1.48-1.77 (m, 4H). HRMS calculated for C$_{24}$H$_{30}$N$_4$O$_4$ 439.2345. found (ESI, [M+H]$^+$), 439.2352. Retention time=2.84 min.

Example 10

2-(4-(4-Fluorobenzoyl)piperidin-1-yl)-N-((4-oxo-3,4,5,6,7,8-hexahydroquinazolin-2-yl)methyl)acetamide

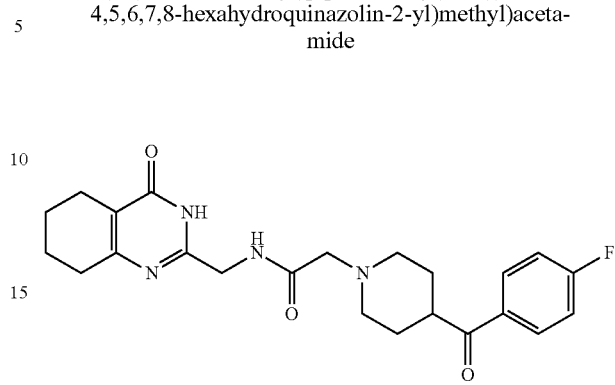

The title compound (14 mg) was prepared following the general procedure of Example 1 from 2-((4-fluorobenzylamino)methyl)-7,8-dihydro-3H-pyrano[4,3-d]pyrimidin-4(5H)-one (53 mg, 0.20 mmol) and 2-(aminomethyl)-5,6,7,8-tetrahydroquinazolin-4(3H)-one (120 mg, 0.67 mmol). $^1$H NMR (400 MHz, CDC$_3$) δ 11.31 (br. s., 1H), 8.08 (br. s., 1H), 7.99 (dd, J=8.8, 5.3 Hz, 2H), 7.17 (t, J=8.5 Hz, 2H), 4.39 (d, J=6.0 Hz, 2H), 3.20-3.39 (m, 1H), 3.17 (br. s., 2H), 3.02 (d, J=10.5 Hz, 2H), 2.61 (t, J=6.0 Hz, 2H), 2.50 (t, J=5.8 Hz, 2H), 2.39 (br. s., 2H), 1.89 (br. s., 4H), 1.57-1.87 (m, 4H). HRMS calculated for C$_{23}$H$_{27}$FN$_4$O$_3$ 427.2145. found (ESI, [M+H]$^+$), 427.2152. Retention time=2.89 min.

Example 11

2-(4-(4-Methoxybenzoyl)piperidin-1-yl)-N-((4-oxo-4,5,6,7-tetrahydro-3H-cyclopenta[d]pyrimidin-2-yl)methyl)acetamide

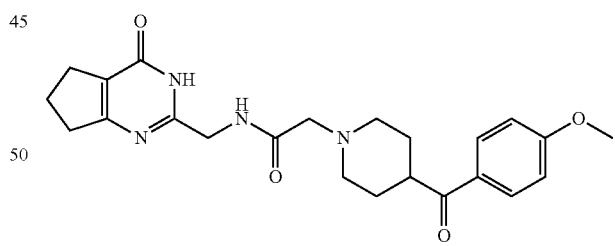

The title compound (70 mg) was prepared following the general procedure of Example 1 from 2-(4-(4-methoxybenzoyl)piperidin-1-yl)acetic acid (307 mg, 0.78 mmol, 70% purity) and 2-(aminomethyl)-6,7-dihydro-3H-cyclopenta[d]pyrimidin-4(5H)-one (128 mg, 0.78 mmol). $^1$H NMR (400 MHz, CDC$_3$) δ 10.58 (br. s., 1H), 8.06 (br. s., 1H), 7.95 (d, J=9.1 Hz, 2H), 6.98 (d, J=9.1 Hz, 2H), 4.41 (d, J=6.1 Hz, 2H), 3.90 (s, 3H), 3.28 (br. s., 3H), 3.02 (br. s., 2H), 2.70-2.95 (m, 4H), 2.43 (br. s., 2H), 2.09 (dq, J=7.8, 7.7 Hz, 2H), 1.91 (br. s., 4H). HRMS calculated for C$_{23}$H$_{28}$N$_4$O$_4$ 425.2189. found (ESI, [M+H]$^+$), 425.2180. Retention time=4.65 min.

Example 12

N-((4,5-Dimethyl-6-oxo-1,6-dihydropyrimidin-2-yl)methyl)-2-(4-(4-methoxybenzoyl)piperidin-1-yl)acetamide

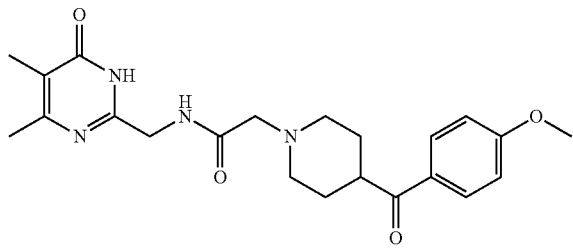

The title compound (183 mg) was prepared following the general procedure of Example 1 from 2-(4-(4-methoxybenzoyl)piperidin-1-yl)acetic acid (357 mg, 0.90 mmol, 70% purity) and 2-(aminomethyl)-5,6-dimethylpyrimidin-4(3H)-one (138 mg, 0.90 mmol). $^1$H NMR (400 MHz, DMSO-$d_6$) δ 12.21 (br. s., 1H), 8.20 (s, 1H), 7.96 (d, J=9.1 Hz, 2H), 7.02-7.06 (m, 2H), 4.14 (d, J=5.6 Hz, 2H), 3.84 (s, 3H), 2.86-3.08 (m, 4H), 2.25-2.39 (m, 2H), 2.22 (s, 1H), 2.16 (s, 3H), 1.88 (s, 3H), 1.63-1.82 (m, 4H). HRMS calculated for $C_{22}H_{28}N_4O_4$ 413.2189. found (ESI, [M+H]$^+$), 413.2195. Retention time=4.44 min.

Example 13

2-(4-(4-Fluorobenzoyl)piperidin-1-yl)-N-((4-oxo-4,5,7,8-tetrahydro-3H-pyrano[4,3-d]pyrimidin-2-yl)methyl)-N-(thiophen-2-ylmethyl)acetamide

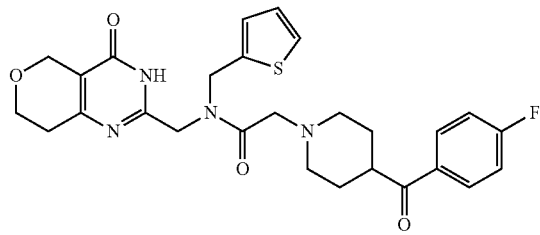 [SMILES: O=C(c1ccc(F)cc1)C1CCN(CC(=O)N(Cc2nc3c(c(=O)[nH]2)COCC3)Cc2cccs2)CC1]

The title compound (296 mg) was prepared following the general procedure of Example from 2-((thiophen-2-ylmethylamino)methyl)-7,8-dihydro-3H-pyrano[4,3-d]pyrimidin-4(5H)-one (710 mg, 2.3 mmol) and 2-(4-(4-fluorobenzoyl)piperidin-1-yl)acetic acid (720 mg, 2.7 mmol). $^1$H NMR (400 MHz, DMSO-$d_6$) δ 11.93 (s, 1H), 8.00 (d, J=8.8, 575 Hz, 2H), 7.38 (d, J=4.4 Hz, 1H), 7.28 (t, J=8.8 Hz, 2H), 7.00 (s, 1H), 6.95 (s, 1H), 4.85 (s, 2H), 4.47 (s, 2H), 4.38 (s, 2H), 3.85 (t, J=5.7 Hz, 2H), 3.18-3.45 (m, 2H), 2.80-3.12 (m, 3H), 2.53 (t, J=5.4 Hz, 2H), 2.29 (t, J=10.7 Hz, 2H), 1.67-1.87 (m, 2H), 1.42-1.63 (m, 2H). HRMS calculated for $C_{27}H_{29}FN_4O_4S$ 525.1972. found (ESI, [M+H]$^+$), 525.1968. MS m/z 525.2 (M+1), retention time=3.08 min.

Example 14

2-(4-(4-Fluorobenzoyl)piperidin-1-yl)-N-neopentyl-N-((4-oxo-4,5,7,8-tetrahydro-3H-pyrano[4,3-d]pyrimidin-2-yl)methyl)acetamide

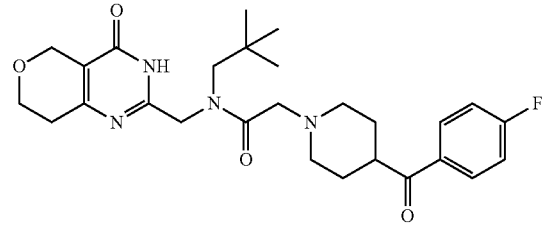 [SMILES: CC(C)(C)CN(Cc1nc2c(c(=O)[nH]1)COCC2)C(=O)CN1CCC(C(=O)c2ccc(F)cc2)CC1]

The title compound (17 mg) was prepared following the general procedure of Example 1 from 2-((neopentylamino)methyl)-7,8-dihydro-3H-pyrano[4,3-d]pyrimidin-4(5H)-one (50 mg, 0.20 mmol) and 2-(4-(4-fluorobenzoyl)piperidin-1-yl)acetic acid (62 mg, 0.20 mmol). $^1$H NMR (400 MHz, CDC$_3$) δ 7.98 (dd, J=9.0, 5.5 Hz, 2H), 7.07-7.21 (m, 2H), 4.61 (s, 2H), 4.49 (br. s., 2H), 3.86-4.05 (m, 2H), 3.30-3.50 (m, 3H), 3.13-3.29 (m, 2H), 2.90-3.13 (m, 2H), 2.52-2.76 (m, 4H), 2.01-2.27 (m, 3H), 1.88 (d, J=3.0 Hz, 1H), 1.02 (s, 3H), 0.96 (s, 7H). HRMS calculated for $C_{27}H_{35}FN_4O_4$ 499.2721. found (ESI, [M+H]$^+$), 499.2738. MS m/z 499.3 (M+1), retention time=3.32 min.

Example 15

2-(4-(4-Fluorobenzoyl)piperidin-1-yl)-N-(4-fluorobenzyl)-N-((4-oxo-4,5,7,8-tetrahydro-3H-pyrano[4,3-d]pyrimidin-2-yl)methyl)acetamide

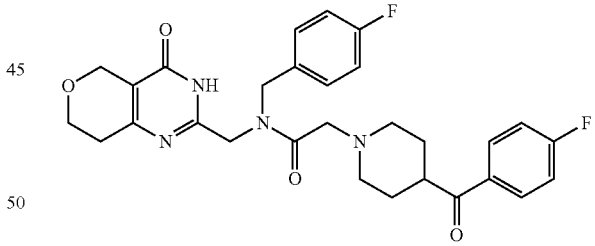

The title compound (20 mg) was prepared following the general procedure of Example 1 from 2-((4-fluorobenzylamino)methyl)-7,8-dihydro-3H-pyrano[4,3-d]pyrimidin-4(5H)-one (80 mg, 0.28 mmol) and 2-(4-(4-fluorobenzoyl)piperidin-1-yl)acetic acid (86 mg, 0.28 mmol, 85% purity). $^1$H NMR (400 MHz, CDC$_3$) δ 7.98 (dd, J=8.0, 5.5 Hz, 2H), 7.10-7.35 (m, 4H), 6.90-7.10 (m, 2H), 4.46-4.67 (m, 3.5H), 4.29 (s, 1.5H), 3.78-4.03 (m, 1H), 3.42 (br. s., 3H), 3.05 (t, J=11.5 Hz, 2H), 2.68 (t, J=5.3 Hz, 3H), 2.59 (t, J=5.5 Hz, 1H), 2.38 (br. s., 1H), 2.09-2.31 (m, 3H), 1.88 (br. s., 1H), 1.74-1.86 (m, 1H). HRMS calculated for $C_{29}H_{30}F_2N_4O_4$ 537.2331. found (ESI, [M+H]$^+$), 537.2313. MS m/z 537.2 (M+1), retention time=3.25 min.

Example 16

2-(4-(4-Fluorobenzoyl)piperidin-1-yl)-N-(4-methoxybenzyl)-N-((4-oxo-4,5,7,8-tetrahydro-3H-pyrano[4,3-d]pyrimidin-2-yl)methyl)acetamide

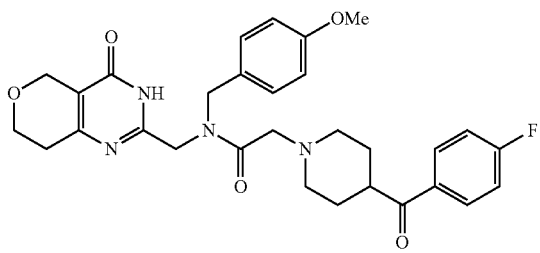 [SMILES: COc1ccc(CN(Cc2nc3c(c(=O)[nH]2)COCC3)C(=O)CN2CCC(C(=O)c3ccc(F)cc3)CC2)cc1]

The title compound (15 mg) was prepared following the general procedures for the preparation of intermediate 13 and Example 15 from 1-(chloromethyl)-4-methoxybenzene (150 mg, 0.83 mmol). $^1$H NMR (400 MHz, CDC$_3$) δ 7.99 (dd, J=8.8, 5.3 Hz, 2H), 7.07-7.35 (m, 4H), 6.71-6.95 (m, 2H), 4.55 (d, J=18.1 Hz, 4H), 4.28 (s, 1H), 3.86-4.02 (m, 2H), 3.68-3.86 (m, 2H), 3.34-3.46 (m, 2H), 3.06 (br. s., 2H), 2.67 (br. s., 3H), 2.57 (br. s., 1H), 2.15-2.34 (m, 3H), 1.80-2.01 (m, 2H), 1.73 (br. s., 2H). HRMS calculated for C$_{30}$H$_{33}$FN$_4$O$_5$ 549.2513. found (ESI, [M+H]$^+$), 549.2516. MS m/z 549.3 (M+1), retention time=3.17 min.

Example 17

N-(Benzo[d]thiazol-2-ylmethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide

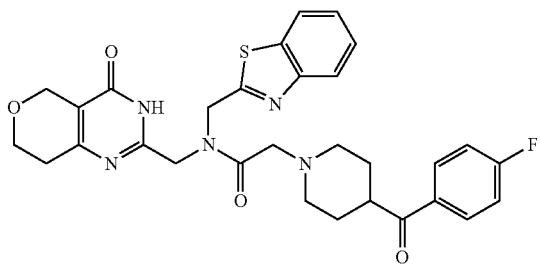 [SMILES: O=C(c1ccc(F)cc1)C1CCN(CC(=O)N(Cc2nc3c(c(=O)[nH]2)COCC3)Cc2nc3ccccc3s2)CC1]

The title compound (4 mg) was prepared following the general procedures for the preparation of intermediate 13 and Example 15 from 2-(chloromethyl)benzo[d]thiazole (122 mg, 0.66 mmol). $^1$H NMR (400 MHz, CDC$_3$) δ 8.46 (d, J=8.0 Hz, 0.5H), 8.24 (d, J=8.0 Hz, 0.5H), 7.75-8.04 (m, 3H), 7.34-7.63 (m, 2H), 7.06-7.23 (m, 2H), 5.43 (s, 1H), 5.01 (s, 1H), 4.69 (s, 1H), 4.58 (d, J=5.0 Hz, 2H), 4.52 (s, 1H), 3.91 (t, J=5.3 Hz, 2H), 3.35 (s, 1H), 3.20-3.31 (m, 1.5H), 2.94-3.05 (m, 1.5H), 2.90 (d, J=11.5 Hz, 1H), 2.62 (d, J=4.0 Hz, 2H), 2.41 (t, J=9.3 Hz, 1H), 2.22 (t, J=11.0 Hz, 1H), 1.83-2.05 (m, 2H), 1.47-1.83 (m, 2H). HRMS calculated for C$_{30}$H$_{30}$FN$_5$O$_4$S 576.2081. found (ESI, [M+H]$^+$), 576.2106. MS m/z 576.2 (M+1), retention time=3.32 min.

Example 18

2-(4-(4-Fluorobenzoyl)piperidin-1-yl)-N-(3-methoxybenzyl)-N-((4-oxo-4,5,7,8-tetrahydro-3H-pyrano[4,3-d]pyrimidin-2-yl)methyl)acetamide

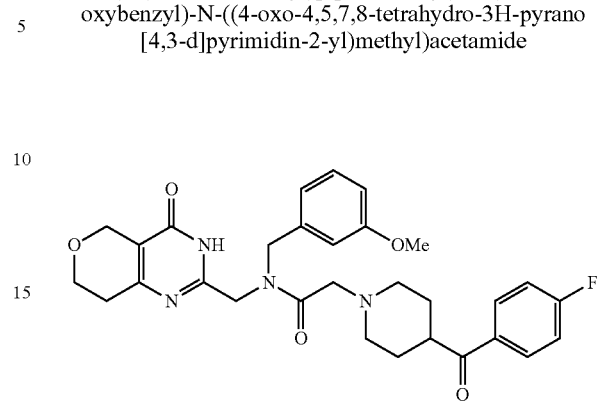

The title compound (11 mg) was prepared following the general procedures for the preparation of intermediate 13 and Example 15 from 1-(bromomethyl)-3-methoxybenzene. $^1$H NMR (400 MHz, CDC$_3$) δ 7.89-8.08 (m, 2H), 7.08-7.37 (m, 3H), 6.73-6.92 (m, 3H), 4.82 (s, 1H), 4.48-4.65 (m, 3H), 4.40 (s, 1H), 4.31 (s, 1H), 3.84-4.04 (m, 2H), 3.72-3.84 (m, 3H), 3.34-3.53 (m, 2H), 2.92-3.16 (m, 2H), 2.52-2.76 (m, 3H), 2.39 (br. s., 1H), 2.05-2.33 (m, 3H), 1.67-1.96 (m, 2H). HRMS calculated for C$_{30}$H$_{33}$FN$_4$O$_3$ 549.2513. found (ESI, [M+H]$^+$), 549.2512. MS m/z 549.3 (M+1), retention time=3.20 min.

Example 19

2-(4-(4-Fluorobenzoyl)piperidin-1-yl)-N-(3-fluorobenzyl)-N-((4-oxo-4,5,7,8-tetrahydro-3H-pyrano[4,3-d]pyrimidin-2-yl)methyl)acetamide

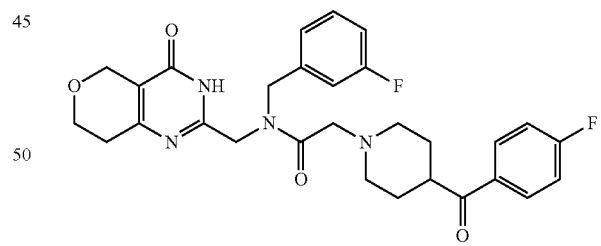

The title compound (46 mg) was prepared following the general procedures for the preparation of intermediate 13 and Example 15 from 1-(bromomethyl)-3-fluorobenzene. $^1$H NMR (400 MHz, CDC$_3$) δ ppm 7.87-8.05 (m, 2H), 7.19-7.41 (m, 1H), 7.14 (t, J=8.5 Hz, 2H), 6.86-7.08 (m, 3H), 4.44-4.85 (m, 4H), 4.33-4.38 (m, 2H), 3.80-4.04 (m, 2H), 3.28-3.49 (m, 3H), 2.92-3.12 (m, 2H), 2.58-2.66 (m, 3H) 2.28 (td, J=10.7, 3.8 Hz, 1H), 1.96-2.22 (m, 3H), 1.69-1.96 (m, 1H). HRMS calculated for C$_{29}$H$_{30}$F$_2$N$_4$O$_4$ 537.2313. found (ESI, [M+H]$^+$), 537.2331. MS m/z 537.2 (M+1), retention time=3.25 min.

Example 20

2-(4-(4-Fluorobenzoyl)piperidin-1-yl)-N-((4-oxo-4,5,7,8-tetrahydro-3H-pyrano[4,3-d]pyrimidin-2-yl)methyl)-N-(pyridin-4-ylmethyl)acetamide

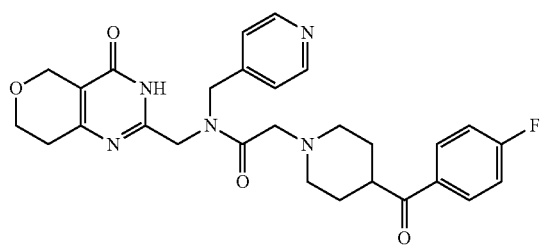 [SMILES: O=C(c1ccc(F)cc1)C1CCN(CC(=O)N(Cc2ccncc2)Cc2nc3c(c(=O)[nH]2)COCC3)CC1]

The title compound (3 mg) was prepared following the general procedures for the preparation of intermediate 13 and Example 15 from 4-(bromomethyl)pyridine. $^1$H NMR (400 MHz, CDC$_3$) δ 8.55 (d, J=6.0 Hz, 2H), 7.83-8.10 (m, 2H), 7.07-7.22 (m, 4H), 4.47-4.70 (m, 4H), 4.32 (s, 2H), 3.85-4.09 (m, 2H), 3.32-3.62 (m, 3H), 3.09 (d, J=2.0 Hz, 1H), 2.62-2.85 (m, 3H), 2.14-2.35 (m, 3H), 1.62-1.92 (m, 1H), 1.18-1.47 (m, 2H). HRMS calculated for C$_{28}$H$_{30}$FN$_5$O$_4$ 520.2360. found (ESI, [M+H]$^+$), 520.2357. MS m/z 520.2 (M+1), retention time=2.15 min.

Example 21

2-(4-(4-Fluorobenzoyl)piperidin-1-yl)-N-((4-oxo-4,5,7,8-tetrahydro-3H-pyrano[4,3-d]pyrimidin-2-yl)methyl)-N-(pyridin-3-ylmethyl)acetamide

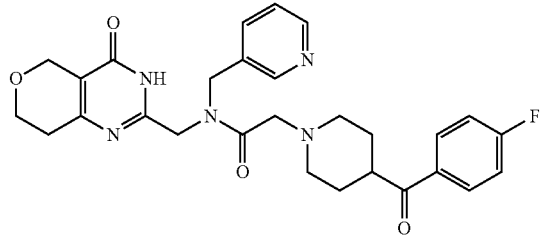 [SMILES: O=C(c1ccc(F)cc1)C1CCN(CC(=O)N(Cc2cccnc2)Cc2nc3c(c(=O)[nH]2)COCC3)CC1]

The title compound (24 mg) was prepared following the general procedures for the preparation of intermediate 13 and Example 15 from 3-(bromomethyl)pyridine. $^1$H NMR (400 MHz, CDC$_3$) δ ppm 8.45-8.65 (m, 2H), 7.97 (dd, J=8.8, 5.3 Hz, 2H), 7.53-7.70 (m, 1H), 7.07-7.37 (m, 3H), 4.61 (s, 2H), 4.46-4.58 (m, 2H), 4.33 (s, 2H), 3.77-4.06 (m, 2H), 3.33-3.53 (m, 2H), 2.90-3.17 (m, 2H), 2.49-2.76 (m, 3H), 1.97-2.26 (m, 3H), 1.85 (br. s., 1H), 0.77-0.97 (m, 2H). HRMS calculated for C$_{28}$H$_{30}$FN$_5$O$_5$ 520.2360. found (ESI, [M+F]$^+$), 520.2385. Retention time=4.17 min.

Example 22

2-(4-(4-Fluorobenzoyl)piperidin-1-yl)-N-((4-oxo-4,5,7,8-tetrahydro-3H-pyrano[4,3-d]pyrimidin-2-yl)methyl)-N-(pyridin-2-ylmethyl)acetamide

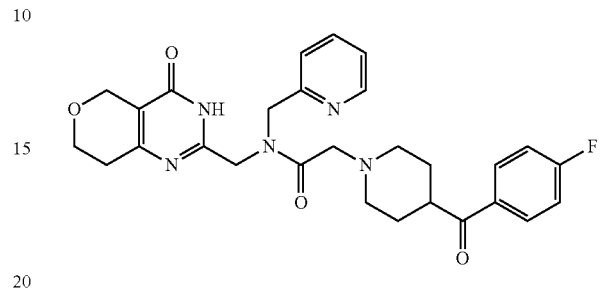

The title compound (20 mg, 8% yield) was prepared following the general procedures for the preparation of intermediate 13 and Example 15 from 2-(bromomethyl)pyridine. $^1$H NMR (400 MHz, CDC$_3$) δ 8.75 (d, J=4.5 Hz, 1H), 7.70-8.00 (m, 3H), 7.35-7.58 (m, 1H), 7.22-7.35 (m, 1H), 6.93-7.22 (m, 2H), 4.74 (s, 1H), 4.68 (s, 3H), 4.59 (s, 1H), 4.48 (s, 1H), 4.09 (t, J=5.5 Hz, 1H), 3.96 (t, J=5.5 Hz, 1H), 3.03-3.30 (m, 3H), 2.80 (d, J=11.5 Hz, 2H), 2.47-2.76 (m, 2H), 2.04-2.31 (m, 2H), 1.75 (d, J=10.5 Hz, 2H), 1.37-1.67 (m, 2H). HRMS calculated for C$_{28}$H$_{33}$FN$_6$O$_6$ 520.2360. found (ESI, [M+520.2367. Retention time=4.44 min.

Example 23

2-[4-(4-Fluoro-benzoyl)-piperidin-1-yl]-N-(4-oxo-3,5,7,8-tetrahydro-4H-pyrano[4,3-d]pyrimidin-2-ylmethyl)-N—((S)-1-phenyl-ethyl)-acetamide

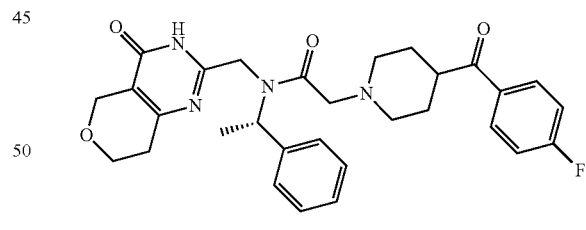

Following the general procedure of Example 4, the title compound was prepared (61.4 mg) from 2-R(S)-1-phenylethylamino)-methyl]-3,5,7,8-tetrahydro-pyrano[4,3-d]pyrimidin-4-one and 2-(4-(4-fluorobenzoyl)piperidin-1-yl)acetic acid. Exact mass calculated for C$_{30}$H$_{33}$FN$_4$O$_4$ 532.61. found 533.7 (ESI, M+H); $^1$H NMR (600 MHz, DMSO-d$_6$) δ ppm 8.00-8.17 (m, 2H) 7.36-7.45 (m, 3H) 7.20-7.36 (m, 4H) 5.79-5.94 (m, 1H) 4.29-4.49 (m, 4H) 4.18-4.29 (m, 2H) 3.76-3.91 (m, 3H) 3.66-3.76 (m, 1H) 3.57-3.66 (m, 1H) 3.54 (d, J=11.71 Hz, 1H) 3.45 (d, J=11.71 Hz, 1H) 3.08-3.27 (m, 2H) 2.54 (br. s., 1H) 2.37-2.49 (m, 1H) 1.99-2.11 (m, 3H) 1.87-1.99 (m, 2H) 1.59-1.69 (m, 1H) 1.34-1.44 (m, 2H).

Example 24

N-Cyclopropylmethyl-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide

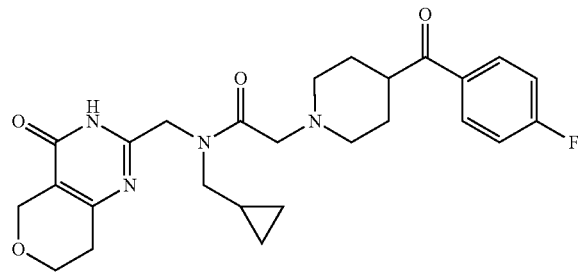

Following the general procedure of Example 4, the title compound was prepared (14.4 mg) from 2-[(Cyclopropylmethyl-amino)-methyl]-3,5,7,8-tetrahydro-pyrano[4,3-d]pyrimidin-4-one and 2-(4-(4-fluorobenzoyl)piperidin-1-yl)acetic acid. Exact mass calculated for $C_{26}H_{31}FN_4O_4$ 482.55. found 483.3 (ESI, M+H); $^1$H NMR (400 MHz, dichloromethane-$d_2$) δ ppm 7.98 (dd, J=8.59, 5.56 Hz, 2H) 7.19 (t, J=8.59 Hz, 2H) 4.65 (s, 1H) 4.58 (br. s., 1H) 4.41-4.55 (m, 2H) 4.26 (br. s., 1H) 4.18 (br. s., 2H) 3.85-3.98 (m, 3H) 3.30 (d, J=7.07 Hz, 1H) 3.22 (d, J=6.57 Hz, 2H) 2.70 (br. s., 1H) 2.64 (br. s., 1H) 2.22 (br. s., 4H) 0.97 (d, J=4.55 Hz, 1H) 0.61 (d, J=7.58 Hz, 1H) 0.42 (d, J=7.07 Hz, 1H) 0.26 (d, J=4.55 Hz, 1H) 0.13-0.22 (m, 1H).

Alternate Method

[4-(4-Fluoro-benzoyl)-piperidin-1-yl]-acetic acid (169 mg, 0.64 mmol) was added with HATU (364 mg, 0.96 mmol) in DMF (2 mL) and DIEA (0.28 mL, 1.60 mmol) was added. This was sonicated, stirred for 30 min and then 2-[(cyclopropylmethyl-amino)-methyl]-3,5,7,8-tetrahydro-pyrano[4,3-d]pyrimidin-4-one (150 mg, 0.64 mmol) in 1 mL DMF was added to the mixture. The mixture was stirred at room temperature for 16 h, concentrated to dryness, purified by silica gel column (eluted with 0-10% methanol in dichloromethane) then triturated with methanol to give a white solid as the title compound (66 mg, 0.14 mmol, 21% yield). m/z=483.3 (M+H).

Example 25

2-[4-(4-Fluoro-benzoyl)-piperidin-1-yl]-N—((S)-2-methyl-butyl)-N-(4-oxo-3,5,7,8-tetrahydro-4H-pyrano[4,3-d]pyrimidin-2-ylmethyl)-acetamide

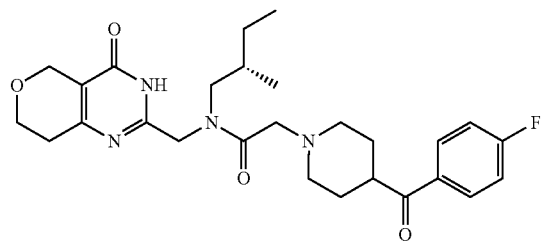 [SMILES: CC[C@H](C)CN(Cc1nc2c(c(=O)[nH]1)COCC2)C(=O)CN1CCC(C(=O)c2ccc(F)cc2)CC1]

Following the general procedure of Example 4, the title compound was prepared (38.2 mg) from (S)-2-((2-methylbutylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{27}H_{35}FN_4O_4$ 498.6. found 499.7 (ESI, M+H); $^1$H NMR (400 MHz, dichloromethane-$d_2$) δ ppm 7.88-8.15 (m, 2H) 7.20 (t, J=8.59 Hz, 2H) 4.44-4.68 (m, 4H) 4.09-4.25 (m, 1H) 3.85-3.99 (m, 2H) 3.80 (d, J=11.12 Hz, 2H) 3.42 (d, J=7.58 Hz, 2H) 3.22-3.36 (m, 2H) 3.17 (br. s., 1H) 2.66-2.76 (m, 1H) 2.20 (br. s., 3H) 1.26-1.47 (m, 1H) 1.06-1.25 (m, 1H) 0.93 (ddd, J=6.82, 3.79, 3.54 Hz, 4H) 0.78-0.90 (m, 2H).

Example 26

2-(4-(4-Fluorobenzoyl)piperidin-1-yl)-N-isobutyl-N-((4-oxo-4,5,7,8-tetrahydro-3H-pyrano[4,3-d]pyrimidin-2-yl)methyl)acetamide

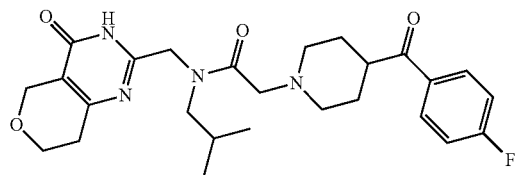 [SMILES: CC(C)CN(Cc1nc2c(c(=O)[nH]1)COCC2)C(=O)CN1CCC(C(=O)c2ccc(F)cc2)CC1]

Following the general procedure of Example 4, the title compound was prepared (36.4 mg) from 2-((isobutylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{26}H_{33}FN_4O_4$ 484.6. found 485.6 (ESI, M+H); $^1$H NMR (400 MHz, dichloromethane-$d_2$) δ ppm 7.98 (dd, J=8.84, 5.31 Hz, 2H) 7.20 (t, J=8.59 Hz, 2H) 4.48-4.67 (m, 4H) 4.21 (br. s., 2H) 3.89-4.01 (m, 2H) 3.82 (br. s., 3H) 3.23 (br. s., 4H) 2.62-2.83 (m, 2H) 2.19 (br. s., 3H) 2.13 (s, 1H) 2.07 (d, J=6.57 Hz, 1H) 0.98 (d, J=6.57 Hz, 4H) 0.88 (d, J=5.56 Hz, 2H).

Example 27

2-(4-(4-Fluorobenzoyl)piperidin-1-yl)-N-((4-oxo-4,5,7,8-tetrahydro-3H-pyrano[4,3-d]pyrimidin-2-yl)methyl)-N-(prop-2-ynyl)acetamide

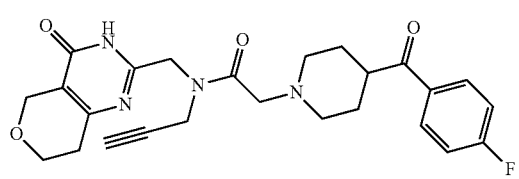 [SMILES: C#CCN(Cc1nc2c(c(=O)[nH]1)COCC2)C(=O)CN1CCC(C(=O)c2ccc(F)cc2)CC1]

Following the general procedure of Example 4, the title compound was prepared (44.3 mg) from 2-((prop-2-ynylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{25}H_{27}FN_4O_4$ 466.5. found 467.7 (ESI, M+H); $^1$H NMR (400 MHz, dichloromethane-$d_2$) δ ppm 7.98 (dd, J=9.09, 5.56 Hz, 2H) 7.20 (t, J=8.59 Hz, 2H) 4.67 (d, J=9.60 Hz, 2H) 4.51 (d, J=15.16 Hz, 2H) 4.26-4.41 (m, 3H) 4.22 (br. s., 2H) 3.88-4.01 (m, 4H) 2.63-2.85 (m, 2H) 2.32 (br. s., 1H) 2.24 (br. s., 4H) 1.46-1.58 (s, 2H).

Example 28

(S)-2-(4-(4-Fluorobenzoyl)piperidin-1-yl)-N-((4-oxo-4,5,7,8-tetrahydro-3H-pyrano[4,3-d]pyrimidin-2-yl)methyl)-N-((tetrahydrofuran-2-yl)methyl)acetamide

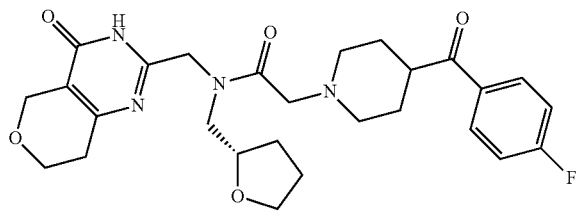 [SMILES: O=C(c1ccc(F)cc1)C1CCN(CC(=O)N(Cc2nc3c(c(=O)[nH]2)COCC3)C[C@@H]2CCCO2)CC1]

Following the general procedure of Example 4, the title compound was prepared (41.2 mg) from (S)-2-(((tetrahydrofuran-2-yl)methylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{27}H_{33}FN_4O_4$ 512.6. found 513.7 (ESI, M+H); $^1$H NMR (400 MHz, dichloromethane-$d_2$) δ ppm 7.98 (dd, J=8.84, 5.31 Hz, 2H) 7.19 (t, J=8.59 Hz, 2H) 4.76 (d, J=16.17 Hz, 2H) 4.47-4.59 (m, 3H) 4.44 (s, 1H) 4.37 (s, 2H) 4.08 (d, J=7.58 Hz, 2H) 3.87-4.01 (m, 3H) 3.69-3.84 (m, 2H) 3.36-3.53 (m, 3H) 2.69-2.84 (m, 2H) 2.18 (br. s., 4H) 1.83-2.10 (m, 4H).

Example 29

(R)-2-(4-(4-Fluorobenzoyl)piperidin-1-yl)-N-((4-oxo-4,5,7,8-tetrahydro-3H-pyrano[4,3-d]pyrimidin-2-yl)methyl)-N-((tetrahydrofuran-2-yl)methyl)acetamide

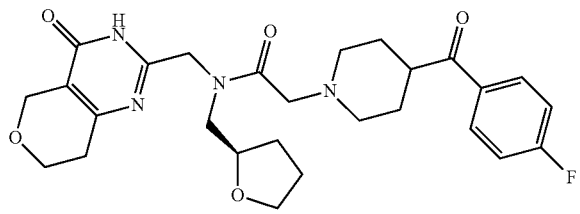 [SMILES: O=C(c1ccc(F)cc1)C1CCN(CC(=O)N(Cc2nc3c(c(=O)[nH]2)COCC3)C[C@H]2CCCO2)CC1]

Following the general procedure of Example 4, the title compound was prepared (20.2 mg) from (R)-2-(((tetrahydrofuran-2-yl)methylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{27}H_{33}FN_4O_4$ 512.6. found 513.7 (ESI, M+H); $^1$H NMR (400 MHz, dichloromethane-$d_2$) δ ppm 7.89 (dd, J=8.84, 5.31 Hz, 2H) 7.11 (t, J=8.59 Hz, 2H) 4.52-4.69 (m, 1H) 4.28-4.52 (m, 4H) 4.09-4.28 (m, 3H) 3.77-3.95 (m, 5H) 3.62-3.74 (m, 2H) 3.28-3.45 (m, 4H) 2.54-2.62 (m, 1H) 2.19 (d, J=7.07 Hz, 1H) 2.12 (br. s., 3H) 1.84-2.02 (m, 4H).

Example 30

2-(4-(4-Fluorobenzoyl)piperidin-1-yl)-N-methyl-N-((4-oxo-4,5,7,8-tetrahydro-3H-pyrano[4,3-d]pyrimidin-2-yl)methyl)acetamide

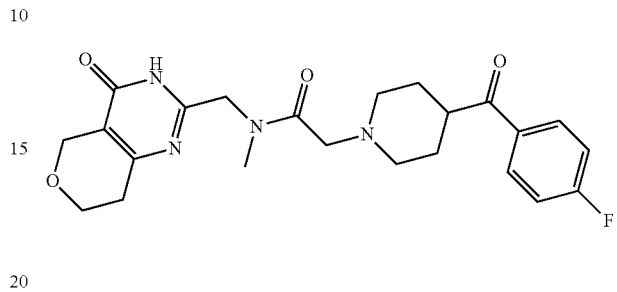

Following the general procedure of Example 4, the title compound was prepared (22.5 mg) from 2-((methylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{23}H_{27}FN_4O_4$ 442.5. found 443.4 (ESI, M+H); $^1$H NMR (400 MHz, dichloromethane-$d_2$) δ ppm 7.98 (dd, J=8.59, 5.56 Hz, 2H) 7.10-7.25 (m, 2H) 4.45-4.57 (m, 2H) 4.27 (s, 2H) 3.92 (t, J=5.56 Hz, 2H) 3.25-3.41 (m, 3H) 3.18 (s, 1H) 3.05-3.16 (m, 2H) 2.89 (s, 3H) 2.65 (t, J=5.56 Hz, 2H) 2.39-2.57 (m, 2H) 2.22 (dd, J=13.64, 2.53 Hz, 2H) 2.00 (br. s., 3H).

Example 31

(S)—N-sec-Butyl-2-(4-(4-fluorobenzoyl)piperidin-1-yl)-N-((4-oxo-4,5,7,8-tetrahydro-3H-pyrano[4,3-d]pyrimidin-2-yl)methyl)acetamide

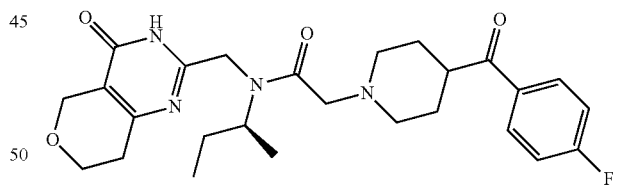

Following general procedure of Example 4, the title compound was prepared (8.7 mg) from (S)-2-((sec-butylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{26}H_{33}FN_4O_4$ 484.6. found 485.4 (ESI, M+H); $^1$H NMR (400 MHz, dichloromethane-$d_2$) δ ppm 7.87-8.08 (m, 2H) 7.09-7.25 (m, 2H) 4.41-4.57 (m, 2H) 4.20-4.40 (m, 3H) 4.16 (d, J=8.08 Hz, 1H) 3.83-3.97 (m, 2H) 3.19-3.42 (m, 3H) 3.11 (d, J=5.56 Hz, 1H) 2.93 (d, J=8.59 Hz, 1H) 2.43-2.71 (m, 3H) 2.17-2.36 (m, 2H) 2.00 (br. s., 1H) 1.68-1.92 (m, 3H) 1.22 (d, J=6.57 Hz, 2H) 1.09 (d, J=7.07 Hz, 1H) 0.66-0.83 (m, 3H).

Example 32

(R)—N-sec-Butyl-2-(4-(4-fluorobenzoyl)piperidin-1-yl)-N-((4-oxo-4,5,7,8-tetrahydro-3H-pyrano[4,3-d]pyrimidin-2-yl)methyl)acetamide

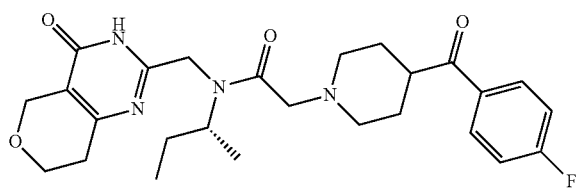 [SMILES: CC[C@@H](C)N(Cc1nc2c(c(=O)[nH]1)COCC2)C(=O)CN1CCC(C(=O)c2ccc(F)cc2)CC1]

Following general procedure of Example 4, the title compound was prepared (11 mg) from (R)-2-((sec-butylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{26}H_{33}FN_4O_4$ 484.6. found 485.4 (ESI, M+H); $^1$H NMR (400 MHz, dichloromethane-$d_2$) δ ppm 7.87-8.07 (m, 2H) 7.16 (t, J=8.59 Hz, 2H) 4.41-4.58 (m, 2H) 4.19-4.41 (m, 3H) 4.13 (d, J=7.07 Hz, 1H) 3.82-3.99 (m, 2H) 3.34 (br. s., 2H) 3.25 (br. s., 1H) 3.13 (br. s., 1H) 2.87-3.07 (m, 1H) 2.55-2.69 (m, 2H) 2.25 (br. s., 2H) 1.98 (br. s., 1H) 1.88 (br. s., 2H) 1.72 (br. s., 1H) 1.16-1.28 (m, 3H) 1.09 (d, J=6.57 Hz, 1H) 0.69-0.89 (m, 3H).

Example 33

2-(4-(4-Fluorobenzoyl)piperidin-1-yl)-N-isopropyl-N-((4-oxo-4,5,7,8-tetrahydro-3H-pyrano[4,3-d]pyrimidin-2-yl)methyl)acetamide

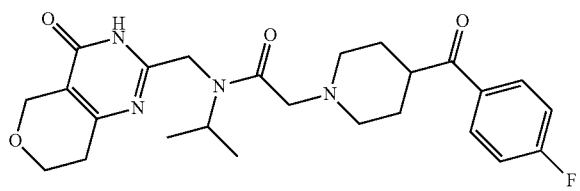 [SMILES: CC(C)N(Cc1nc2c(c(=O)[nH]1)COCC2)C(=O)CN1CCC(C(=O)c2ccc(F)cc2)CC1]

Following general procedure of Example 4, the title compound was prepared (26.4 mg) from 2-((isopropylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{25}H_{31}FN_4O_4$ 470.5. found 471.6 (ESI, M+H); $^1$H NMR (400 MHz, dichloromethane-$d_2$) δ ppm 7.91-8.18 (m, 2H) 7.19 (t, J=8.59 Hz, 2H) 4.53-4.69 (m, 2H) 4.50 (s, 1H) 4.24-4.43 (m, 1H) 4.19 (br. s., 1H) 3.86-4.08 (m, 3H) 3.80 (d, J=7.58 Hz, 1H) 3.58 (br. s., 2H) 3.33-3.50 (m, 1H) 3.28 (br. s., 1H) 2.74 (t, J=5.31 Hz, 2H) 2.19 (d, J=10.61 Hz, 2H) 2.13 (s, 1H) 1.11-1.33 (m, 5H) 1.07 (d, J=6.06 Hz, 1H).

Example 34

2-(4-(4-Fluorobenzoyl)piperidin-1-yl)-N-((4-oxo-4,5,7,8-tetrahydro-3H-pyrano[4,3-d]pyrimidin-2-yl)methyl)-N-propylacetamide

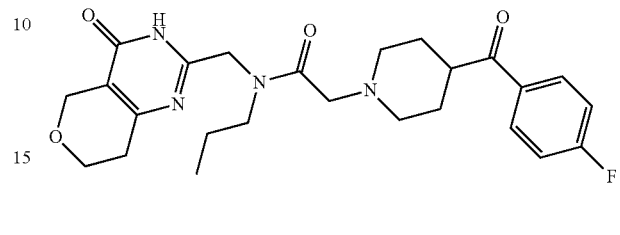

Following general procedure of Example 4, the title compound was prepared (37.3 mg) from 2-((propylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{25}H_{31}FN_4O_4$ 470.5. found 471.6 (ESI, M+H); $^1$H NMR (400 MHz, dichloromethane-$d_2$) δ ppm 7.89-8.08 (m, 2H) 7.19 (t, J=8.34 Hz, 2H) 4.60 (s, 2H) 4.42-4.57 (m, 2H) 4.27 (br. s., 2H) 3.85-4.01 (m, 3H) 3.81 (br. s., 1H) 3.57 (br. s., 1H) 3.39 (br. s., 1H) 3.31 (br. s., 2H) 3.12-3.28 (m, 1H) 2.72 (br. s., 1H) 2.13 (s, 4H) 1.58-1.80 (m, 1H) 1.40-1.58 (m, 1H) 0.76-1.00 (m, 3H).

Example 35

(S)-2-(4-(4-Fluorobenzoyl)piperidin-1-yl)-N-(1-(4-fluorophenyl)ethyl)-N-((4-oxo-4,5,7,8-tetrahydro-3H-pyrano[4,3-d]pyrimidin-2-yl)methyl)acetamide

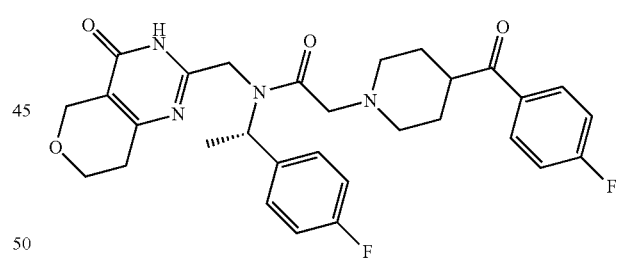

Following general procedure of Example 4, the title compound was prepared (40.7 mg) from (S)-2-((1-(4-fluorophenyl)ethylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{30}H_{32}FN_4O_4$ 550.6. found 551.4 (ESI, M+H); $^1$H NMR (400 MHz, dichloromethane-$d_2$) δ ppm 7.97 (dd, J=8.84, 5.31 Hz, 2H) 7.31 (dd, J=8.59, 5.05 Hz, 1H) 7.13-7.27 (m, 3H) 6.88 (t, J=7.83 Hz, 1H) 6.03 (q, J=7.07 Hz, 1H) 4.27-4.57 (m, 5H) 4.11 (br. s., 2H) 3.85-4.03 (m, 4H) 3.36 (br. s., 1H) 3.30 (br. s., 2H) 2.97 (s, 1H) 2.70 (br. s., 2H) 2.59 (d, J=4.04 Hz, 1H) 2.12 (s, 4H) 1.68 (d, J=7.07 Hz, 1H) 1.49 (d, J=7.07 Hz, 2H).

Example 36

(R)-2-(4-(4-Fluorobenzoyl)piperidin-1-yl)-N-(1-(4-fluorophenyl)ethyl)-N-((4-oxo-4,5,7,8-tetrahydro-3H-pyrano[4,3-d]pyrimidin-2-yl)methyl)acetamide

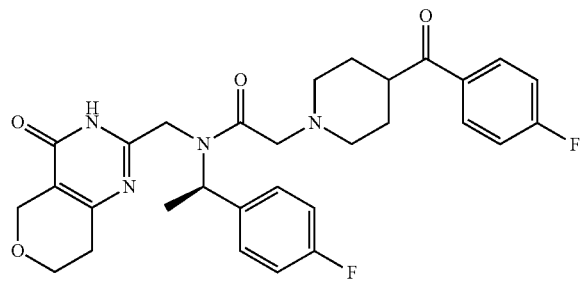 [SMILES: C[C@H](c1ccc(F)cc1)N(Cc1nc2c(c(=O)[nH]1)COCC2)C(=O)CN1CCC(C(=O)c2ccc(F)cc2)CC1]

Following general procedure of Example 4, the title compound was prepared (26.9 mg) from (R)-2-((1-(4-fluorophenyl)ethylamino)methyl)-7,8-dihydro-3H-pyrano[4,3-d]pyrimidin-4(5H)-one and 2-(4-(4-fluorobenzoyl)piperidin-1-yl) acetic acid. Exact mass calculated for $C_{30}H_{32}FN_4O_4$ 550.6. found 551.4 (ESI, M+H); $^1$H NMR (400 MHz, dichloromethane-$d_2$) δ ppm 7.97 (dd, J=8.84, 5.31 Hz, 2H) 7.31 (dd, J=8.59, 5.05 Hz, 1H) 7.13-7.27 (m, 3H) 6.88 (t, J=7.83 Hz, 1H) 6.03 (q, J=7.07 Hz, 1H) 4.27-4.57 (m, 5H) 4.11 (br. s., 2H) 3.85-4.03 (m, 4H) 3.36 (br. s., 1H) 3.30 (br. s., 2H) 2.97 (s, 1H) 2.70 (br. s., 2H) 2.59 (d, J=4.04 Hz, 1H) 2.12 (s, 4H) 1.68 (d, J=7.07 Hz, 1H) 1.49 (d, J=7.07 Hz, 2H).

Example 37

N-(1-(2,4-Difluorophenyl)ethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide

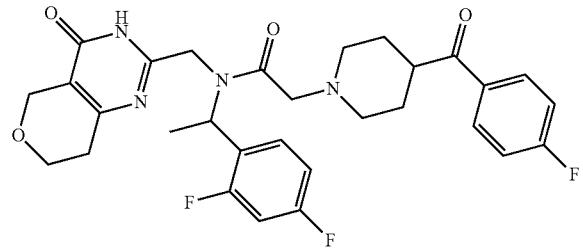 [SMILES: CC(c1ccc(F)cc1F)N(Cc1nc2c(c(=O)[nH]1)COCC2)C(=O)CN1CCC(C(=O)c2ccc(F)cc2)CC1]

Following general procedure of Example 4, the title compound was prepared (43.3 mg) from 2-((1-(2,4-difluorophenyl)ethylamino)methyl)-7,8-dihydro-3H-pyrano[4,3-d]pyrimidin-4(5H)-one and 2-(4-(4-fluorobenzoyl)piperidin-1-yl) acetic acid. Exact mass calculated for $C_{30}H_{31}F_2N_4O_4$ 568.6. found 569.4 (ESI, M+H); $^1$H NMR (400 MHz, dichloromethane-$d_2$) δ ppm 7.80-8.00 (m, 2H) 7.23-7.41 (m, 1H) 7.11 (t, J=8.59 Hz, 3H) 6.81-6.95 (m, 2H) 6.67-6.81 (m, 2H) 6.41-6.61 (m, 1H) 4.32-4.58 (m, 4H) 4.17-4.32 (m, 1H) 3.70-3.96 (m, 4H) 3.47 (d, J=11.12 Hz, 1H) 3.15-3.37 (m, 1H) 3.09 (br. s., 1H) 2.62 (br. s., 1H) 2.50 (br. s., 1H) 2.36 (br. s., 1H) 2.14 (br. s., 2H) 2.04 (s, 1H) 1.60 (d, J=6.57 Hz, 1H) 1.39 (d, J=6.57 Hz, 2H).

Example 38

N-Benzyl-2-(4-(4-fluorobenzoyl)piperidin-1-yl)-N-((4-oxo-4,5,7,8-tetrahydro-3H-pyrano[4,3-d]pyrimidin-2-yl)methyl)acetamide

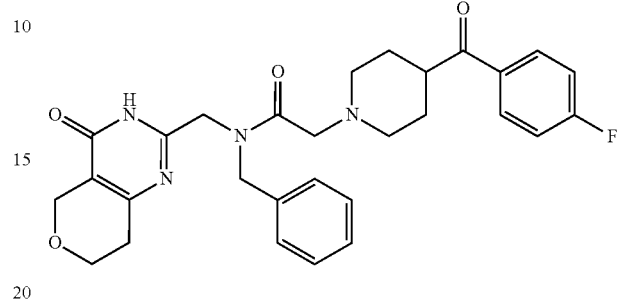

Following general procedure of Example 4, the title compound was prepared (17.7 mg) from 2-((benzylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{29}H_{31}FN_4O_4$ 518.58. found 519.4 (ESI, M+H); $^1$H NMR (400 MHz, dichloromethane-$d_2$) δ ppm 7.98 (br. s., 2H) 7.28-7.52 (m, 1H) 7.21 (d, J=7.58 Hz, 4H) 4.66 (d, J=8.08 Hz, 2H) 4.60 (br. s., 1H) 4.48 (br. s., 2H) 3.85-4.08 (m, 5H) 3.81 (br. s., 2H) 3.42 (d, J=7.07 Hz, 2H) 3.28 (br. s., 2H) 2.70 (d, J=15.66 Hz, 2H) 2.06-2.36 (m, 3H) 1.17-1.41 (m, 2H)

Example 39

2-(4-(4-Fluorobenzoyl)piperidin-1-yl)-N-(2-fluorobenzyl)-N-((4-oxo-4,5,7,8-tetrahydro-3H-pyrano[4,3-d]pyrimidin-2-yl)methyl)acetamide

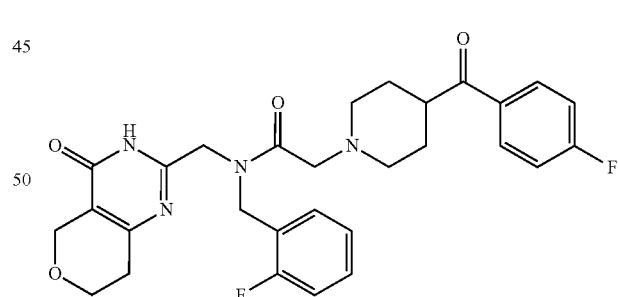

Following general procedure of Example 4, the title compound was prepared (52 mg) from 2-((2-fluorobenzylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{29}H_{30}F_2N_4O_4$ 536.6. found 537.4 (ESI, M+H); $^1$H NMR (400 MHz, dichloromethane-$d_2$) δ ppm 7.87-8.12 (m, 2H) 7.16-7.45 (m, 5H) 7.04-7.14 (m, 1H) 4.69 (br. s., 1H) 4.61 (d, J=11.62 Hz, 3H) 4.48 (d, J=4.55 Hz, 3H) 4.31 (br. s., 1H) 3.84-4.08 (m, 7H) 3.39 (br. s., 1H) 3.28 (br. s., 1H) 2.63-2.79 (m, 2H) 2.28 (br. s., 2H) 1.97-2.20 (m, 2H).

Example 40

N-(2,4-Difluorobenzyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide

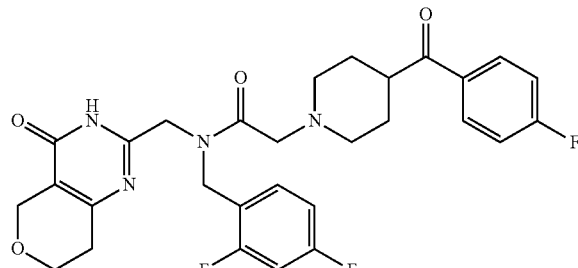

Following general procedure of Example 4, the title compound was prepared (33 mg) from 2-((2,4-difluorobenzylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{29}H_{29}F_3N_4O_4$ 554.7. found 555.4 (ESI, M+H); $^1$H NMR (400 MHz, dichloromethane-$d_2$) δ ppm 7.26-7.43 (m, 1H) 7.20 (t, J=8.59 Hz, 2H) 6.80-6.99 (m, 1H) 4.54-4.75 (m, 4H) 4.49 (d, J=10.61 Hz, 4H) 3.86-4.00 (m, 3H) 3.74 (br. s., 3H) 3.43 (br. s., 5H) 2.63-2.79 (m, 2H) 2.44 (br. s., 1H) 2.24 (br. s., 2H) 2.12 (s, 1H).

Example 41

(R)—N-(1-Cyclopropylethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide

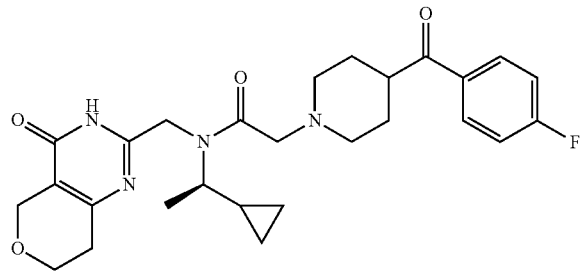 [SMILES: C[C@H](C1CC1)N(Cc1nc2c(c(=O)[nH]1)COCC2)C(=O)CN1CCC(C(=O)c2ccc(F)cc2)CC1]

Following general procedure of Example 4, the title compound was prepared (9 mg) from (R)-2-((1-cyclopropylethylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{27}H_{33}FN_4O_4$ 496.6. found 497.6 (ESI, M+H); $^1$H NMR (400 MHz, DMSO-$d_6$) δ ppm 7.98-8.21 (m, 2H) 7.40 (t, J=8.84 Hz, 2H) 4.25-4.54 (m, 5H) 3.84 (ddd, J=17.31, 5.56, 5.43 Hz, 3H) 3.70 (d, J=6.06 Hz, 1H) 3.56 (br. s., 2H) 3.23 (br. s., 1H) 2.99-3.20 (m, 2H) 1.99 (br. s., 4H) 1.00-1.29 (m, 4H) 0.68-0.94 (m, 1H) 0.46-0.68 (m, 1H) 0.38 (d, J=5.05 Hz, 1H) 0.24-0.34 (m, 1H) 0.15-0.24 (m, 1H).

Example 42

(S)—N-(1-Cyclopropylethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide

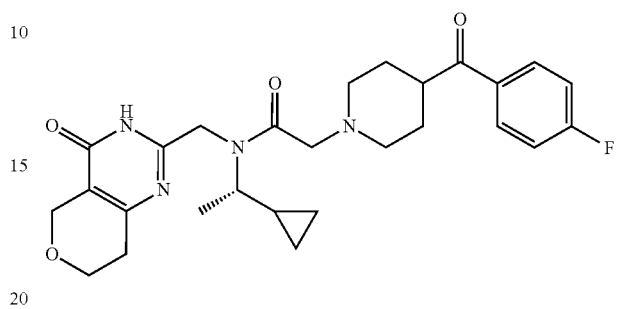

Following general procedure of Example 4, the title compound was prepared (29 mg) from (S)-2-((1-cyclopropylethylamino)methyl)-7,8-dihydro-3H-pyrano[4,3-d]pyrimidin-4(5H)-one and 2-(4-(4-fluorobenzoyl)piperidin-1-yl)acetic acid. Exact mass calculated for $C_{27}H_{33}FN_4O_4$ 496.6. found 497.6 (ESI, M+H); $^1$H NMR (400 MHz, DMSO-$d_6$) δ ppm 7.98-8.21 (m, 2H) 7.40 (t, J=8.84 Hz, 2H) 4.25-4.54 (m, 5H) 3.84 (ddd, J=17.31, 5.56, 5.43 Hz, 3H) 3.70 (d, J=6.06 Hz, 1H) 3.56 (br. s., 2H) 3.23 (br. s., 1H) 2.99-3.20 (m, 2H) 1.99 (br. s., 4H) 1.00-1.29 (m, 4H) 0.68-0.94 (m, 1H) 0.46-0.68 (m, 1H) 0.38 (d, J=5.05 Hz, 1H) 0.24-0.34 (m, 1H) 0.15-0.24 (m, 1H).

Example 43

N-Cyanomethyl-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide

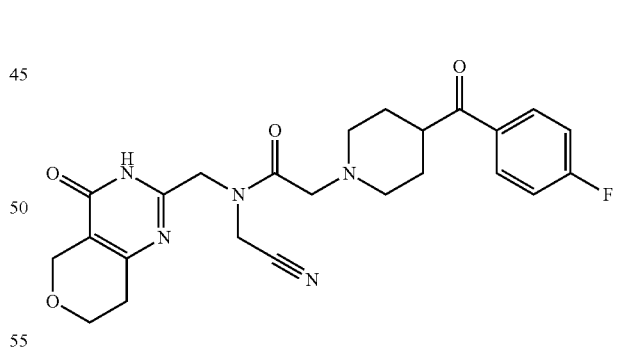

Following general procedure of Example 4, the title compound was prepared (5.4 mg) from [(4-oxo-3,5,7,8-tetrahydro-4H-pyrano[4,3-d]pyrimidin-2-ylmethyl)-amino]-acetonitrile and 2-(4-(4-fluorobenzoyl)piperidin-1-yl)acetic acid. Exact mass calculated for $C_{24}H_{26}FN_5O_4$ 467.5. found 468.5 (ESI, M+H); $^1$H NMR (400 MHz, DMSO-$d_6$) δ ppm 12.61 (br. s., 1H) 9.80 (br. s., 1H) 7.96-8.19 (m, 2H) 7.40 (t, J=8.84 Hz, 2H) 4.58 (s, 2H) 4.50 (s, 2H) 4.26-4.46 (m, 4H) 3.80-3.92 (m, 3H) 3.61-3.75 (m, 1H) 3.52 (br. s., 2H) 3.17 (br. s., 1H) 3.09 (br. s., 1H) 2.00 (br. s., 4H).

Example 44

2-[4-(4-Fluoro-benzoyl)-piperidin-1-yl]-N-(2-fluoro-ethyl)-N-(4-oxo-3,5,7,8-tetrahydro-4H-pyrano[4,3-d]pyrimidin-2-ylmethyl)-acetamide

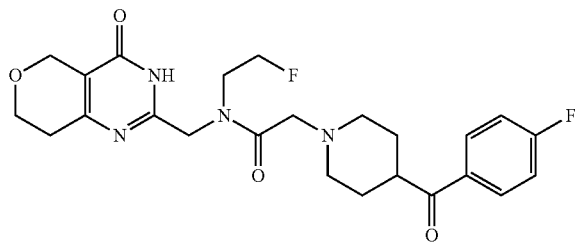 [SMILES: O=C(c1ccc(F)cc1)C1CCN(CC(=O)N(CCF)Cc2nc3c(c(=O)[nH]2)COCC3)CC1]

Following the general procedure of Example 5, the title compound was prepared (0.09 g) from 2-((2-fluoroethylamino)methyl)-7,8-dihydro-3H-pyrano[4,3-d]pyrimidin-4(5H)-one (0.18 g, 0.79 mmol, 1 eq.) and 2-(4-(4-fluorobenzoyl)piperidin-1-yl)acetic acid (0.19 g, 0.71 mmol, 0.9 eq.). $^1$H NMR (400 MHz, MeOD) δ ppm 8.04-8.18 (m, 2H), 7.26 (m, 2H), 4.71-4.80 (m, 1H), 4.60-4.67 (m, 1H), 4.59 (s, 2H), 4.48-4.53 (m, 1H), 4.46 (s, 1H), 4.37 (s, 2H), 3.89-3.96 (m, 2H), 3.83-3.90 (m, 1H), 3.77-3.84 (m, 1H), 3.66-3.78 (m, 3H), 3.46-3.61 (m, 1H), 3.16-3.28 (m, 1H), 2.49-2.73 (m, 2H), 1.91-2.25 (m, 4H). HRMS calculated for $C_{24}H_{29}F_2N_4O_4$ 475.2157. found (ESI, [M+H]+) 475.2178. MS (ESI) m/z 475.2 (M+H)$^+$. Retention time: 4.08 min (5-95% $CH_3CN/H_2O$ over 7.75 min with 0.1% formic acid, Inertsil ODS3 100×3 mm C18 column with flow rate of 1.0 mL/min).

Example 45

N-(2,2-Difluoro-ethyl)-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide

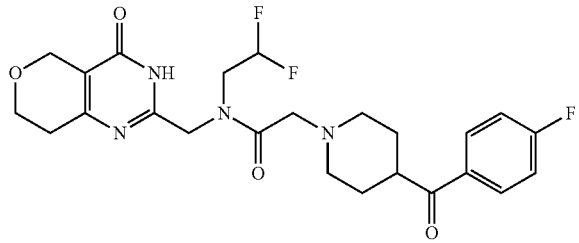 [SMILES: O=C(c1ccc(F)cc1)C1CCN(CC(=O)N(Cc2nc3c(c(=O)[nH]2)COCC3)CC(F)F)CC1]

Following general procedure of Example 5, the title compound was prepared (0.046 g) from 2-((2,2-difluoroethylamino)methyl)-7,8-dihydro-3H-pyrano[4,3-d]pyrimidin-4(5H)-one (0.18 g, 0.73 mmol, 1 eq.) and 2-(4-(4-fluorobenzoyl)piperidin-1-yl)acetic acid (0.20 g, 0.73 mmol, 1 eq.). $^1$H NMR (400 MHz, MeOD) δ ppm 8.00-8.18 (m, 2H), 7.17-7.36 (m, 2H), 5.83-6.44 (m, 1H), 4.56-4.68 (m, 2H), 4.42-4.52 (m, 2H), 4.30-4.42 (m, 2H), 3.80-4.08 (m, 4H), 3.66-3.79 (m, 3H), 3.42-3.61 (m, 1H), 3.09-3.26 (m, 1H), 2.56-2.71 (m, 2H), 1.93-2.28 (m, 4H). HRMS calculated for $C_{24}H_{28}F_3N_4O_4$ 493.2063. found (ESI, [M+H]+) 493.2062. MS (ESI) m/z 493.2 (M+H)$^+$. Retention time: 4.65 min (5-95% $CH_3CN/H_2O$ over 7.75 min with 0.1% formic acid, Inertsil ODS3 100×3 mm C18 column with flow rate of 1.0 mL/min).

Example 46

N-(5-Cyano-thiophen-2-ylmethyl)-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide

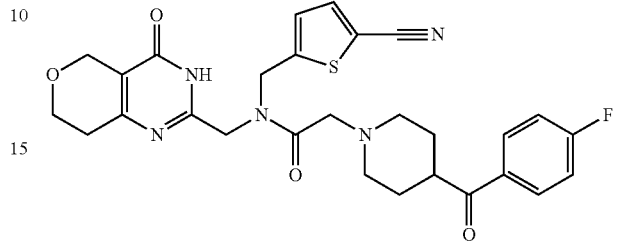

Following general procedure of Example 5, the title compound was prepared (0.01 g) from 5-(((4-oxo-4,5,7,8-tetrahydro-3H-pyrano[4,3-d]pyrimidin-2-yl)methylamino)methyl)thiophene-2-carbonitrile and 2-(4-(4-fluorobenzoyl)piperidin-1-yl)acetic acid. $^1$H NMR (400 MHz, MeOD) δ ppm 8.03-8.18 (m, 2H), 7.50-7.79 (m, 1H), 7.21-7.34 (m, 2H), 7.01-7.14 (m, 1H), 4.81-4.89 (m, 2H), 4.51-4.62 (m, 2H), 4.33-4.49 (m, 4H), 3.85-4.04 (m, 2H), 3.67-3.82 (m, 2H), 3.38-3.65 (m, 1H), 3.08-3.28 (m, 2H), 2.46-2.68 (m, 2H), 1.98-2.27 (m, 4H). HRMS calculated for $C_{28}H_{28}F_1N_5O_4S_1$ 550.1924. found (ESI, [M+H]+) 550.1933. MS (ESI) m/z 550.6 (M+H)$^+$. Retention time: 3.3 min (5-95% $CH_3CN/H_2O$ over 7.75 min with 0.1% formic acid, Inertsil ODS3 100×3 mm C18 column with flow rate of 1.0 mL/min).

Example 47

2-[4-(4-Fluoro-benzoyl)-piperidin-1-yl]-N-[5-(morpholine-4-sulfonyl)-thiophen-2-ylmethyl]-N-(4-oxo-3,5,7,8-tetrahydro-4H-pyrano[4,3-d]pyrimidin-2-ylmethyl)-acetamide

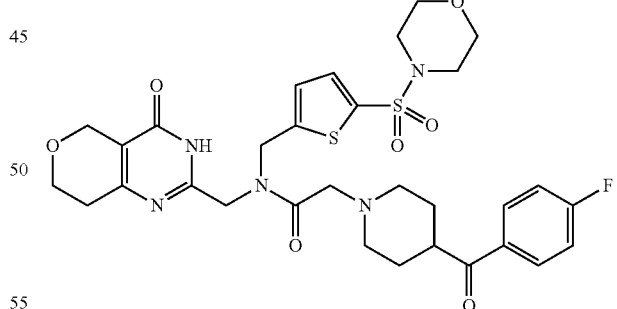

Following general procedure of Example 5, the title compound was prepared (0.044 g) from 2-(((5-(morpholinosulfonyl)thiophen-2-yl)methylamino)methyl)-7,8-dihydro-3H-pyrano[4,3-d]pyrimidin-4(5H)-one and 2-(4-(4-fluorobenzoyl)piperidin-1-yl)acetic acid. $^1$H NMR (400 MHz, MeOD) δ ppm 8.04-8.16 (m, 2H), 7.33-7.59 (m, 1H), 7.23-7.31 (m, 2H), 7.05-7.15 (m, 1H), 4.84-4.89 (m, 2H), 4.54-4.63 (m, 2H), 4.36-4.52 (m, 4H), 3.85-3.98 (m, 2H), 3.67-3.83 (m, 6H), 3.17-3.28 (m, 3H), 2.87-2.98 (m, 4H), 2.47-2.67 (m, 2H), 1.98-2.26 (m, 4H). HRMS calculated for $C_{31}H_{37}F_1N_5O_7S_2$ 674.2118. found (ESI, [M+H]+) 674.2119.

MS (ESI) m/z 674.2. (M+H)+. Retention time: 3.3 min (5-95% CH₃CN/H₂O over 7.75 min with 0.1% formic acid, Inertsil ODS3 100×3 mm C18 column with flow rate of 1.0 mL/min).

Example 48

2-[4-(4-Fluoro-benzoyl)-piperidin-1-yl]-N-(4-oxo-3,5,7,8-tetrahydro-4H-pyrano[4,3-d]pyrimidin-2-ylmethyl)-N-(2,2,2-trifluoro-ethyl)-acetamide

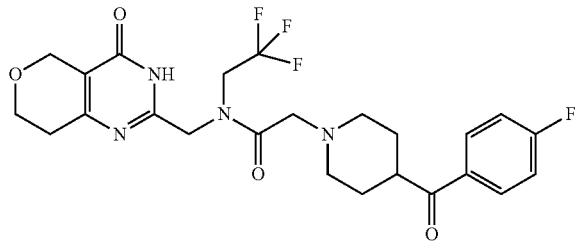 [SMILES: O=C(c1ccc(F)cc1)C1CCN(CC(=O)N(Cc2nc3c(c(=O)[nH]2)COCC3)CC(F)(F)F)CC1]

Following the general procedure of Example 1, the title compound was prepared (0.015 g) from 2-((2,2,2-trifluoroethylamino)methyl)-7,8-dihydro-3H-pyrano[4,3-d]pyrimidin-4(5H)-one and 2-(4-(4-fluorobenzoyl)piperidin-1-yl)acetic acid. $^1$H NMR (400 MHz, MeOD) δ ppm 8.04-8.18 (m, 2H), 7.21-7.33 (m, 2H), 4.62-4.70 (m, 2H), 4.36-4.53 (m, 5H), 4.17-4.30 (m, 1H), 3.87-4.00 (m, 2H), 3.66-3.80 (m, 2H), 3.38-3.59 (m, 1H), 3.08-3.26 (m, 2H), 2.54-2.69 (m, 2H), 1.93-2.27 (m, 4H). HRMS calculated for $C_{24}H_{27}F_4N_4O_4$ 511.1968. found (ESI, [M+H]+) 511.1963. MS (ESI) m/z 511.2. (M+H)+. Retention time: 3.02 min (5-95% CH₃CN/H₂O over 7.75 min with 0.1% formic acid, Inertsil ODS3 100×3 mm C18 column with flow rate of 1.0 mL/min).

Example 49

2-[4-(4-Fluoro-benzoyl)-piperidin-1-yl]-N-(4-oxo-3,5,7,8-tetrahydro-4H-pyrano[4,3-d]pyrimidin-2-ylmethyl)-N-(1-thiophen-2-yl-ethyl)-acetamide

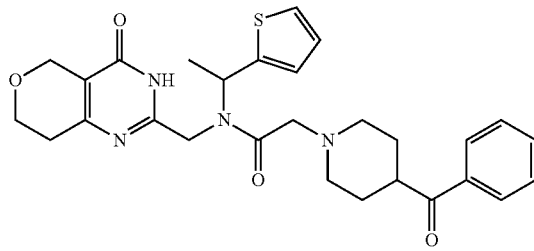

Following the general procedure of Example 1, the title compound was prepared (0.02 g) from 2-((1-(thiophen-2-yl)ethylamino)methyl)-7,8-dihydro-3H-pyrano[4,3-d]pyrimidin-4(5H)-one and 2-(4-(4-fluorobenzoyl)piperidin-1-yl)acetic acid. $^1$H NMR (400 MHz, MeOD) δ ppm 8.04-8.17 (m, 2H), 7.22-7.46 (m, 3H), 6.99-7.17 (m, 1H), 6.86-6.95 (m, 1H), 6.09-6.24 (m, 1H), 5.36-5.47 (m, 1H), 4.24-4.64 (m, 6H), 3.85-3.95 (m, 2H), 3.69-3.83 (m, 2H), 3.38-3.64 (m, 1H), 3.11-3.27 (m, 1H), 2.49-2.68 (m, 2H), 1.99-2.26 (m, 4H), 1.74-1.85 (m, 1H), 1.55 (d, J=7.03 Hz, 2H). HRMS calculated for $C_{29}H_{31}F_1N_4O_4S_1$ 539.2128. found (ESI, [M+H]+) 539.2128. MS (ESI) m/z 539.2. (M+H)+. Retention time: 3.21 min (5-95% CH₃CN/H₂O over 7.75 min with 0.1% formic acid, Inertsil ODS3 100×3 mm C18 column with flow rate of 1.0 mL/min).

Example 50

N-(2,2-Difluoro-ethyl)-2-[4-(4-methoxy-benzoyl)-piperidin-1-yl]-N-(4-oxo-3,5,7,8-tetrahydro-4H-pyrano[4,3-d]pyrimidin-2-ylmethyl)-acetamide

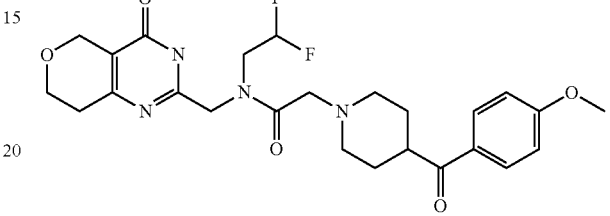

Following the general procedure of Example 1, the title compound was prepared (0.07 g) from 2-(4-methoxy-benzoylpiperidin-1-yl)acetic acid (0.24 g, 0.69 mmol, 1.3 eq.). $^1$H NMR (400 MHz, MeOD) δ ppm 7.88-8.02 (m, 2H), 6.91-7.07 (m, 2H), 5.71-6.44 (m, 1H), 4.63-4.69 (m, 1H), 4.54-4.59 (m, 1H), 4.42-4.52 (m, 1H), 4.02-4.25 (m, 1H), 3.92-3.99 (m, 3H), 3.86 (s, 3H), 3.34-3.51 (m, 2H), 2.93-3.17 (m, 1H), 2.82-2.94 (m, 1H), 2.49-2.73 (m, 2H), 2.11-2.35 (m, 2H), 1.63-1.89 (m, 3H), 1.19-1.52 (m, 3H). HRMS calculated for $C_{25}H_{31}F_2N_4O_5$ 505.2263. found (ESI, [M+H]+) 505.2271. MS (ESI) m/z 504.8. (M+H)+. Retention time: 2.7 min (5-95% CH₃CN/H₂O over 7.75 min with 0.1% formic acid, Inertsil ODS3 100×3 mm C18 column with flow rate of 1.0 m L/m in).

Example 51

2-(4-(6-Fluorobenzo[d]isoxazol-3-yl)piperidin-1-yl)-N-((4-oxo-4,5,7,8-tetrahydro-3H-pyrano[4,3-d]pyrimidin-2-yl)methyl)acetamide

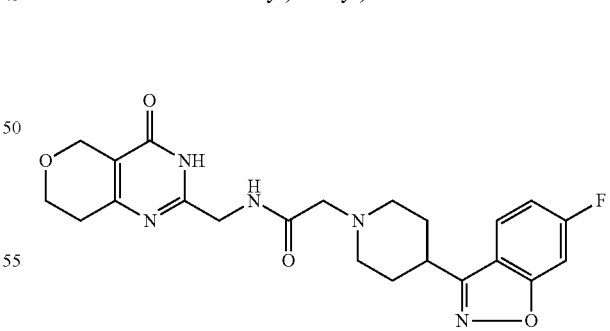

The title compound (46 mg) was prepared following the general procedures for the synthesis of 2-(4-(4-fluorobenzoyl)piperidin-1-yl)acetic acid and Example 1 from 6-fluoro-3-(piperidin-4-yl)benzo[d]isoxazole. $^1$H NMR (400 MHz, CDCl₃) δ 11.22 (s, 1H), 8.31 (s, 1H), 7.69 (s, 1H), 7.29 (dd, J=8.0, 2.0 Hz, 1H), 7.10 (dt, J=8.5, 2.0 Hz, 1H), 4.58 (s, 2H), 4.43 (d, J=6.0 Hz, 2H), 3.96 (t, J=5.5 Hz, 2H), 2.96-3.41 (m, 5H), 2.65-2.75 (m, 2H), 2.37-2.63 (m, 2H), 2.02-2.29 (m, 4H). HRMS calculated for C$_{22}$H$_{24}$FN$_5$O$_4$ 442.1891. found (ESI, [M+H]$^+$), 442.1889. MS m/z 442.3 (M+1), retention time=1.40 min.

Example 52

N-(4-Oxo-3,5,7,8-tetrahydro-4H-pyrano[4,3-d]pyrimidin-2-ylmethyl)-2-[4-(5-phenyl-[1,3,4]oxadiazol-2-yl)-piperidin-1-yl]-acetamide

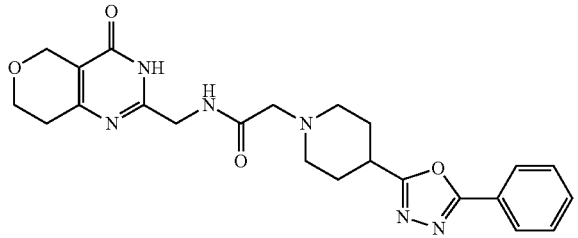 [SMILES: O=C(CN1CCC(c2nnc(-c3ccccc3)o2)CC1)NCc1nc2c(c(=O)[nH]1)COCC2]

To a stirred solution of [4-5-phenyl-[1,3,4]oxadiazol-2-yl)-piperidin-1-yl]-acetic acid in DMF were added HBTU (79 mg, 0.209 mmol, 1.5 eq.) and DIPEA (49 μL 0.278 mmol, 2 eq.). The mixture was stirred for 5 min and 2-aminomethyl-3,5,7,8-tetrahydro-pyrano[4,3-d]pyrimidin-4-one was added and the mixture stirred for 1 h. Upon reaction completion, ethyl acetate (3 mL) was added and the reaction mixture was washed with water (2×3 mL) and brine (3 mL). The organic layers were combined, dried over Na$_2$SO$_4$ and the solvent evaporated in vacuo, leaving a yellow oil, which was purified by column chromatography (MeOH/CH$_2$Cl$_2$) yielding a clear oil. Addition of acetonitrile and sonication gave a white solid precipitate which was filtered and washed with acetonitrile to yield the title compound (20 mg, 0.044 mmol, 25%). $^1$H NMR (400 MHz, DMSO-d$_6$) δ ppm 12.44 (br s, 1H) 8.23-8.31 (m, 1H) 7.98 (d, J=1.52 Hz, 2H) 7.57-7.64 (m, 2H) 4.34 (s, 2H) 4.21 (d, J=5.56 Hz, 2H) 3.80-3.83 (m, 2H) 3.25-3.46 (m, 2H) 3.06 (s, 2H) 2.94-3.03 (m, 3H) 2.83-2.94 (m, 1H) 2.32-2.37 (m, 2H) 2.10 (d, J=10.61 Hz, 2H) 1.92-2.02 (m, 2H). HR-MS (m/z, MH+): 451.2105, 452.2155. HPLC retention time: 7.11 min (Agilent column 3.0×100 mm 3 um C$_{18}$ column; flow rate of 1.0 mL/min with gradient from 2% to 20% in 5 min then 20% to 95% acetonitrile in 10 min, 5 mM ammonium formate)

Example 53

2-(4-Benzoyl-piperidin-1-yl)-N-(2-methoxy-ethyl)-N-(4-oxo-3,5,7,8-tetrahydro-4H-pyrano[4,3-d]pyrimidin-2-ylmethyl)-acetamide

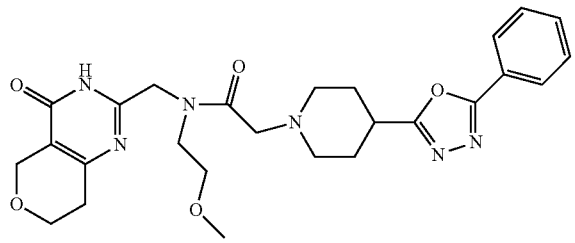 [SMILES: COCCN(Cc1nc2c(c(=O)[nH]1)COCC2)C(=O)CN1CCC(c2nnc(-c3ccccc3)o2)CC1]

The title compound (16.7 mg, 0.033 mmol) was prepared following the general procedure of Example 1 from [4-(5-phenyl-[1,3,4]oxadiazol-2-yl)-piperidin-1-yl]-acetic acid (75 mg, 0.196 mmol, 1 eq) and 2-[(2-methoxy-ethylamino)-methyl]-3,5,7,8-tetrahydro-pyrano[4,3-d]pyrimidin-4-one (54.0 mg, 0.196 mmol, 1.0 eq). $^1$H NMR (400 MHz, chloroform-d) δ ppm 7.84-8.11 (m, 2H) 7.36-7.51 (m, 3H) 4.34-4.55 (m, 4H) 3.77-3.96 (m, 2H) 3.59-3.77 (m, 1H) 3.44-3.58 (m, 3H) 3.17-3.34 (m, 4H) 2.95 (dd, J=15.66, 12.13 Hz, 3H) 2.50-2.69 (m, 2H) 2.26-2.46 (m, 2H) 1.94-2.20 (m, 4H) 1.23-1.48 (m, 2H). HR-MS (m/z, MH+): 509.2519, 510.2566, 511.2614. HPLC retention time: 2.68 min (Agilent column 3.0×100 mm 3 um C18 column; flow rate of 1.0 mL/min with gradient from 5% to 95% acetonitrile in 10 min, 0.1% FA).

Example 54

2-[4-(4-Methoxy-benzoyl)-piperidin-1-yl]-N-(2-methoxy-ethyl)-N-(4-oxo-3,5,7,8-tetrahydro-4H-pyrano[4,3-d]pyrimidin-2-ylmethyl)-acetamide

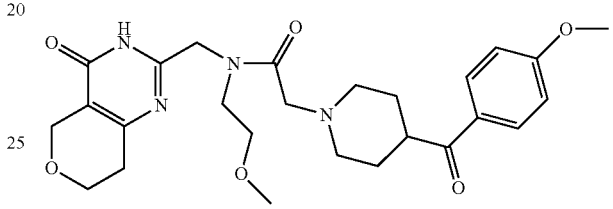

The title compound (22 mg, 0.044 mmol) was prepared following the general procedure of Example 1 from [4-(4-methoxy-benzoyl)-piperidin-1-yl]-acetic acid (65 mg, 0.188 mmol, 1.0 eq) and 2-[(2-methoxy-ethylamino)-methyl]-3,5,7,8tetrahydro-pyrano[4,3-d]pyrimidin-4-one (51.7 mg, 0.188 mmol, 1.0 eq). $^1$H NMR (400 MHz, DMSO-d$_6$) δ ppm 7.88-8.02 (m, 2H) 6.98-7.10 (m, 2H) 4.52 (br s, 1H) 4.36 (d, J=16.67 Hz, 3H) 3.75-3.92 (m, 5H) 3.52-3.58 (m, 3H) 3.42-3.45 (m, 3H) 3.27 (d, J=5.05 Hz, 15H) 3.17 (br s, 2H). HR-MS (m/z, MH+): 499.2580, 500.2607, 501.2628. HPLC retention time: 2.62 min (Ascentis column 3.0×100 mm 3 um C$_{18}$ column; flow rate of 1.0 mL/min with gradient from 5% to 95% acetonitrile in 10 min, 0.1% FA).

Example 55

2-{4-[5-(4-Fluoro-phenyl)-[1,3,4]oxadiazol-2-yl]piperidin-1-yl}-N-(4-oxo-3,5,7,8-tetrahydro-4H-pyrano[4,3-d]pyrimidin-2-ylmethyl)-acetamide

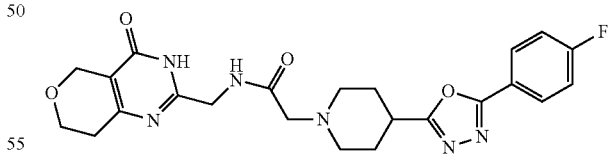

The title compound (14.8 mg, 0.031 mmol) was prepared following the general procedure of Example 1 from {4-[5-(4-fluoro-phenyl)-[1,3,4]oxadiazol-2-yl]-piperidin-1-yl}-acetic acid (90 mg, 0.206 mmol, 1 eq) and 2-aminomethyl-3,5,7,8-tetrahydro-pyrano[4,3-d]pyrimidin-4-one (41.1 mg, 0.227 mmol, 1.1 eq). $^1$H NMR (400 MHz, DMSO-d$_6$) δ ppm 12.38 (br s, 1H) 8.23-8.26 (m, 1H) 8.05 (dd, J=8.84, 5.31 Hz, 2H) 7.43-7.47 (m, 2H) 4.34 (s, 2H) 4.20 (d, J=5.56 Hz, 2H) 4.04-4.11 (m, 1H) 3.80-3.83 (m, 2H) 3.17 (d, J=5.05 Hz, 2H) 3.03-3.11 (m, 1H) 3.01 (s, 2H) 2.93-2.99 (m, 2H) 2.27-2.33 (m, 2H) 2.05-2.10 (m, 2H) 1.85-2.01 (m, 2H). HR-MS (m/z, MH+): 469.2001, 470.2061. HPLC retention time: 2.66 min (Agilent column 3.0×100 mm 3 um $C_{18}$ column; flow rate of 1.0 mL/min with gradient from 5% to 95% acetonitrile in 10 min, 0.1% FA).

Example 56

2-{4-[5-(4-Methoxy-phenyl)-[1,3,4]oxadiazol-2-yl]-piperidin-1-yl}-N-(4-oxo-3,5,7,8-tetrahydro-4H-pyrano[4,3-d]pyrimidin-2-ylmethyl)-acetamide

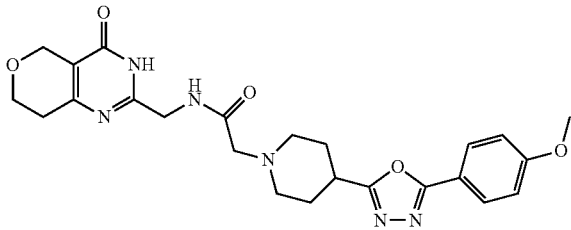 [SMILES: COc1ccc(-c2nnc(C3CCN(CC(=O)NCc4nc5c(c(=O)[nH]4)COCC5)CC3)o2)cc1]

The title compound (10 mg, 0.018 mmol) was prepared following the general procedure of Example 1 from {4-[5-(4-methoxy-phenyl)-[1,3,4]oxadiazol-2-yl]-piperidin-1-yl}-acetic acid (100 mg, 0.246 mmol, 1.0 eq) and 2-aminomethyl-3,5,7,8-tetrahydro-pyrano[4,3-d]pyrimidin-4-one (46.8 mg, 0.258 mmol, 1.05 eq). $^1$H NMR (400 MHz, DMSO-$d_6$) δ ppm 12.43 (br s, 1H) 8.27 (br s, 1H) 7.92 (d, J=9.03 Hz, 2H) 7.14 (d, J=9.03 Hz, 2H) 4.34 (s, 2H) 4.20 (d, J=5.52 Hz, 2H) 3.73-3.92 (m, 5H) 2.86-3.11 (m, 5H) 2.18-2.36 (m, 2H) 2.01-2.10 (m, 2H) 1.87-1.98 (m, 2H). HR-MS (m/z, MH+): 481.2205, 482.2262. HPLC retention time: 2.69 min (Agilent column 3.0×100 mm 3 um C18 column; flow rate of 1.0 mL/min with gradient from 5% to 95% acetonitrile in 10 min, 0.1% FA).

Example 57

2-[4-(6-Fluoro-1H-indazol-3-yl)-piperidin-1-yl]-N-(4-oxo-3,5,7,8-tetrahydro-4H-pyrano[4,3-d]pyrimidin-2-ylmethyl)acetamide

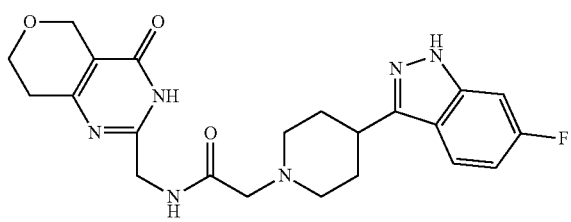 [SMILES: O=C(CN1CCC(c2n[nH]c3cc(F)ccc23)CC1)NCc1nc2c(c(=O)[nH]1)COCC2]

To a solution of EDCl (0.22 g, 1.17 mmol), HOBT (0.16 g, 1.17 mmol) in 10 mL of DMF were added [4-(6-fluoro-1H-indazol-3-yl)-piperidin-1-yl]-acetic acid (0.27 g, 1.0 mmol), 2-aminomethyl-3,5,7,8-tetrahydro-pyrano[4,3-d]pyrimidin-4-one (0.19 g, 1.1 mmol), and $Et_3N$ (0.40 g, 3.9 mmol). The reaction mixture was stirred at ambient temperature for 15 hours then poured into a separatory funnel containing brine. After separation, the aqueous layer was extracted with DCM (50 mL). The combined organic layers were washed with saturated aqueous $NaHCO_3$ solution, dried over $Na_2SO_4$, filtered and concentrated in vacuo to yield an oily liquid. Purification by flash chromatography gave the title compound (89.0 mg, 0.19 mmol, 20% yield) as a yellow solid. MS (ESI) m/z 440.8 (M+H+); HPLC (Novapak 150×3.9 mm C-18 column: mobile phase: 35-90% acetonitrile/water with 0.1% TFA, at 2 mL/min over 2 min.) t 0.96 min. $^1$H NMR (400 MHz, MeOD) δ ppm 1.94-2.27 (m, 4H), 2.36-2.56 (m, 2H), 2.64 (br. s., 2H), 2.98-3.46 (m, 4H), 3.90 (br. s., 2H), 4.27-4.59 (m, 2H), 4.72-5.01 (m, 3H), 6.91 (br. s., 1H), 7.14 (br. s., 1H), 7.82 (br. s., 1H). HRMS calculated for $C_{22}H_{26}FN_6O_3$: 441.2050 (M+H). found (ESI, [M+H]+): 441.2067.

Example 58

2-[4-(6-Methoxy-1H-indazol-3-yl)-piperidin-1-yl]-N-(4-oxo-3,5,7,8-tetrahydro-4H-pyrano[4,3-c]pyrimidin-2-ylmethyl)-acetamide

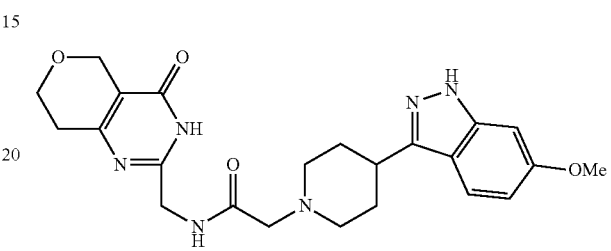

The title compound (20.1 mg, 0.042 mmol) was prepared following the general procedure of Example 1 from [4-(6-methoxy-1H-indazol-3-yl)-piperidin-1-yl]-acetic acid (which was in turn prepared following the general procedure for the synthesis of [4-(6-fluoro-1H-indazol-3-yl)-piperidin-1-yl]-acetic acid from 1-fluoro-3-methoxy-benzene (1.7 g, 13.2 mmol)). MS (ESI) m/z 452.8 (M+H+); HPLC (Insertsil ODS3 100×3 mm C-18 column: mobile phase: 5-95% acetonitrile/water with 0.1% TFA, at 1 mL/min over 7.75 min.), t=0.91 min. $^1$H NMR (400 MHz, MeOD) δ ppm 2.05-2.29 (m, 4H), 2.36-2.47 (m, 2H), 2.60-2.70 (m, 2H), 3.09-3.20 (m, 2H), 3.30-3.33 (m, 2H), 3.79 (s, 3H), 3.88-3.95 (m, 2H), 4.31-4.52 (m, 2H), 4.83 (s, 3H), 6.91 (d, J=8.59 Hz, 1H), 7.45 (d, J=8.59 Hz, 1H), 7.72-8.02 (m, 1H). HRMS calculated for $C_{23}H_{29}N_6O_4$: 453.2250 (M+H). found (ESI, [M+H]+): 453.2251.

Example 59

N-(4-Oxo-3,5,7,8-tetrahydro-4H-pyrano[4,3-d]pyrimidin-2-ylmethyl)-2-[4-(4-phenyl-pyrazol-1-yl)-piperidin-1-yl]-acetamide

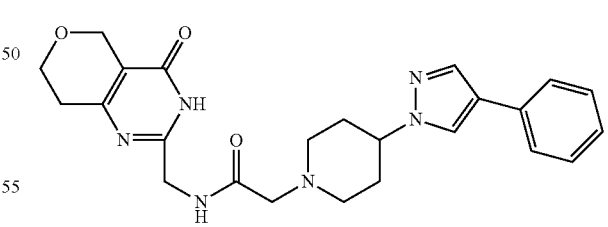

The title compound (84.5 mg, 0.18 mmol) was prepared following the general procedure of Example 1 from 4-(4-phenyl-1H-pyrazol-1-yl)piperidine (1.0 g, 4.4 mmol). MS (ESI) m/z 449.4 (M+H+); HPLC (Insertsil ODS3 100×3 mm C-18 column: mobile phase: 5-95% acetonitrile/water with 0.1% TFA, at 1 mL/min over 7.75 min.) t=1.16 min. $^1$H NMR (400 MHz, DMSO-$d_6$) δ ppm 2.01-2.18 (m, 4H), 2.23-2.35 (m, 1H), 2.45-2.53 (m, 4H), 3.00-3.08 (m, 2H), 3.31 (s, 1H), 3.82 (t, J=5.56 Hz, 2H), 4.13-4.25 (m, 3H), 4.34 (s, 2H), 7.18 (t, J=7.33 Hz, 1H), 7.34 (t, J=7.83 Hz, 2H), 7.57 (d, J=7.07

Hz, 2H), 7.89 (s, 1H), 8.18-8.32 (m, 2H), 12.39 (br. s., 1H). HRMS calculated for $C_{24}H_{29}N_6O_3$: 449.2301 (M+H). found (ESI, [M+H]$^+$): 449.2323.

Example 60

2-{4-[4-(4-Methoxy-phenyl)-pyrazol-1-yl]-piperidin-1-yl}-N-(4-oxo-3,5,7,8-tetrahydro-4H-pyrano[4,3-d]pyrimidin-2-ylmethyl)-acetamide

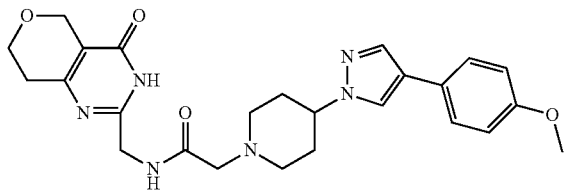 [SMILES: COc1ccc(-c2cnn(C3CCN(CC(=O)NCc4nc5c(c(=O)[nH]4)COCC5)CC3)c2)cc1]

The title compound (59.3 mg, 0.12 mmol) was prepared following the general procedure of Example 1 from 4-[4-(4-methoxy-phenyl)-pyrazol-1-yl]-piperidine (0.30 g, 1.2 mmol). MS (ESI) m/z 479.5 (M+H$^+$); HPLC (Insertsil ODS3 100×3 mm C-18 column: mobile phase: 5-95% acetonitrile/water with 0.1% TFA, at 1 mL/min over 7.75 min.) t=1.16 min. $^1$H NMR (400 MHz, MeOD) δ ppm 2.06-2.16 (m, 2H) 2.16-2.29 (m, 2H) 2.35-2.48 (m, 2H) 2.61-2.69 (m, 2H) 3.09-3.20 (m, 4H) 3.79 (s, 3H) 3.87-3.95 (m, 2H) 4.15-4.27 (m, 1H) 4.36 (s, 2H) 4.47 (s, 2H) 6.91 (d, J=8.59 Hz, 2H) 7.46 (d, J=8.59 Hz, 2H) 7.76 (s, 1H) 7.95 (s, 1H). HRMS calculated for $C_{25}H_{31}N_6O_4$: 479.2407 (M+H). found (ESI, [M+H]$^+$): 479.2414.

Example 61

2-(5-Fluoro-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide

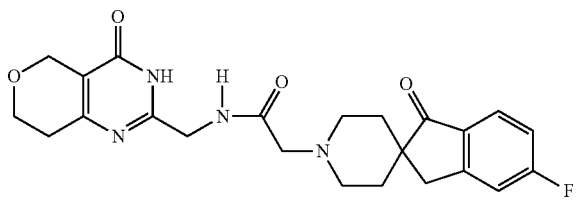 [SMILES: O=C(CN1CCC2(CC1)Cc1cc(F)ccc1C2=O)NCc1nc2c(c(=O)[nH]1)COCC2]

To a stirred solution of 2-(5-fluoro-1-oxo-1,3-dihydrospiro[indene-2,4'-piperidine]-t-yl)acetic acid (118 mg, 0.166 mmol) in DMF (3 mL) at 25° C. was added DIPEA (0.087 mL, 0.497 mmol) and HBTU (69.3 mg, 0.182 mmol). After being stirred at ambient temperature for 15 min, 2-aminomethyl-3,5,7,8-tetrahydro-pyrano[4,3-d]pyrimidin-4-one (30 mg, 0.166 mmol) in 1 mL of DMF was added. After being stirred at 25° C. for 1 hr, the reaction mixture was quenched with 20 mL of water and extracted twice with 15 mL of ethyl acetate, dried over Na$_2$SO$_4$ and concentrated in vacuo. The crude product is purified by HPLC (column: Waters Sunfire 5 um 50×50 mm; mobile phase: acetonitrile 20%/H$_2$O 80% (with 0.1% TFA) to acetonitrile 50%/H$_2$O 50% (with 0.1% TFA) over 10 min and with flow at rate 60 mL/min, concentrated to give 28.1 mg of white solid as TFA salt which was dissolved in 1 mL of MeOH and neutralized by passing through PL-HCO$_3$ MP-Resin, and concentrated to give the title compound (19 mg, 0.043 mmol). HRMS calculated for $C_{23}H_{26}FN_4O_4$ 441.1860. found (ESI) m/z 441.1944 [M+H]$^+$), retention time 2.38 min.

Example 62

N-(Cyclopropylmethyl)-2-(5-fluoro-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide

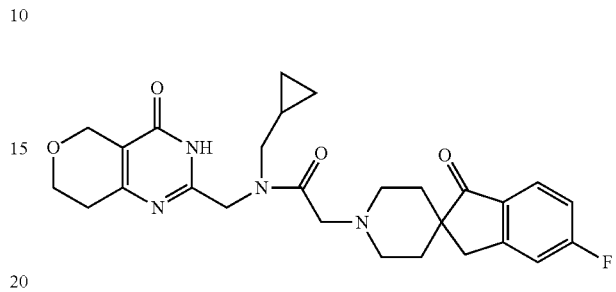

Following general procedure of Example 1, the title compound (9.0 mg, 0.018 mmol, 11.27% yield) was prepared from 2-(5-fluoro-1-oxo-1,3-dihydrospiro[indene-2,4'-piperidine]-1'-yl)acetic acid (115 mg, 0.162 mmol). HRMS calculated for $C_{27}H_{32}FN_4O_4$ 495.2408. found (ESI) m/z 495.2386 (M+H)$^+$, retention time 2.78 min.

Example 63

N-(Cyclopropylmethyl)-2-(5-methoxy-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide

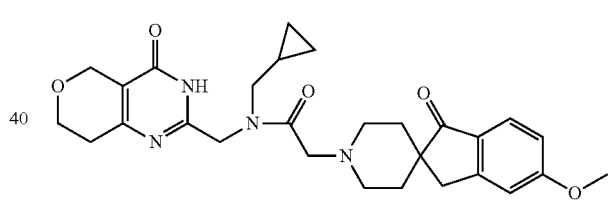

To a stirred solution of 2-(5-methoxy-1-oxo-1,3-dihydrospiro[indene-2,4'-piperidine]-1'-yl)acetic acid (96 mg, 0.332 mmol) in DMF (5 mL) was added DIPEA (0.174 mL, 0.995 mmol) and HBTU (139 mg, 0.365 mmol) at 25° C. After being stirred for 10 min at ambient temperature, 2-[(cyclopropylmethyl-amino)-methyl]-3,5,7,8-tetrahydro-pyrano[4,3-d]pyrimidin-4-one (90 mg, 0.332 mmol) was added to the reaction mixture and stirred at ambient temperature for 2 h. The reaction mixture was diluted with 20 mL of ethyl acetate and washed with 5 mL of water, dried over Na$_2$SO$_4$ and concentrated in vacuo. The crude product was purified by HPLC (column Waters Sunfire 5 um 50×50 mm; mobile phase acetonitrile 20%/H$_2$O 80% (with 0.1% TFA) to acetonitrile 50%/H$_2$O 50% (with 0.1% TFA) over 10 min; flow rate: 60 mL/min) and concentrated to give 15 mg of white solid as TFA salt which was dissolved in 1 mL of MeOH and neutralized by passing through PL-HCO$_3$ MP-Resin, and concentrated to give the title compound (63.5 mg, 0.125 mmol). $^1$H NMR (CD$_3$OD) δ 7.67 (d, J=8.6 Hz, 1H), 7.07 (d, J=6.5 Hz, 1H), 7.01 (d, J=8.0 Hz, 1H), 4.69 (s, 1H), 4.61 (s, 1H), 4.49 (s, 1H), 4.46 (s, 2H), 4.40 (s, 1H), 3.98 (s, 1H), 3.95-3.9 (m, 1H), 3.92 (d, J=2.5 Hz, 2H), 3.90 (s, 1H), 3.78-3.75 (m, 2H), 3.59 (s, 1H), 3.38 (d, J=7.0 Hz, 2H), 3.32-3.31 (m, 3H), 3.22 (s, 1H), 3.19 (s, 1H), 3.11 (s, 1H), 2.67-2.62 (m, 2H), 2.27 (s, 1H), 2.11 (s, 1H), 1.72 (d, J=14, 1H), 0.65-0.61 (m, 1H), 0.49-0.44 (m, 1H), 0.35-0.31 (m, 1H), 0.24-0.21 (m, 1H); $^{13}$C NMR (CD$_3$OD) δ 207.88, 168.06, 163.36, 161.18, 160.80, 158.45, 157.27, 128.85, 127.13, 119.59, 117.53, 111.03, 65.15, 63.63, 57.95, 56.44, 53.78, 52.52, 52.22, 47.81, 38.70, 31.63, 31.08, 30.85, 10.48, 10.05, 4.24. HRMS calculated for C$_{28}$H$_{35}$N$_4$O$_5$ 507.2607. found (ESI) m/z 507.2613 (M+H)$^+$, retention time 2.81 min.

Example 64

N-(2,2-Difluoro-ethyl)-2-(5-methoxy-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide

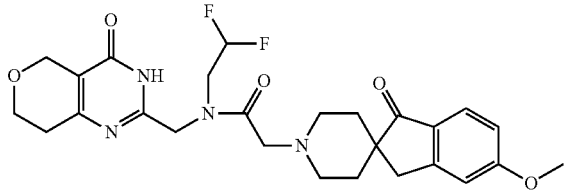 [SMILES: COc1ccc2c(c1)CC1(CCN(CC(=O)N(Cc3nc4c(c(=O)[nH]3)COCC4)CC(F)F)CC1)C2=O]

Following the general procedure of Example 1 the title compound (20.0 mg, 0.039 mmol) was prepared from 2-(5-methoxy-1-oxo-1,3-dihydrospiro[indene-2,4'piperidine]-1'-yl)acetic acid (96 mg, 0.332 mmol). HRMS calculated for C$_{26}$H$_{30}$F$_2$N$_4$O$_5$ 517.2263. found (ESI) m/z 517.2261 (M+H)$^+$, retention time: 2.75 min.

Example 65

2-(1-oxo-3,4-dihydro-1H-spiro[naphthalene-2,4'-piperidine]-1'-yl)-N-((4-oxo-4,5,7,8-tetrahydro-3H-pyrano[4,3-d]pyrimidin-2-yl)methyl)acetamide

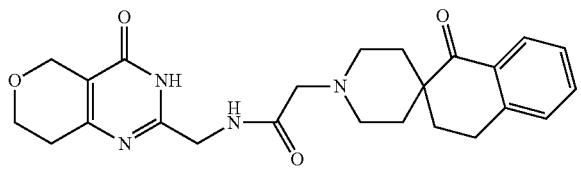 [SMILES: O=C(CN1CCC2(CCc3ccccc3C2=O)CC1)NCc1nc2c(c(=O)[nH]1)COCC2]

To a solution of 2-(1-oxo-3,4-dihydro-1H-spiro[naphthalene-2,4'-piperidine]-1'-yl)acetic acid (37 mg, 0.135 mmol) in DMF (3 mL) at 25° C. was added DIPEA (0.071 mL, 0.406 mmol) and HBTU (56.5 mg, 0.149 mmol). After being stirred at 25° C. for 15 min, 2-aminomethyl-3,5,7,8-tetrahydro-pyrano[4,3-d]pyrimidin-4-one (24.53 mg, 0.135 mmol) in 1 mL of DMF was added. After being stirred at 25° C. for 2 h, the reaction mixture was quenched with 20 mL of water, extracted twice with 15 mL of ethyl acetate, dried with Na$_2$SO$_4$ and concentrated. The crude product was purified by HPLC (column: Waters Sunfire 5 um 50×50 mm; mobile phase: gradient of acetonitrile 20%/H$_2$O 75% (with 0.1% TFA) to acetonitrile 50%/H$_2$O 50% over 10 min; flow rate: 60 mL/min). After concentrating and lyophilization the TFA salt of the title compound was obtained as a white solid (12.8 mg). HRMS calculated for C$_{18}$H$_{24}$NO$_4$ 437.2189. found (ESI) m/z 437.2188 (M+H)$^+$, retention time 2.54 min.

Example 66

2-(4-(4-Ethoxybenzoyl)piperidin-1-yl)-N-((4-oxo-4,5,7,8-tetrahydro-3H-pyrano[4,3-d]pyrimidin-2-yl)methyl)acetamide

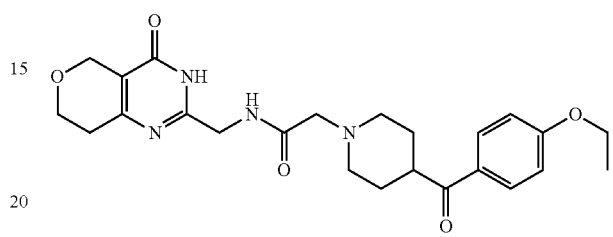

The title compound (150 mg) was prepared following the general procedure of Example 1 from 2-aminomethyl-3,5,7,8-tetrahydro-pyrano[4,3-d]pyrimidin-4-one (300 mg, 1.66 mmol) and 2-(4-(4-ethoxybenzoyl)piperidin-1-yl)acetic acid (603 mg, 1.66 mmol). 1H NMR (400 MHz, CDC$_3$) δ 10.67 (s, 1H), 8.07 (t, J=6.0 Hz, 1H), 7.92 (d, J=9.0 Hz, 2H), 6.94 (t, J=9.0 Hz, 2H), 4.56 (s, 2H), 4.37 (d, J=6.0 Hz, 2H), 4.10 (q, J=7.0 Hz, 2H), 3.95 (t, J=5.5 Hz, 2H), 3.20-3.29 (m, 1H), 2.91-3.00 (m, 2H), 2.66-2.72 (m, 2H), 2.30-2.40 (m, 2H), 1.80-1.90 (m, 4H), 1.45 (t, J=7.0 Hz, 3H). HRMS calculated for C$_{24}$H$_{30}$N$_4$O$_5$ 455.2294. found (ESI, [M+H]$^+$), 455.2308. MS m/z 455.2 (M+1), retention time=2.70 min.

Example 67

2-(4-(4-Methoxybenzoyl)piperidin-1-yl)-N-((4-oxo-4,5,7,8-tetrahydro-3H-pyrano[4,3-d]pyrimidin-2-yl)methyl)acetamide

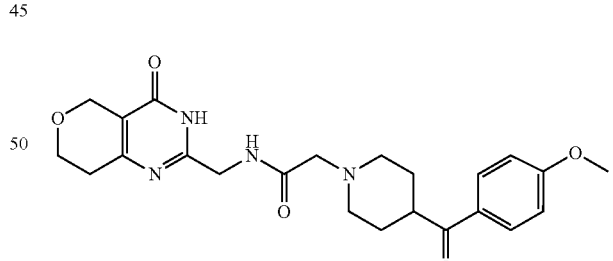

The title compound (25 mg) was prepared following the general procedure of Example 1 from 2-(4-(4-fluorobenzoyl)piperidin-1-yl)acetic acid. $^1$H NMR (400 MHz, DMSO-d$_6$) δ 8.24 (s, 1H), 7.97 (d, J=9.0 Hz, 2H), 7.04 (d, J=9.0 Hz, 2H), 4.27 (s, 2H), 4.02 (d, J=4.5 Hz, 2H), 3.84 (s, 3H), 3.79 (q, J=6.0 Hz, 2H), 3.15-3.19 (m, 1H), 2.89-2.99 (m, 4H), 2.40-2.47 (m, 2H), 2.18-2.30 (m, 2H), 1.68-1.77 (m, 4H). HRMS calculated for C$_{23}$H$_{28}$N$_4$O$_5$ 441.2138. found (ESI, [M+H]$^+$), 441.2141. MS m/z 445.2 (M+1), retention time=2.70 min.

Example 68

2-(4-Benzoyl-piperidin-1-yl)-N-(2,2-difluoro-ethyl)-N-(4-oxo-3,5,7,8-tetrahydro-4H-pyrano[4,3-d]pyrimidin-2-ylmethyl)-acetamide

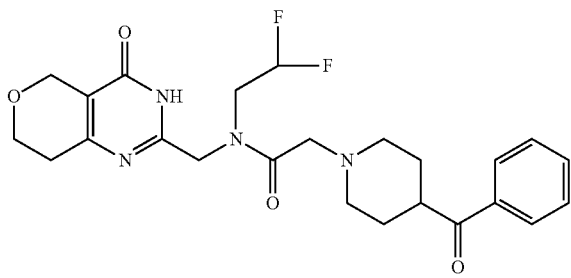 [SMILES: O=C(c1ccccc1)C1CCN(CC(=O)N(Cc2nc3c(c(=O)[nH]2)COCC3)CC(F)F)CC1]

The title compound (0.07 g) was prepared following the general procedure of Example 1 from 2-(4-benzoylpiperidin-1-yl)acetic acid and 2-((2,2-difluoroethylamino)methyl)-7,8-dihydro-3H-pyrano[4,3-d]pyrimidin-4(5H)-one. $^1$H NMR (400 MHz, MeOD) δ ppm 7.89-8.03 (m, 2H), 7.44-7.66 (m, 3H), 5.88-6.43 (m, 1H), 4.61-4.69 (m, 1H), 4.53-4.60 (m, 1H), 4.40-4.48 (m, 1H), 3.78-4.23 (m, 5H), 3.36-3.59 (m, 2H), 3.02-3.18 (m, 1H), 2.83-2.93 (m, 1H), 2.54-2.69 (m, 3H), 2.13-2.36 (m, 2H), 1.65-1.97 (m, 3H), 1.37-1.54 (m, 1H). HRMS calculated for $C_{24}H_{29}F_2N_4O_4$ 475.2157. found (ESI, [M+H]+) 475.2180. MS (ESI) m/z 475.2. (M+H)$^+$. Retention time: 3.04 min (5-95% $CH_3CN/H_2O$ over 7.75 min with 0.1% formic acid, Inertsil ODS3 100×3 mm C18 column with flow rate of 1.0 mL/min).

Example 69

2-[4-(4-Chloro-benzoyl)-piperidin-1-yl]-N-(2,2-difluoro-ethyl)-N-(4-oxo-3,5,7,8-tetrahydro-4H-pyrano[4,3-c]pyrimidin-2-ylmethyl)-acetamide

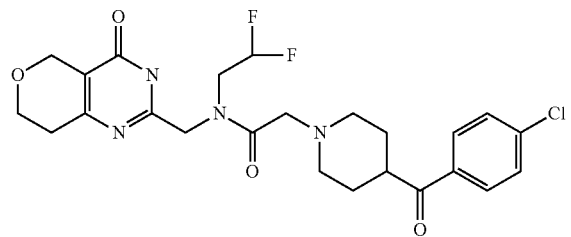 [SMILES: O=C(c1ccc(Cl)cc1)C1CCN(CC(=O)N(Cc2nc3c(c(=O)[nH]2)COCC3)CC(F)F)CC1]

The title compound (0.063 g) was prepared following the general procedure of Example 1 from 2-((2,2-difluoroethylamino)methyl)-7,8-dihydro-3H-pyrano[4,3-d]pyrimidin-4(5H)-one hydrochloride (0.1 g, 0.36 mmol, 1 eq.) and 2-(4-chloro-benzoylpiperidin-1-yl)acetic acid (0.1 g, 0.39 mmol, 1.1 eq.). $^1$H NMR (400 MHz, MeOD) δ ppm 7.85-8.02 (m, 2H), 7.50 (t, 2H), 5.86-6.45 (m, 1H), 4.65 (s, 1H), 4.56 (s, 1H), 4.42-4.52 (m, 1H), 4.07-4.23 (m, 1H), 3.77-3.99 (m, 4H), 3.33-3.41 (m, 3H), 3.21-3.28 (m, 1H), 2.99-3.11 (m, 1H), 2.82-2.93 (m, 1H), 2.53-2.69 (m, 1H), 2.11-2.34 (m, 2H), 1.67-1.91 (m, 2H), 1.37-1.54 (m, 2H). HRMS calculated for $C_{24}H_{28}Cl_1F_2N_4O_4$ 509.1767. found (ESI, [M+H]+) 509.1779. MS (ESI) m/z 509.2. (M+H)$^+$. Retention time: 5.29 min (5-95% $CH_3CN/H_2O$ over 7.75 min with 0.1% formic acid, Inertsil ODS3 100×3 mm C18 column with flow rate of 1.0 mL/min).

Example 70

N-Cyclopropylmethyl-N-(4-oxo-3,5,7,8-tetrahydro-4H-pyrano[4,3-c]pyrimidin-2-ylmethyl)-2-[4-(4-trifluoromethoxy-benzoyl)-piperidin-1-yl]-acetamide

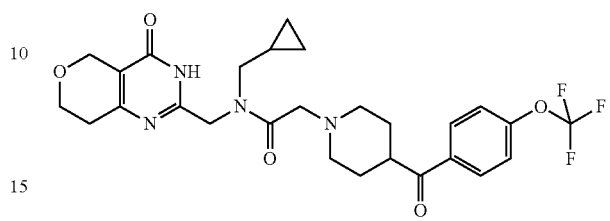

To a mixture of 1-{[cyclopropylmethyl-(4-oxo-3,4a,5,7,8,8a-hexahydro-4H-pyrano[4,3-d]pyrimidin-2-ylmethyl)-carbamoyl]-methyl}-piperidine-4-carbothioic acid S-phenyl ester (0.05 g, 0.101 mmol, 1 eq.), ligand TFP (0.005 g, 0.02 mmol, 0.2 eq.), $Pd_2(dba)_3$ (0.009 g, 0.010 mmol, 0.1 eq.), copper (I) thiophene-2-carboxylate (0.058 g, 0.3 mmol, 3 eq.) was added a solution of 4-(trifluoromethoxy)phenylboronic acid (0.062 g, 0.3 mmol, 3 eq.) in 1 mL of DME while purging with nitrogen. The resulting mixture was stirred at room temperature overnight. After 18 h, the reaction mixture was filtered through celite, washed with dichloromethane and concentrated in vacuo to give an oil. This oil was purified by silica gel column chromatography (98/1/1 to 95/4/1 dichloromethane/MeOH/$NH_4OH$) to give the title compound as a white solid (0.008 g). $^1$H NMR (400 MHz, MeOD) δ ppm 8.02-8.14 (m, 2H), 7.35-7.46 (m, 2H), 4.63-4.77 (m, 1H), 4.51-4.60 (m, 2H), 4.40-4.49 (m, 1H), 3.86-3.99 (m, 2H), 3.46-3.56 (m, 1H), 3.32-3.45 (m, 2H), 2.91-3.16 (m, 2H), 2.55-2.69 (m, 2H), 2.21-2.39 (m, 2H), 1.74-1.95 (m, 3H), 1.56-1.71 (m, 1H), 1.24-1.41 (m, 2H), 0.82-1.10 (m, 1H), 0.42-0.61 (m, 2H), 0.16-0.31 (m, 2H). HRMS calculated for $C_{27}H_{32}F_3N_4O_3$ 549.2325. found (ESI, [M+H]+) 549.2336. MS (ESI) m/z 549.2. (M+H)$^+$. Retention time: 3.39 min (5-95% $CH_3CN/H_2O$ over 7.75 min with 0.1% formic acid, Inertsil ODS3 100×3 mm C18 column with flow rate of 1.0 mL/min).

Example 71

N-(2,2-Difluoro-ethyl)-N-(4-oxo-3,5,7,8-tetrahydro-4H-pyrano[4,3-d]pyrimidin-2-ylmethyl)-2-[4-(4-trifluoromethoxy-benzoyl)-piperidin-1-yl]-acetamide

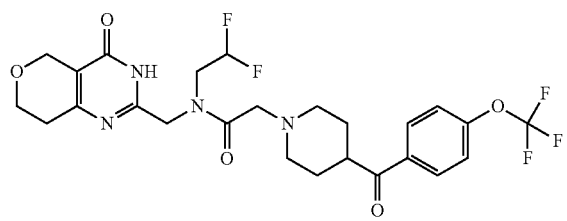 [SMILES: O=C(c1ccc(OC(F)(F)F)cc1)C1CCN(CC(=O)N(Cc2nc3c(c(=O)[nH]2)COCC3)CC(F)F)CC1]

tert-Butyl 4-(4-(trifluoromethoxy)benzoyl)piperidine-1-carboxylate (0.38 g, 1.02 mmol) was converted to the corresponding piperidin-1-yl-acetic acid following the general procedures for the synthesis of piperidin-4-yl-(2-trifluoromethoxy-phenyl)-methanone and was then used to prepare the title compound (0.30 g) following the general procedure of Example 1 from 2-((2,2-difluoroethylamino)methyl)-7,8-dihydro-3H-pyrano[4,3-d]pyrimidin-4(5H)-one. $^1$H NMR (400 MHz, MeOD) δ ppm 7.98-8.17 (m, 2H), 7.32-7.45 (m, 2H), 4.61-4.69 (m, 1H), 4.52-4.58 (m, 1H), 4.40-4.52 (m, 1H), 3.74-4.02 (m, 4H), 3.39-3.52 (m, 1H), 2.94-3.17 (m, 1H), 2.81-2.95 (m, 1H), 2.53-2.71 (m, 1H), 2.12-2.34 (m, 1H), 1.66-1.95 (m, 2H), 1.40-1.58 (m, 1H), 1.18-1.38 (m, 5H), 0.78-0.97 (m, 2H). HRMS calculated for $C_{23}H_{28}F_3N_4O_3$ 559.1980. found (ESI, [M+H]+) 559.1984. MS (ESI) m/z 558.5. (M+H)$^+$. Retention time: 5.68 min (5-95% $CH_3CN/H_2O$ over 7.75 min with 0.1% formic acid, Inertsil ODS3 100×3 mm C18 column with flow rate of 1.0 mL/min).

Example 72

N-(2,2-Difluoro-ethyl)-2-[4-(2-methoxy-benzoyl)-piperidin-1-yl]-N-(4-oxo-3,5,7,8-tetrahydro-4H-pyrano[4,3-d]pyrimidin-2-ylmethyl)-acetamide

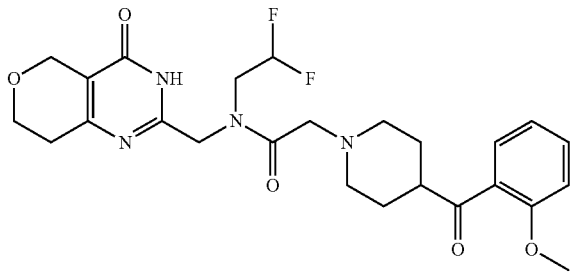 [SMILES: COc1ccccc1C(=O)C1CCN(CC(=O)N(Cc2nc3c(c(=O)[nH]2)COCC3)CC(F)F)CC1]

tert-Butyl 4-(2-methoxybenzoyl)piperidine-1-carboxylate (0.16 g) was converted to the corresponding piperidin-1-yl-acetic acid following the general procedures for the synthesis of piperidin-4-yl-(2-trifluoromethoxy-phenyl)-methanone and was then used to prepare the title compound (0.076 g) following the general procedure of Example 1 from 2-((2,2-difluoroethylamino)methyl)-7,8-dihydro-3H-pyrano[4,3-d]pyrimidin-4(5H)-one. $^1$H NMR (400 MHz, MeOD) δ ppm 7.40-7.53 (m, 2H), 7.05-7.14 (m, 1H), 6.95-7.05 (m, 1H), 5.86-6.41 (m, 1H), 4.60-4.67 (m, 1H), 4.53-4.57 (m, 1H), 4.44-4.50 (m, 1H), 4.05-4.18 (m, 1H), 3.89-3.98 (m, 4H), 3.88 (s, 3H), 3.54-3.70 (m, 2H), 3.07-3.21 (m, 3H), 2.95-3.04 (m, 1H), 2.77-2.88 (m, 1H), 2.53-2.68 (m, 2H), 2.04-2.24 (m, 2H), 1.62-1.93 (m, 2H). HRMS calculated for $C_{25}H_{31}F_2N_4O_5$ 505.2263. found (ESI, [M+H]+) 505.2279. MS (ESI) m/z 504.6 (M+H)$^+$. Retention time: 4.75 min (5-95% $CH_3CN/H_2O$ over 7.75 min with 0.1% formic acid, Inertsil ODS3 100×3 mm C18 column with flow rate of 1.0 mL/min).

Example 73

N-(2,2-Difluoro-ethyl)-2-[4-(3-methoxy-benzoyl)-piperidin-1-yl]-N-(4-oxo-3,5,7,8-tetrahydro-4H-pyrano[4,3-d]pyrimidin-2-ylmethyl)-acetamide

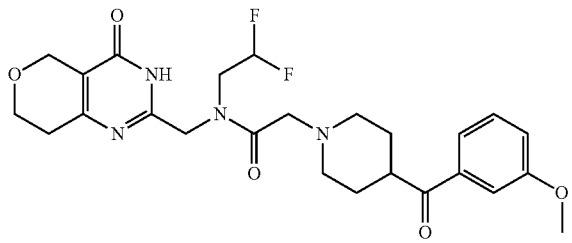 [SMILES: COc1cccc(C(=O)C2CCN(CC(=O)N(Cc3nc4c(c(=O)[nH]3)COCC4)CC(F)F)CC2)c1]

tert-Butyl 4-(3-methoxybenzoyl)piperidine-1-carboxylate (0.1 g) was converted to the corresponding piperidin-1-yl-acetic acid following the general procedures for the synthesis of piperidin-4-yl-(2-trifluoromethoxy-phenyl)-methanone and was then used to prepare the title compound (0.044 g) following the general procedure of Example 1 from 2-((2,2-difluoroethylamino)methyl)-7,8-dihydro-3H-pyrano[4,3-d]pyrimidin-4(5H)-one. $^1$H NMR (400 MHz, MeOD) δ ppm 7.56-7.64 (m, 1H), 7.40-7.54 (m, 2H), 7.15-7.27 (m, 1H), 5.81-6.44 (m, 1H), 4.56-4.67 (m, 2H), 4.42-4.53 (m, 2H), 4.31-4.42 (m, 2H), 3.88-4.08 (m, 4H), 3.85 (s, 3H), 3.64-3.79 (m, 3H), 3.38-3.63 (m, 1H), 3.08-3.28 (m, 1H), 2.56-2.71 (m, 2H), 1.95-2.27 (m, 4H). HRMS calculated for $C_{25}H_{31}F_2N_4O_5$ 505.2263. found (ESI, [M+H]+) 505.2279. MS (ESI) m/z 504.8 (M+H)$^+$. Retention time: 3.04 min (5-95% $CH_3CN/H_2O$ over 7.75 min with 0.1% formic acid, Inertsil ODS3 100×3 mm C18 column with flow rate of 1.0 mL/min).

Example 74

N-(2,2-Difluoro-ethyl)-N-(4-oxo-3,5,7,8-tetrahydro-4H-pyrano[4,3-d]pyrimidin-2-ylmethyl)-2-[4-(3-trifluoromethoxy-benzoyl)-piperidin-1-yl]-acetamide

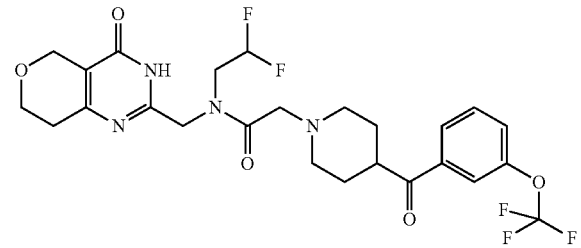 [SMILES: O=C(c1cccc(OC(F)(F)F)c1)C1CCN(CC(=O)N(Cc2nc3c(c(=O)[nH]2)COCC3)CC(F)F)CC1]

(tert-Butyl 4-(3-(trifluoromethoxy)benzoyl)piperidine-1-carboxylate (0.31 g) was converted to the corresponding piperidin-1-yl-acetic acid following the general procedures for the synthesis of piperidin-4-yl-(2-trifluoromethoxy-phenyl)-methanone and was then used to prepare the title compound (0.006 g) following the general procedure of Example 1 from 2-((2,2-difluoroethylamino)methyl)-7,8-dihydro-3H-pyrano[4,3-d]pyrimidin-4(5H)-one. $^1$H NMR (400 MHz, MeOD) δ ppm 7.99-8.09 (m, 1H), 7.85-7.93 (m, 1H), 7.64-7.73 (m, 1H), 7.54-7.61 (m, 1H), 5.78-6.43 (m, 1H), 4.58-4.66 (m, 2H), 4.44-4.52 (m, 2H), 4.40 (s, 2H), 3.79-4.06 (m, 4H), 3.64-3.79 (m, 3H), 3.09-3.27 (m, 2H), 2.52-2.72 (m, 2H), 1.90-2.27 (m, 4H). HRMS calculated for $C_{25}H_{28}F_5N_4O_5$ 559.1980. found (ESI, [M+H]+) 559.2008. MS (ESI) m/z 560.0 (M+H)$^+$. Retention time: 3.57 min (5-95% $CH_3CN/H_2O$ over 7.75 min with 0.1% formic acid, Inertsil ODS3 100×3 mm C18 column with flow rate of 1.0 mL/min).

Example 75

N-(2,2-Difluoro-ethyl)-N-(4-oxo-3,5,7,8-tetrahydro-4H-pyrano[4,3-d]pyrimidin-2-ylmethyl)-2-[4-(4-trifluoromethyl-benzoyl)-piperidin-1-yl]-acetamide

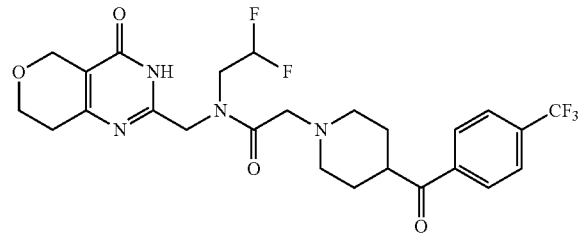 [SMILES: O=C(c1ccc(C(F)(F)F)cc1)C1CCN(CC(=O)N(Cc2nc3c(c(=O)[nH]2)COCC3)CC(F)F)CC1]

tert-Butyl 4-(4-(trifluoromethyl)benzoyl)piperidine-1-carboxylate (0.30 g) was converted to the corresponding piperidin-1-yl-acetic acid following the general procedures for the synthesis of piperidin-4-yl-(2-trifluoromethoxy-phenyl)-methanone and was then used to prepare the title compound (0.034 g) following the general procedure of Example 1 from 2-((2,2-difluoroethylamino)methyl)-7,8-dihydro-3H-pyrano[4,3-d]pyrimidin-4(5H)-one. $^1$H NMR (400 MHz, MeOD) δ ppm 8.04-8.20 (m, 2H), 7.71-7.89 (m, 2H), 4.61-4.69 (m, 1H), 4.53-4.60 (m, 1H), 4.40-4.51 (m, 1H), 4.06-4.23 (m, 1H), 3.75-4.02 (m, 6H), 3.42-3.55 (m, 1H), 2.99-3.17 (m, 1H), 2.79-2.97 (m, 1H), 2.51-2.70 (m, 2H), 2.13-2.39 (m, 2H), 1.69-1.96 (m, 3H), 1.36-1.54 (m, 2H). HRMS calculated for $C_{25}H_{28}F_5N_4O_4$ 543.2031. found (ESI, [M+H]+) 543.2048. MS (ESI) m/z 542.9 (M+H)$^+$. Retention time: 3.47 min (5-95% CH$_3$CN/H$_2$O over 7.75 min with 0.1% formic acid, Inertsil ODS3 100×3 mm C18 column with flow rate of 1.0 mL/min).

Example 76

N-Cyclopropylmethyl-N-(4-oxo-3,5,7,8-tetrahydro-4H-pyrano[4,3-d]pyrimidin-2-ylmethyl)-2-[4-(pyridine-2-carbonyl)-piperidin-1-yl]-acetamide

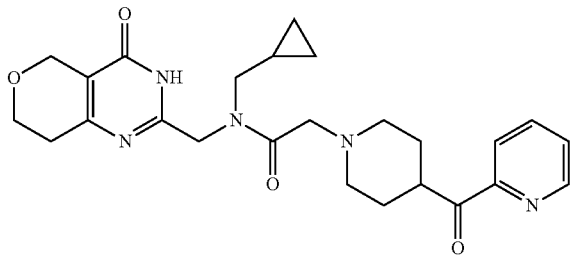 [SMILES: O=C(c1ccccn1)C1CCN(CC(=O)N(Cc2nc3c(c(=O)[nH]2)COCC3)CC2CC2)CC1]

To a solution of compound [4-(pyridine-2-carbonyl)-piperidin-1-yl]-acetic acid (178 mg, 0.72 mmol) and 2-[(cyclopropylmethyl-amino)-methyl]-3,5,7,8-tetrahydro-pyrano[4,3-d]pyrimidin-4-one (169 mg, 0.72 mmol) in DMF (5 mL) and DCM (5 mL) at 0° C. is added DIPEA (0.50 mL, 2.87 mmol) and then HATU (313 mg, 0.82 mmol). The reaction is then stirred at 25° C. for 36 hours. The solvent was removed under vacuum and then solubilized in methanol and filtered. The compound was then purified by reverse phase using sunfire C18 ODB using water acetonitrile and TFA as a buffer to afford the title compound (140 mg). $^1$H NMR (400 MHz, MeOD) δ: 8.68 (s, 1H), 7.99 (m, 2H), 7.59 (s, 1H), 4.68 (s, 1H), 4.57 (s, 2H), 4.49 (s, 1H), 3.97 (t, J=5.6 Hz, 3H), 3.51 (d, J=7.1 Hz, 1H), 3.40 (s, 2H), 3.36 (s, 2H), 3.35-3.31 (m, 2H), 3.30 (d, J=11.6 Hz, 2H), 2.68-2.58 (m, 2H), 2.37-2.24 (m, 2H), 1.96-1.91 (m, 2H), 1.13-0.97 (m, 1H), 0.62-0.45 (m, 2H), 0.33-0.22 (m, 2H). HRMS calculated for $C_{25}H_{31}N_5O_4$=465, 2376. found (ESI, [M+H]$^+$), 465, 2369. LRMS m/z: ES+=466.0 (M+H), retention time 1.04.

Example 77

N-Cyclopropylmethyl-N-(4-oxo-3,5,7,8-tetrahydro-4H-pyrano[4,3-d]pyrimidin-2-ylmethyl)-2-[4-(4-phenoxy-benzoyl)-piperidin-1-yl]-acetamide

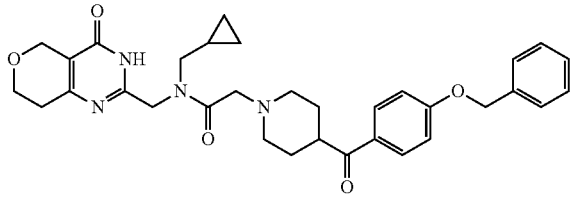 [SMILES: O=C(c1ccc(OCc2ccccc2)cc1)C1CCN(CC(=O)N(Cc2nc3c(c(=O)[nH]2)COCC3)CC2CC2)CC1]

The title compound (30 mg) was prepared according to the general procedure of Example 1 from 2-[(cyclopropylmethyl-amino)-methyl]-3,5,7,8-tetrahydro-pyrano[4,3-d]pyrimidin-4-one (73 mg, 0.31 mmol) and [4-(4-benzyloxy-benzoyl)-piperidin-1-yl]-acetic acid (110 mg, 0.31 mmol). $^1$H NMR (400 MHz, MeOD) δ: 8.01 (d, J=9.1 Hz, 2H), 7.44 (d, J=7.1 Hz, 2H), 7.38 (t, J=7.1 Hz, 2H), 7.33 (d, J=7.1 Hz, 1H), 7.12 (d, J=9.1 Hz, 2H), 4.66 (s, 1H), 4.57 (s, 2H), 4.38 (s, 2H), 3.91 (t, J=5.6 Hz, 2H), 3.78-3.66 (m, 4H), 3.36 (d, J=7.1 Hz, 2H), 3.33-3.29 (m, 5H), 2.68-2.58 (m, 2H), 2.18-2.02 (m 4H), 1.11-0.87 (m, 1H), 0.65-0.43 (m, 2H), 0.32-0.21 (m, 2H). HRMS calculated for $C_{33}H_{38}N_4O_5$=571.2920. found (ESI, [M+H]$^+$), 571.2949. LRMS m/z: ES+=571.1 (M+H), retention time 1.49.

Example 78

2-[4-(4-But-2-ynyloxy-benzoyl)-piperidin-1-yl]-N-cyclopropylmethyl-N-(4-oxo-3,5,7,8-tetrahydro-4H-pyrano[4,3-d]pyrimidin-2-ylmethyl)-acetamide

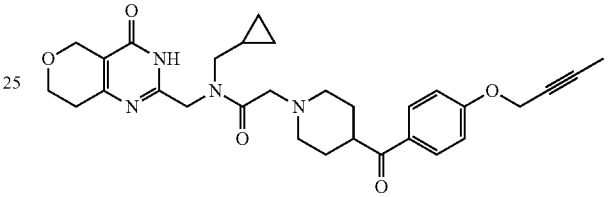

The title compound (90 mg) was prepared following the general procedure of Example 1 from 2-[(cyclopropylmethyl-amino)-methyl]-3,5,7,8-tetrahydro-pyrano[4,3-d]pyrimidin-4-one (140 mg, 0.59 mmol) and [4-(4-but-2-ynyloxy-benzoyl)-piperidin-1-yl]-acetic acid (187 mg, 0.59 mmol). 1H NMR (400 MHz, MeOD) δ: 8.01 (d, J=8.6 Hz, 2H), 7.08 (d, J=9.1 Hz, 2H), 4.79-4.76 (m, 2H), 4.66 (s, 1H), 4.57 (s, 1H), 4.50-4.45 (m, 2H), 4.39 (s, 2H), 3.92 (t, J=5.6 Hz, 2H), 3.80-3.67 (m, 2H), 3.36 (d, J=7.1 Hz, 2H), 3.33-3.28 (m, 6H), 2.69-2.58 (m, 2H), 2.22-2.02 (m, 4H), 1.83 (t, J=2.5 Hz, 3H), 1.11-0.89 (m, 1H), 0.66-0.43 (m, 2H), 0.34-0.19 (m, 2H). HRMS calculated for $C_{33}H_{38}N_4O_3$=533.2764. found (ESI, [M+H]$^+$), 533.2788. LRMS m/z: ES+=533.7 (M+H), retention time 1.08.

Example 79

N-((4-Oxo-4,5,7,8-tetrahydro-3H-pyrano[4,3-d]pyrimidin-2-yl)methyl)-2-(4-(1,2,3,4-tetrahydroisoquinoline-2-carbonyl)piperidin-1-yl)acetamide

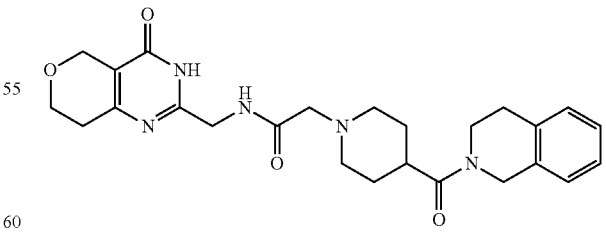

The title compound (23 mg) was prepared following the general procedure of Example 1 from 1-(2-oxo-2-((4-oxo-4,5,7,8-tetrahydro-3H-pyrano[4,3-d]pyrimidin-2-yl)methylamino)ethyl)piperidine-4-carboxylic acid (250 mg, 0.50 mmol) and 1,2,3,4-tetrahydroisoquinoline (66 mg, 0.50 mmol). $^1$H NMR (400 MHz, CDC$_3$) δ 8.19 (br. s., 1H), 6.94-7.16 (m, 3H), 4.66 (s, 1H), 4.59 (s, 1H), 4.46 (s, 2H), 4.32 (d, J=5.1 Hz, 2H), 3.85 (t, J=5.3 Hz, 2H), 3.76 (t, J=6.1 Hz, 1H), 3.65 (t, J=5.8 Hz, 1H), 3.40 (br. s., 1H), 3.06 (br. s., 1H), 3.01 (s, 2H), 2.68-2.95 (m, 4H), 2.60 (br. s., 2H), 2.33-2.57 (m, 1H), 2.17 (t, J=11.4 Hz, 2H), 1.87 (dq, J=11.1, 10.9 Hz, 2H). HRMS calculated for $C_{25}H_{31}N_5O_4$ 466.2454. found (ESI, [M+H]$^+$), 466.2466. Retention time=1.25 min.

Example 80

2-(4-(6-Methoxy-1,2,3,4-tetrahydroquinoline-1-carbonyl)piperidin-1-yl)-N-((4-oxo-4,5,7,8-tetrahydro-3H-pyrano[4,3-d]pyrimidin-2-yl)methyl)acetamide

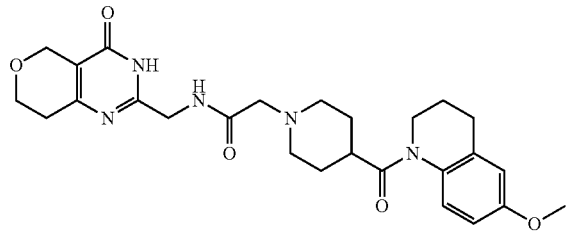 [SMILES: COc1ccc2c(c1)CCCN2C(=O)C1CCN(CC(=O)NCc2nc3c(c(=O)[nH]2)COCC3)CC1]

The title compound (56 mg, 22% yield) was prepared following the general procedure of Example 1 from 1-(2-oxo-2-((4-oxo-4,5,7,8-tetrahydro-3H-pyrano[4,3-d]pyrimidin-2-yl)methylamino)ethyl)piperidine-4-carboxylic acid (250 mg, 0.50 mmol) and 6-methoxy-1,2,3,4-tetrahydroquinoline (82 mg, 0.50 mmol). $^1$H NMR (400 MHz, CDC$_3$) δ 10.68 (br. s., 1H), 8.12 (br. s, 0.5H), 6.97 (br. s., 0.5H), 6.73-6.80 (m, 2H), 4.58 (s, 2H), 4.38 (d, J=5.6 Hz, 2H), 3.97 (t, J=5.6 Hz, 2H), 3.63-3.89 (m, 5H), 3.10 (br. s., 2H), 2.89 (br. s., 3H), 2.71 (t, J=5.3 Hz, 4H), 2.15 (br. s., 2H), 1.82-2.09 (m, 5H), 1.68 (br. s., 1H). HRMS calculated for $C_{26}H_{33}N_5O_5$ 496.2560. found (ESI, [M+H]$^+$), 496.2561. Retention time=1.29 min.

Example 81

2-(4-(5-Chloro-1,2,3,4-tetrahydroisoquinoline-2-carbonyl)piperidin-1-yl)-N-((4-oxo-4,5,7,8-tetrahydro-3H-pyrano[4,3-d]pyrimidin-2-yl)methyl)acetamide

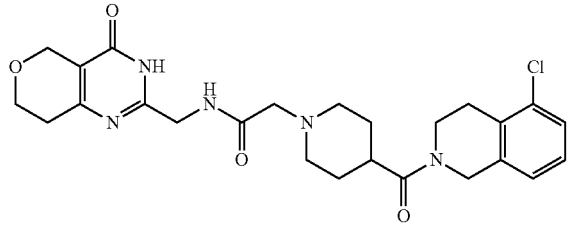 [SMILES: O=C(CN1CCC(C(=O)N2CCc3c(Cl)cccc3C2)CC1)NCc1nc2c(c(=O)[nH]1)COCC2]

The title compound (44 mg, 18% yield) was prepared following the general procedure of Example 1 from 1-(2-oxo-2-((4-oxo-4,5,7,8-tetrahydro-3H-pyrano[4,3-d]pyrimidin-2-yl)methylamino)ethyl)piperidine-4-carboxylic acid (250 mg, 0.50 mmol) and 5-chloro-1,2,3,4-tetrahydroisoquinoline (84 mg, 0.50 mmol). $^1$H NMR (400 MHz, DMSO-d$_6$) δ 8.20 (br. s., 1H), 7.32 (d, J=6.6 Hz, 1H), 7.22 (d, J=8.1 Hz, 2H), 4.74 (br. s., 1H), 4.64 (s, 1H), 4.34 (s, 2H), 4.18 (d, J=5.6 Hz, 2H), 3.66-3.87 (m, 4H), 3.09-3.20 (m, 1H), 2.95 (s, 4H), 2.79-2.91 (m, 2H), 2.73 (br. s., 1H), 2.67 (br. s., 1H), 2.02-2.23 (m, 2H), 1.74 (br. s., 4H). HRMS calculated for $C_{25}H_{30}ClN_5O_4$ 500.2065. found (ESI, [M+H]$^+$), 500.2066. Retention time=1.36 min.

Example 82

2-(4-(2-Oxo-2,3-dihydro-1H-benzo[d]imidazol-1-yl)piperidin-1-yl)-N-((4-oxo-4,5,7,8-tetrahydro-3H-pyrano[4,3-d]pyrimidin-2-yl)methyl)acetamide

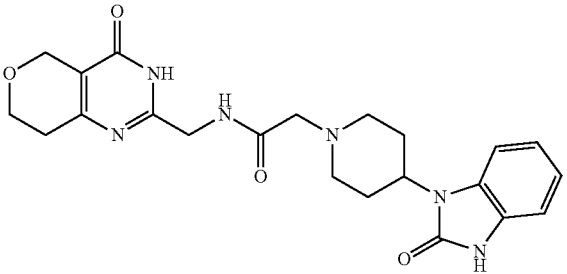 [SMILES: O=C(CN1CCC(n2c(=O)[nH]c3ccccc32)CC1)NCc1nc2c(c(=O)[nH]1)COCC2]

The title compound (27 mg,) was prepared following the general procedure of Example 1 from 1-(piperidin-4-yl)-1H-benzo[d]imidazol-2(3H)-one (200 mg, 0.92 mmol). $^1$H NMR (400 MHz, CD$_3$OD) δ 7.26 (d, J=5.5 Hz, 1H), 7.00-7.16 (m, 3H), 4.55 (s, 2H), 4.37 (s, 2H), 4.23-4.34 (m, 1H), 3.93 (t, J=5.5 Hz, 2H), 3.39 (d, J=15.1 Hz, 2H), 3.14-3.22 (m, 2H), 3.10 (d, J=9.5 Hz, 2H), 2.69 (br. s., 2H), 2.51-2.66 (m, 2H), 2.43 (t, J=11.5 Hz, 2H). HRMS calculated for $C_{22}H_{26}N_6O_4$ 439.2094. found (ESI, [M+H]$^+$), 439.2097.

Example 83

2-[4-(4-Methyl-benzoyl)-piperidin-1-yl]-N-(4-oxo-3,5,7,8-tetrahydro-4H-pyrano[4,3-d]pyrimidin-2-ylmethyl)-acetamide

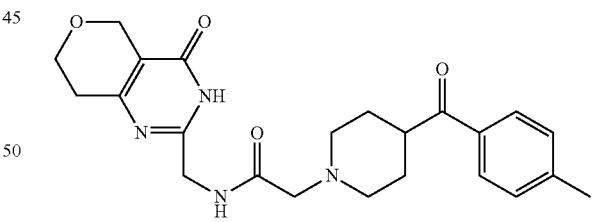

Following the procedure of Example 2, the title compound was synthesized from piperidin-4-yl-p-tolyl-methanone (150 mg, 0.57 mmol). The title product was obtained as a white solid (88.0 mg, 0.21 mmol). MS (ESI) m/z 425.5 (M+H$^+$); HPLC (Insertsil ODS3 100×3 mm C-18 column: mobile phase: 5-95% acetonitrile/water with 0.1% TFA, at 1 mL/min over 7.75 min.) t=1.00 min. $^1$H NMR (400 MHz, DMSO-d$_6$) δ ppm 1.63-1.83 (m, 6H), 2.25 (br. s., 1H), 2.38 (br. s., 2H), 2.50 (br. s., 3H), 2.87-3.10 (m, 3H), 3.31 (br. s., 2H), 3.34-3.45 (m, 1H), 3.82 (br. s., 1H), 4.19 (br. s., 1H), 4.34 (br. s., 2H), 7.33 (d, J=2.53 Hz, 2H), 7.87 (br. s., 2H), 8.20 (s, 1H) 12.40 (s, 1H). HRMS calculated for $C_{23}H_{29}N_4O_4$: 425.2189 (M+H). found (ESI, [M+H]$^+$): 425.2192.

Example 84

N-(4-Oxo-3,5,7,8-tetrahydro-4H-pyrano[4,3-d]pyrimidin-2-ylmethyl)2-[4-(4-propoxy-benzoyl)-piperidin-1-yl]acetamide

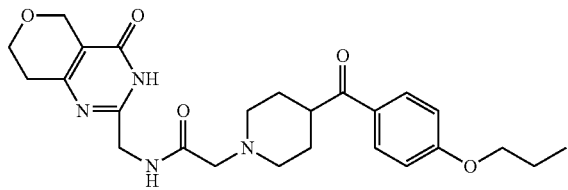 [SMILES: CCCOc1ccc(C(=O)C2CCN(CC(=O)NCc3nc4c(c(=O)[nH]3)COCC4)CC2)cc1]

2-(4-(4-Propoxybenzoyl)piperidin-1-yl)acetic acid was prepared following the general procedures for the synthesis of 2-(4-(4-ethoxybenzoyl)piperidin-1-yl)acetic acid from 2-(4-(4-fluorobenzoyl)piperidin-1-yl)acetic acid and propan-1-ol. The title compound (76.1 mg, 0.15 mmol) was prepared following the general procedure of Example 1 from 2-(4-(4-propoxybenzoyl)piperidin-1-yl)acetic acid and 2-aminomethyl-3,5,7,8-tetrahydro-pyrano[4,3-d]pyrimidin-4-one. MS (ESI) m/z 469.4 (M+H⁺); HPLC (Insertsil ODS3 100×3 mm C-18 column: mobile phase: 5-95% acetonitrile/water with 0.1% TFA, at 1 mL/min over 7.75 min.) t=1.39 min. ¹H NMR (400 MHz, DMSO-d₆) δ ppm 0.99 (t, 3H), 1.60-1.88 (m, 6H), 2.14-2.33 (m, 2H), 2.43-2.65 (m, 4H), 2.98 (br. s., 2H), 3.23-3.42 (m, 1H), 3.83 (br. s., 2H), 3.95-4.10 (m, 2H), 4.20 (br. s., 2H), 4.34 (br. s., 2H), 7.03 (d, J=4.55 Hz, 2H), 7.95 (d, J=4.55 Hz, 2H), 8.22 (br. s., 1H), 12.38 (br. s., 1H). HRMS calculated for $C_{26}H_{33}N_4O_6$: 469.2451 (M+H). found (ESI, [M+H]⁺): 469.2459.

Example 85

2-[4-(4-Cyclopropylmethoxy-benzoyl)-piperidin-1-yl]-N-(4-oxo-3,5,7,8-tetrahydro-4H-pyrano[4,3-d]pyrimidin-2-ylmethyl)-acetamide

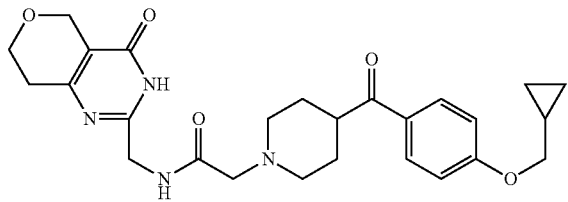 [SMILES: O=C(CN1CCC(C(=O)c2ccc(OCC3CC3)cc2)CC1)NCc1nc2c(c(=O)[nH]1)COCC2]

2-[4-(4-Cyclopropylmethoxy-benzoyl)-piperidin-1-yl]-acetic acid was prepared following the general procedures for the synthesis of 2-(4-(4-ethoxybenzoyl)piperidin-1-yl)acetic acid from 2-(4-(4-fluorobenzoyl)piperidin-1-yl)acetic acid and cyclopropyl-methanol. The title compound (44.7 mg, 0.088 mmol) was prepared following the general procedure of Example 1 from 2-[4-(4-cyclopropylmethoxy-benzoyl)-piperidin-1-yl]-acetic acid and 2-aminomethyl-3,5,7,8-tetrahydro-pyrano[4,3-d]pyrimidin-4-one. MS (ESI) m/z 481.5 (M+H⁺); HPLC (Insertsil ODS3 100×3 mm C-18 column: mobile phase: 5-95% acetonitrile/water with 0.1% TFA, at 1 mL/min over 7.75 min.) t=1.27 min. ¹H NMR (400 MHz, DMSO-d₆) δ ppm 0.26-0.41 (m, 2H), 0.48-0.68 (m, 2H), 1.14-1.29 (m, 1H), 1.65-1.83 (m, 4H), 2.18-2.33 (m, 2H), 2.51 (br. s., 2H), 2.84-3.08 (m, 3H), 3.32 (br. s., 2H), 3.83 (br. s., 2H), 3.91 (d, J=6.06 Hz, 2H), 4.20 (br. s., 2H), 4.34 (br. s., 2H), 7.03 (d, J=7.07 Hz, 2H), 7.94 (d, J=7.58 Hz, 2H), 8.21 (br. s., 1H), 12.38 (br. s., 1H). HRMS calculated for $C_{26}H_{33}N_4O_5$: 481.2451 (M+H). found (ESI, [M+H]⁺): 481.2459.

Example 86

2-[4-(4-Cyclobutylmethoxy-benzoyl)-piperidin-1-yl]-N-(4-oxo-3,5,7,8-tetrahydro-4H-pyrano[4,3-d]pyrimidin-2-ylmethyl)-acetamide

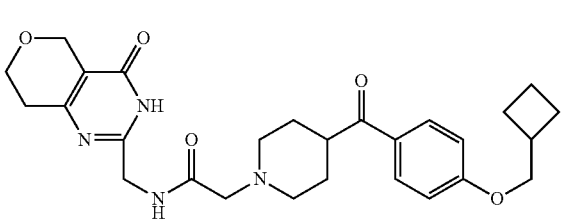 [SMILES: O=C(CN1CCC(C(=O)c2ccc(OCC3CCC3)cc2)CC1)NCc1nc2c(c(=O)[nH]1)COCC2]

2-[4-(4-Cyclobutylmethoxy-benzoyl)-piperidin-1-yl]-acetic acid was prepared following the general procedures for the synthesis of 2-(4-(4-ethoxybenzoyl)piperidin-1-yl)acetic acid from 2-(4-(4-fluorobenzoyl)piperidin-1-yl)acetic acid and cyclobutyl-methanol. The title compound (24.7 mg, 0.047 mmol) was prepared following the general procedure of Example 1 from 2-[4-(4-cyclobutylmethoxy-benzoyl)-piperidin-1-yl]-acetic acid and 2-aminomethyl-3,5,7,8-tetrahydro-pyrano[4,3-d]pyrimidin-4-one. MS (ESI) m/z 495.5 (M+H⁺); HPLC (Insertsil ODS3 100×3 mm C-18 column: mobile phase: 5-95% acetonitrile/water with 0.1% TFA, at 1 mL/min over 7.75 min.) t=1.53 min. ¹H NMR (400 MHz, DMSO-d₆) δ ppm 1.72 (d, J=2.53 Hz, 2H), 1.77-1.96 (m, 5H), 2.03-2.13 (m, 2H), 2.19-2.32 (m, 2H), 2.50 (br. s., 3H), 2.66-2.82 (m, 1H), 2.90-3.03 (m, 3H), 3.24-3.40 (m, 2H), 3.82 (t, J=5.56 Hz, 2H), 4.04 (d, J=6.57 Hz, 2H), 4.19 (d, J=5.56 Hz, 2H), 4.34 (s, 2H), 7.03 (d, J=9.09 Hz, 2H), 7.94 (d, J=8.59 Hz, 2H), 8.21 (t, J=5.81 Hz, 1H), 12.37 (br. s., 1H). HRMS calculated for $C_{27}H_{35}N_4O_5$: 495.2607 (M+H). found (ESI, [M+H]⁺): 495.2627.

Example 87

N-(4-Oxo-3,5,7,8-tetrahydro-4H-pyrano[4,3-d]pyrimidin-2-ylmethyl)-2-{4-[4-(tetrahydro-pyran-4-yloxy)-benzoyl]-1-yl}-acetamide

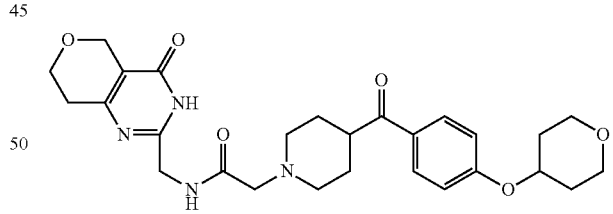

{4-[4-(Tetrahydro-pyran-4-yloxy)-benzoyl]-piperidin-1-yl}-acetic acid was prepared following the general procedures for the synthesis of 2-(4-(4-ethoxybenzoyl)piperidin-1-yl)acetic acid from 2-(4-(4-fluorobenzoyl)piperidin-1-yl) acetic acid and tetrahydro-pyran-4-ol. The title compound (21.0 mg, 0.039 mmol) was prepared following the general procedure of Example 1 from {4-[4-(tetrahydro-pyran-4-yloxy)-benzoyl]-piperidin-1-yl}-acetic acid and 2-aminomethyl-3,5,7,8-tetrahydro-pyrano[4,3-d]pyrimidin-4-one. MS (ESI) m/z 511.6 (M+H⁺); HPLC (Insertsil ODS3 100×3 mm C-18 column: mobile phase: 5-95% acetonitrile/water with 0.1% TFA, at 1 mL/min over 7.75 min.) t=1.13 min. ¹H NMR (400 MHz, DMSO-d₆) δ ppm 1.51-1.82 (m, 6H), 1.93-2.07 (m, 2H), 2.17-2.32 (m, 2H), 2.48-2.56 (m, 5H), 3.00 (br. s., 2H), 3.29-3.42 (m, 4H), 3.47-3.58 (m, 1H), 3.75-3.95 (m, 2H), 4.19 (br. s., 2H), 4.34 (br. s., 2H), 7.09 (d, J=6.02 Hz, 2H), 7.95 (d, J=6.53 Hz, 2H), 8.25 (br. s., 1H), 12.43 (br. s., 1H). HRMS calculated for $C_{27}H_{35}N_4O_6$: 511.2557 (M+H). found (ESI, [M+H]$^+$): 511.2570.

Example 88

2-{4-[4-(2-Methoxy-ethoxy)-benzoyl]-piperidin-1-yl}-N-(4-oxo-3,5,7,8-tetrahydro-4H-pyrano[4,3-d]pyrimidin-2-ylmethyl)-acetamide

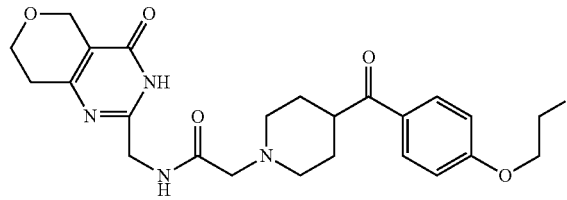

{4-[4-(2-Methoxy-ethoxy)-benzoyl]-piperidin-1-yl}-acetic acid was prepared following the general procedures for the synthesis of 2-(4-(4-ethoxybenzoyl)piperidin-1-yl)acetic acid from 2-(4-(4-fluorobenzoyl)piperidin-1-yl)acetic acid and 2-methoxy-ethanol. The title compound (190 mg, 0.373 mmol) was prepared following the general procedure of Example 1 from {4-[4-(2-methoxy-ethoxy)-benzoyl]-piperidin-1-yl}-acetic acid and 2-aminomethyl-3,5,7,8-tetrahydro-pyrano[4,3-d]pyrimidin-4-one. MS (ESI) m/z 484.8 (M+H+); HPLC (Insertsil ODS3 100×3 mm C-18 column: mobile phase: 5-95% acetonitrile/water with 0.1% TFA, at 1 mL/min over 7.75 min.) t=1.46 min. $^1$H NMR (400 MHz, DMSO-d$_6$) δ ppm 1.51-1.83 (m, 6H), 2.20-2.33 (m, 2H), 2.51 (br. s., 2H), 2.92-3.03 (m, 4H), 3.24-3.41 (m, 4H), 3.65-3.71 (m, 2H), 3.82 (t, J=5.31 Hz, 2H), 4.16-4.24 (m, 2H), 4.34 (s, 2H), 7.05 (d, J=8.59 Hz, 2H), 7.95 (d, J=8.59 Hz, 2H), 8.24 (br. s., 1H), 12.38 (br. s., 1H). HRMS calculated for $C_{25}H_{33}N_4O_6$: 485.2400 (M+H). found (ESI, [M+H]$^+$): 485.2394.

Example 89

2-{4-[4-(2-Cyclopropyl-ethoxy)-benzoyl]-piperidin-1-yl}-N-(4-oxo-3,5,7,8-tetrahydro-4H-pyrano[4,3-d]pyrimidin-2-ylmethyl)-acetamide

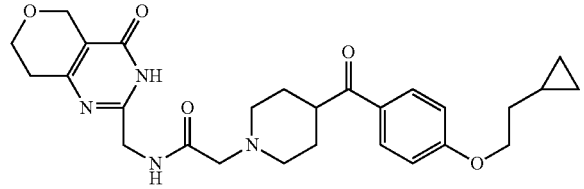 [SMILES: O=C(CN1CCC(C(=O)c2ccc(OCCC3CC3)cc2)CC1)NCc1nc2c(c(=O)[nH]1)COCC2]

{4-[4-(2-Cyclopropyl-ethoxy)-benzoyl]-piperidin-1-yl}-acetic acid was prepared following the general procedures for the synthesis of 2-(4-(4-ethoxybenzoyl)piperidin-1-yl)acetic acid from 2-(4-(4-fluorobenzoyl)piperidin-1-yl)acetic acid and 2-cyclopropyl-ethanol. The title compound (74.3 mg, 0.143 mmol) was prepared following the general procedure of Example 1 from {4-[4-(2-cyclopropyl-ethoxy)-benzoyl]-piperidin-1-yl}-acetic acid and 2-aminomethyl-3,5,7,8-tetrahydro-pyrano[4,3-d]pyrimidin-4-one. MS (ESI) m/z 495.5 (M+H+); HPLC (Insertsil ODS3 100×3 mm C-18 column: mobile phase: 5-95% acetonitrile/water with 0.1% TFA, at 1 mL/min over 7.75 min.) t=1.51 min. $^1$H NMR (400 MHz, DMSO-d$_6$) δ ppm –0.07-0.05 (m, 2H), 0.23-0.36 (m, 2H), 0.58-0.75 (m, 1H), 1.47-1.65 (m, 6H), 2.01-2.18 (m, 2H), 2.37 (br. s., 2H), 2.78-2.89 (m, 3H), 3.20 (dd, J=15.41, 6.32 Hz, 2H), 3.69 (t, J=5.56 Hz, 2H), 3.98 (t, J=6.57 Hz, 2H), 4.05 (d, J=5.56 Hz, 2H), 4.20 (s, 2H), 6.90 (d, J=9.09 Hz, 2H), 7.81 (d, J=8.59 Hz, 2H), 8.08 (t, J=5.81 Hz, 1H), 12.24 (br. s., 1H). HRMS calculated for $C_{27}H_{35}N_4O_5$: 495.2607 (M+H). found (ESI, [M+H]$^+$): 495.2622.

Example 90

2-[4-(3,4-Dimethoxy-benzoyl)-piperidin-1-yl]-N-(4-oxo-3,5,7,8-tetrahydro-4H-pyrano[4,3-c]pyrimidin-2-ylmethyl)-acetamide

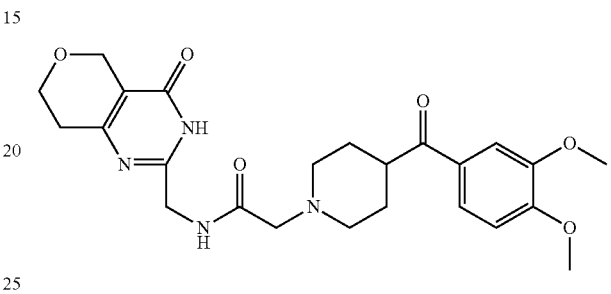

A solution of [4-(3,4-dimethoxy-benzoyl)-piperidin-1-yl]-acetic acid (0.25 g, 0.81 mmol), EDCl (0.19 g, 0.98 mmol), HOBT (0.13 g, 0.98 mmol) and triethylamine (0.33 g, 3.3 mmol) in 10 mL of DMF was stirred at ambient temperature for 20 min., then 2-aminomethyl-3,5,7,8-tetrahydro-pyrano[4,3-d]pyrimidin-4-one (0.15 g, 0.81 mmol) was added. The reaction mixture was stirred at ambient temperature for 15 hours. The reaction mixture was diluted with 50 mL of water, extracted with DCM (100 mL) and the combined organic layers were washed with saturated aqueous NaHCO$_3$ solution. The organic layer was dried over Na$_2$SO$_4$, filtered and concentrated in vacuo to provide crude product. Purification by flash chromatography gave the title compound (42.2 mg, 0.085 mmol) as a white solid. MS (ESI) m/z 470.8 (M+H$^+$); HPLC (Insertsil ODS3 100×3 mm C-18 column: mobile phase: 5-95% acetonitrile/water with 0.1% TFA, at 1 mL/min over 7.75 min.), t=0.95 min. $^1$H NMR (400 MHz, dichloromethane-d$_2$) δ ppm 1.75-1.98 (m, 4H), 2.24-2.48 (m, 2H), 2.61-2.78 (m, 2H), 3.02 (d, J=10.11 Hz, 2H), 3.15 (br. s., 2H), 3.29 (d, J=9.60 Hz, 2H), 3.94 (br. s., 6H), 4.39 (br. s., 1H), 4.49-4.64 (m, 2H), 5.36 (br. s., 2H), 6.95 (d, J=8.08 Hz, 1H), 7.52 (br. s., 1H), 7.61 (d, J=7.58 Hz, 1H). HRMS calculated for $C_{24}H_{31}N_4O_6$. 471.2244 (M+H) found (ESI, [M+H]$^+$): 471.2250.

Example 91

2-[4-(2,3-Dihydro-benzofuran-5-carbonyl)-piperidin-1-yl]-N-(4-oxo-3,5,7,8-tetrahydro-4H-pyrano[4,3-c]pyrimidin-2-ylmethyl)-acetamide

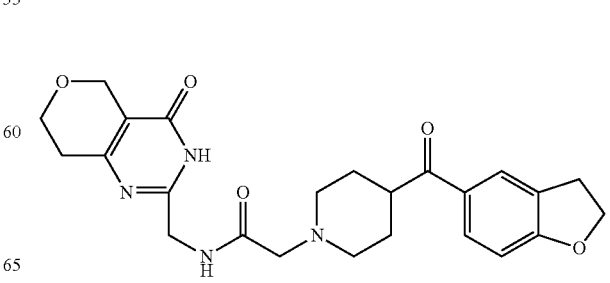

A solution of [4-(2,3-dihydro-benzofuran-5-carbonyl)-piperidin-1-yl]-acetic acid (0.16 g, 0.55 mmol), EDCl (0.13 g, 0.66 mmol), HOBT (0.09 g, 0.66 mmol) and triethylamine (0.28 g, 2.8 mmol) in 10 mL of DMF was stirred at ambient temperature for 20 min., then 2-aminomethyl-3,5,7,8-tetrahydro-pyrano[4,3-d]pyrimidin-4-one (0.10 g, 0.55 mmol) was added. The reaction mixture was stirred at ambient temperature for 15 hours. The reaction mixture was diluted with 50 mL of water, extracted with DCM (100 mL) and the combined organic layers were washed with saturated aqueous NaHCO$_3$ solution. The organic layer was dried over Na$_2$SO$_4$, filtered and concentrated in vacuo to provide crude product. Purification by flash chromatography gave the title compound (16.9 mg, 0.037 mmol) as a white solid. MS (ESI) m/z 452.8 (M+H$^+$); HPLC (Insertsil ODS3 100×3 mm C-18 column: mobile phase: 5-95% acetonitrile/water with 0.1% TFA, at 1 mL/min over 7.75 min.), t=1.01 min. $^1$H NMR (400 MHz, methanol-d$_4$) δ ppm 1.76-1.93 (m, 4H), 2.28-2.43 (m, 2H), 2.62-2.76 (m, 2H), 2.99-3.08 (m, 2H), 3.08-3.16 (m, 2H), 3.30-3.34 (m, 3H), 3.93 (t, J=5.31 Hz, 2H), 4.31-4.37 (m, 1H), 4.45-4.50 (m, 1H), 4.64 (t, J=8.08 Hz, 2H), 4.79-4.85 (m, 2H), 6.80 (d, J=8.08 Hz, 1H), 7.78-8.00 (m, 2H). HRMS calculated for C$_{24}$H$_{29}$N$_4$O$_5$: 453.2138 (M+H) found (ESI, [M+H]$^+$): 453.2151.

Example 92

2-[4-(Benzo[1,3]dioxole-5-carbonyl)-piperidin-1-yl]-N-(4-oxo-3,5,7,8-tetrahydro-4H-pyrano[4,3-c]pyrimidin-2-ylmethyl)-acetamide

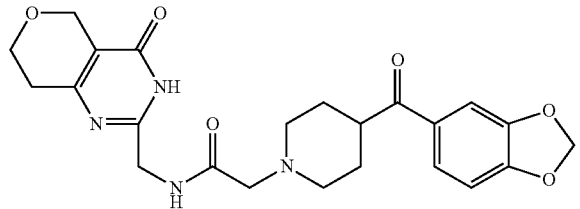 [SMILES: O=C(CN1CCC(C(=O)c2ccc3c(c2)OCO3)CC1)NCc1nc2c(c(=O)[nH]1)COCC2]

A solution of [4-(benzo[1,3]dioxole-5-carbonyl)-piperidin-1-yl]-acetic acid (0.32 g, 1.1 mmol), EDCl (0.25 g, 1.3 mmol), HOBT (0.18 g, 1.3 mmol) and triethylamine (0.56 g, 5.5 mmol) in 10 mL of DMF was stirred at ambient temperature for 20 min., then 2-aminomethyl-3,5,7,8-tetrahydro-pyrano[4,3-d]pyrimidin-4-one (0.20 g, 1.1 mmol) was added. The reaction mixture was stirred at ambient temperature for 15 hours. The reaction mixture was diluted with 50 mL of water, extracted with DCM (100 mL) and the combined organic layers were washed with saturated aqueous NaHCO$_3$ solution. The organic layer was dried over Na$_2$SO$_4$, filtered and concentrated in vacuo to provide crude product. Purification by flash chromatography gave the title compound (54.9 mg, 0.12 mmol) as a white solid. MS (ESI) m/z 454.8 (M+H$^+$); HPLC (Insertsil ODS3 100×3 mm C-18 column: mobile phase: 5-95% acetonitrile/water with 0.1% TFA, at 1 mL/min over 7.75 min.), t=1.67 min. $^1$H NMR (400 MHz, methanol-d$_4$) δ ppm 1.74-1.90 (m, 4H), 2.22-2.41 (m, 2H), 2.58-2.75 (m, 2H), 2.97-3.08 (m, 2H), 3.27-3.39 (m, 3H), 3.86-3.99 (m, 2H), 4.30-4.48 (m, 2H), 4.88 (s, 2H), 6.05 (s, 2H), 6.91 (d, J=6.57 Hz, 1H), 7.38-7.44 (m, 1H), 7.58-7.69 (m, 1H). HRMS calculated for C$_{23}$H$_{27}$N$_4$O$_6$: 455.1931 (M+H) found (ESI, [M+H]$^+$): 455.1939.

Example 93

2-[4-(4-Methoxy-3-methyl-benzoyl)-piperidin-1-yl]-N-(4-oxo-3,5,7,8-tetrahydro-4H-pyrano[4,3-d]pyrimidin-2-ylmethyl)-acetamide

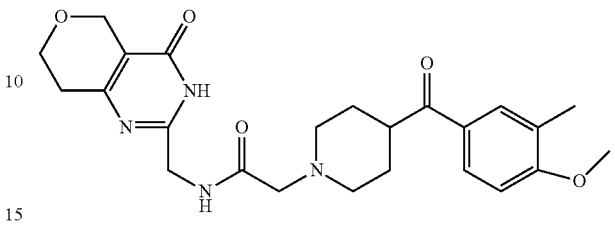

A solution of [4-(4-methoxy-3-methyl-benzoyl)-piperidin-1-yl]-acetic acid (0.10 g, 0.34 mmol), EDCl (0.08 g, 0.41 mmol), HOBT (0.06 g, 0.41 mmol) and triethylamine (0.17 g, 1.7 mmol) in 10 mL of DMF was stirred at ambient temperature for 20 min., then 2-aminomethyl-3,5,7,8-tetrahydro-pyrano[4,3-d]pyrimidin-4-one (0.06 g, 0.34 mmol) was added. The reaction mixture was stirred at ambient temperature for 15 hours. The reaction mixture was diluted with 50 mL of water, extracted with DCM (100 mL) and the combined organic layers were washed with saturated aqueous NaHCO$_3$ solution. The organic layer was dried over Na$_2$SO$_4$, filtered and concentrated in vacuo to provide crude product. Purification by flash chromatography gave the title compound (42.8 mg, 0.09 mmol) as a yellow solid. MS (ESI) m/z 454.8 (M+H$^+$); HPLC (Insertsil ODS3 100×3 mm C-18 column: mobile phase: 5-95% acetonitrile/water with 0.1% TFA, at 1 mL/min over 7.75 min.), t=1.21 min. $^1$H NMR (400 MHz, dichloromethane-d$_2$) δ ppm 1.77-1.97 (m, 4H), 2.28 (br. s., 3H), 2.42-2.55 (m, 2H), 2.64-2.77 (m, 2H), 2.90-3.11 (m, 3H), 3.17-3.24 (m, 2H), 3.25-3.36 (m, 1H), 3.93 (br. s., 3H), 4.31-4.41 (m, 2H), 4.48-4.65 (m, 3H), 6.89-7.02 (m, 1H), 7.78 (br. s., 1H), 7.84 (d, J=8.59 Hz, 1H), 8.20 (br. s., 1H), 10.84 (s, 1H). HRMS calculated for C$_{24}$H$_{31}$N$_4$O$_5$: 455.2294 (M+H). found (ESI, [M+H]$^+$): 455.2311.

Example 94

2-[4-(3-Chloro-4-methoxy-benzoyl)-piperidin-1-yl]-N-(4-oxo-3,5,7,8-tetrahydro-4H-pyrano[4,3-d]pyrimidin-2-ylmethyl)-acetamide

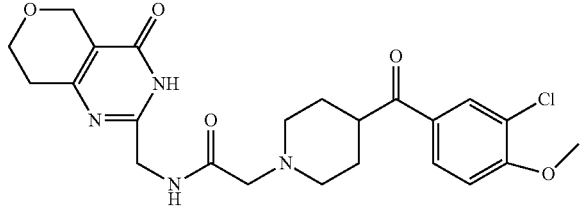 [SMILES: COc1ccc(C(=O)C2CCN(CC(=O)NCc3nc4c(c(=O)[nH]3)COCC4)CC2)cc1Cl]

A solution of [4-(3-chloro-4-methoxy-benzoyl)-piperidin-1-yl]-acetic acid (0.41 g, 1.3 mmol), EDCl (0.25 g, 1.3 mmol), HOBT (0.18 g, 1.3 mmol) and triethylamine (0.56 g, 5.5 mmol) in 10 mL of DMF was stirred at ambient temperature for 20 min., then 2-aminomethyl-3,5,7,8-tetrahydro-pyrano[4,3-d]pyrimidin-4-one (0.20 g, 1.1 mmol) was added. The reaction mixture was stirred at ambient temperature for 15 hours. The reaction mixture was diluted with 50 mL of water, extracted with DCM (100 mL) and the combined organic layers were washed with saturated aqueous NaHCO$_3$ solution. The organic layer was dried over Na$_2$SO$_4$, filtered and concentrated in vacuo to provide crude product. Purification by flash chromatography gave the title compound (155.2 mg, 0.3 mmol) as a white solid. MS (ESI) m/z 475.4 (M+H$^+$); HPLC (Insertsil ODS3 100×3 mm C-18 column: mobile phase: 5-95% acetonitrile/water with 0.1% TFA, at 1 mL/min over 7.75 min.), t=0.97 min. $^1$H NMR (400 MHz, methanol-d$_4$) δ ppm 2.01-2.19 (m, 6H) 2.65 (t, 4H) 3.31 (s, 2H) 3.63-3.80 (m, 3H) 3.93 (t, J=5.56 Hz, 1H) 3.98 (s, 3H) 4.07 (s, 1H) 4.38 (s, 1H) 4.47 (s, 1H) 7.20 (d, J=8.59 Hz, 1H) 7.98-8.02 (m, 1H) 8.03-8.06 (m, 1H) HRMS calculated for C$_{23}$H$_{28}$ClN$_4$O$_5$: 475.1748 (M+H). found (ESI, [M+H]$^+$): 475.1755.

Example 95

2-[4-(4-Ethoxy-3-fluoro-benzoyl)-piperidin-1-yl]-N-(4-oxo-3,5,7,8-tetrahydro-4H-pyrano[4,3-c]pyrimidin-2-ylmethyl)-acetamide

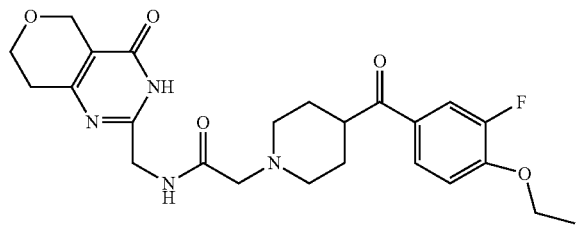 [SMILES: CCOc1ccc(C(=O)C2CCN(CC(=O)NCc3nc4c(c(=O)[nH]3)COCC4)CC2)cc1F]

A solution of [4-(4-ethoxy-3-fluoro-benzoyl)-piperidin-1-yl]-acetic acid (0.20 g, 0.65 mmol), EDCl (0.05 g, 0.25 mmol), HOBT (0.03 g, 0.25 mmol) and triethylamine (0.10 g, 1.0 mmol) in 10 mL of DMF was stirred at ambient temperature for 20 min., then 2-aminomethyl-3,5,7,8-tetrahydro-pyrano[4,3-d]pyrimidin-4-one (0.04 g, 0.2 mmol) was added. The reaction mixture was stirred at ambient temperature for 15 hours. The reaction mixture was diluted with 50 mL of water, extracted with DCM (100 mL) and the combined organic layers were washed with saturated aqueous NaHCO$_3$ solution. The organic layer was dried over Na$_2$SO$_4$, filtered and concentrated in vacuo to provide crude product. Purification by flash chromatography gave the title compound (41.2 mg, 0.08 mmol) as a white solid. MS (ESI) m/z 473.5 (M+H$^+$); HPLC (Insertsil ODS3 100×3 mm C-18 column: mobile phase: 5-95% acetonitrile/water with 0.1% TFA, at 1 mL/min over 7.75 min.), t=0.88 min. $^1$H NMR (400 MHz, MeOD) δ ppm 1.45 (t, J=6.57 Hz, 3H) 2.12 (br. s., 6H) 2.65 (br. s., 4H) 3.31 (br. s., 2H) 3.57-3.81 (m, 3H) 3.93 (br. s., 2H) 4.08 (br. s., 1H) 4.21 (d, J=6.57 Hz, 1H) 4.38 (br. s., 1H) 4.47 (br. s., 1H) 7.15-7.26 (m, 1H) 7.71-7.81 (m, 1H) 7.82-7.91 (m, 1H). HRMS calculated for C$_{24}$H$_{30}$FN$_4$O$_5$: 473.2200 (M+H). found (ESI, [M+H]$^+$): 473.2190.

Example 96

2-[4-(4-methoxy-benzoyl)-piperidin-1-yl]-N-(1-oxo-5,8-dihydro-1H,6H-pyrano[3,4-c]pyran-3-ylmethyl)-acetamide

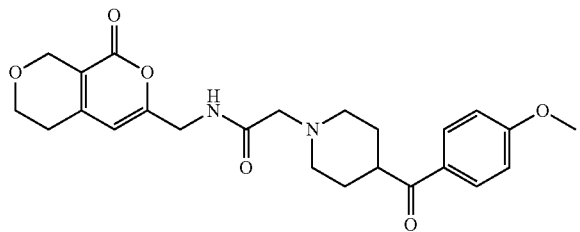 [SMILES: COc1ccc(C(=O)C2CCN(CC(=O)NCc3cc4c(c(=O)o3)COCC4)CC2)cc1]

Dissolved (1-oxo-5,8-dihydro-1H,6H-pyrano[3,4-c]pyran-3-ylmethyl)-carbamic acid tert-butyl ester (20 mg, 0.07 mmol) in 4N HCl dioxane solution (2 mL) and stirred for twenty minutes. The solution was concentrated in vacuo and used as is without purification. Dissolved the residue in dichloromethane (5 mL) and added [4-(4-methoxy-benzoyl)-piperidin-1-yl]-acetic acid (40 mg, 0.14 mmol), 1-ethyl-3-(3-dimethylaminopropyl) carbodiimide hydrochloride (36 mg, 0.19 mmol), N-hydroxybenzotriazole (17 mg, 0.11 mmol), triethylamine (0.077 mL, 0.55 mmol) and a catalytic amount of N,N-dimethylaminopyridine (~1 mg). The mixture was stirred sixteen hours and then concentrated in vacuo. The crude residue was purified by HPLC (Phenomenex Gemini® 30×100 mm 110 Å, 5 μm, C18; 5-45% acetonitrile in 0.1% trifluoroacetic acid) to obtain title compound as the trifluoroacetate salt. The TFA salt was dissolved in methanol (2 mL), added to a 0.5 g Stratospheres® PL-HCO3 SPE cartridge under gravity, then eluted with three times 2 mL 50% methanol in dichloromethane and then concentrated in vacuo to obtain title compound as a white powder (3 mg). $^1$H NMR (400 MHz, MeOD) δ ppm 7.97 (d, J=9.1 Hz, 2H), 7.01 (d, J=9.1 Hz, 2H), 6.15 (s, 1H), 4.37 (s, 2H), 4.24 (s, 2H), 3.87 (s, 3H), 3.85 (t, J=5.6 Hz, 2H), 3.32-3.41 (m, 1H), 3.11 (s, 2H), 2.91-3.02 (m, 2H), 2.54-2.61 (m, 2H), 2.38-2.32 (m, 2H), 1.79-1.86 (m, 4H). MS (ESI) m/z 441.5 (M+1), retention time=1.38 min.

Example 97

2-[4-(4-Methoxy-benzoyl)-piperidin-1-yl]-N-(8-oxo-3,4,7,8-tetrahydro-1H-pyrano[3,4-c]pyridin-6-ylmethyl)-acetamide

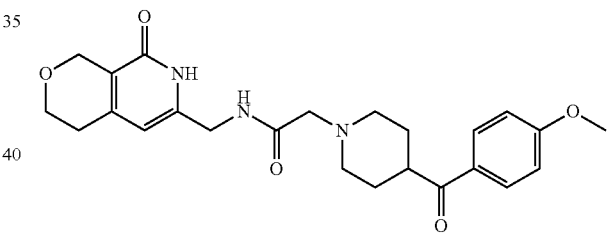

To a 4 N HCl solution in dioxane (4 mL) was added (8-oxo-3,4,7,8-tetrahydro-1H-pyrano[3,4-c]pyridin-6-ylmethyl)-carbamic acid tert-butyl ester (109 mg, 0.39 mmol), stirred for twenty minutes and the solution was then concentrated in vacuo. The resulting residue was dissolved in dichloromethane (5 mL) and to this was added [4-(4-methoxy-benzoyl)-piperidin-1-yl]-acetic acid (140 mg, 0.51 mmol), 1-ethyl-3-(3-dimethylaminopropyl) carbodiimide hydrochloride (127 mg, 0.66 mmol), N-hydroxybenzotriazole (60 mg, 0.39 mmol), triethylamine (0.271 mL, 1.9 mmol) and a catalytic amount of N,N-dimethylaminopyridine (~1 mg). The reaction was stirred 16 h then concentrated in vacuo. The resulting reside was purified by HPLC (Phenomenex Gemini®30×100 mm 110 Å, 5 μm, C18; 5-45% acetonitrile in 0.1% trifluoroacetic acid) to obtain title compound as the trifluoroacetate salt which was then dissolved in dichloromethane (20 mL), washed with three 20 mL volumes of saturated aqueous sodium bicarbonate then concentrated in vacuo to obtain title compound (12 mg). $^1$H NMR (400 MHz, MeOD) δ ppm 7.97 (d, J=9.1 Hz, 2H), 7.01 (d, J=9.1 Hz, 2H), 6.11 (s, 1H), 4.47 (s, 2H), 4.27 (s, 2H), 3.87 (s, 3H), 3.86 (t, J=5.6 Hz, 2H), 3.35-3.45 (m, 1H), 3.14 (s, 2H), 2.93-3.01 (m, 2H) 2.59-2.67 (m, 2H), 2.32-2.44 (m, 2H), 1.78-1.92 (m, 4H).

MS (ESI) m/z 440.5 (M+1), retention time=0.70 min. HRMS ESI m/z (M+H)$^+$ exact mass calculated for $C_{24}H_{29}N_3O_5$: 440.2185. found 440.2170.

Example 98

2-(4-(4-Fluorobenzoyl)piperidin-1-yl)-N-methyl-N-(1-(4-oxo-4,5,7,8-tetrahydro-3H-pyrano[4,3-d]pyrimidin-2-yl)ethyl)acetamide

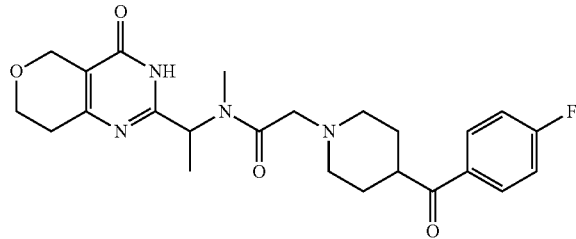 [SMILES: CC(c1nc2c(c(=O)[nH]1)COCC2)N(C)C(=O)CN1CCC(C(=O)c2ccc(F)cc2)CC1]

The title compound (170 mg) was prepared according to the general procedure of Example 1 from 2-(1-(methylamino)ethyl)-7,8-dihydro-3H-pyrano[4,3-d]pyrimidin-4(5H)-one (320 mg, 1.5 mmol) and 2-(4-(4-fluorobenzoyl)piperidin-1-yl)acetic acid (450 mg, 1.7 mmol). $^1$H NMR (400 MHz, CDC$_3$) δ 12.88 (br. s., 1H), 7.97 (dd, J=8.8, 5.3 Hz, 2H), 7.05-7.21 (m, 2H), 4.48-4.70 (m, 2H), 3.95 (t, J=5.5 Hz, 2H), 3.68 (d, J=12.5 Hz, 1H), 3.39 (br. s., 1H), 3.16-3.36 (m, 1H), 3.07-3.16 (m, 1H), 2.83-3.07 (m, 3H), 2.62-2.77 (m, 5H), 2.56 (t, J=9.8 Hz, 1H), 2.27-2.47 (m, 1H), 1.97-2.27 (m, 2H), 1.76-1.94 (m, 1H), 1.46-1.69 (m, 3H). HRMS calculated for $C_{24}H_{23}FN_4O_4$ 457.2251. found (ESI, [M+H]$^+$), 457.2257. Retention time=1.83 min.

Biological Assays and Data
Biochemical Assay to Determine Compound Inhibition of TNKS Enzyme Activity The human tankyrase 1 PARP catalytic domain, TNKS1P, was cloned into a pDONR221 vector using the Invitrogen Gateway Technology. This entry clone was then subcloned into the destination vector pDEST20 to obtain the N-terminal Glutathione S-transferase (GST)-tagged fusion protein. GST-TNKS1P was then expressed in Sf21 cells using the Invitrogen baculovirus expression system (Invitrogen-Bac-to-Bac® Baculovirus Expression System, Version D). The protein was purified by a GSTrap column (GE Healthcare). The N-terminal GST-tagged tankyrase 2 protein PARP domain, TNKS2P, was cloned, expressed, and purified in a similar manner. Human PARP1 (Cat. No. 4668-100-01) and activated DNA (Cat. No. 4671-096-06) were purchased from Trevigen, Inc. PARP2 (Cat. No. ALX-201-064-C020) was purchased from Alexis Biochemical.

The autoparsylation activity of the TNKS 1/2 or PARP1/2 enzymes was measured by the liquid chromatography-mass spectrometry (LC/MS) detection of nicotinamide as readout. Compound activity in inhibiting the TNKS and PARP autoparsylation was evaluated by IC$_{50}$ measurements. In the compound screening assays, the reaction is composed of 5 μL of compound in 8-point serial dilutions with concentrations ranging from 0.0086 to 18.75 μM, 20 nM of purified enzyme, and 250 μM of β-NAD$^+$ in the 1× Assay Buffer. After 60 min incubation at room temperature, the reactions were quenched by the addition of 10 μL of 5× quenching solution (20% formic acid and 500 nM [d]-nicotinamide in water). For the background control wells, 10 μL of the 5× quenching solution per well was added prior to the addition of β-NAD$^+$. The % Inhibition was calculated as: (Control−Sample)/(Control−Background)*100. "Control" is the average value of 8 wells without compound; and "Background" is the average of 8 wells mixed with 5× quenching solution measured prior to initiation of the reaction.

Examples 1-98 were tested in one or more of the above enzymatic assays, the results of which are given in Table 1.

TABLE 1

| Example | TNKS1 AP IC$_{50}$ (μM) | TNKS2 AP IC$_{50}$ (μM) | PARP1 IC$_{50}$ (μM) | PARP2 IC$_{50}$ (μM) |
| --- | --- | --- | --- | --- |
| 1 | 0.064 ± 0.008 | 0.023 ± 0.009 | 10.4 ± 1.8 | 3.1 ± 1.1 |
| 2 | 0.037 ± 0.002 | 0.007 | 9.1 ± 1.0 | 2.59 ± 0.29 |
| 3 | 0.035 ± 0.009 | 0.014 ± 0.001 | 5.63 ± 0.73 | 2.10 ± 0.24 |
| 4 | 0.063 ± 0.005 | 0.016 ± 0.001 | >19 | >19 |
| 5 | 0.0155 ± 0.0035 | 0.006 ± 0.001 | >19 | >19 |
| 6 | 0.575 ± 0.025 | 0.353 ± 0.008 | | |
| 7 | 0.714 ± 0.005 | 0.371 ± 0.003 | | |
| 8 | 0.031 ± 0.001 | 0.016 ± 0.002 | 16.4 ± 0.7 | 9.14 ± 0.21 |
| 9 | 0.021 ± 0.003 | 0.014 ± 0.001 | 1.08 ± 0.11 | 0.243 ± 0.066 |
| 10 | 0.055 ± 0.003 | 0.036 ± 0.002 | 2.7 ± 0.8 | 0.70 ± 0.08 |
| 11 | 0.0285 ± 0.0035 | 0.11 ± 0.14 | 17.9 ± 1.8 | 4.62 ± 0.02 |
| 12 | 0.040 ± 0.002 | 0.020 ± 0.003 | >19 | >19 |
| 13 | 0.0154 ± 0.0023 | 0.0075 ± 0.0020 | >19 | >19 |
| 14 | 0.060 ± 0.007 | 0.020 ± 0.001 | >19 | >19 |
| 15 | 0.138 ± 0.001 | 0.032 ± 0.001 | >19 | >19 |
| 16 | 0.066 ± 0.004 | 0.015 ± 0.002 | >19 | >19 |
| 17 | 0.073 ± 0.003 | 0.018 ± 0.001 | >19 | >19 |
| 18 | 0.094 ± 0.001 | 0.023 | >19 | >19 |
| 19 | 0.084 ± 0.007 | 0.021 ± 0.001 | >19 | >19 |
| 20 | 0.845 ± 0.012 | 0.206 ± 0.002 | | |
| 21 | 0.214 ± 0.002 | 0.042 ± 0.001 | | |
| 22 | 0.120 ± 0.002 | 0.031 ± 0.002 | >19 | >19 |
| 23 | 0.209 ± 0.003 | 0.050 ± 0.001 | >19 | >19 |
| 24 | 0.035 ± 0.010 | 0.0107 ± 0.0049 | >19 | >19 |
| 25 | 0.037 ± 0.004 | 0.013 ± 0.001 | >19 | >19 |
| 26 | 0.070 ± 0.007 | 0.018 ± 0.002 | >19 | >19 |
| 27 | 0.043 ± 0.001 | 0.014 ± 0.001 | >19 | >19 |
| 28 | 0.024 ± 0.001 | 0.010 ± 0.001 | >19 | >19 |
| 29 | 0.148 ± 0.01 | 0.038 ± 0.001 | >19 | >19 |
| 30 | 0.241 ± 0.03 | 0.057 ± 0.001 | | |
| 31 | 0.038 ± 0.003 | 0.013 ± 0.001 | >19 | >19 |

TABLE 1-continued

| Example | TNKS1 AP IC$_{50}$ (μM) | TNKS2 AP IC$_{50}$ (μM) | PARP1 IC$_{50}$ (μM) | PARP2 IC$_{50}$ (μM) |
|---|---|---|---|---|
| 32 | 0.043 ± 0.002 | 0.013 ± 0.001 | >19 | >19 |
| 33 | 0.095 ± 0.001 | 0.020 ± 0.001 | >19 | >19 |
| 34 | 0.046 ± 0.001 | 0.011 ± 0.001 | >19 | >19 |
| 35 | 0.256 ± 0.004 | 0.068 ± 0.001 | | |
| 36 | 0.104 ± 0.028 | 0.025 ± 0.007 | >19 | >19 |
| 37 | 0.155 ± 0.034 | 0.0395 ± 0.0078 | >19 | >19 |
| 38 | 0.082 ± 0.001 | 0.016 ± 0.001 | >19 | >19 |
| 39 | 0.043 ± 0.001 | 0.009 ± 0.001 | >19 | >19 |
| 40 | 0.077 ± 0.005 | 0.014 ± 0.001 | >19 | >19 |
| 41 | 0.016 ± 0.001 | 0.032 ± 0.001 | >19 | >19 |
| 42 | 0.042 ± 0.003 | 0.010 ± 0.001 | >19 | >19 |
| 43 | >19 | | >19 42.9 | |
| 44 | 0.0720 ± 0.0014 | 0.0190 ± 0.0014 | >19 | >19 |
| 45 | 0.037 ± 0.017 | 0.0102 ± 0.0074 | >19 | >19 |
| 46 | 0.053 ± 0.004 | 0.0160 ± 0.0014 | >19 | >19 |
| 47 | 0.561 ± 0.049 | 0.066 ± 0.002 | | |
| 48 | 0.055 ± 0.003 | 0.014 ± 0.001 | >19 | >19 |
| 49 | 0.0475 ± 0.0035 | 0.0165 ± 0.0007 | >19 | >19 |
| 50 | 0.018 ± 0.007 | 0.012 ± 0.001 | >19 | >19 |
| 51 | 0.207 ± 0.017 | 0.043 ± 0.002 | 7.63 ± 0.32 | 3.09 ± 0.39 |
| 52 | 1.19 ± 0.15 | 0.17 ± 0.03 | | |
| 53 | 1.13 ± 0.27 | 0.142 ± 0.019 | | |
| 54 | 0.035 ± 0.006 | 0.014 ± 0.003 | >19 | >19 |
| 55 | 0.487 ± 0.016 | 0.078 ± 0.004 | | |
| 56 | 0.548 ± 0.039 | 0.089 ± 0.003 | | |
| 57 | 1.21 ± 0.10 | 0.27 ± 0.01 | | |
| 58 | 1.49 ± 0.05 | 0.311 ± 0.039 | | |
| 59 | 2.25 ± 0.023 | 0.188 ± 0.016 | | |
| 60 | 3.8 ± 0.1 | 0.386 ± 0.007 | | |
| 61 | 0.025 ± 0.006 | 0.0080 ± 0.0026 | 6.5 ± 1.7 | >19 |
| 62 | 0.017 ± 0.001 | 0.004 ± 0.001 | | |
| 63 | 0.0100 ± 0.0014 | 0.0010 ± 0.0014 | | |
| 64 | 0.0100 ± 0.0014 | 0.0025 ± 0.0007 | | |
| 65 | 3.1 ± 0.4 | 0.760 ± 0.015 | | |
| 66 | 0.027 ± 0.010 | 0.009 ± 0.007 | 6.5 ± 1.3 | 3.2 ± 1.0 |
| 67 | 0.028 ± 0.006 | 0.012 ± 0.002 | 10.0 ± 3.2 | 3.64 ± 0.63 |
| 68 | 0.031 ± 0.001 | 0.005 ± 0.001 | | |
| 69 | 0.035 ± 0.004 | 0.018 ± 0.001 | | |
| 70 | 0.037 ± 0.002 | 0.008 | >19 | >19 |
| 71 | 0.043 ± 0.001 | 0.015 ± 0.001 | >19 | 11.76 ± 0.05 |
| 72 | 0.42 ± 0.11 | 0.085 ± 0.02 | | |
| 73 | 0.049 ± 0.001 | 0.016 ± 0.002 | >19 | >19 |
| 74 | 0.155 ± 0.015 | 0.038 ± 0.004 | | |
| 75 | 0.073 ± 0.005 | 0.017 ± 0.001 | | |
| 76 | 0.105 ± 0.001 | 0.032 ± 0.001 | | |
| 77 | 1.17 ± 0.05 | 0.764 ± 0.051 | | |
| 78 | 0.029 ± 0.002 | 0.015 ± 0.002 | 14.7 ± 4.6 | >19 |
| 79 | 3.02 ± 0.049 | 0.815 ± 0.028 | | |
| 80 | >19 | 31.2 | | |
| 81 | 0.761 ± 0.018 | 0.244 ± 0.024 | | |
| 82 | 0.222 ± 0.002 | 0.039 ± 0.003 | 32.4 ± 4.6 | 2.9 ± 0.9 |
| 83 | 0.064 | 0.018 ± 0.002 | 8.3 ± 3.0 | 2.30 ± 0.36 |
| 84 | 0.023 ± 0.005 | 0.013 ± 0.002 | 4.80 ± 0.25 | 2.13 ± 0.44 |
| 85 | 0.023 ± 0.002 | 0.010 ± 0.002 | 4.50 ± 0.58 | 1.97 ± 0.26 |
| 86 | 0.030 ± 0.003 | 0.012 ± 0.001 | 2.05 ± 0.37 | 0.885 ± 0.037 |
| 87 | 0.067 ± 0.004 | 0.029 | 5.8 ± 1.3 | 2.84 ± 0.33 |
| 88 | 0.026 ± 0.001 | 0.006 | 6.8 ± 2.0 | 2.37 ± 0.52 |
| 89 | 0.021 ± 0.002 | 0.012 ± 0.002 | 1.75 ± 0.020 | 0.92 ± 0.34 |
| 90 | 0.042 ± 0.002 | 0.018 | | |
| 91 | 0.04 ± 0.01 | 0.020 | 16.7 ± 0.4 | 4.53 ± 0.07 |
| 92 | 0.129 ± 0.001 | 0.043 | | |
| 93 | 0.033 ± 0.014 | 0.012 | 17.1 ± 0.8 | 4.26 ± 0.21 |
| 94 | 0.029 ± 0.003 | 0.0105 ± 0.0007 | | |
| 95 | 0.038 ± 0.003 | 0.016 ± 0.005 | | |
| 96 | 0.328 ± 0.001 | 0.133 ± 0.031 | | |
| 97 | 0.10 ± 0.01 | 0.027 ± 0.001 | 7.5 ± 0.4 | 1.15 ± 0.009 |
| 98 | 4.1 ± 0.5 | 0.723 ± 0.01 | | |

Cellular Reporter Gene Assay to Determine Compound Inhibition of Wnt Signaling Activity Compound activity in inhibiting Wnt ligand-induced signaling was measured using a Wnt-responsive Super-TOp-Flash (STF) luciferase reporter gene assay in HEK293 cells. On day 1 of the assay, cells were plated at a density of 8000 cells per well of 384-well plate in 25 μl medium containing 5% fetal bovine serum (FBS). On the second day, 20 Wnt3A condition medium (CM) produced from mouse L cells was added to the cells to induce Wnt signaling, followed by addition of 5 μL of compounds each well in 10-point serial dilution. On the third day, the luciferase activity was measured by the Bright-Glo™ Luciferase Assay System following manufacture's protocol (Promega, E2620). The Inhibition was calculated as: (Maximum Wnt-induced signaling−Sample)/(Maximum Wnt-induced signaling−Background)*100. "Maximum Wnt-induced signaling" is the STF signal level induced by 20% Wnt3A CM without compound; and "Background" is the STF signal level without the addition of Wnt3A CM or compound.

Cellular ELISA Assay to Determine Compound Effect on Stabilizing the Axin2 Protein Compound activity in stabilizing the Axin2 protein was measured by Sandwich Enzyme-Linked Immuosorbent (ELISA) assay in the colorectal cell line SW480. 30,000 SW480 cells were seeded per well in 96-well plate and incubated overnight prior to compound treatment. Cells were then treated with compounds in 6-point dilution starting at 10 µM for 24 hrs. Cells were then washed with 100 µL of cold Phosphate Buffer Saline (PBS), and lysed in 125 µl of cold 1× lysis buffer (Cell Signaling Technology, 9803) supplemented with Protease inhibitor (Roche, 11836170) and Phosphatase inhibitors (Sigma, P2850, P5726). For the ELISA assay, anti Axin-2 capture antibody (Strategic Diagnostics) antibody was diluted to a concentration of 1 µg/ml (1:1000) in Carbonate Coating buffer, pH 9.2 (Sigma, C3041-50CAP). 100µ, of the diluted anti Axin-2 capture antibody per well was then used to coat the 96-well ELISA plate (Thermo Electron Corp., MicroLite 1 flat bottom plate #7571) overnight at 4° C. Plates were then washed three times with 300 of wash solution, PBST20 (PBS+0.05% Tween), and blocked with 300 µl/well 1% BSA/PBS (BSA, Millipore Probumin #82-045-1) for 1.5 hours at room temperature while shaking gently. After blocking, plates were then washed three times with 300 µl/well of wash solution. 100 µL of prepared SW480 cell lysate was then added to each well and incubated at room temperature for 2 hours while shaking gently. After washing, 100 µL of Biotinylated anti-Axin2 antibody (CST, 2151) was added to each well and incubated room temperature for 2 hours. 100 µL of Streptavidin-HRP (R&D systems, DY998) diluted 1:200 in 1% BSA/PBS was then added in each well and incubate for 30 mins at R/T in the dark. Signal was detected by Chemiluminescence (Pierce SuperSignal ELISA Femto #3704), and measured on PerkinElmer Wallac 1420 plate reader.

Cellular Proliferation Assay to Determine Compound Inhibition of Cancer Cell Growth Non-small lung cancer ABC-1 cells were plated at 5000 cells per well in 96-well plates and treated with 8 serial compound dilutions starting from 10 µM as the highest concentration. Viable cells were measured after 3 days of compound treatment using the CellTiter-Glo assay (Promega, G7570). Assay was performed following the manufacture protocol. Excel XLfit 4 was used for plotting of the growth curves and calculation of $IC_{50}$ values. % growth following compound treatment was calculated as: (treated sample/(DMSO control)*100. $IC_{50}$ values are concentrations of the compound at which cell growth is inhibited by 50%.

Examples 1-98 were tested in one or more of the above cellular assays, the results of which are given in Table 2.

TABLE 2

| Example | STF $IC_{50}$ (µM) | Axin $AC_{50}$ (µM) | ABC-1 $IC_{50}$ (µM) |
|---|---|---|---|
| 1 | 0.038 ± 0.021 | 0.88 ± 0.21 | 1.05 ± 0.39 |
| 2 | 0.010 ± 0.002 | 0.205 ± 0.061 | 0.393 |
| 3 | 0.023 ± 0.002 | 0.062 ± 0.016 | 0.105 |
| 4 | 0.059 ± 0.017 | 0.363 ± 0.037 | |
| 5 | 0.0033 ± 0.0017 | 0.06 ± 0.06 | 0.032 ± 0.004 |
| 6 | 0.056 ± 0.007 | 0.293 ± 0.008 | 0.484 |
| 7 | 0.18 ± 0.07 | 0.68 ± 0.09 | 0.691 |
| 8 | 0.003 ± 0.001 | 0.013 ± 0.003 | 0.022 |
| 9 | 0.003 ± 0.003 | 0.009 ± 0.002 | 0.041 |
| 10 | 0.027 ± 0.015 | 0.479 ± 0.024 | 0.393 |
| 11 | 0.003 ± 0.001 | 0.015 ± 0.004 | 0.018 |
| 12 | 0.007 ± 0.004 | 0.032 ± 0.014 | 0.053 |
| 13 | 0.0040 ± 0.0024 | 0.026 ± 0.008 | 0.040 |
| 14 | 0.049 ± 0.023 | 0.501 ± 0.029 | 0.270 |
| 15 | 0.101 ± 0.074 | 0.804 ± 0.091 | 0.54 |
| 16 | 0.049 ± 0.043 | 0.587 ± 0.087 | 0.34 |
| 17 | 0.049 ± 0.037 | 0.125 ± 0.018 | 0.42 |
| 18 | 0.072 ± 0.062 | 0.493 ± 0.087 | 0.535 ± 0.007 |
| 19 | 0.092 ± 0.077 | 0.779 ± 0.083 | |
| 20 | 2.39 ± 0.25 | | |
| 21 | 0.46 ± 0.28 | | |
| 22 | 0.052 ± 0.029 | 0.36 ± 0.19 | 0.54 ± 0.28 |
| 23 | 0.189 ± 0.076 | | |
| 24 | 0.0167 ± 0.0044 | 0.32 ± 0.18 | 0.276 ± 0.037 |
| 25 | 0.030 ± 0.009 | 0.179 ± 0.026 | |
| 26 | 0.028 ± 0.016 | 0.473 ± 0.036 | 0.545 |
| 27 | 0.053 ± 0.045 | 3.64 ± 0.66 | |
| 28 | 0.015 ± 0.004 | 0.101 ± 0.019 | |
| 29 | 0.079 ± 0.08 | 0.99 ± 0.22 | 1.43 |
| 30 | 0.2 ± 0.2 | 6.0 ± 0.5 | |
| 31 | 0.037 ± 0.009 | 1.10 ± 0.18 | 0.63 ± 0.40 |
| 32 | 0.049 ± 0.014 | 0.91 ± 0.15 | 0.37 |
| 33 | 0.059 ± 0.02 | 2.8 ± 1.4 | 0.69 ± 0.10 |
| 34 | 0.034 ± 0.012 | 1.01 ± 0.07 | |
| 35 | 0.179 ± 0.020 | | |
| 36 | 0.127 ± 0.047 | 1.85 ± 0.31 | 2.63 |
| 37 | 0.096 ± 0.019 | 0.96 ± 0.52 | 0.51 |
| 38 | 0.065 ± 0.004 | 0.372 ± 0.086 | 0.833 |
| 39 | 0.017 ± 0.003 | 0.112 ± 0.018 | 0.230 ± 0.099 |
| 40 | 0.028 ± 0.004 | 0.431 ± 0.040 | 0.520 ± 0.014 |
| 41 | 0.0320 ± 0.0014 | 0.72 ± 0.15 | 0.476 |
| 42 | 0.0457 ± 0.0049 | 0.589 ± 0.06 | 0.29 |
| 43 | 0.362 | | |
| 44 | 1.47 ± 0.36 | >10 | 6.4 |
| 45 | 0.016 ± 0.009 | 0.45 ± 0.09 | 0.509 ± 0.047 |
| 46 | 0.036 ± 0.008 | 0.275 ± 0.084 | |
| 47 | 1.83 ± 0.39 | 5.0 ± 2.3 | |
| 48 | 0.014 ± 0.006 | 0.61 ± 0.24 | 0.79 ± 0.18 |
| 49 | 0.016 ± 0.004 | 0.086 ± 0.003 | 0.17 |
| 50 | 0.0095 ± 0.0005 | 0.030 ± 0.006 | 0.045 |
| 52 | 0.155 ± 0.008 | 1.09 ± 0.17 | 2.80 |
| 53 | 0.43 ± 0.05 | 2.1 ± 0.2 | 2.16 |
| 54 | 0.091 ± 0.013 | 1.2 ± 0.1 | 1.84 |
| 55 | 0.0047 ± 0.0018 | 0.025 ± 0.005 | 0.083 |
| 56 | 0.207 ± 0.021 | | 0.641 |
| 57 | 0.207 ± 0.035 | | 0.649 |
| 58 | 4.5 ± 0.4 | | >10 |
| 59 | 3.94 ± 0.12 | | 8.17 |
| 60 | 1.10 ± 0.11 | | 5.85 |
| 61 | 1.6 ± 0.8 | | 8.12 |
| 62 | 0.115 ± 0.017 | 0.56 ± 0.15 | 0.470 |
| 63 | 0.0119 ± 0.0031 | 0.137 ± 0.031 | 0.158 |
| 64 | 0.0012 ± 0.0005 | 0.009 ± 0.003 | 0.012 |
| 65 | 0.0007 ± 0.0002 | 0.012 ± 0.003 | 0.026 |
| 66 | 5.69 ± 0.17 | >10 | |
| 67 | 0.0053 ± 0.0041 | 0.016 ± 0.003 | 0.045 |
| 68 | 0.0052 ± 0.0008 | 0.041 ± 0.007 | 0.075 |
| 69 | 0.020 ± 0.009 | 0.93 ± 0.45 | 0.709 |
| 70 | 0.0080 ± 0.0016 | 0.135 ± 0.007 | 0.392 |
| 71 | 0.0175 ± 0.0066 | 0.058 ± 0.012 | 0.100 |
| 72 | 0.0087 ± 0.0003 | 0.052 ± 0.028 | 0.096 |
| 73 | 0.47 ± 0.15 | >10 | |
| 74 | 0.0351 ± 0.0034 | 0.508 ± 0.05 | 0.590 |
| 75 | 0.29 ± 0.13 | | 6.05 |
| 76 | 0.032 ± 0.010 | 0.176 ± 0.014 | 0.236 |
| 77 | 0.055 ± 0.008 | 4.48 ± 0.09 | 2.71 |
| 78 | 0.155 ± 0.008 | 1.92 ± 0.24 | 2.01 |
| 79 | 0.0065 ± 0.0027 | 0.027 ± 0.003 | 0.026 |
| 80 | 6.4 ± 1.1 | | |
| 81 | >10 | | |
| 82 | 0.787 ± 0.023 | | |
| 83 | >10 | >10 | >10 |
| 84 | 0.011 ± 0.003 | 0.162 ± 0.019 | 0.301 |
| 85 | 0.0052 ± 0.0001 | 0.015 ± 0.002 | 0.034 |

TABLE 2-continued

| Example | STF IC$_{50}$ (μM) | Axin AC$_{50}$ (μM) | ABC-1 IC$_{50}$ (μM) |
|---|---|---|---|
| 86 | 0.82 ± 0.41 | 0.029 ± 0.008 | 0.041 |
| 87 | 0.014 ± 0.001 | 0.040 ± 0.006 | 0.032 |
| 88 | 0.021 ± 0.005 | 0.069 ± 0.007 | 0.087 |
| 89 | 0.017 ± 0.004 | 0.052 ± 0.002 | 0.087 |
| 90 | 0.0103 ± 0.0008 | 0.020 ± 0.005 | 0.038 |
| 91 | 0.010 ± 0.007 | 0.053 ± 0.025 | 0.116 |
| 92 | 0.0091 ± 0.0012 | 0.154 ± 0.025 | 0.346 |
| 93 | 0.052 ± 0.012 | 1.16 ± 0.15 | 2.01 |
| 94 | 0.0024 ± 0.0003 | 0.011 ± 0.002 | 0.016 |
| 95 | 0.0066 ± 0.0007 | 0.026 ± 0.007 | 0.032 ± 0.005 |
| 96 | 0.013 ± 0.003 | 0.024 ± 0.008 | 0.065 ± 0.023 |
| 97 | | 0.266 ± 0.058 | |
| 98 | 0.017 ± 0.008 | 0.072 ± 0.015 | 0.258 |
| 99 | 3.19 ± 0.27 | | |

What is claimed is:

1. A compound according to formula (I)

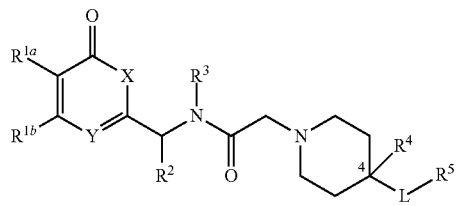

wherein:
X is NH or O;
Y is N or CH;
$R^{1a}$ and $R^{1b}$ are each independently $C_{1-3}$ alkyl; or
$R^{1a}$ and $R^{1b}$ are joined together with the atoms to which they are attached forming an optionally substituted $C_{5-7}$ cycloalkenyl ring, an optionally substituted 3,6-dihydro-2H-pyranyl ring, or an optionally substituted 1,2,3,6-tetrahydropyridinyl ring,
wherein said $C_{5-7}$ cycloalkenyl, 3,6-dihydro-2H-pyranyl, and 1,2,3,6-tetrahydropyridinyl are each optionally substituted with one to three substituents each independently selected from the group consisting of: halo, hydroxy, $C_{1-3}$ alkyl, and benzyl;
$R^2$ is H or $C_{1-3}$ alkyl;
$R^3$ is hydrogen, $C_{1-3}$ haloalkyl, $C_{3-6}$ alkynyl, or $C_{1-6}$ alkyl optionally substituted with one substituent selected from the group consisting of: methoxy, cyano, $C_{3-5}$ cycloalkyl, optionally substituted phenyl, optionally substituted 5-10 membered heteroaryl, and 5-6 membered heterocyclyl,
wherein said phenyl, 5-10 membered heteroaryl and 5-6 membered heterocycloalkyl are each optionally substituted with one or two substituents each independently selected from the group consisting of: halo, $C_{1-3}$ alkoxy, cyano, and morpholinyl-S(O)$_2$—; and
$R^4$ is hydrogen, L is C(O),

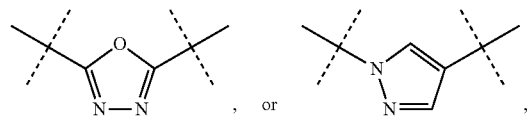

and
$R^5$ is optionally substituted phenyl, optionally substituted 5-6 membered heteroaryl, optionally substituted 2,3-dihydrobenzofuran-6-yl, optionally substituted benzyl[1,3]dioxol-5-yl; optionally substituted 1,2,3,4-tetrahydro-quinolin-1-yl, or optionally substituted 1,2,3,4-tetrahydro-isoquinolin-2-yl,
wherein each $R^5$ is optionally substituted with one or two substituents each independently selected from the group consisting of:
(a) halo,
(b) hydroxy,
(c) $C_{1-6}$ alkyl,
(d) $C_{1-3}$ haloalkyl,
(e) $C_{1-3}$ alkoxy optionally substituted with one methoxy, $C_{3-5}$ cycloalkyl, or phenyl,
(f) $C_{1-3}$ haloalkoxy,
(g) $C_{3-6}$ alkynyloxy,
(h) tetrahydropyranyl-O—, and
(i) $C_{1-3}$ alkyl-C(O)NH—;
or
$R^4$ is hydrogen, L is absent, and $R^5$ is optionally substituted benzo[d]isoxazol-3-yl, optionally substituted 1H-indazol-3-yl, or optionally substituted 1,3-dihydro-benzimidazol-2-one-1-yl, wherein each $R^5$ is optionally substituted with one or two substituents each independently selected from the group consisting of: halo, hydroxy, $C_{1-6}$ alkyl, $C_{1-3}$ haloalkyl, and $C_{1-3}$ alkoxy;
or
$R^4$ and L-$R^5$, wherein L is C(O), are joined together with the atoms to which they are attached forming an optionally substituted indan-1-one-2-yl group or an optionally substituted 3,4-dihydro-2H-naphthalen-1-one-2-yl each of which are attached to the piperidine ring of formula (I) through spiro carbon 4 and are optionally substituted with one to three substituents each independently selected from the group consisting of: halo and $C_{1-6}$ alkoxy; or a pharmaceutically acceptable salt thereof.

2. The compound according to claim 1 wherein X is NH and Y is N; or a pharmaceutically acceptable salt thereof.

3. The compound according to claim 1 wherein $R^{1a}$ and $R^{1b}$ are both methyl; or a pharmaceutically acceptable salt thereof.

4. The compound according to claim 1 wherein $R^{1a}$ and $R^{1b}$ are joined together with the atoms to which they are attached forming an optionally substituted $C_{5-7}$ cycloalkenyl ring, an optionally substituted 3,6-dihydro-2H-pyranyl ring, or an optionally substituted 1,2,3,6-tetrahydropyridinyl ring; or a pharmaceutically acceptable salt thereof.

5. The compound according to claim 1 wherein $R^{1a}$ and $R^{1b}$ are joined together with the atoms to which they are attached forming an optionally substituted 3,6-dihydro-2H-pyranyl ring; or a pharmaceutically acceptable salt thereof.

6. The compound according to claim 1 wherein $R^2$ is H or methyl; or a pharmaceutically acceptable salt thereof.

7. The compound according to claim 1 wherein $R^3$ is H, $C_{1-3}$ haloalkyl, $C_{3-6}$ alkynyl, or unsubstituted $C_{1-6}$ alkyl; or a pharmaceutically acceptable salt thereof.

8. The compound according to claim 1 wherein $R^3$ is optionally substituted $C_{1-6}$ alkyl; or a pharmaceutically acceptable salt thereof.

9. The compound according to claim 1 wherein $R^4$ is H, L is C(O), and $R^5$ is optionally substituted phenyl, optionally substituted 5-6 membered heteroaryl; optionally substituted 2,3-dihydrobenzofuran-6-yl, optionally substituted benzyl[1,3]dioxol-5-yl; optionally substituted 1,2,3,4-tetrahydro-quinolin-1-yl, or optionally substituted 1,2,3,4-tetrahydro-isoquinolin-2-yl; or a pharmaceutically acceptable salt thereof.

10. The compound according to claim 9 wherein $R^5$ is optionally substituted phenyl; or a pharmaceutically acceptable salt thereof.

11. The compound according to claim 1 wherein $R^4$ and L-$R^5$, wherein L is C(O), are joined together with the atoms to which they are attached forming an optionally substituted indan-1-one-2-yl group or an optionally substituted 3,4-dihydro-2H-naphthalen-1-one-2-yl both of which are attached to the piperidine ring of formula (I) through spiro carbon 4 and are optionally substituted with one to three substituents each independently selected from the group consisting of: halo and $C_{1-6}$ alkoxy; or a pharmaceutically acceptable salt thereof.

12. The compound according to claim 1 which is:
- 2-(4-(4-Fluorobenzoyl)piperidin-1-yl)-N-((4-oxo-4,5,7,8-tetrahydro-3H-pyrano[4,3-d]pyrimidin-2-yl)methyl)acetamide;
- 2-[4-(4-Chloro-benzoyl)-piperidin-1-yl]-N-(4-oxo-3,5,7,8-tetrahydro-4H-pyrano[4,3-d]-pyrimidin-2-ylmethyl)-acetamide;
- 2-[4-(4-Isopropoxy-benzoyl)-piperidin-1-yl]-N-(4-oxo-3,5,7,8-tetrahydro-4H-pyrano[4,3-d]pyrimidin-2-ylmethyl)-acetamide;
- 2-[4-(4-Fluoro-benzoyl)-piperidin-1-yl]-N-(4-oxo-3,5,7,8-tetrahydro-4H-pyrano[4,3-d]pyrimidin-2-ylmethyl)-N-((R)-1-phenyl-ethyl)-acetamide;
- N-Cyclopropylmethyl-2-[4-(4-methoxy-benzoyl)-piperidin-1-yl]-N-(4-oxo-3,5,7,8-tetrahydro-4H-pyrano[4,3-d]pyrimidin-2-ylmethyl)-acetamide;
- 2-(4-(4-Methoxybenzoyl)piperidin-1-yl)-N-((4-oxo-4,5,6,7,8,9-hexahydro-3H-cyclohepta[d]pyrimidin-2-yl)methyl)acetamide;
- N-(Cyclopropylmethyl)-2-(4-(4-methoxybenzoyl)piperidin-1-yl)-N-((4-oxo-4,5,6,7,8,9-hexahydro-3H-cyclohepta[d]pyrimidin-2-yl)methyl)acetamide;
- N-(Cyclopropylmethyl)-2-(4-(4-methoxybenzoyl)piperidin-1-yl)-N-((4-oxo-3,4,5,6,7,8-hexahydroquinazolin-2-yl)methyl)acetamide;
- 2-(4-(4-Methoxybenzoyl)piperidin-1-yl)-N-((4-oxo-3,4,5,6,7,8-hexahydroquinazolin-2-yl)methyl)acetamide;
- 2-(4-(4-Fluorobenzoyl)piperidin-1-yl)-N-((4-oxo-3,4,5,6,7,8-hexahydroquinazolin-2-yl)methyl)acetamide;
- 2-(4-(4-Methoxybenzoyl)piperidin-1-yl)-N-((4-oxo-4,5,6,7-tetrahydro-3H-cyclopenta[d]pyrimidin-2-yl)methyl)acetamide;
- N-((4,5-Dimethyl-6-oxo-1,6-dihydropyrimidin-2-yl)methyl)-2-(4-(4-methoxybenzoyl)piperidin-1-yl)acetamide;
- 2-(4-(4-Fluorobenzoyl)piperidin-1-yl)-N-((4-oxo-4,5,7,8-tetrahydro-3H-pyrano[4,3-d]pyrimidin-2-yl)methyl)-N-(thiophen-2-ylmethyl)acetamide;
- 2-(4-(4-Fluorobenzoyl)piperidin-1-yl)-N-neopentyl-N-((4-oxo-4,5,7,8-tetrahydro-3H-pyrano[4,3-d]pyrimidin-2-yl)methyl)acetamide;
- 2-(4-(4-Fluorobenzoyl)piperidin-1-yl)-N-(4-fluorobenzyl)-N-((4-oxo-4,5,7,8-tetrahydro-3H-pyrano[4,3-d]pyrimidin-2-yl)methyl)acetamide;
- 2-(4-(4-Fluorobenzoyl)piperidin-1-yl)-N-(4-methoxybenzyl)-N-((4-oxo-4,5,7,8-tetrahydro-3H-pyrano[4,3-d]pyrimidin-2-yl)methyl)acetamide;
- N-(Benzo[d]thiazol-2-ylmethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;
- 2-(4-(4-Fluorobenzoyl)piperidin-1-yl)-N-(3-methoxybenzyl)-N-((4-oxo-4,5,7,8-tetrahydro-3H-pyrano[4,3-d]pyrimidin-2-yl)methyl)acetamide;
- 2-(4-(4-Fluorobenzoyl)piperidin-1-yl)-N-(3-fluorobenzyl)-N-((4-oxo-4,5,7,8-tetrahydro-3H-pyrano[4,3-d]pyrimidin-2-yl)methyl)acetamide;
- 2-(4-(4-Fluorobenzoyl)piperidin-1-yl)-N-((4-oxo-4,5,7,8-tetrahydro-3H-pyrano[4,3-d]pyrimidin-2-yl)methyl)-N-(pyridin-4-ylmethyl)acetamide;
- 2-(4-(4-Fluorobenzoyl)piperidin-1-yl)-N-((4-oxo-4,5,7,8-tetrahydro-3H-pyrano[4,3-d]pyrimidin-2-yl)methyl)-N-(pyridin-3-ylmethyl)acetamide;
- 2-(4-(4-Fluorobenzoyl)piperidin-1-yl)-N-((4-oxo-4,5,7,8-tetrahydro-3H-pyrano[4,3-d]pyrimidin-2-yl)methyl)-N-(pyridin-2-ylmethyl)acetamide;
- 2-[4-(4-Fluoro-benzoyl)-piperidin-1-yl]-N-(4-oxo-3,5,7,8-tetrahydro-4H-pyrano[4,3-d]pyrimidin-2-ylmethyl)-N-((S)-1-phenyl-ethyl)-acetamide;
- N-Cyclopropylmethyl-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide;
- 2-[4-(4-Fluoro-benzoyl)-piperidin-1-yl]-N-((S)-2-methyl-butyl)-N-(4-oxo-3,5,7,8-tetrahydro-4H-pyrano[4,3-d]pyrimidin-2-ylmethyl)-acetamide;
- 2-(4-(4-Fluorobenzoyl)piperidin-1-yl)-N-isobutyl-N-((4-oxo-4,5,7,8-tetrahydro-3H-pyrano[4,3-d]pyrimidin-2-yl)methyl)acetamide;
- 2-(4-(4-Fluorobenzoyl)piperidin-1-yl)-N-((4-oxo-4,5,7,8-tetrahydro-3H-pyrano[4,3-d]pyrimidin-2-yl)methyl)-N-(prop-2-ynyl)acetamide;
- (S)-2-(4-(4-Fluorobenzoyl)piperidin-1-yl)-N-((4-oxo-4,5,7,8-tetrahydro-3H-pyrano[4,3-d]pyrimidin-2-yl)methyl)-N-((tetrahydrofuran-2-yl)methyl)acetamide;
- (R)-2-(4-(4-Fluorobenzoyl)piperidin-1-yl)-N-((4-oxo-4,5,7,8-tetrahydro-3H-pyrano[4,3-d]pyrimidin-2-yl)methyl)-N-((tetrahydrofuran-2-yl)methyl)acetamide;
- 2-(4-(4-Fluorobenzoyl)piperidin-1-yl)-N-methyl-N-((4-oxo-4,5,7,8-tetrahydro-3H-pyrano[4,3-d]pyrimidin-2-yl)methyl)acetamide;
- (S)—N-sec-Butyl-2-(4-(4-fluorobenzoyl)piperidin-1-yl)-N-((4-oxo-4,5,7,8-tetrahydro-3H-pyrano[4,3-d]pyrimidin-2-yl)methyl)acetamide;
- (R)—N-sec-Butyl-2-(4-(4-fluorobenzoyl)piperidin-1-yl)-N-((4-oxo-4,5,7,8-tetrahydro-3H-pyrano[4,3-d]pyrimidin-2-yl)methyl)acetamide;
- 2-(4-(4-Fluorobenzoyl)piperidin-1-yl)-N-isopropyl-N-((4-oxo-4,5,7,8-tetrahydro-3H-pyrano[4,3-d]pyrimidin-2-yl)methyl)acetamide;
- 2-(4-(4-Fluorobenzoyl)piperidin-1-yl)-N-((4-oxo-4,5,7,8-tetrahydro-3H-pyrano[4,3-d]pyrimidin-2-yl)methyl)-N-propylacetamide;
- (S)-2-(4-(4-Fluorobenzoyl)piperidin-1-yl)-N-(1-(4-fluorophenyl)ethyl)-N-((4-oxo-4,5,7,8-tetrahydro-3H-pyrano[4,3-d]pyrimidin-2-yl)methyl)acetamide;
- (R)-2-(4-(4-Fluorobenzoyl)piperidin-1-yl)-N-(1-(4-fluorophenyl)ethyl)-N-((4-oxo-4,5,7,8-tetrahydro-3H-pyrano[4,3-d]pyrimidin-2-yl)methyl)acetamide;
- N-(1-(2,4-Difluorophenyl)ethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;
- N-Benzyl-2-(4-(4-fluorobenzoyl)piperidin-1-yl)-N-((4-oxo-4,5,7,8-tetrahydro-3H-pyrano[4,3-d]pyrimidin-2-yl)methyl)acetamide;
- 2-(4-(4-Fluorobenzoyl)piperidin-1-yl)-N-(2-fluorobenzyl)-N-((4-oxo-4,5,7,8-tetrahydro-3H-pyrano[4,3-d]pyrimidin-2-yl)methyl)acetamide;
- N-(2,4-Difluorobenzyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;
- (R)—N-(1-Cyclopropylethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;
- (S)—N-(1-Cyclopropylethyl)-2-(4-(4-fluorobenzoyl)piperidin-1-yl)-N-((4-oxo-4,5,7,8-tetrahydro-3H-pyrano[4,3-d]pyrimidin-2-yl)methyl)acetamide;
- N-Cyanomethyl-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide;

2-[4-(4-Fluoro-benzoyl)-piperidin-1-yl]-N-(2-fluoro-ethyl)-N-(4-oxo-3,5,7,8-tetrahydro-4H-pyrano[4,3-d]pyrimidin-2-ylmethyl)-acetamide;

N-(2,2-Difluoro-ethyl)-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide;

N-(5-Cyano-thiophen-2-ylmethyl)-2-[4-(4-fluoro-benzoyl)-piperidin-1-yl]-N-(4-oxo-3,5,7,8-tetrahydro-4H-pyrano[4,3-d]pyrimidin-2-ylmethyl)-acetamide;

2-[4-(4-Fluoro-benzoyl)-piperidin-1-yl]-N-[5-(morpholine-4-sulfonyl)-thiophen-2-ylmethyl]-N-(4-oxo-3,5,7,8-tetrahydro-4H-pyrano[4,3-d]pyrimidin-2-ylmethyl)-acetamide;

2-[4-(4-Fluoro-benzoyl)-piperidin-1-yl]-N-(4-oxo-3,5,7,8-tetrahydro-4H-pyrano[4,3-d]pyrimidin-2-ylmethyl)-N-(2,2,2-trifluoro-ethyl)-acetamide;

2-[4-(4-Fluoro-benzoyl)-piperidin-1-yl]-N-(4-oxo-3,5,7,8-tetrahydro-4H-pyrano[4,3-d]pyrimidin-2-ylmethyl)-N-(1-thiophen-2-yl-ethyl)-acetamide;

N-(2,2-Difluoro-ethyl)-2-[4-(4-methoxy-benzoyl)-piperidin-1-yl]-N-(4-oxo-3,5,7,8-tetrahydro-4H-pyrano[4,3-d]pyrimidin-2-ylmethyl)-acetamide;

2-(4-(6-Fluorobenzo[d]isoxazol-3-yl)piperidin-1-yl)-N-((4-oxo-4,5,7,8-tetrahydro-3H-pyrano[4,3-d]pyrimidin-2-yl)methyl)acetamide;

N-(4-Oxo-3,5,7,8-tetrahydro-4H-pyrano[4,3-d]pyrimidin-2-ylmethyl)-2-[4-(5-phenyl-[1,3,4]oxadiazol-2-yl)-piperidin-1-yl]-acetamide;

2-(4-Benzoyl-piperidin-1-yl)-N-(2-methoxy-ethyl)-N-(4-oxo-3,5,7,8-tetrahydro-4H-pyrano[4,3-d]pyrimidin-2-ylmethyl)-acetamide;

2-[4-(4-Methoxy-benzoyl)-piperidin-1-yl]-N-(2-methoxy-ethyl)-N-(4-oxo-3,5,7,8-tetrahydro-4H-pyrano[4,3-d]pyrimidin-2-ylmethyl)-acetamide;

2-{4-[5-(4-Fluoro-phenyl)-[1,3,4]oxadiazol-2-yl]-piperidin-1-yl}-N-(4-oxo-3,5,7,8-tetrahydro-4H-pyrano[4,3-d]pyrimidin-2-ylmethyl)-acetamide;

2-{4-[5-(4-Methoxy-phenyl)-[1,3,4]oxadiazol-2-yl]-piperidin-1-yl}-N-(4-oxo-3,5,7,8-tetrahydro-4H-pyrano[4,3-d]pyrimidin-2-ylmethyl)-acetamide;

2-[4-(6-Fluoro-1H-indazol-3-yl)-piperidin-1-yl]-N-(4-oxo-3,5,7,8-tetrahydro-4H-pyrano[4,3-d]pyrimidin-2-ylmethyl)acetamide;

2-[4-(6-Methoxy-1H-indazol-3-yl)-piperidin-1-yl]-N-(4-oxo-3,5,7,8-tetrahydro-4H-pyrano[4,3-d]pyrimidin-2-ylmethyl)-acetamide;

N-(4-Oxo-3,5,7,8-tetrahydro-4H-pyrano[4,3-d]pyrimidin-2-ylmethyl)-2-[4-(4-phenyl-pyrazol-1-yl)-piperidin-1-yl]-acetamide;

2-{4-[4-(4-Methoxy-phenyl)-pyrazol-1-yl]-piperidin-1-yl}-N-(4-oxo-3,5,7,8-tetrahydro-4H-pyrano[4,3-d]pyrimidin-2-ylmethyl)-acetamide;

2-(5-Fluoro-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide;

N-(Cyclopropylmethyl)-2-(5-fluoro-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide;

N-(Cyclopropylmethyl)-2-(5-methoxy-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide;

N-(2,2-Difluoro-ethyl)-2-(5-methoxy-1-oxo-1,3-dihydrospiro[indene-2,4'-piperidine]-1'-yl)-N-((4-oxo-4,5,7,8-tetrahydro-3H-pyrano[4,3-d]pyrimidin-2-yl)methyl)acetamide;

2-(1-oxo-3,4-dihydro-1H-spiro[naphthalene-2,4'-piperidine]-1'-yl)-N-((4-oxo-4,5,7,8-tetrahydro-3H-pyrano[4,3-d]pyrimidin-2-yl)methyl)acetamide;

2-(4-(4-Ethoxybenzoyl)piperidin-1-yl)-N-((4-oxo-4,5,7,8-tetrahydro-3H-pyrano[4,3-d]pyrimidin-2-yl)methyl)acetamide;

2-(4-(4-Methoxybenzoyl)piperidin-1-yl)-N-((4-oxo-4,5,7,8-tetrahydro-3H-pyrano[4,3-d]pyrimidin-2-yl)methyl)acetamide;

2-(4-Benzoyl-piperidin-1-yl)-N-(2,2-difluoro-ethyl)-N-(4-oxo-3,5,7,8-tetrahydro-4H-pyrano[4,3-d]pyrimidin-2-ylmethyl)-acetamide;

2-[4-(4-Chloro-benzoyl)-piperidin-1-yl]-N-(2,2-difluoro-ethyl)-N-(4-oxo-3,5,7,8-tetrahydro-4H-pyrano[4,3-d]pyrimidin-2-ylmethyl)-acetamide;

N-Cyclopropylmethyl-N-(4-oxo-3,5,7,8-tetrahydro-4H-pyrano[4,3-d]pyrimidin-2-ylmethyl)-2-[4-(4-trifluoromethoxy-benzoyl)-piperidin-1-yl]-acetamide;

N-(2,2-Difluoro-ethyl)-N-(4-oxo-3,5,7,8-tetrahydro-4H-pyrano[4,3-d]pyrimidin-2-ylmethyl)-2-[4-(4-trifluoromethoxy-benzoyl)-piperidin-1-yl]-acetamide;

N-(2,2-Difluoro-ethyl)-2-[4-(2-methoxy-benzoyl)-piperidin-1-yl]-N-(4-oxo-3,5,7,8-tetrahydro-4H-pyrano[4,3-d]pyrimidin-2-ylmethyl)-acetamide;

N-(2,2-Difluoro-ethyl)-2-[4-(3-methoxy-benzoyl)-piperidin-1-yl]-N-(4-oxo-3,5,7,8-tetrahydro-4H-pyrano[4,3-d]pyrimidin-2-ylmethyl)-acetamide;

N-(2,2-Difluoro-ethyl)-N-(4-oxo-3,5,7,8-tetrahydro-4H-pyrano[4,3-d]pyrimidin-2-ylmethyl)-2-[4-(3-trifluoromethoxy-benzoyl)-piperidin-1-yl]-acetamide;

N-(2,2-Difluoro-ethyl)-N-(4-oxo-3,5,7,8-tetrahydro-4H-pyrano[4,3-d]pyrimidin-2-ylmethyl)-2-[4-(4-trifluoromethyl-benzoyl)-piperidin-1-yl]-acetamide;

N-Cyclopropylmethyl-N-(4-oxo-3,5,7,8-tetrahydro-4H-pyrano[4,3-d]pyrimidin-2-ylmethyl)-2-[4-(pyridine-2-carbonyl)-piperidin-1-yl]-acetamide;

N-Cyclopropylmethyl-N-(4-oxo-3,5,7,8-tetrahydro-4H-pyrano[4,3-d]pyrimidin-2-ylmethyl)-2-[4-(4-phenoxy-benzoyl)-piperidin-1-yl]-acetamide;

2-[4-(But-2-ynyloxy-benzoyl)-piperidin-1-yl]-N-cyclopropylmethyl-N-(4-oxo-3,5,7,8-tetrahydro-4H-pyrano[4,3-d]pyrimidin-2-ylmethyl)-acetamide;

N-((4-Oxo-4,5,7,8-tetrahydro-3H-pyrano[4,3-d]pyrimidin-2-yl)methyl)-2-(4-(1,2,3,4-tetrahydroisoquinoline-2-carbonyl)piperidin-1-yl)acetamide;

2-(4-(6-Methoxy-1,2,3,4-tetrahydroquinoline-1-carbonyl)piperidin-1-yl)-N-((4-oxo-4,5,7,8-tetrahydro-3H-pyrano[4,3-d]pyrimidin-2-yl)methyl)acetamide;

2-(4-(5-Chloro-1,2,3,4-tetrahydroisoquinoline-2-carbonyl)piperidin-1-yl)-N-((4-oxo-4,5,7,8-tetrahydro-3H-pyrano[4,3-d]pyrimidin-2-yl)methyl)acetamide;

2-(4-(2-Oxo-2,3-dihydro-1H-benzo[d]imidazol-1-yl)piperidin-1-yl)-N-((4-oxo-4,5,7,8-tetrahydro-3H-pyrano[4,3-d]pyrimidin-2-yl)methyl)acetamide;

2-[4-(4-Methyl-benzoyl)-piperidin-1-yl]-N-(4-oxo-3,5,7,8-tetrahydro-4H-pyrano[4,3-d]pyrimidin-2-ylmethyl)-acetamide;

N-(4-Oxo-3,5,7,8-tetrahydro-4H-pyrano[4,3-d]pyrimidin-2-ylmethyl)2-[4-(4-propoxy-benzoyl)-piperidin-1-yl]-acetamide;

2-[4-(4-Cyclopropylmethoxy-benzoyl)-piperidin-1-yl]-N-(4-oxo-3,5,7,8-tetrahydro-4H-pyrano[4,3-d]pyrimidin-2-ylmethyl)-acetamide;

2-[4-(4-Cyclobutylmethoxy-benzoyl)-piperidin-1-yl]-N-(4-oxo-3,5,7,8-tetrahydro-4H-pyrano[4,3-d]pyrimidin-2-ylmethyl)-acetamide;

N-(4-Oxo-3,5,7,8-tetrahydro-4H-pyrano[4,3-d]pyrimidin-2-ylmethyl)-2-{4-[4-(tetrahydro-pyran-4-yloxy)-benzoyl]-piperidin-1-yl}-acetamide;

2-{4-[4-(2-Methoxy-ethoxy)-benzoyl]-piperidin-1-yl}-N-(4-oxo-3,5,7,8-tetrahydro-4H-pyrano[4,3-d]pyrimidin-2-ylmethyl)-acetamide;

2-{4-[4-(2-Cyclopropyl-ethoxy)-benzoyl]-piperidin-1-yl}-N-(4-oxo-3,5,7,8-tetrahydro-4H-pyrano[4,3-d]pyrimidin-2-ylmethyl)-acetamide;

2-[4-(3,4-Dimethoxy-benzoyl)-piperidin-1-yl]-N-(4-oxo-3,5,7,8-tetrahydro-4H-pyrano[4,3-d]pyrimidin-2-ylmethyl)-acetamide;

2-[4-(2,3-Dihydro-benzofuran-5-carbonyl)-piperidin-1-yl]-N-(4-oxo-3,5,7,8-tetrahydro-4H-pyrano[4,3-d]pyrimidin-2-ylmethyl)-acetamide;

2-(4-(Benzo[1,3]dioxole-5-carbonyl)-piperidin-1-yl]-N-(4-oxo-3,5,7,8-tetrahydro-4H-pyrano[4,3-d]pyrimidin-2-ylmethyl)-acetamide;

2-[4-(4-Methoxy-3-methyl-benzoyl)-piperidin-1-yl]-N-(4-oxo-3,5,7,8-tetrahydro-4H-pyrano[4,3-d]pyrimidin-2-ylmethyl)-acetamide;

2-(4-(3-Chloro-4-methoxy-benzoyl)-piperidin-1-yl]-N-(4-oxo-3,5,7,8-tetrahydro-4H-pyrano[4,3-d]pyrimidin-2-ylmethyl)-acetamide;

2-[4-(4-Ethoxy-3-fluoro-benzoyl)-piperidin-1-yl]-N-(4-oxo-3,5,7,8-tetrahydro-4H-pyrano[4,3-d]pyrimidin-2-ylmethyl)-acetamide;

2-(4-(4-methoxy-benzoyl)-piperidin-1-yl]-N-(1-oxo-5,8-dihydro-1H,6H-pyrano[3,4-c]pyran-3-ylmethyl)-acetamide;

2-(4-(4-Methoxy-benzoyl)-piperidin-1-yl]-N-(8-oxo-3,4,7,8-tetrahydro-1H-pyrano[3,4-c]pyridin-6-ylmethyl)-acetamide; or 2-(4-(4-Fluorobenzoyl)piperidin-1-yl)-N-methyl-N-(1-(4-oxo-4,5,7,8-tetrahydro-3H-pyrano[4,3-d]pyrimidin-2-yl)ethyl)acetamide.

13. A pharmaceutical composition comprising a compound according to claim 1 or a pharmaceutically acceptable salt thereof and a pharmaceutically acceptable excipient.

\* \* \* \* \*